(12) United States Patent
Giovannini et al.

(10) Patent No.: US 9,012,489 B2
(45) Date of Patent: Apr. 21, 2015

(54) PHENYL-3-AZA-BICYCLO[3.1.0]HEX-3-YL-METHANONES AND THE USE THEREOF AS MEDICAMENT

(75) Inventors: Riccardo Giovannini, Verona (IT); Barbara Bertani, Castiglione delle Stiviere (IT); Marco Ferrara, San Donato Milanese (IT); Iain Lingard, Monza (IT); Rocco Mazzaferro, San Giuliano Milanese (IT); Holger Rosenbrock, Mittelbiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 56 days.

(21) Appl. No.: 13/560,063

(22) Filed: Jul. 27, 2012

(65) Prior Publication Data

US 2013/0197011 A1 Aug. 1, 2013

(30) Foreign Application Priority Data

Aug. 3, 2011 (EP) .................................. 11176468

(51) Int. Cl.
*A61K 31/40* (2006.01)
*A61K 31/41* (2006.01)
*C07D 413/04* (2006.01)
*C07D 209/52* (2006.01)
*C07D 417/04* (2006.01)
*C07D 403/04* (2006.01)
*C07D 413/14* (2006.01)
*C07D 401/04* (2006.01)
*C07D 471/04* (2006.01)

(52) U.S. Cl.
CPC ............ *C07D 413/04* (2013.01); *C07D 209/52* (2013.01); *C07D 417/04* (2013.01); *C07D 403/04* (2013.01); *C07D 413/14* (2013.01); *C07D 401/04* (2013.01); *C07D 471/04* (2013.01)

(58) Field of Classification Search
CPC .. C07D 209/52; C07D 401/04; C07D 403/04; C07D 413/04; C07D 413/14; C07D 417/04; C07D 471/04
USPC ......... 514/256, 300, 339, 364, 365, 374, 378, 514/383, 412, 421; 546/121, 276.7; 548/131, 143, 181, 236, 238, 247, 548/262.2, 512, 515
See application file for complete search history.

(56) References Cited

U.S. PATENT DOCUMENTS 7,557,114 B2 * 7/2009 Jolidon et al. ............. 514/265.1
8,188,139 B2 * 5/2012 Jolidon et al. ................ 514/416
8,288,435 B2 * 10/2012 Aissaoui et al. .............. 514/443

FOREIGN PATENT DOCUMENTS

WO 2004089363 A1 10/2004
WO 2005037216 A2 4/2005

OTHER PUBLICATIONS

Baldovini et al., 3-Oxa- and 3-Azabicyclo[3.1.0]hexan-2-ones via Tandem Radical Cydlization-Intramolecular SN2 Reactions, J of Organic Chemistry, 1996, vol. 61, p. 3205-3208.
Gilligan et al., Divergent mechanisms for the Dealkoxycarbonylation of a 2-(3-Azetidiny)malonate by Chloide and Cyanide, Tetrahedron Letters, 1994, vol. 35, No. 21, pp. 3441-3444.
International Search Report, PCT/ISA/210, and Written Opinion, form PCT/ISA/237, for corresponding application PCT/EP2012/065140, date of mailing Aug. 27, 2012.
Medda et al., 3,4-Methano-β-Proline: A Conformationally Constrained β-Amino Acid, Synlett, vol. 2009, No. 06, p. 921-924.

* cited by examiner

*Primary Examiner* — My-Chau T Tran
(74) *Attorney, Agent, or Firm* — Michael P. Morris; Alan R. Stempel

(57) ABSTRACT

Substituted phenyl-3-aza-bicyclo[3.1.0]hex-3-yl-methanones which are glycine transporter-1 (GlyT1) inhibitors. These are useful for the treatment of schizophrenia, Alzheimer's Disease and other neurological and psychiatric disorders.

47 Claims, No Drawings

PHENYL-3-AZA-BICYCLO[3.1.0]HEX-3-YL-METHANONES AND THE USE THEREOF AS MEDICAMENT

The present inventions relate to substituted phenyl-3-aza-bicyclo[3.1.0]hex-3-yl-methanones of general formula (I)

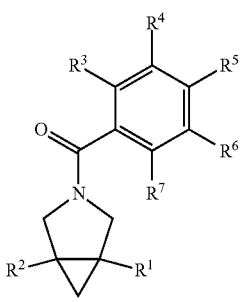

wherein
$R^1$, $R^2$, $R^3$, $R^4$, $R^5$ and $R^6$ are as herein described or salts thereof, preferably pharmaceutically acceptable salts thereof.

The invention further relates to the manufacture of said compounds, pharmaceutical compositions comprising a compound according to general formula (I), and the use of said compounds for the treatment of various conditions such as conditions concerning positive and negative symptoms of schizophrenia as well as cognitive impairments associated with schizophrenia, Alzheimer's Disease and other neurological and psychiatric disorders.

The compounds of the invention according to general formula (I) show glycine transporter-1 (GlyT1) inhibiting properties.

Another subject of the present invention concerns intermediates for the manufacture of the pharmaceutically active compounds of the invention.

BACKGROUND OF THE INVENTION

A general overview of the role of glycine transporter-1 (GlyT1) inhibitors for the treatment of diseases can be taken for example from WO2010/086251. This role of glycine transporter-1 (GlyT1) inhibitors is applicable for the present invention.

Schizophrenia is a progressive and devastating psychiatric disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, 2000, Neuron, 28: 325-33). For decades research has focused on the "dopaminergic hyperactivity" hypothesis which has led to therapeutic interventions involving blockade of the dopaminergic system (Vandenberg R J and Aubrey K R., 2001, Exp. Opin. Ther. Targets, 5(4): 507-518; Nakazato A and Okuyama S, et al., 2000, Exp. Opin. Ther. Patents, 10(1): 75-98). However, this pharmacological approach does not effectively treat negative and cognitive symptoms which are the best predictors of functional outcome (Sharma T., 1999, Br. J. Psychiatry, 174(suppl. 28):44-51).

A complementary model of schizophrenia was proposed in the mid-1960' based upon the psychotomimetic action caused by the blockade of the glutamate system by compounds like phencyclidine (PCP) and related agents (e.g. ketamine) which are non-competitive antagonists of the glutamate N-methyl-D-aspartate (NMDA) receptor. Interestingly in healthy volunteers, PCP-induced psychotomimetic action incorporates positive and negative symptoms as well as cognitive dysfunction, thus closely resembling schizophrenia in patients (Javitt D C et al., 1999, Biol. Psychiatry, 45:668-679; see also Jentsch and Roth, 1999, Neuropsychopharmacology 20:201-225. Therefore, increasing NMDA-receptor neurotransmission in the central nervous system offers an opportunity for the development of novel treatment approaches for schizophrenia and also other neurological and psychiatric diseases related to NMDA-receptor and/or glutamatergic dysfunction. The NMDA-receptor is a ligand-gated ion channel composed of a combination of two NR1 and two NR2 subunits and requires the concomitant binding of glutamate at the NR2 subunit and glycine as a co-agonist at the NR1 subunit to be activated (Johnson and Ascher, 1987, Nature 325:529-531). While glutamate is released in an activity-dependent manner from synaptic terminals, glycine is apparently present at a more constant level and seems to modulate/control the receptor for its response to glutamate. One of the most effective ways to control synaptic concentrations of neurotransmitter is to influence their re-uptake at the synapses. In forebrain areas like prefrontal and frontal cortex, hippocampus, striatum and thalamus, glycine has been shown to be necessary for glutamatergic NMDA-receptor activity and to modulate NMDA-receptor dependent excitatory neurotransmission (Johnson and Ascher, 1987, Nature 325: 529-531; Danysz and Parsons, 1998, Pharmacol. Rev. 50: 597-664). The ability of glycine to modulate NMDA-receptor mediated neurotransmission suggests that pharmacological manipulation of synaptic glycine could prove effective in the treatment of conditions involving a hypofunction of the NMDA-receptor such as schizophrenia. Thus, one strategy to enhance NMDA receptor activity is to elevate the glycine concentration in the local microenvironment of synaptic NMDA receptors by inhibition of GlyT1 (Bergeron R. et al., 1998, Proc. Natl. Acad. Sci. USA 95:15730-15734). In fact, clinical studies with direct glycine site agonists D-serine and a prototype GlyT1-inhibitor, sarcosine, which increases glycine in the synaptic cleft, have demonstrated some efficacy for the treatment of negative symptoms and to a lesser extent, positive and cognitive symptoms of schizophrenia (Tsai et al., 2004, Biol. Psychiatry 44:1081-1089; Lane et al., 2005, Biol. Psychiatry 63:9-12). Recently, clinical efficacy regarding negative symptoms in schizophrenia patients was reported for the GlyT1-inhibitor RG1678 tested in a clinical phase II trial as adjunctive treatment to marketed antipsychotics (Umbricht et al., 2011, Schizophr. Bull. 37(Suppl.1):324).

Efficacy in various animal models/tests for positive and negative symptoms of schizophrenia as well as in several memory tasks has been reported in the literature for different GlyT1-inhibitors. In detail, the selective GlyT1-inhibitors SSR504734 and SSR103800 were shown to be efficacious in two models for antipsychotic activity, i.e. reversal of NMDA-receptor antagonist induced hyperlocomotion and pre-pulse-inhibition, well known models for positive symptoms of schizophrenia (Depoortere et al., 2005, Neuropsychopharmacology 30:1963-1985; Boulay et al., 2008, Pharmacol. Biochem. Behav. 91:47-58). Regarding negative symptoms, SSR504734 was demonstrated to increase dopamine in the prefrontal cortex, a mechanistic in-vivo model for negative symptoms in schizophrenia (Depoortere et al., 2005, Neuropsychopharmacology 30:1963-1985). Regarding memory enhancement, both GlyT1-inhibitors were efficacious in the social recognition test (Depoortere et al., 2005, Neuropsychopharmacology 30:1963-1985; Boulay et al., 2008, Pharmacol. Biochem. Behav. 91:47-58). Another GlyT1-inhibitor, NFPS, was shown to be active in the object recognition and social recognition test regarding reversal of MK-801-induced cognitive deficits (Karasawa et al., 2008, Behav. Brain Res. 186:78-83; Shimazaki et al., 2010, Psychopharmacology 209:263-270). In addition, an enhancing effect on long-term potentiation in hippocampal slices could be shown with NIPS demonstrating that inhibition of GlyT1 leads to strengthening of synaptic plasticity which is crucial for memory formation on a cellular level (Kinney et al., 2003, J. Neurosci. 23:7586-7591). In fact, glutamate neurotransmission, in particular NMDA receptor activity, plays a critical role in synaptic plasticity, learning and memory, such as the NMDA receptors appears to serve as a graded switch for gating the threshold of synaptic plasticity and memory formation (Bliss T V and Collingridge G L, 1993, Nature, 361:31-39).

In addition, GlyT1-inhibitors were shown to be efficacious in animal models of depression, anxiety and sleep, such as chronic mild stress, ultrasonic distress calls in rat pups and increased latency of paradoxical sleep (Depoortere et al., 2005, Neuropsychopharmacology 30:1963-1985).

Two distinct glycine transporter genes have been cloned (GlyT1 and GlyT2) from mammalian brain, which give rise to two transporters with ~50% amino acid sequence homology. GlyT1 presents four isoforms arising from alternative splicing and alternative promoter usage (1a, 1b, 1c and 1d). Only two of these isoforms have been found in rodent brain (GlyT1a and GlyT1b). GlyT2 also presents some degree of heterogeneity. Two GlyT2 isoforms (2a and 2b) have been identified in rodent brains. GlyT1 is known to be located in CNS and in some peripheral tissues, whereas GlyT2 is specific to the CNS, primarily in the hindbrain and spinal cord (Zafra et al., 1995, J. Neurosci. 15:3952-3969). GlyT1 is expressed in glia and neurons, and it is found to be located at glutamatergic synapses (Cubelos et al., 2005, Cereb. Cortex 15:448-459).

Glycine transporter inhibitors are suitable for the treatment of neurological and psychiatric disorders. The majority of diseases states implicated are psychoses, schizophrenia (Armer R E and Miller D J, 2001, Exp. Opin. Ther. Patents 11:563-572), psychotic mood disorders such as severe major depressive disorder, mood disorders associated with psychotic disorders such as acute mania or depression, associated with bipolar disorders and mood disorders, associated with schizophrenia, (Pralong E T et al., 2002, Prog. Neurobiol., 67:173-202), autistic disorders (Carlsson M L, 1998, J. Neural Trans. 105:525-535), cognitive disorders such as dementias, including age related dementia and senile dementia of the Alzheimer type, memory disorders in a mammal, including a human, attention deficit disorders and pain (Armer R E and Miller D J, 2001, Exp. Opin. Ther. Patents, 11:563-572). Thus, increasing activation of NMDA receptors via GlyT1 inhibition may lead to agents that treat psychosis, schizophrenia (positive, negative and cognitive symptoms), dementia and other diseases in which cognitive processes are impaired, such as attention deficit disorders, Alzheimer's disease, or other neurological and psychiatric disorders.

All these concepts to medicinally benefit from the inhibition of GlyT1 are of high interest, in particular with respect to cognitive impairment associated with Alzheimer's disease or Schizophrenia.

BRIEF SUMMARY OF THE INVENTION

The present inventions relate to substituted phenyl-3-azabicyclo[3.1.0]hex-3-yl-methanones of general formula (I)

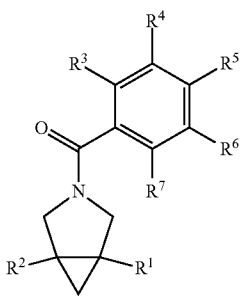

wherein
$R^1$, $R^2$, $R^3$, $R^4$, $R^5$, $R^6$ and $R^7$ are as herein described or salts thereof, preferably a pharmaceutically acceptable salt thereof.

The invention further relates to the manufacture of said active compounds, pharmaceutical compositions comprising a compound according to general formula (I), and the use of said active compounds for the treatment of various conditions such as conditions concerning positive and negative symptoms of schizophrenia as well as cognitive impairments associated with schizophrenia, Alzheimer's Disease and other neurological and psychiatric disorders.

The use comprises the manufacture of medicaments for the treatment of the corresponding diseases.

DETAILED DESCRIPTION OF THE INVENTION

The present inventions relate to substituted phenyl-3-azabicyclo[3.1.0]hex-3-yl-methanones of general formula (I)

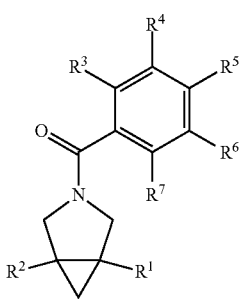

wherein
$R^1$ is defined according to a definition selected from a group of $R^{1a}$, $R^{1b}$, $R^{1c}$ and $R^{1d}$;
$R^2$ is defined according to a definition selected from a group of $R^{2a}$, $R^{2b}$ and $R^{2c}$;
$R^3$ is defined according to a definition selected from a group of $R^{3a}$, $R^{3b}$, $R^{3c}$ and $R^{3d}$; $R^4$ is defined according to definition $R^{4a}$;
or $R^3$ and $R^4$ together are defined according to definition $R^{3/4}$ which is selected from the group of $R^{3/4a}$, $R^{3/4b}$ and $R^{3/4c}$;
$R^5$ is defined according to definition $R^{5a}$;
$R^6$ is defined according to a definition selected from a group of $R^{6a}$, $R^{6b}$ and $R^{6c}$;
$R^7$ is defined according to definition $R^{7a}$;
or one of the pairs a) $R^6$ and $R^7$ or b) $R^6$ and $R^5$ together are defined according to definition $R^{5/6/7}$ which is selected from the group of $R^{5/6/7a}$ and $R^{5/6/7b}$;

and wherever appropriate the salts, preferably pharmaceutically acceptable salts, solvates and the solvates of the salts thereof.

DEFINITIONS OF SUBSTITUENTS ACCORDING TO GENERAL FORMULA (I)

Definitions for $R^1$ $R^{1a}$: $R^1$ is selected from the group of
a) 5 or 6 membered monocyclic heteroaryl, having 1, 2, 3 or 4 heteroatoms independently selected from the group of O, N and $S(O)_r$,
b) 5 or 6 membered monocyclic partially saturated heterocycloalkyl, having 1, 2 or 3 heteroatoms independently selected from the group of O, N and $S(O)_r$, and
c) 9 or 10 membered bicyclic heteroaryl, having 1, 2 or 3 heteroatoms independently selected from the group of O, N and $S(O)_r$,
wherein r is 0, 1 or 2;
wherein each of said groups a), b) and c) is optionally substituted with 1 or more substituents independently selected from the group of $C_{1-4}$-alkyl-, $C_{1-4}$-alkyl-O—, oxetanyl, tetrahydrofuranyl, tetrahydropyranyl, $C_{3-6}$-cycloalkyl- and $C_{3-6}$-cycloalkyl-O— and in case a substituent is attached to a nitrogen ring atom said substituent is selected from the group of $C_{1-4}$-alkyl-, $C_{3-6}$-cycloalkyl- and $C_{3-6}$-cycloalkyl-CO—,
and wherein each of said $C_{1-4}$-alkyl-, $C_{1-4}$-alkyl-O—, $C_{1-4}$-alkyl-CO—, oxetanyl, tetrahydrofuranyl, tetrahydropyranyl, $C_{3-6}$-cycloalkyl-, $C_{3-6}$-cycloalkyl-CO— or $C_{3-6}$-cycloalkyl-O-substituents may be substituted by 1 or more substituents independently other from the group of fluoro, —$CF_3$, —$CHF_2$, —$CH_2F$ and —CN;

Examples for the 5 or 6 membered heteroaryls according to group a) in definition $R^{1a}$ above are:

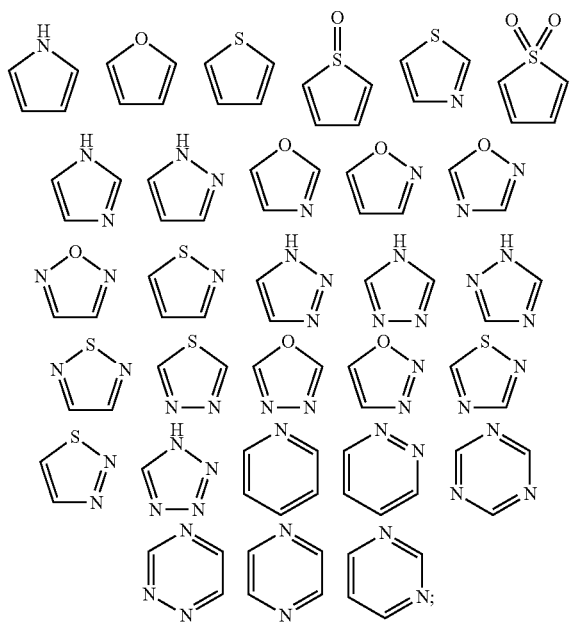

$R^{1b}$: $R^1$ is a 5 or 6 membered monocyclic heteroaryl, having 1, 2 or 3 heteroatoms independently selected from the group of O, N or S,
wherein said heteroaryl is optionally substituted with 1 or more substituents independently selected from the group of $C_{1-2}$-alkyl-, $C_{1-2}$-alkyl-O—, oxetanyl, tetrahydrofuranyl, tetrahydropyranyl, cyclopropyl-, cyclobutyl-, cyclopropyl-O— and cyclobutyl-O— and in case a substituent is attached to a nitrogen ring atom said substituent is selected from the group of $C_{1-2}$-alkyl- and $C_{1-2}$-alkyl-CO—,
and wherein each of said $C_{1-2}$-alkyl-, $C_{1-2}$-alkyl-O—, $C_{1-2}$-alkyl-CO—, oxetanyl, tetrahydrofuranyl, tetrahydropyranyl, cyclopropyl- or cyclopropyl-O— substituents may be substituted with 1 or more substituents independently selected from the group of fluoro, —$CF_3$, —$CHF_2$, —$CH_2F$ and —CN, preferably fluoro;

Examples for the 5 or 6 membered heteroaryls according to group a) in definition $R^{1b}$ above are:

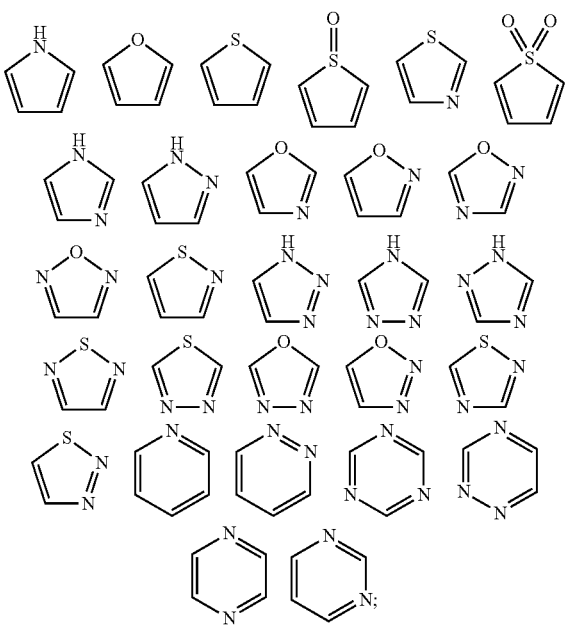

$R^{1c}$: $R^1$ is a 5 or 6 membered monocyclic heteroaryl being selected from the group of oxadiazolyl, oxazolyl, isoxazolyl, thiazolyl, pyrazolyl, triazoyl, pyridinyl and pyrimidinyl,
wherein said heteroaryl is optionally substituted with 1 or more substituents independently selected from the group of $C_{1-2}$-alkyl-, $C_{1-2}$-alkyl-O—, cyclopropyl- and cyclopropyl-O— and in case it is a substituent of a nitrogen ring atom said substituent is selected from the group of $C_{1-2}$-alkyl- and $C_{1-2}$-alkyl-CO—,
and wherein each of said $C_{1-2}$-alkyl-, $C_{1-2}$-alkyl-O—, $C_{1-2}$-alkyl-CO—, cyclopropyl- or cyclopropyl-O-substituents may be substituted with 1 or more substituents independently selected from the group of fluoro, —$CF_3$, —$CHF_2$, —$CH_2F$ and —CN, preferably fluoro;

$R^{1d}$: $R^1$ is a 5 or 6 membered monocyclic heteroaryl being selected from the group of oxadiazolyl, oxazolyl, isoxazolyl, thiazolyl, pyridinyl and pyrimidinyl,
wherein said heteroaryl is optionally substituted with 1 or more substituents independently selected from the group of $C_{1-2}$-alkyl-, $C_{1-2}$-alkyl-O—, cyclopropyl-, cyclopropyl-O— and in case it is a substituent of a nitrogen ring atom is selected from the group of $C_{1-2}$-alkyl- and $C_{1-2}$-alkyl-CO—,
and wherein each of said $C_{1-2}$-alkyl-, $C_{1-2}$-alkyl-O—, $C_{1-2}$-alkyl-CO—, cyclobutyl, cyclopropyl-O— or cyclobutyl-O— substituents may be substituted with 1 or more substituents independently selected from the group of fluoro, —$CF_3$, —$CHF_2$, —$CH_2F$ and —CN, preferably fluoro;

Definitions for $R^2$ $R^{2a}$: $R^2$ is selected from the group of hydrogen, $C_{1-4}$-alkyl-, $C_{1-4}$-alkyl-O—, —CN and $C_{3-6}$-cycloalkyl-,
wherein each of said $C_{1-4}$-alkyl-, $C_{1-4}$-alkyl-O— and $C_{3-6}$-cycloalkyl-group may be optionally substituted with 1, 2, 3 or more substituents independently selected from the group of fluoro, —$CF_3$, —$CHF_2$, —$CH_2F$ and —CN;

$R^{2b}$: $R^2$ is selected from the group of hydrogen, methyl, ethyl, methoxy, ethoxy, —CN and cyclopropyl-,
wherein each of said groups may be optionally substituted with 1, 2 or 3 substituents independently selected from the group of fluoro, —$CF_3$, —$CHF_2$, —$CH_2F$ and —CN;

$R^{2c}$: $R^2$ is hydrogen or methyl;

$R^{2d}$: $R^2$ is hydrogen;

Definitions for $R^3$ $R^{3a}$: $R^3$ is selected from the group of $C_{1-6}$-alkyl-O—, $C_{3-6}$-cycloalkyl-O—, morpholino, pyrazolyl and a 4 to 7 membered, monocyclic heterocycloalkyl-O— with 1 oxygen atom as ring member and optionally 1 or 2 heteroatoms independently selected from the group of O, N and $S(O)_s$ with s=0, 1 or 2, preferably with 1 oxygen atom as the only heteroatom in said heterocycloalkyl-O— ring,
wherein said $C_{1-6}$-alkyl-O— and said $C_{3-6}$-cycloalkyl-O— may be optionally substituted with 1, 2, 3 or more substituents independently selected from the group of fluoro, —$CF_3$, —$CHF_2$, —$CH_2F$, —CN, $C_{1-4}$-alkyl-, $C_{3-6}$-cycloalkyl-, $C_{1-6}$-alkyl-O— and $C_{3-6}$-cycloalkyl-O—;

$R^{3b}$: $R^3$ is selected from the group of $C_{1-6}$-alkyl-O—, oxetanyl-O—, tetrahydrofuranyl-O—, tetrahydropyranyl-O— wherein said $C_{1-6}$-alkyl-O—, oxetanyl-O—, tetrahydrofuranyl-O—, tetrahydropyranyl-O— may be optionally substituted with 1, 2 or 3 substituents independently selected from the group of fluoro, —$CF_3$, —$CHF_2$, —$CH_2F$, —CN, $C_{1-4}$-alkyl and $C_{1-6}$-alkyl-O—;

$R^{3c}$: $R^3$ is selected from the group of $C_{1-3}$-alkyl-O—, oxetanyl-O—, tetrahydrofuranyl-O— and tetrahydropyranyl-O—, wherein said $C_{1-3}$-alkyl-O—, oxetanyl-O—, tetrahydrofuranyl-O—, tetrahydropyranyl-O— may be optionally substituted with 1, 2 or 3 substituents independently selected from the group of fluoro and —$CF_3$;

$R^{3d}$: $R^3$ is selected from the group of R-1,1,1-trifluoro-2-ethoxy and S-1,1,1-trifluoro-2-ethoxy and isopropoxy;
whenever $R^3$ is a representative of a member of the group selected from $C_{1-6}$-alkyl-O—, a $C_{3-6}$-cycloalkyl-O— or the 4 to 7 membered, monocyclic heterocycloalkyl-O— and if there is a substituent selected from the group of $C_{1-6}$-alkyl-O— or $C_{3-6}$-cycloalkyl-O— substituent, said substituent preferably is not attached geminal to the "oxy" group (—O—) by which said $R^3$ is connected to the remaining part of the molecule. Specifically, if $R^3$ is a heterocycloalkyl-O— with 1 or more oxygen atom(s) as ring member, such as oxetanyl-O—, tetrahydrofuranyl-O—, tetrahydropyranyl-O—, i.e. as defined in $R^{3a}$, $R^{3b}$, $R^{3c}$, an oxygen atom that is a ring member preferably shall not be directly attached to said carbon atom to which the oxy substituent is bound by which said heterocycloalkyl-O— is attached to the group to which it is a substituent in order to avoid a geminal diether motif.

In case of oxetanyl-O— the preferred isomer is always 3-oxetanyl-O—, in case of tetrahydrofuranyl-O— the preferred isomer is always 3-tetrahydrofuranyl and in case of tetrahydropyranyl-O— the preferred isomers are always 3- or 4-tetrahydropyranyl-O—.

The analogue principle shall apply in case of other heteroatoms in a heterocycloalkyl-O— group.

Definitions for $R^4$ $R^{4a}$: $R^4$ is hydrogen

Definitions for $R^{3/4}$ $R^{3/4a}$: $R^3$ and $R^4$ together with the ring atoms of the phenyl group to which they are bound may form a 4, 5 or 6 membered, monocyclic, partially saturated heterocycloalkyl or a heteroaryl each of which having 1, 2 or 3 heteroatoms independently selected from the group of O, N and $S(O)_s$ with s=0, 1 or 2, wherein there must be 1 ring oxygen atom that is directly attached to the ring carbon atom of said phenyl group to which $R^3$ is attached to in general formula (I);
wherein
with respect to oxetanyl-O— the preferred isomer is 3-oxetanyl-O—,
with respect to tetrahydrofuranyl-O— the preferred isomer is 3-tetrahydrofuranyl and
with respect to tetrahydropyranyl-O— the preferred isomers are 3- or 4-tetrahydropyranyl-O—;
wherein said heterocycloalkyl group may be optionally substituted with 1, 2, 3 or more substituents independently selected from the group of fluoro, —$CF_3$, —$CHF_2$, —$CH_2F$, —CN, $C_{1-4}$-alkyl-, $C_{3-6}$-cycloalkyl-, $C_{1-6}$-alkyl-O—, $C_{3-6}$-cycloalkyl-O—, oxetanyl-O—, tetrahydrofuranyl-O— and tetrahydropyranyl-O—;

$R^{3/4b}$: $R^3$ and $R^4$ together with the ring atoms of the phenyl group to which they are bound may form a 4, 5 or 6 membered, monocyclic, partially saturated heterocycloalkyl group having 1 or 2 oxygen atoms, wherein 1 ring oxygen atom is directly attached to the ring carbon atom of said phenyl group to which $R^3$ is attached to in general formula (I);
wherein said heterocycloalkyl group may be optionally substituted with 1, 2, 3 or more substituents independently selected from the group of fluoro, —$CF_3$, —$CHF_2$, —CN, $C_{1-3}$-alkyl-, cyclopropyl-, $C_{1-3}$-alkyl-O— and cyclopropyl-O—;

$R^{3/4c}$: $R^3$ and $R^4$ together with the ring atoms of the phenyl group to which they are bound may form a oxetan-, tetrahydrofuran-, tetrahydropyran- or dioxolan-group, wherein 1 oxygen atom is directly attached to the ring carbon atom of said phenyl group to which $R^3$ is attached to in general formula (I);
wherein said oxetan-, tetrahydrofuran-, tetrahydropyran- or dioxolan-group, may be optionally substituted with 1, 2, 3 or more substituents independently selected from the group of fluoro, —$CF_3$, —$CHF_2$, —$CH_2F$, —CN, $C_{1-3}$-alkyl-, cyclopropyl-, $C_{1-3}$-alkyl-O and cyclopropyl-O—;

Definitions for $R^5$ $R^{5a}$: $R^5$ is hydrogen;

Definitions for $R^6$ $R^{6a}$: $R^6$ selected from the group of hydrogen, $C_{1-4}$-alkyl-$SO_2$—, $C_{3-6}$-cycloalkyl-$SO_2$— and —CN;

$R^{6b}$: $R^6$ is selected from the group of $C_{1-4}$-alkyl-$SO_2$— and —CN;

$R^{6c}$: $R^6$ is selected from the group of methyl-$SO_2$—, ethyl-$SO_2$—; CN; preferably being selected from the group of methyl-$SO_2$— and ethyl-$SO_2$—;

Definitions for $R^7$ $R^{7a}$: $R^7$ is hydrogen

Definitions for $R^{5/6/7}$ $R^{5/6/7a}$: one of the pairs a) $R^6$ and $R^7$ or b) $R^6$ and $R^5$ form together with the ring atoms of the phenyl group to which they are hound, a 5 or 6 membered, partially saturated monocyclic heterocycloalkyl group having 1, 2 or 3 heteroatoms independently selected from the group of O, N and $S(O)_u$ with u=0, 1 or 2, wherein there must be 1 —$SO_2$— member that is directly attached to the ring carbon atom of said phenyl group to which $R^6$ is attached to in general formula (I),
wherein said heterocycloalkyl group may be optionally substituted with 1, 2, 3 or more substituents independently selected from the group of fluoro, —$CF_3$, —$CHF_2$, —$CH_2F$, —CN, $C_{1-4}$-alkyl-, $C_{1-6}$-alkyl-O— and $C_{3-6}$-cycloalkyl-O—;

$R^{5/6/7b}$: one of the pairs a) $R^6$ and $R^7$ or b) $R^6$ and $R^5$ form together with the ring atoms of the phenyl group to which they are hound, a 5 or 6 membered, partially saturated monocyclic heterocycloalkyl group having 1, 2 or 3 heteroatoms independently selected from the group of O, N and $S(O)_u$ with u=0, 1 or 2, wherein there must be 1 —$SO_2$— member that is directly attached to the ring carbon atom of said phenyl group to which $R^6$ is attached to in general formula (I),
wherein said heterocycloalkyl group may be optionally substituted with 1, 2, 3 or more substituents independently selected from the group of fluoro, —$CF_3$, —$CHF_2$, —$CH_2F$ and —$C_{1-4}$-alkyl-.

EMBODIMENTS ACCORDING TO THE INVENTION

General Remark

Substituents are defined herein as $R^1$, $R^2$ etc. The definitions for these substituents are abbreviated by the name of the substituent directly followed by a superscript Latin letter. To illustrate this principle, the herein irrelevant substituent $R^0$ shall be taken as an example: If the corresponding definition for said substituent is "$R^0$ is as defined by $R^{0a}$", the wording means that the definition $R^{0a}$ applies in order to define substituent $R^0$. If $R^{0a}$ defines: $R^0$ is hydrogen, then the term "$R^0$ is as defined by $R^{0a}$" is to be read "$R^0$ is hydrogen".

Embodiment 1

Genius

A compound according to general formula (I), wherein
$R^1$ is as defined by $R^{1a}$;
$R^2$ is as defined by $R^{2a}$;
$R^3$ is as defined by $R^{3a}$, preferably $R^{3b}$; more preferably $R^{3c}$, more preferably $R^{3d}$;
$R^4$ is defined by $R^{4a}$;
or $R^3$ and $R^4$ together are as defined by $R^{3/4a}$;
$R^5$ is defined according to definition $R^{5a}$;
$R^6$ is as defined by $R^{6a}$;
$R^7$ is as defined by $R^{7a}$;
or one of the pairs a) $R^6$ and $R^7$ or b) $R^6$ and $R^5$ together are defined by $R^{5/6/7a}$; preferably by $R^{5/6/7b}$;
and wherever appropriate a specific diastereoisomer or a mixture thereof, a salt, preferably a pharmaceutically acceptable salt, a solvate and the solvate of a salt thereof.

Embodiment 2

Genius

A compound according to general formula (I), wherein
$R^1$ is as defined by $R^{1b}$;
$R^2$ is as defined by $R^{2b}$; preferably by $R^{2c}$;
$R^3$ is as defined by $R^{3b}$; preferably by $R^{3c}$;
$R^4$ is as defined by $R^{4a}$;
or $R^3$ and $R^4$ together are as defined by $R^{3/4b}$;
$R^5$ is as defined according to definition $R^{5a}$;
$R^6$ is as defined by $R^{6a}$; preferably $R^{6b}$;
$R^7$ is as defined by $R^{7a}$;
and wherever appropriate a specific diastereoisomer or a mixture thereof, a salt, preferably a pharmaceutically acceptable salt, a solvate and the solvate of a salt thereof.

Embodiment 3

According to the Invention (Genius)

A compound according to general formula (I), wherein
$R^1$ is as defined by $R^{1c}$;
$R^2$ is as defined by $R^{2b}$; preferably by $R^{2c}$;
$R^3$ is as defined by $R^{3b}$; preferably by $R^{3c}$;
$R^4$ is as defined by $R^{4a}$;
or $R^3$ and $R^4$ together are as defined by $R^{3/4c}$;
$R^5$ is as defined according to definition $R^{5a}$;
$R^6$ is as defined by $R^{6a}$; preferably $R^{6b}$; more preferably $R^{6c}$;
$R^7$ is as defined by $R^{7a}$;
and wherever appropriate a specific diastereoisomer or a mixture thereof, a salt, preferably a pharmaceutically acceptable salt, a solvate and the solvate of a salt thereof.

Embodiment 4

According to the Invention (Genius)

A compound according to general formula (I), wherein
$R^1$ is as defined by $R^{1d}$;
$R^2$ is as defined by $R^{2c}$, preferably $R^{2d}$;
$R^3$ is as defined by $R^{3b}$; preferably by $R^{3c}$;
$R^4$ is as defined by $R^{4a}$;
or $R^3$ and $R^4$ together are as defined by $R^{3/4c}$;
$R^5$ is as defined according to definition $R^{5a}$;
$R^6$ is as defined by $R^{6b}$; preferably $R^{6c}$;
$R^7$ is as defined by $R^{7a}$;
and wherever appropriate a specific diastereoisomer or a mixture thereof, a salt, preferably a pharmaceutically acceptable salt, a solvate and the solvate of a salt thereof.

Embodiment 5

According to the Invention (Genius)

A compound according to general formula (I), wherein
$R^1$ is as defined by $R^{1d}$;
$R^2$ is as defined by $R^{2c}$; preferably as defined by $R^{2d}$;
$R^3$ is as defined by $R^{3c}$;
$R^4$ is as defined by $R^{4a}$;
$R^5$ is as defined according to definition $R^{5a}$;
$R^6$ is as defined by $R^{6b}$; preferably $R^{6c}$;
$R^7$ is as defined by $R^{7a}$;
and wherever appropriate a specific diastereoisomer or a mixture thereof, a salt, preferably a pharmaceutically acceptable salt, a solvate and the solvate of a salt thereof.

Embodiment 6

According to the Invention (Genius)

A compound according to general formula (I), wherein
$R^1$ is as defined by $R^{1d}$;
$R^2$ is as defined by $R^{2d}$;
$R^3$ is as defined by $R^{3d}$;
$R^4$ is as defined by $R^{4a}$;
$R^5$ is as defined according to definition $R^{5a}$;
$R^6$ is as defined by $R^{6b}$; preferably $R^{6c}$;
$R^7$ is as defined by $R^{7a}$;
and wherever appropriate a specific diastereoisomer or a mixture thereof, a salt, preferably a pharmaceutically acceptable salt, a solvate and the solvate of a salt thereof.

USED TERMS AND DEFINITIONS

General Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In case a compound of the present invention is depicted in form of a chemical name and as a formula in case of any discrepancy the formula shall prevail.

An asterisk is may be used in sub-formulas to indicate the bond which is connected to the core molecule as defined.

Scope of the Term Compound/Scope of a Chemical Structure/Stereochemistry/Solvates/Hydrates Unless specifically indicated, throughout the specification and the appended claims, a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The terms "compound of the invention" or "compound according to formula (I)" and the like refer to the compounds according to general formula (I)—be it generically or specifically. Such compounds are also called "active compounds", meaning that they are supposed to be the active ingredients of medicaments or pharmaceutical compositions.

These "active compounds" shall not be mixed up with the term "intermediate compounds" as defined by the general formulas (II), (III), (IV), (V) and (VI).

Whenever the term compound is used it may be any compound or specifically an active compound, what will be evident from the context. An intermediate compound according to the general formulas (II), (III), (IV), (V) and (VI) will be addressed "intermediate compound"

Bonds

"Bonds": If within a chemical formula of a ring system or a defined group a substituent is directly linked to an atom or a group like "RyR" in below formula this shall mean that the substituent is only attached to the corresponding atom. If however from another substituent like "RxR" a bond is not specifically linked to an atom of the ring system but drawn towards the centre of the ring or group this means that this substituent "RxR" may be linked to any meaningful atom of the ring system/group unless stated otherwise.

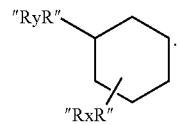

The bond symbol "–" (=minus sign) or the symbol "–*" (=minus sign followed by an asterisk sign) stands for the bond through which a substituent is bound to the corresponding remaining part of the molecule/scaffold. In cases in that the minus sign does not seem to be sufficiently clear, there may be added an asterisk to the bond symbol "–" in order to determine the point of attachment of said bond with the corresponding main part of the molecule/scaffold.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "$C_{1-4}$-alkyl-O—$C_{1-3}$-alkyl-" means a $C_{1-4}$-alkyl-group that is bound to an oxygen that with its second valence is bound to another $C_{1-3}$-alkyl-group or in other word an alkoxyalkyl group. If to a substituent a hyphen is added with a loose end, this end indicates the position of said substituent which is connected to the remaining part of the compound as defined. In the above example "$C_{1-4}$-alkyl-O—$C_{1-3}$-alkyl-" it is the $C_{1-3}$-alkyl group that is bound to the remaining part of the compound, while the $C_{1-4}$-alkyl-O— group is a substituent for the $C_{1-3}$-alkyl group. In the following illustrative examples "—CN", "—$CF_3$" it is the carbon atom that is attached to the remaining part of the compound. An alternative writing of the groups such as the latter two ones is: "NC—" or "$F_3$—" for addressing a C-bound cyano or trifluoromethyl-group.

Metabolites

"Metabolites" are considered derivatives of the active compounds according to the present invention that are formed in-vivo. Active metabolites are such metabolites that cause a pharmacological effect. It will be appreciated that metabolites of the active compounds according to the present inventions are subject to the present invention as well, in particular active metabolites.

Prodrugs

A "Prodrug" is considered a compound that is designed to release a biologically active compound according to the present invention in-vivo when such prodrug is administered to a mammalian subject. Prodrugs of active compounds according to the present invention are prepared by modifying functional groups present in the active compound of the invention in such a way that these modifications are retransformed to the original functional groups under physiological conditions. It will be appreciated that prodrugs of the compounds according to the present inventions are subject to the present invention as well.

Prevention/Prophylaxis

Expressions like "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis. Thus the expression "prevention of a disease" as used herein means the management and care of an individual at risk of developing the disease prior to the clinical onset of the disease. The purpose of prevention is to combat the development of the disease, condition or disorder and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

Solvates

Some of the compounds of the invention may form "solvates". For the purposes of the invention the term "solvates" refers to those forms of the compounds which form, in the solid or liquid state, a complex by coordination with solvent molecules. Hydrates are a specific form of solvates in which the coordination takes place with water. According to the present invention, the term preferably is used for solid solvates, such as amorphous or more preferably crystalline solvates.

Treatment/Therapy

The expression "treatment" or "therapy" preferably means therapeutic treatment of (e.g. preferably human) patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition, disorder or a symptom thereof. Treatment includes the administration of the active compounds to eliminate or control the disease, condition or disorder as well as to alleviate the symptoms or complications associated with the disease, condition or disorder.

Scaffold

The following formula represents the scaffold of the compounds according to the present inventions, specifically the compounds according to general formula (I), inclusively the numbering of the atoms (position numbers) in the two ring systems, the 3-azabicyclo[3.1.0]hex-3-yl-ring system and the phenyl ring system:

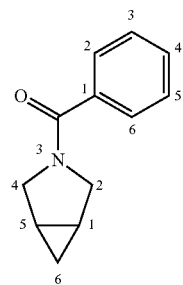

The positions 1 and 5 of the 3-aza-bicyclo[3.1.0]hexane ring are the bridgehead positions. Specifically $R^1$ is attached to one of said bridgehead positions.

Salts:

The active compounds of the present invention shall provide a pharmacological effect in an animal or a human being. The pharmacological effect may be provided by the neutral active compound or in the case of some active compound according to the invention by a salt thereof. Among salt forms, pharmaceutically acceptable salts are preferred for the final destination of the active compound, i.e. as pharmacologically active ingredient in a drug product. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed active compounds wherein the parent compound is modified by making acid or base salts thereof. Examples of potential pharmaceutically acceptable salts can be found in: Pharmaceutical salts, Berge, S. M. et al., J. Pharm. Sci., (1977), 66, 1-19.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts,) also comprise a part of the invention.

Solvates

Some of the compounds may form "solvates". For the purposes of the invention the term "solvates" refers to those forms of the compounds which form, in the solid or liquid state, a complex by coordination with solvent molecules. Hydrates are a specific form of solvates in which the coordination takes place with water. According to the present invention, the term preferably is used for solid solvates, such as amorphous or more preferably crystalline solvates.

Substitution

The term "substituted" as used herein explicitly or implicitly, means that any one or more hydrogen(s) on the designated atom is replaced with a member of the indicated group of substituents, provided that the designated atom's normal valence is not exceeded. In case a substituent is bound via a double bond, e.g. an oxo substituent, such substituent replaces two hydrogen atoms on the designated atom. The substitution shall result in a stable compound. "Stable" in the context with an active compound preferably means a compound that from a pharmaceutical point of view is chemically and physically sufficiently stable under ambient conditions in order to be used as an active pharmaceutical ingredient of a pharmaceutical composition. If a substituent is not defined, it shall be hydrogen. By the term "optionally substituted" is meant that either the corresponding group is substituted or it is not. A characterization that substituents of the same group may be "selected independently" shall mean that the corresponding substituents may be the same or may be different.

Definitions for Substituents

Alkyl:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-4}$-alkyl embraces the radicals:
C1-alkyl: $H_3C$—,
C2-alkyl: $H_3C$—$CH_2$—,
C3-alkyl: $H_3C$—$CH_2$—$CH_2$—, $H_3C$—$CH(CH_3)$—,
C4-alkyl: $H_3C$—$CH_2$—$CH_2$—$CH_2$—, $H_3C$—$CH_2$—$CH$($CH_3$)—, $H_3C$—$CH(CH_3)$—$CH_2$—, $H_3C$—$C(CH_3)_2$—.

Cycloalkyl:

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-6}$-cycloalkyl includes cyclopropyl, cyclobutyl, cyclopentyl and cyclohexyl.

Heteroaryl

The term "heteroaryl" means an aromatic-ring systems containing heteroatoms. A heteroaryl comprises at least one heteroatom selected from N, O or S, wherein an atom like S may be oxidized without disturbing the aromatic character of the ring system which is why it is referred to as $S(O)_r$, wherein r=0, 1 or 2. The ring is composed of atoms or groups of atoms such as carbon, oxygen, nitrogen, sulfur, —S(O)— or —S(O)$_2$—. Such atoms or groups are ring members. For example, a 5 membered heteroaryl is composed by 5 such atoms/groups. The term "heteroaryl" is intended to include all the possible isomeric forms. In cases in which there is tautomeric forms are possible which allow an aromatic and a non-aromatic character, the system shall be considered aromatic if the aromatic form dominates under ambient and/or in-vivo conditions.

In principle, a "heteroaryl" may be attached to the group of which it is a substituent either by a carbon ring atom or a nitrogen ring atom.

Heterocycloalkyl

The term "heterocycloalkyl" means a cycloalkyl ring in which one or more carbon atoms are replaced by heteroatoms. A heterocycloalkyl comprises at least one heteroatom selected from N, O or S, wherein an atom like S may be oxidized, which is why it is referred to as $S(O)_r$, wherein r=0, 1 or 2. The ring is composed of atoms or groups of atoms such as carbon, oxygen, nitrogen, sulfur, —S(O)— or —S(O)$_2$—. Such atoms or groups are ring members. A 5 membered heterocycloalkyl is composed by 5 such atoms/groups. The term "heterocycloalkyl" is intended to include all the possible isomeric forms. A heterocycloalkyl is a non-aromatic ring system, that even if substituted will maintain its non-aromatic character. If not specified otherwise it is a saturated ring system.

PREFERRED EMBODIMENTS

Specifically preferred in the context of the present invention are the following compound family groups (compound family groups of active compounds). The following compound family groups and individual isomers (=compound family members) are particularly preferred embodiments of compounds according to the invention. Each such compound family group and individual isomer is an individual embodiment of the invention. For each of these compound family groups one or more isomer(s) or mixture of specific isomers is/are among the compounds as exemplified in the section "Exemplary embodiments of active compounds".

The following tabular scheme is used to list said active compound families and their members individually. In the presentation, the structure prevails the chemical name in case of discrepancy.

| Compound family with alphanumerical abbreviation: chemical name thereof | | |
|---|---|---|
| chemical structure[1] | Compound family members[2] | Exemplified species[3] |
| | (R;R) and | |
| | (S;S) and | |
| | (R;S) and | |
| | (S;R) and | |
| | and mixtures thereof[2a] | |

[1] Structure of compound family is presented as diastereomeric or racemic mixture.

[2] The compound family encompasses all stereoisomers that are encompassed by the chemical structure of the left hand column as well as the mixtures of the corresponding stereoisomers. In the table form only the individualized stereoisomers are presented as the preferred representatives of the compound family. The specific stereochemistry is presented with respect to $R^1$ and $R^3$ according to formula (I). Stereochemistry of the two stereocentres bearing $R^1$ and the one within $R^3$ is presented as ($R^1;R^3$), wherein ($R^1;R^3$) = (configuration at $R^1$; configuration at $R^3$). The name and the structure are directly determinable from the remaining information provided. While the absolute configuration for $R^3$ is known, as this is R-1,1,1-trifluoro-2-propoxy substituent, S-1,1,1-trifluoro-2-propoxy, (S)-Tetrahydro-furan-3-oxy or (R)-Tetrahydro-furan-3-oxy, the absolute configuration for $R^1$ is not known. For $R^1$, only the relative configuration with respect to $R^2$ is known: their relative configuration is always syn.

The following abbreviations for the absolute configuration of the corresponding stereocentres are used: M: mixture of compounds with R and S configuration at the corresponding stereocentres $R^1$ and $R^3$; R: R-configuration at $R^3$; S: S-configuration at $R^3$; X, Y, U, V: specific configuration $R^1$, however the absolute configuration is not known. X and Y are used to indicate the two different stereoisomers with regard to $R^1$ if $R^3$ has S-configuration, U and V are used to indicate the two different stereoisomers with regard to $R^1$ if $R^3$ has R-configuration. The absolute configuration behind X, Y, U and Y may vary over the different compound families. For example the configurations (X; S) and (Y,S) decribes the two stereoismers wherein for both compounds $R^3$ shows S-configuration while for one of them $R^1$ shows R-configuration and for the other one $R^1$ shows S-configuration; In case $R^3$ lacks a stereogenic center, only the specific stereochemistry at $R^1$ is presented by the capital letters W for enantiomer 1, Z for enantiomer 2; M1 indicates a mixture at $R^1$. This is as again the absolute configuration is not known. Consequently for a compound family lacking a stereogenic center at $R^3$ only the stereochemical property for $R^1$ is to be considered. In the below table this is indicated as ($R^1$; $R^3$ = no stereogenic center). In case $R^1$ in itself includes a stereogenic center, stereochemistry is presented by a pair of three time of the corresponding letters for R and S configuration: as before the first letter stands for the stereochemistry of the carbon atom bearing $R^1$, the second letter stands for the stereochemistry within substitutent $R^3$ and the third one for the stereochemistry within $R^1$. For example: (R;S;R) means, stereochemistry at the bridgehead bearing $R^1$ is R; stereo-chemistry within substituent $R^3$ is S and stereochemstry within $R^1$ is R. The absolute configuration for the stereogenic center bearing $R^1$ and the stereogenic center within $R^1$ may be not known. In these cases the following abbreviations for the absolute configuration of the corresponding stereocentres are used: M: mixture of compounds with R and S configuration at the corresponding stereocentres.

[2a] The compound family encompasses all mixtures of the corresponding stereoisomers of said family, i.e. mixtures of 2, 3 or 4 stereoisomers that belong to the same compound family. (= binary, ternary and quaternary mixtures). Example of the binary mixtures (in the terminology ($R^1;R^3$) as discussed above): (S;S) and (R;R); (S;S) and (R;S); (S;S) and (S;R); (R;R) and (R;S); (R;R) and (S;R).

[3] For details it is referred to the experimental part, section "Exemplary embodiments". The example number and the stereochemistry are presented as discussed above under 2).

List of Active Compound Families and the Individual Family Members as Further Preferred Embodiments of the Invention (Table 1)

TABLE 1

Compound family A: [5-Methanesulfonyl-2-(2,2,2-trifluoro-1-methyl-ethoxy)-phenyl]-[1-(5-trifluoromethyl-[1,2,4]oxadiazol-3-yl)-3-aza-bicyclo[3.1.0]hex-3-yl]-methanone

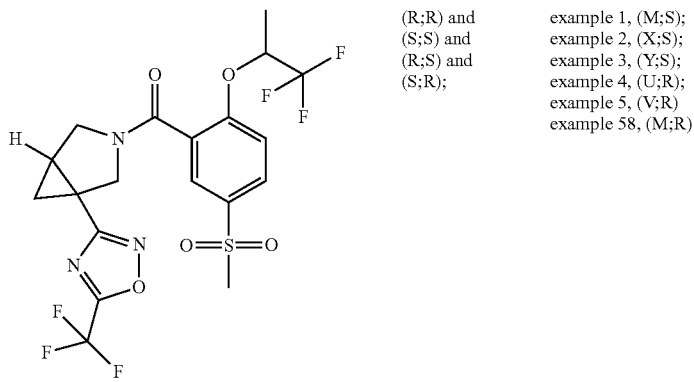

(R;R) and    example 1, (M;S);
(S;S) and    example 2, (X;S);
(R;S) and    example 3, (Y;S);
(S;R);    example 4, (U;R);
    example 5, (V;R)
    example 58, (M;R)

Compound family B: [5-Methanesulfonyl-2-(2,2,2-trifluoro-1-methyl-ethoxy)-phenyl]-[1-(5-methyl-[1,2,4]oxadiazol-3-yl)-3-aza-bicyclo[3.1.0]hex-3-yl]-methanone

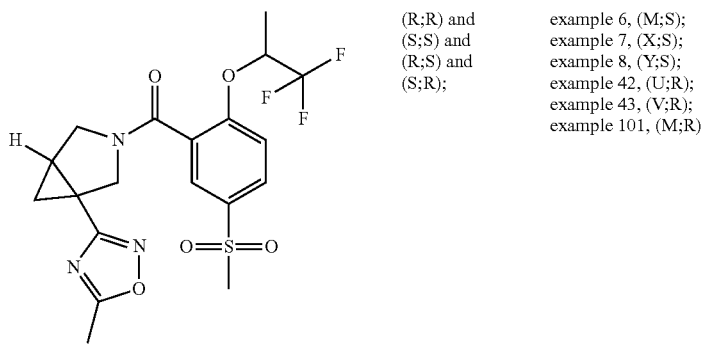

(R;R) and    example 6, (M;S);
(S;S) and    example 7, (X;S);
(R;S) and    example 8, (Y;S);
(S;R);    example 42, (U;R);
    example 43, (V;R);
    example 101, (M;R)

Compound family C: [1-(5-Cyclopropyl-[1,2,4]oxadiazol-3-yl)-3-aza-bicyclo[3.1.0]hex-3-yl]-[5-methanesulfonyl-2-(2,2,2-trifluoro-1-methyl-ethoxy)-phenyl]-methanone

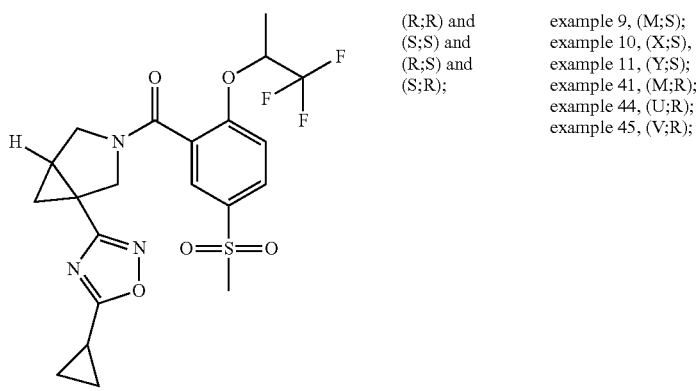

(R;R) and    example 9, (M;S);
(S;S) and    example 10, (X;S),
(R;S) and    example 11, (Y;S);
(S;R);    example 41, (M;R);
    example 44, (U;R);
    example 45, (V;R);

TABLE 1-continued

Compound family D: [5-Methanesulfonyl-2-(2,2,2-trifluoro-1-methyl-ethoxy)-phenyl]-{1-[5-(2,2,2-trifluoro-1,1-dimethyl-ethyl)-[1,2,4]oxadiazol-3-yl]-3-aza-bicyclo[3.1.0]hex-3-yl}-methanone

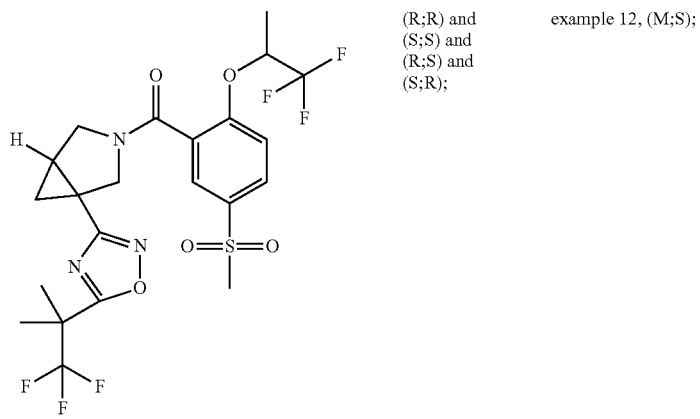

(R;R) and (S;S) and (R;S) and (S;R);

example 12, (M;S);

Compound family E: {1-[5-(3,3-Difluoro-cyclobutyl)-[1,2,4]oxadiazol-3-yl]-3-aza-bicyclo[3.1.0]hex-3-yl}-[5-methanesulfonyl-2-(2,2,2-trifluoro-1-methyl-ethoxy)-phenyl]-methanone

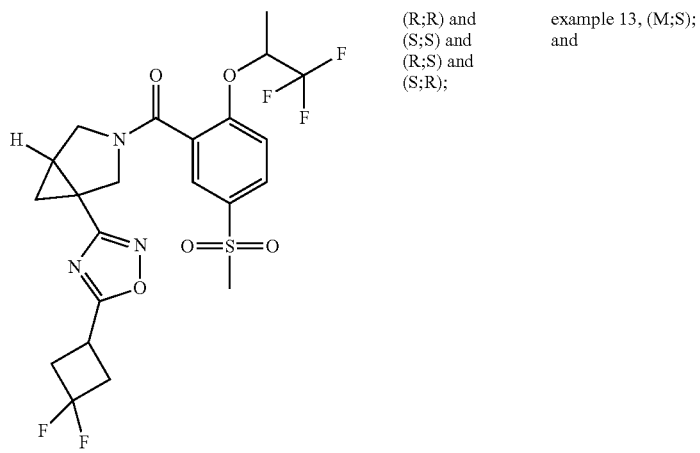

(R;R) and (S;S) and (R;S) and (S;R);

example 13, (M;S); and

Compound family F: [5-Methanesulfonyl-2-(2,2,2-trifluoro-1-methyl-ethoxy)-phenyl]-(1-pyrimidin-2-yl-3-aza-bicyclo[3.1.0]hex-3-yl)-methanone

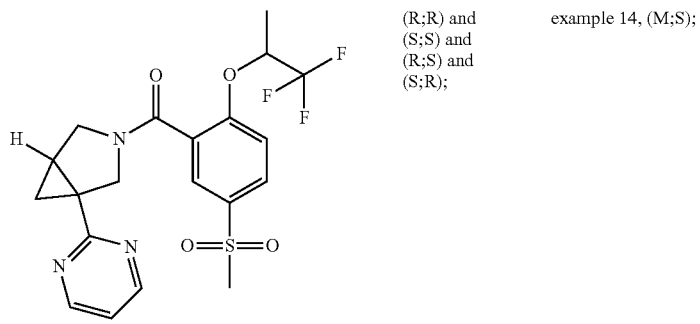

(R;R) and (S;S) and (R;S) and (S;R);

example 14, (M;S);

TABLE 1-continued

Compound family G: [5-Methanesulfonyl-2-(2,2,2-trifluoro-1-methyl-ethoxy)-phenyl]-
[1-(4-trifluoromethyl-pyrimidin-2-yl)-3-aza-bicyclo[3.1.0]hex-3-yl]-methanone

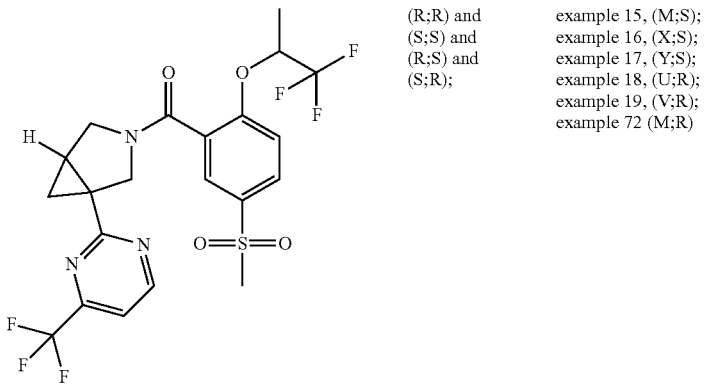

(R;R) and  example 15, (M;S);
(S;S) and  example 16, (X;S);
(R;S) and  example 17, (Y;S);
(S;R);     example 18, (U;R);
           example 19, (V;R);
           example 72 (M;R)

Compound family H: [5-Methanesulfonyl-2-(2,2,2-trifluoro-1-methyl-ethoxy)-phenyl]-
(1-oxazol-2-yl-3-aza-bicyclo[3.1.0]hex-3-yl)-methanone

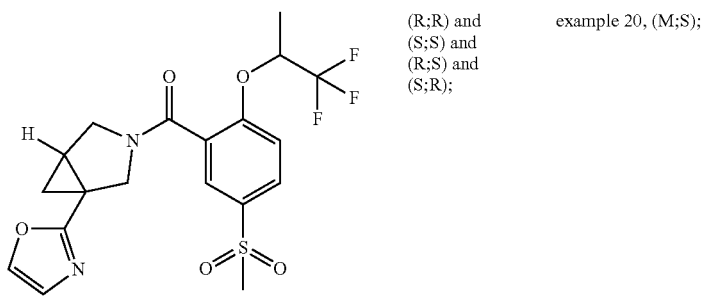

(R;R) and  example 20, (M;S);
(S;S) and
(R;S) and
(S;R);

Compound family I: [5-Methanesulfonyl-2-(2,2,2-trifluoro-1-methyl-ethoxy)-phenyl]-[1-
(5-methyl-oxazol-2-yl)-3-aza-bicyclo[3.1.0]hex-3-yl]-methanone

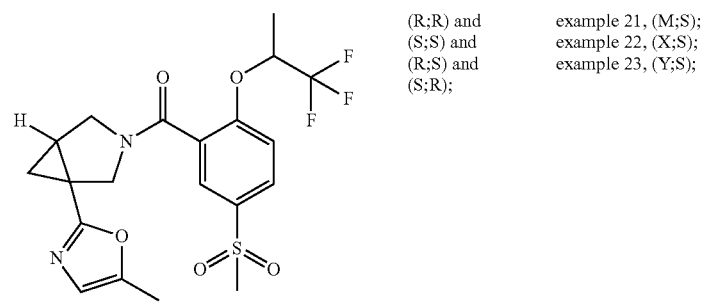

(R;R) and  example 21, (M;S);
(S;S) and  example 22, (X;S);
(R;S) and  example 23, (Y;S);
(S;R);

Compound family J: (1-Imidazo[1,2-a]pyridin-2-yl-3-aza-bicyclo[3.1.0]hex-3-yl)-[5-
methanesulfonyl-2-(2,2,2-trifluoro-1-methyl-1-ethoxy)-phenyl]-methanone

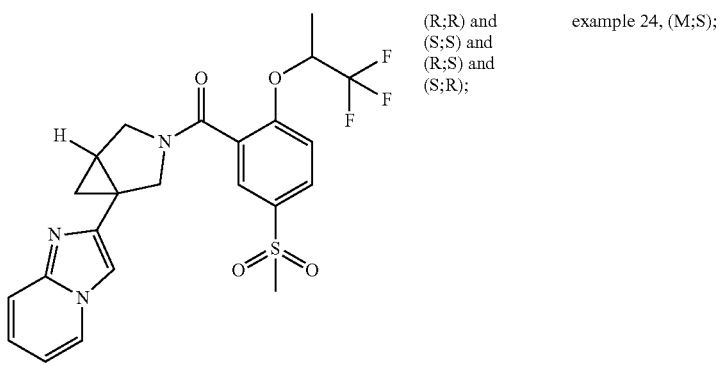

(R;R) and  example 24, (M;S);
(S;S) and
(R;S) and
(S;R);

TABLE 1-continued

Compound family K: [5-Methanesulfonyl-2-(2,2,2-trifluoro-1-methyl-ethoxy)-phenyl]-
[1-(2-methyl-thiazol-4-yl)-3-aza-bicyclo[3.1.0]hex-3-yl]-methanone

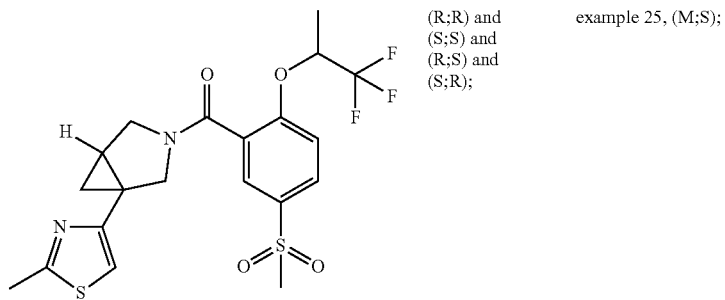

(R;R) and  example 25, (M;S);
(S;S) and
(R;S) and
(S;R);

Compound family L: [5-Methanesulfonyl-2-(2,2,2-trifluoro-1-methyl-ethoxy)-phenyl]-[1-
(2-trifluoromethyl-thiazol-4-yl)-3-aza-bicyclo[3.1.0]hex-3-yl]-methanone

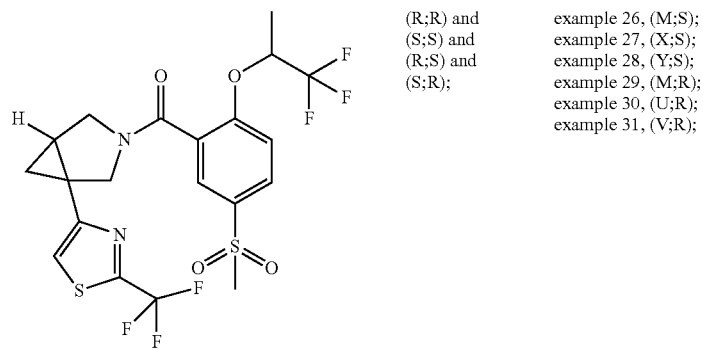

(R;R) and  example 26, (M;S);
(S;S) and  example 27, (X;S);
(R;S) and  example 28, (Y;S);
(S;R);     example 29, (M;R);
           example 30, (U;R);
           example 31, (V;R);

Compound family M: [5-Methanesulfonyl-2-(2,2,2-trifluoro-1-methyl-ethoxy)-phenyl]-
[1-(2-methyl-oxazol-4-yl)-3-aza-bicyclo[3.1.0]hex-3-yl]-methanone

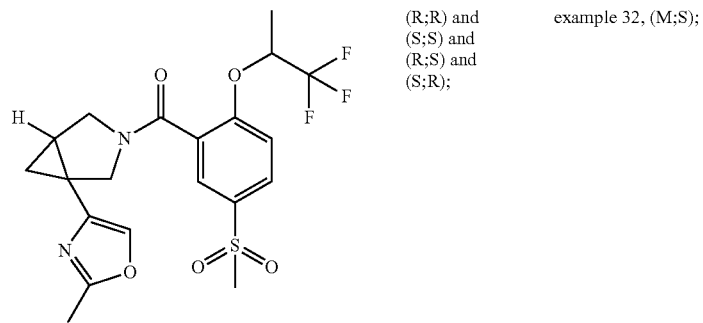

(R;R) and  example 32, (M;S);
(S;S) and
(R;S) and
(S;R);

Compound family N: [5-Methanesulfonyl-2-(2,2,2-trifluoro-1-methyl-ethoxy)-phenyl]-
[1-(4-methyl-oxazol-2-yl)-3-aza-bicyclo[3.1.0]hex-3-yl]-methanone

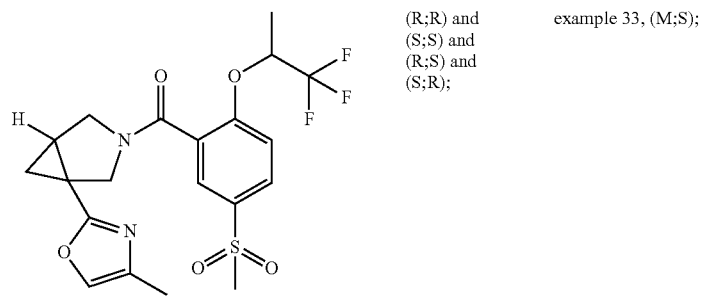

(R;R) and  example 33, (M;S);
(S;S) and
(R;S) and
(S;R);

TABLE 1-continued

Compound family O: [5-Methanesulfonyl-2-(2,2,2-trifluoro-1-methyl-ethoxy)-phenyl]-
[1-(3-methyl-[1,2,4]oxadiazol-5-yl)-3-aza-bicyclo[3.1.0]hex-3-yl]-methanone

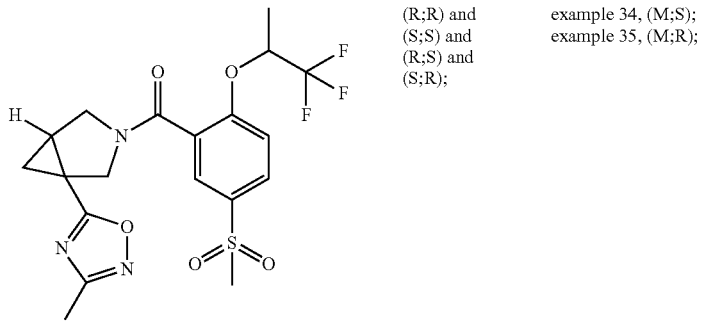

(R;R) and    example 34, (M;S);
(S;S) and    example 35, (M;R);
(R;S) and
(S;R);

Compound family P: [5-Methanesulfonyl-2-(2,2,2-trifluoro-1-methyl-ethoxy)-phenyl]-[1-
(3-trifluoromethyl-[1,2,4]oxadiazol-5-yl)-3-aza-bicyclo[3.1.0]hex-3-yl]-methanone

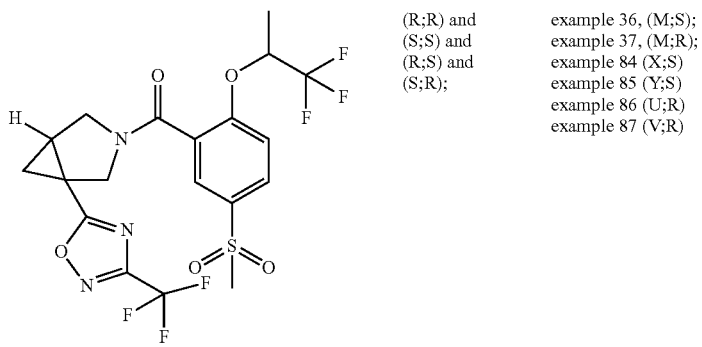

(R;R) and    example 36, (M;S);
(S;S) and    example 37, (M;R);
(R;S) and    example 84 (X;S)
(S;R);       example 85 (Y;S)
             example 86 (U;R)
             example 87 (V;R)

Compound family Q: [5-Methanesulfonyl-2-(2,2,2-trifluoro-1-methyl-ethoxy)-phenyl]-
[1-(5-methyl-[1,3,4]oxadiazol-2-yl)-3-aza-bicyclo[3.1.0]hex-3-yl]-methanone

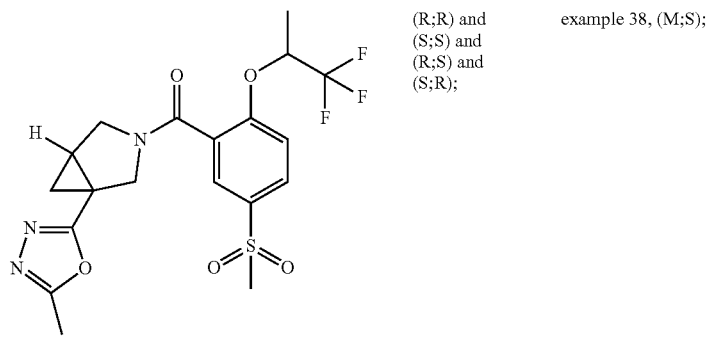

(R;R) and    example 38, (M;S);
(S;S) and
(R;S) and
(S;R);

Compound family R: 4-(2,2,2-Trifluoro-1-methyl-ethoxy)-3-[1-(5-trifluoromethyl-
[1,2,4]oxadiazol-3-yl)-3-aza-bicyclo[3.1.0]hexane-3-carbonyl]-benzonitrile

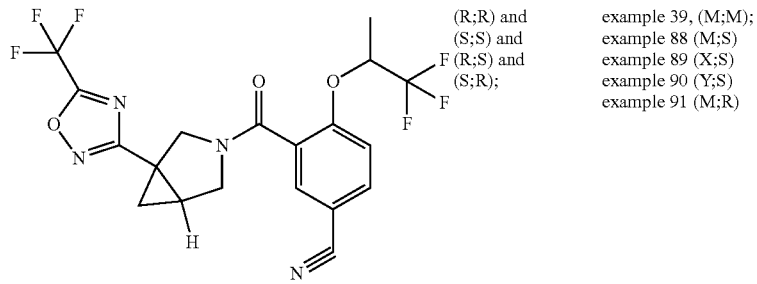

(R;R) and    example 39, (M;M);
(S;S) and    example 88 (M;S)
(R;S) and    example 89 (X;S)
(S;R);       example 90 (Y;S)
             example 91 (M;R)

TABLE 1-continued

Compound family S: [5-Ethanesulfonyl-2-(2,2,2-trifluoro-1-methyl-ethoxy)-phenyl]-[1-(5-trifluoromethyl-[1,2,4]oxadiazol-3-yl)-3-aza-bicyclo[3.1.0]hex-3-yl]-methanone

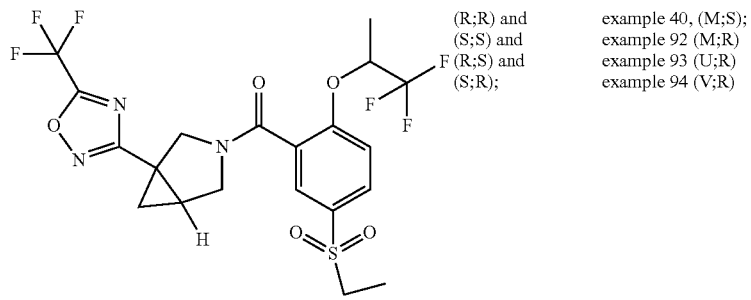

(R;R) and (S;S) and (R;S) and (S;R);

example 40, (M;S); example 92 (M;R) example 93 (U;R) example 94 (V;R)

Compound family T: [5-Methanesulfonyl-2-(2,2,2-trifluoro-1-methyl-ethoxy)-phenyl]-[1-(5-trifluoromethyl-isoxazol-3-yl)-3-aza-bicyclo[3.1.0]hex-3-yl]-methanone

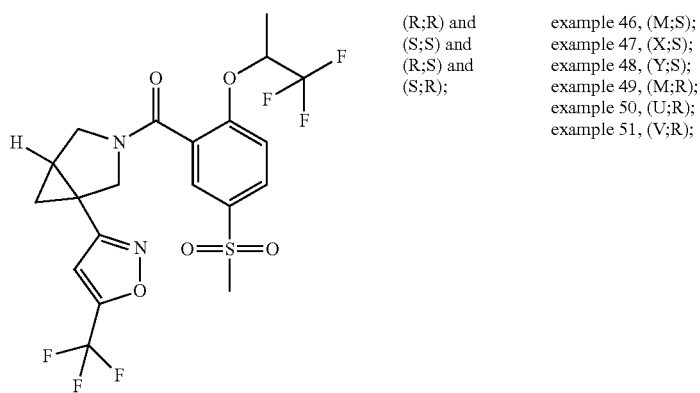

(R;R) and (S;S) and (R;S) and (S;R);

example 46, (M;S); example 47, (X;S); example 48, (Y;S); example 49, (M;R); example 50, (U;R); example 51, (V;R);

Compound family U: [5-Methanesulfonyl-2-(2,2,2-trifluoro-1-methyl-ethoxy)-phenyl]-[1-(5-methyl-isoxazol-3-yl)-3-aza-bicyclo[3.1.0]hex-3-yl]-methanone

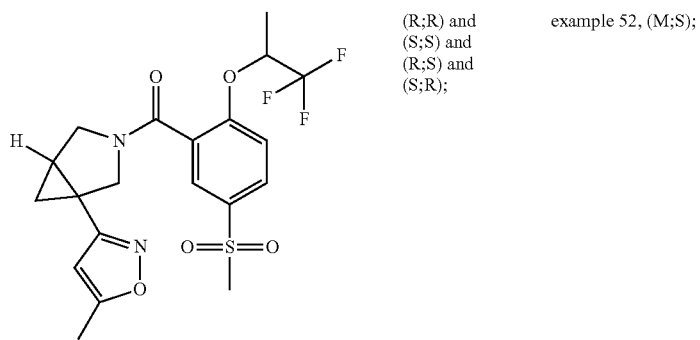

(R;R) and (S;S) and (R;S) and (S;R);

example 52, (M;S);

Compound family V: [5-Methanesulfonyl-2-(2,2,2-trifluoro-1-methyl-ethoxy)-phenyl]-[1-(5-trifluoromethyl-pyridin-3-yl)-3-aza-bicyclo[3.1.0]hex-3-yl]-methanone

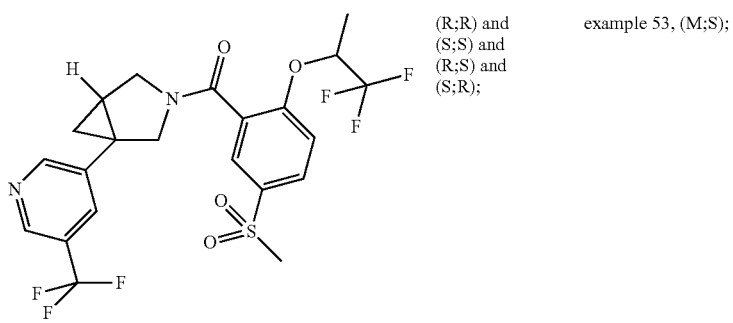

(R;R) and (S;S) and (R;S) and (S;R);

example 53, (M;S);

TABLE 1-continued

Compound family W: [5-Methanesulfonyl-2-(2,2,2-trifluoro-1-methyl-ethoxy)-phenyl]-
[1-(6-trifluoromethyl-pyridin-2-yl)-3-aza-bicyclo[3.1.0]hex-3-yl]-methanone

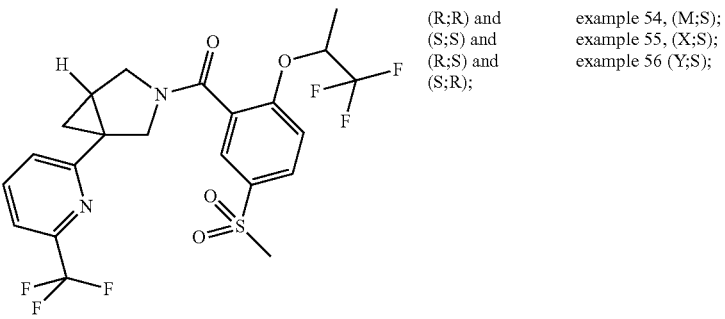

(R;R) and  example 54, (M;S);
(S;S) and  example 55, (X;S);
(R;S) and  example 56 (Y;S);
(S;R);

Compound family X: [5-Methanesulfonyl-2-(2,2,2-trifluoro-1-methyl-ethoxy)-phenyl]-
[1-(5-trifluoromethyl-4,5-dihydro-oxazol-2-yl)-3-aza-bicyclo[3.1.0]hexyl-3-yl]-methanone

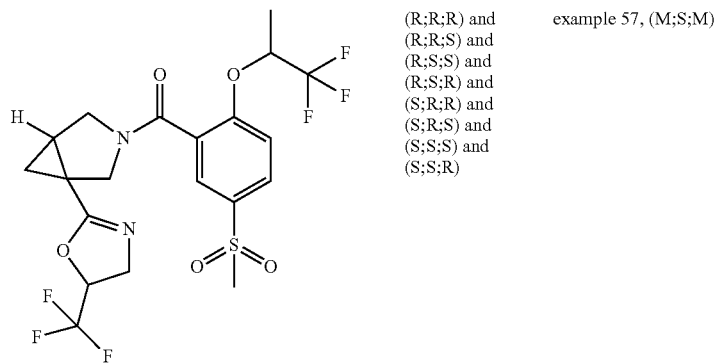

(R;R;R) and  example 57, (M;S;M)
(R;R;S) and
(R;S;S) and
(R;S;R) and
(S;R;R) and
(S;R;S) and
(S;S;S) and
(S;S;R)

Compound family Y: [5-Methanesulfonyl-2-(2,2,2-trifluoro-1-methyl-ethoxy)-phenyl]-
{1-[5-(2,2,2-trifluoro-ethyl)-[1,2,4]oxadiazol-3-yl]-3-aza-bicyclo[3.1.0]hex-3-yl}-
methanone

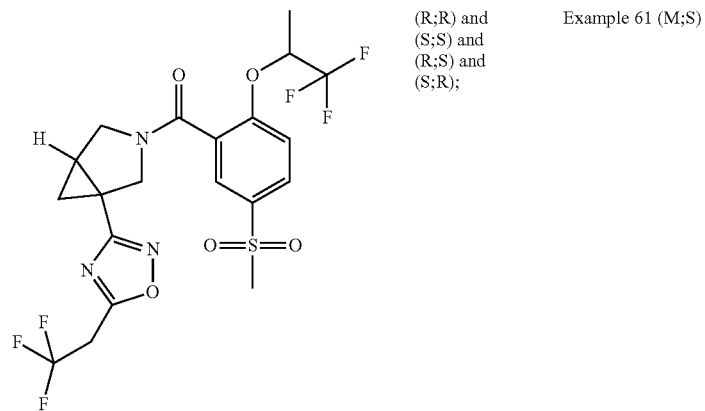

(R;R) and  Example 61 (M;S)
(S;S) and
(R;S) and
(S;R);

TABLE 1-continued

Compound family Z: [5-Methanesulfonyl-2-(2,2,2-trifluoro-1-methyl-ethoxy)phenyl]-
{1-[5-(3-methyl-oxetan-3-yl)-[1,2,4]oxadiazol-3-yl]-3-aza-bicyclo[3.1.0]hex-3-yl}-
methanone

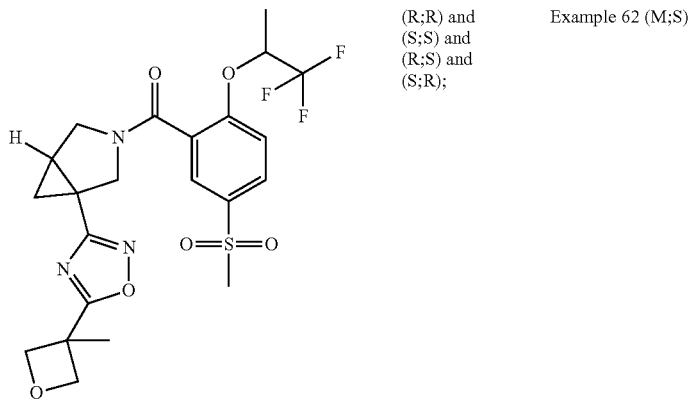

(R;R) and  Example 62 (M;S)
(S;S) and
(R;S) and
(S;R);

Compound family Za: {1-[5-(2,2-Difluoro-cyclopropyl)-[1,2,4]oxadiazol-3-yl]-3-aza-
bicyclo[3.1.0]hex-3-yl}-[5-methanesulfonyl-2-(2,2,2-trifluoro-1-methyl-ethoxy)-
phenyl]-methanone

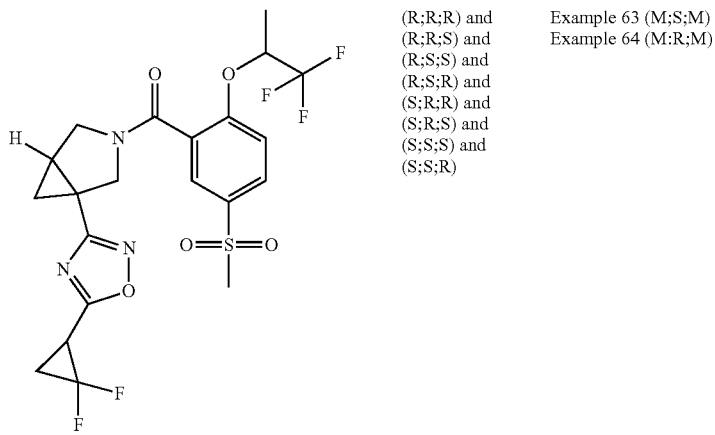

(R;R;R) and  Example 63 (M;S;M)
(R;R;S) and  Example 64 (M;R;M)
(R;S;S) and
(R;S;R) and
(S;R;R) and
(S;R;S) and
(S;S;S) and
(S;S;R)

Compound family Zb: [5-Methanesulfonyl-2-(2,2,2-trifluoro-1-methyl-ethoxy)-phenyl]-
{1-[5-(1-trifluoromethyl-cyclopropyl)-[1,2,4]oxadiazol-3-yl]-3-aza-bicyclo[3.1.0]
hex-3-yl}-methanone

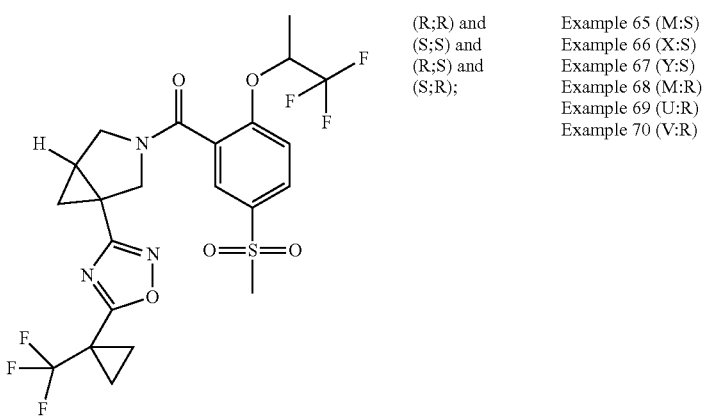

(R;R) and  Example 65 (M;S)
(S;S) and  Example 66 (X;S)
(R;S) and  Example 67 (Y;S)
(S;R);     Example 68 (M;R)
           Example 69 (U;R)
           Example 70 (V;R)

TABLE 1-continued

Compound family Zc: [5-Methanesulfonyl-2-(2,2,2-trifluoro-1-methyl-ethoxy)-phenyl]-[1-(1-methyl-5-trifluoromethyl-1H-[1,2,4]triazol-3-yl)-3-aza-bicyclo[3.1.0]hex-3-yl]-methanone

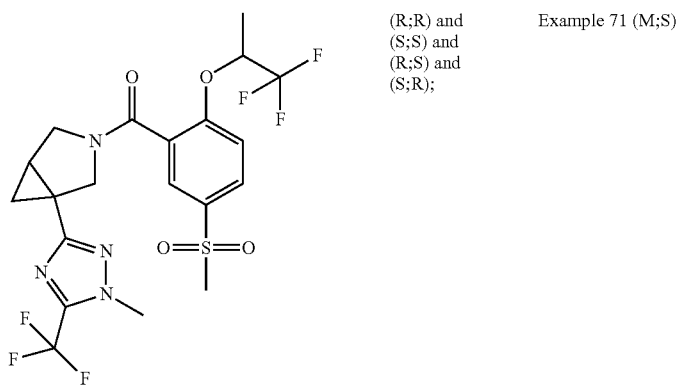

(R;R) and (S;S) and (R;S) and (S;R);

Example 71 (M;S)

Compound family Zd: [5-Ethanesulfonyl-2-(2,2,2-trifluoro-1-methyl-ethoxy)-phenyl]-[1-(4-trifluoromethyl-pyrimidin-2-yl)-3-aza-bicyclo[3.1.0]hex-3-yl]-methanone

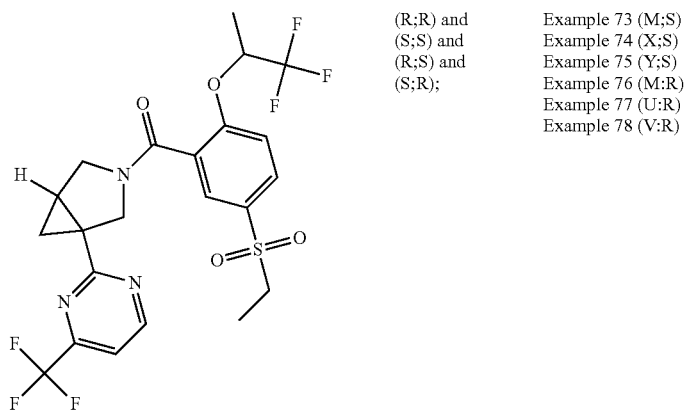

(R;R) and (S;S) and (R;S) and (S;R);

Example 73 (M;S)
Example 74 (X;S)
Example 75 (Y;S)
Example 76 (M;R)
Example 77 (U;R)
Example 78 (V;R)

Compound family Ze: [1-(4-Cyclopropyl-pyrimidin-2-yl)-3-aza-bicyclo[3.1.0]hex-3-yl]-[5-methanesulfonyl-2-(2,2,2-trifluoro-1-methyl-ethoxy)-phenyl]-methanone

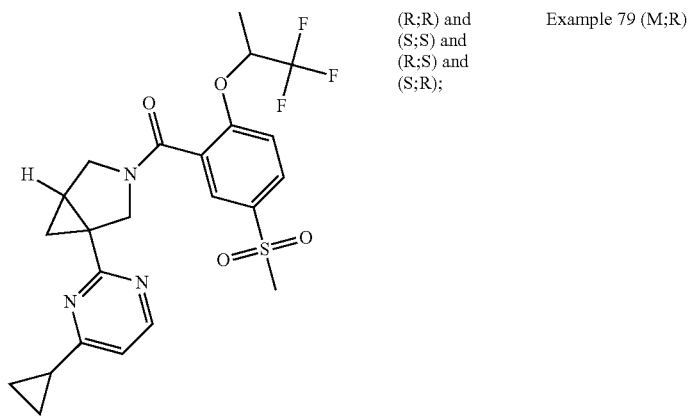

(R;R) and (S;S) and (R;S) and (S;R);

Example 79 (M;R)

TABLE 1-continued

Compound family Zf: [1-(2-Cyclopropyl-oxazol-4-yl)-3-aza-bicyclo[3.1.0]hex-3-yl]-[5-methanesulfonyl-2-((S)-2,2,2-trifluoro-1-methyl-ethoxy)-phenyl]-methanone

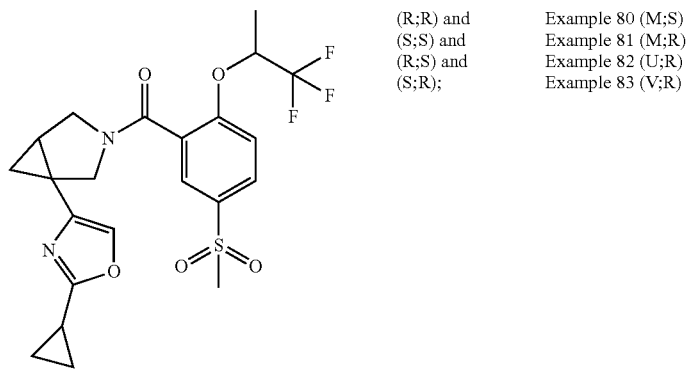

(R;R) and     Example 80 (M;S)
(S;S) and     Example 81 (M;R)
(R;S) and     Example 82 (U;R)
(S;R);         Example 83 (V;R)

Compound family Zg: (2-Isobutoxy-5-methxnesulfonyl-phenyl)-[1-(5-trifluoromethyl-[1,2,4]oxadiazol-3-yl)-3-aza-bicyclo[3.10]hex-3-yl]-methanone

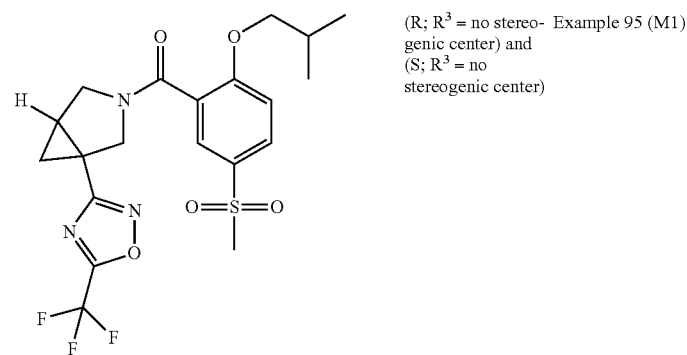

(R; $R^3$ = no stereo-   Example 95 (M1)
genic center) and
(S; $R^3$ = no
stereogenic center)

Compound family Zh: (2-Isopropoxy-5-methanesulfonyl-phenyl)-[1-(5-trifluoromethyl-[1,2,4]oxadiazol-3-yl)-3-aza-bicyclo[3.1.0]hex-3-yl]-methanone

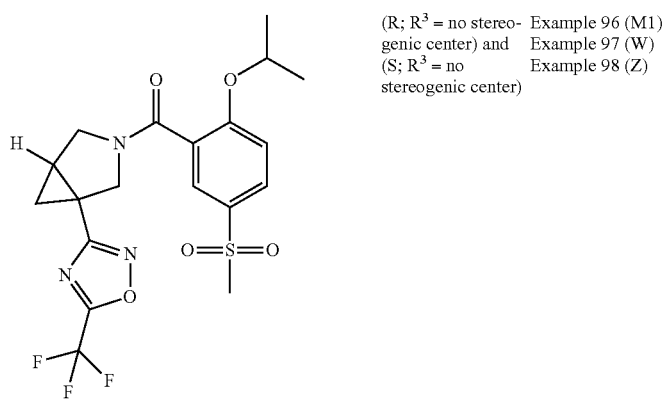

(R; $R^3$ = no stereo-   Example 96 (M1)
genic center) and    Example 97 (W)
(S; $R^3$ = no         Example 98 (Z)
stereogenic center)

TABLE 1-continued

Compound family Zi: (5-Methanesulfonyl-2,2-dimethyl-2,3-dihydro-benzofuran-7-yl)-[1-(5-trifluoromethyl-[1,2,4]oxadiazol-3-yl)-3-aza-bicyclo[3.1.0]-3-yl]-methanone

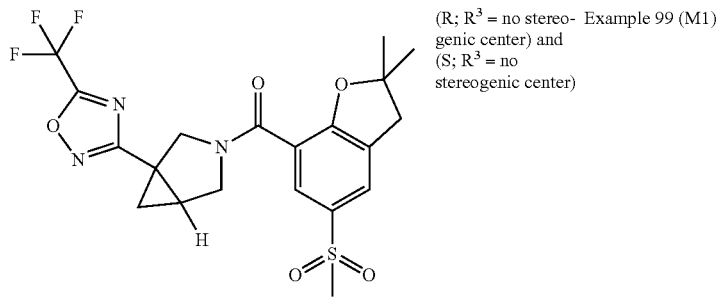

(R; $R^3$ = no stereogenic center) and (S; $R^3$ = no stereogenic center)   Example 99 (M1)

Compound family Zj: [5-Oxazol-2-yl-2-(2,2,2-trifluoro-1-methyl-ethoxy)-phenyl]-[1-(5-trifluoromethyl-[1,2,4]oxadiazol-3-yl)-3-aza-bicyclo[3.1.0]hex-3-yl]-methanone

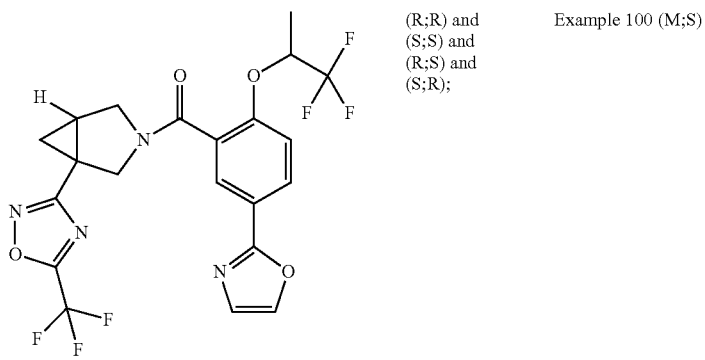

(R;R) and (S;S) and (R;S) and (S;R);   Example 100 (M;S)

Compound family Zl: [5-Ethanesulfonyl-2-(2,2,2-trifluoro-1-methyl-ethoxy)-phenyl]-[1-(5-trifluoromethyl-isoxazol-3-yl)-3-aza-bicyclo[3.1.0]hex-3-yl]-methanone

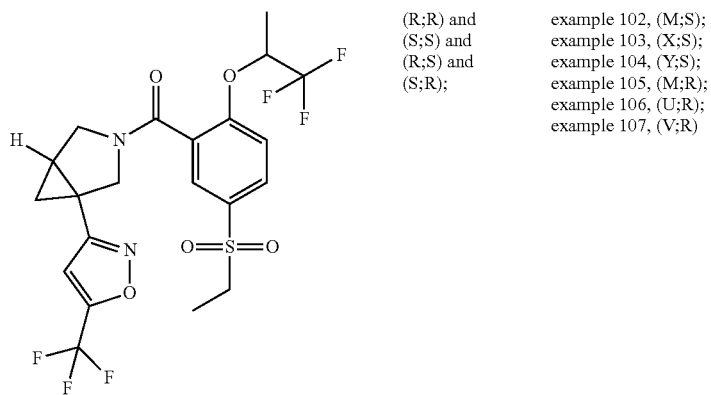

(R;R) and (S;S) and (R;S) and (S;R);   example 102, (M;S); example 103, (X;S); example 104, (Y;S); example 105, (M;R); example 106, (U;R); example 107, (V;R)

Compound family Zm: [5-Methanesulfonyl-2-(2,2,2-trifluoro-1-methyl-ethoxy)-phenyl]-[1-(4-methyl-isoxazol-3-yl)-3-aza-bicyclo[3.1.0]hex-3-yl]-methanone

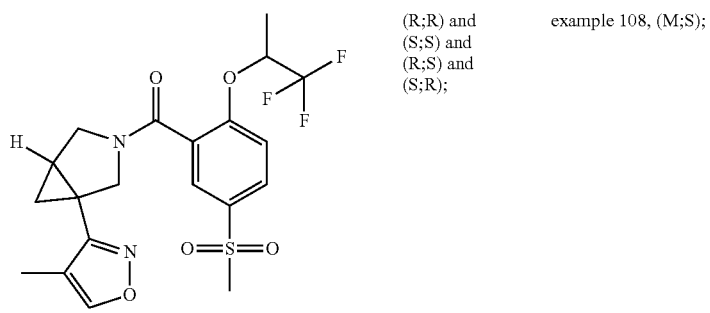

(R;R) and (S;S) and (R;S) and (S;R);   example 108, (M;S);

TABLE 1-continued

Compound family Zn: [5-Methanesulfonyl-2-(2,2,2-trifluoro-1-methyl-ethoxy)-phenyl]-[1-(4-trifluoromethyl-isoxazol-3-yl)-3-aza-bicyclo[3.1.0]hex-3-yl]-methanone

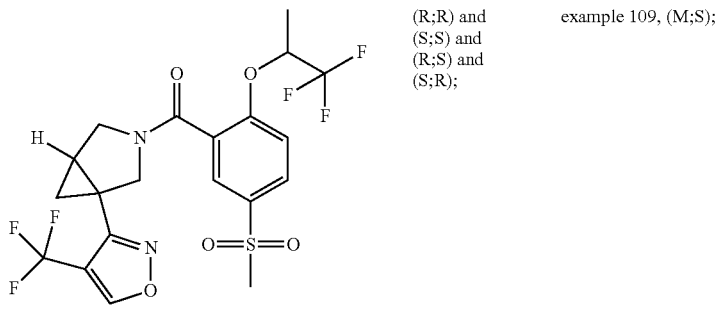

(R;R) and (S;S) and (R;S) and (S;R);  example 109, (M;S);

Compound family Zo: (2-Isopropoxy-5-methanesulfonyl-phenyl)-[1-(4-trifluoromethyl-oxazol-2-yl)-3-aza-bicyclo[3.1.0]hex-3-yl]-methanone

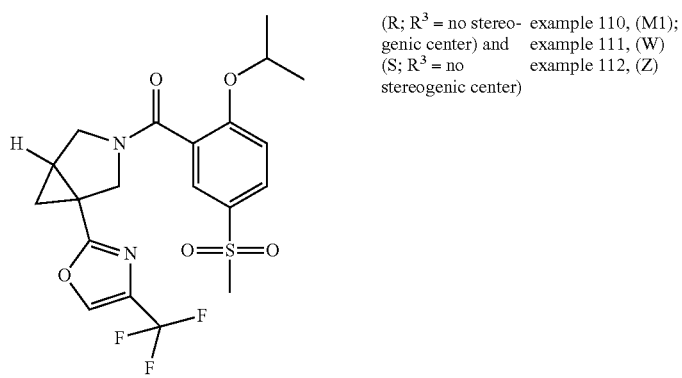

(R; $R^3$ = no stereogenic center) and (S; $R^3$ = no stereogenic center)  example 110, (M1); example 111, (W) example 112, (Z)

Compound family Zp: [5-Methanesulfonyl-2-(2,2,2-trifluoro-1-methyl-ethoxy)-phenyl]-[1-(4-trifluoromethyl-oxazol-2-yl)-3-aza-bicyclo[3.1.0]hex-3-yl]-methanone

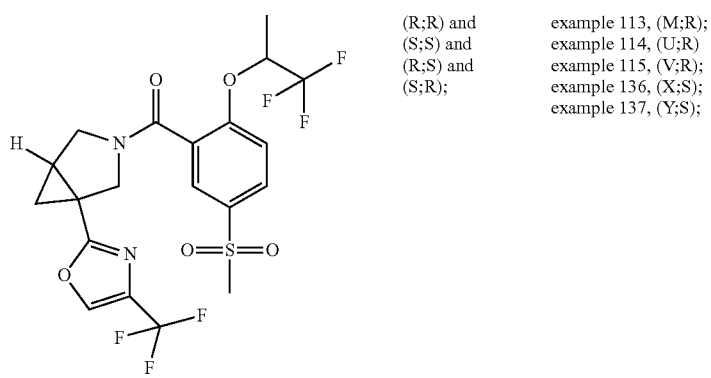

(R;R) and (S;S) and (R;S) and (S;R);  example 113, (M;R); example 114, (U;R) example 115, (V;R); example 136, (X;S); example 137, (Y;S);

TABLE 1-continued

Compound family: Zq: [5-Methanesulfonyl-2-(2,2,2-trifluoro-1-methyl-ethoxy)-phenyl]-{1-[5-(1-methoxy-cyclopropyl)-[1,2,4]oxadiazol-3-yl]-3-aza-bicyclo[3.1.0]hex-3-yl}-methanone

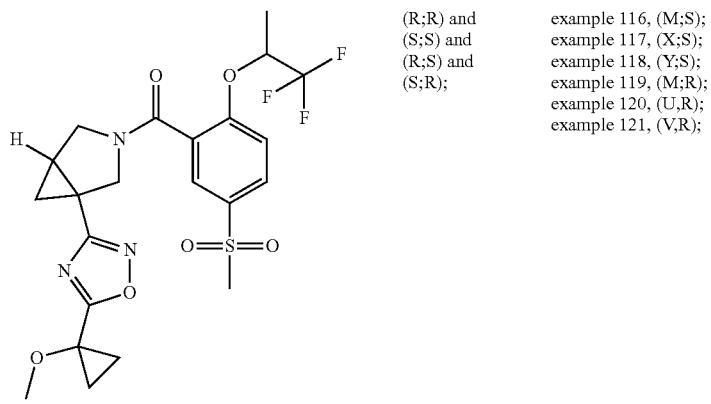

(R;R) and    example 116, (M;S);
(S;S) and    example 117, (X;S);
(R;S) and    example 118, (Y;S);
(S;R);       example 119, (M;R);
             example 120, (U,R);
             example 121, (V,R);

Compound family: Zr: [5-Methanesulfonyl-2-(2,2,2-trifluoro-1-methyl-ethoxy)-phenyl]-[1-(5-trifluoromethyl-[1,3,4]oxadiazol-2-yl)-3-aza-bicyclo[3.1.0]hex-3-yl]-methanone

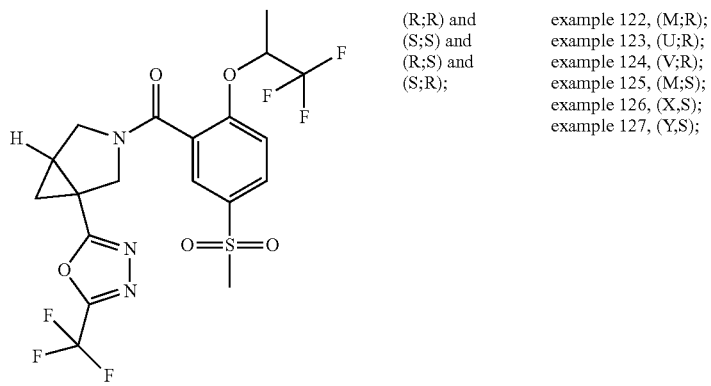

(R;R) and    example 122, (M;R);
(S;S) and    example 123, (U;R);
(R;S) and    example 124, (V;R);
(S;R);       example 125, (M;S);
             example 126, (X,S);
             example 127, (Y,S);

Compound family: Zs: [5-Methanesulfonyl-2-(2,2,2-trifluoro-1-methyl-ethoxy)-phenyl]-[1-(5-trifluoromethyl-oxazol-2-yl)-3-aza-bicyclo[3.1.0]hex-3-yl]-methanone

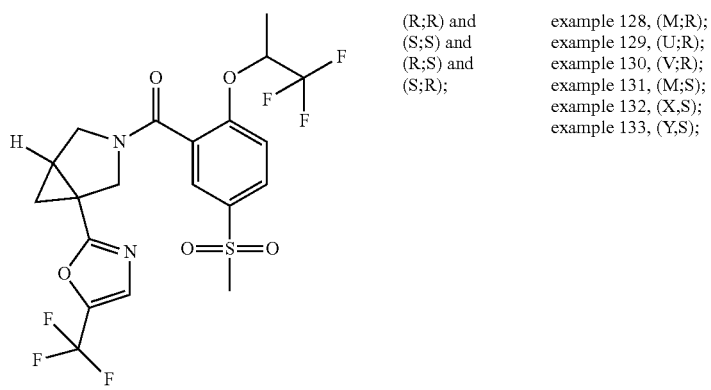

(R;R) and    example 128, (M;R);
(S;S) and    example 129, (U;R);
(R;S) and    example 130, (V;R);
(S;R);       example 131, (M;S);
             example 132, (X,S);
             example 133, (Y,S);

TABLE 1-continued

Compound family: Zt: [5-Methanesulfonyl-2-(2,2,2-trifluoro-1-methyl-ethoxy)-phenyl]-{1-[5-(1-methyl-cyclopropyl)-[1,2,4]oxadiazol-3-yl]-3-aza-bicyclo[3.1.0]hex-3-yl}-methanone

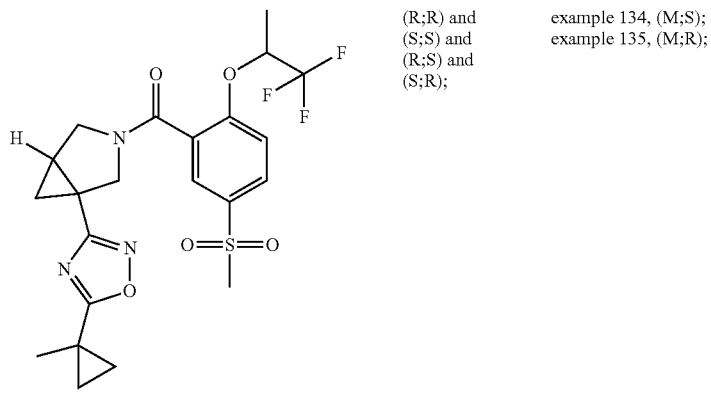

(R;R) and (S;S) and (R;S) and (S;R);

example 134, (M;S); example 135, (M;R);

Compound family: Zu: [5-Methanesulfonyl-2-(tetrahydro-furan-3-yloxy)-phenyl]-[1-(5-trifluoromethyl-[1,2,4]oxadiazol-3-yl)-3-aza-bicyclo[3.1.0]hex-3-yl]-methanone

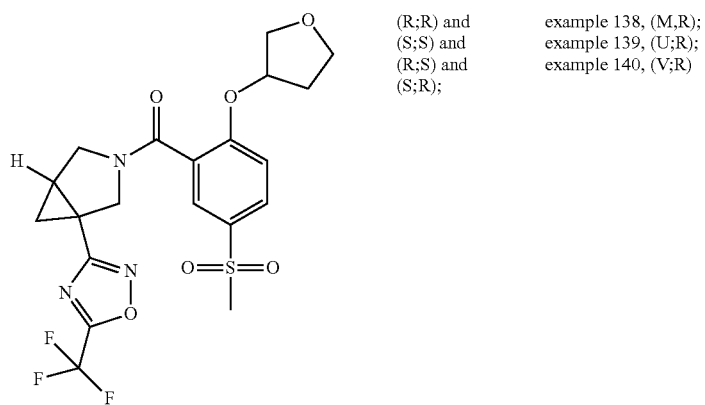

(R;R) and (S;S) and (R;S) and (S;R);

example 138, (M,R); example 139, (U;R); example 140, (V;R)

Compound family: Zv: [5-Methanesulfonyl-2-(3-trifluoromethyl-pyrazol-1-yl)-phenyl]-[1-(5-trifluoromethyl-[1,2,4]oxadiazol-3-yl)-3-aza-bicyclo[3.1.0]hex-3-yl]-methanone

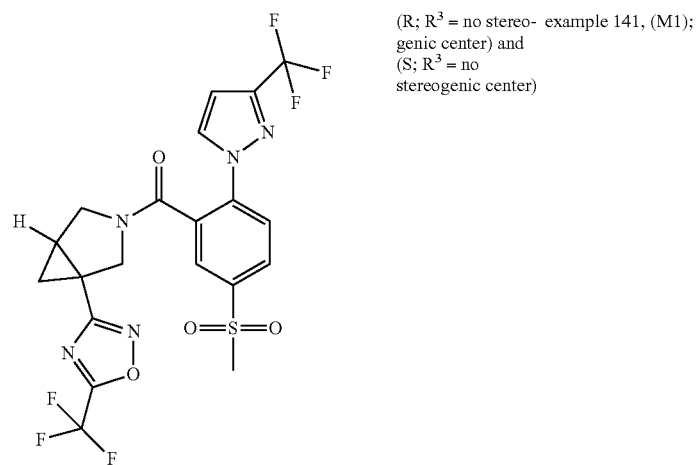

(R; $R^3$ = no stereogenic center) and (S; $R^3$ = no stereogenic center)

example 141, (M1);

TABLE 1-continued

Compound family: Zw: (2-Isopropoxy-5-methanesulfonyl-phenyl)-{1-[5-(1-trifluoromethyl-cyclopropyl)-[1,2,4]oxadiazol-3-yl]-3-aza-bicyclo[3.1.0]hex-3-yl}-methanone

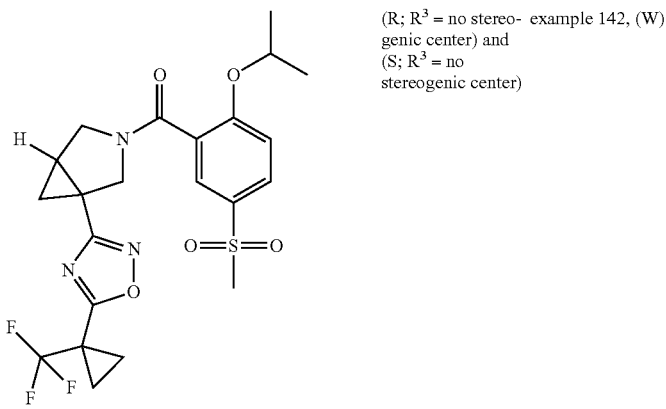

(R; $R^3$ = no stereogenic center) and  
(S; $R^3$ = no stereogenic center)

example 142, (W)

Compound family: Zx: [1-(3-Cyclopropyl-[1,2,4]oxadiazol-5-yl)-3-aza-bicyclo[3.1.0]hex-3-yl]-[5-methanesulfonyl-2-(2,2,2-trifluoro-1-methyl-ethoxy)-phenyl]-methanone

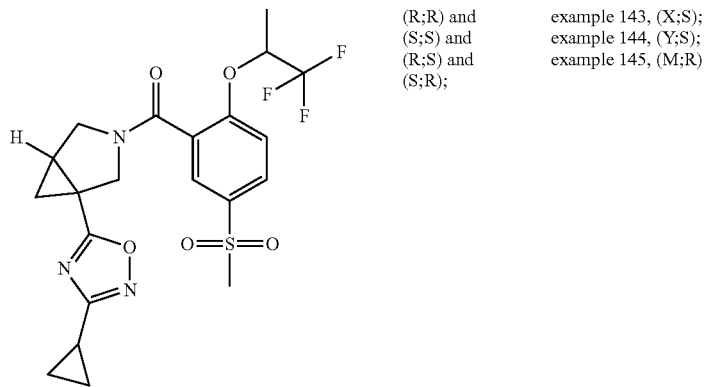

(R;R) and  
(S;S) and  
(R;S) and  
(S;R);

example 143, (X;S);  
example 144, (Y;S);  
example 145, (M;R)

Compound family: Zy: [1-(5-Cyclopropyl-[1,3,4]oxadiazol-2-yl)-3-aza-bicyclo[3.1.0]hex-3-yl]-[5-methanesulfonyl-2-(2,2,2-trifluoro-1-methyl-ethoxy)-phenyl]-methanone

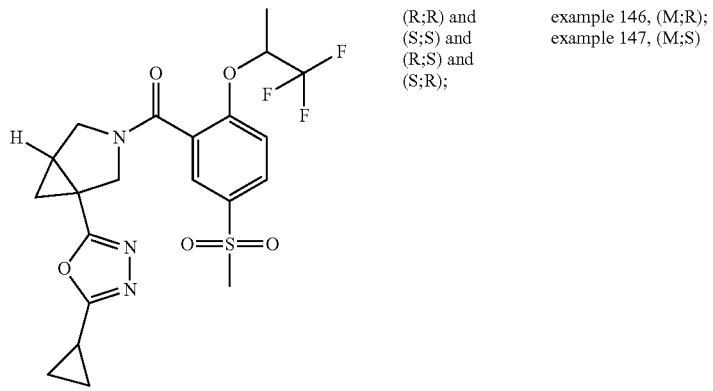

(R;R) and  
(S;S) and  
(R;S) and  
(S;R);

example 146, (M;R);  
example 147, (M;S)

TABLE 1-continued

Compound family: Zz: [5-Methanesulfonyl-2-(2,2,2-trifluoro-1-methyl-ethoxy)-phenyl]-{1-[5-(1-trifluoromethyl-cyclopropyl)-[1,3,4]oxadiazol-2-yl]-3-aza-bicyclo[3.1.0]hex-3-yl}-methanone

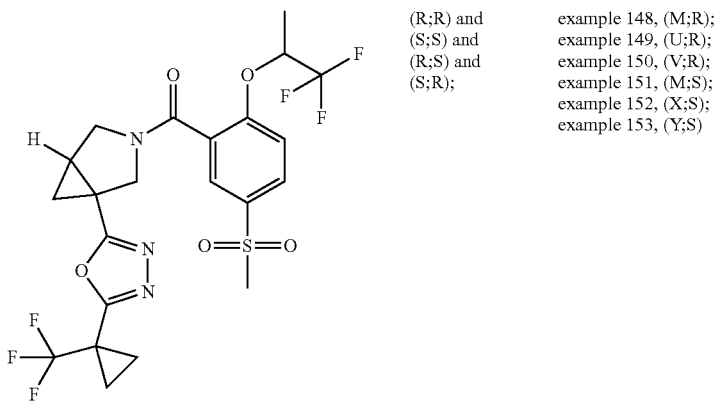

(R;R) and
(S;S) and
(R;S) and
(S;R);

example 148, (M;R);
example 149, (U;R);
example 150, (V;R);
example 151, (M;S);
example 152, (X;S);
example 153, (Y;S)

Compound family: Zza: (2-Isopropoxy-5-methanesulfonyl-phenyl)-{1-[3-(1-trifluoromethyl-cyclopropyl)-[1,2,4]oxadiazol-5-yl]-3-aza-bicyclo[3.1.0]hex-3-yl}-methanone

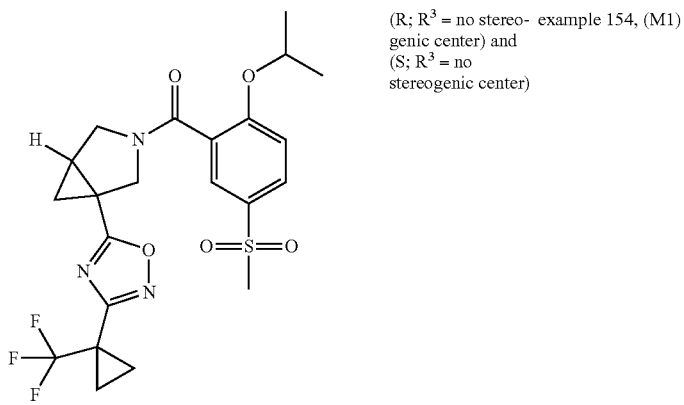

(R; $R^3$ = no stereogenic center) and
(S; $R^3$ = no stereogenic center)

example 154, (M1)

Compound family: Zzb: [5-Methanesulfonyl-2-(2,2,2-trifluoro-1-methyl-ethoxy)-phenyl]-{1-[3-(1-trifluoromethyl-cyclopropyl)-[1,2,4]oxadiazol-5-yl]-3-aza-bicyclo[3.1.0]hex-3-yl}-methanone

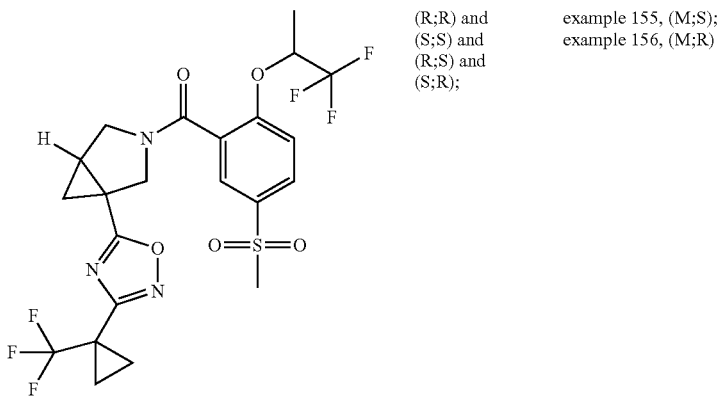

(R;R) and
(S;S) and
(R;S) and
(S;R);

example 155, (M;S);
example 156, (M;R)

TABLE 1-continued

Compound family: Zzc: [5-Methanesulfonyl-2-(2,2,2-trifluoro-1-methyl-ethoxy)-phenyl]-[1-methyl-5-(5-trifluoromethyl-[1,2,4]oxadiazol-3-yl)-3-aza-bicyclo[3.1.0]hex-3-yl]-methanone

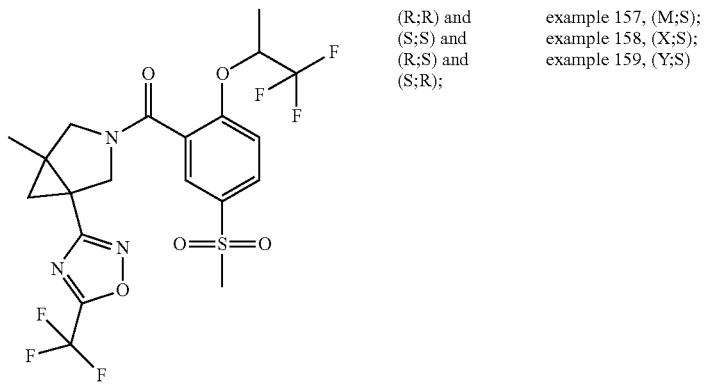

(R;R) and (S;S) and (R;S) and (S;R);

example 157, (M;S); example 158, (X;S); example 159, (Y;S)

Compound family: Zzd: [5-Methanesulfonyl-2-(2,2,2-trifluoro-1-methyl-ethoxy)-phenyl]-[1-(4-methyl-5-(trifluoromethyl-isoxazol-3-yl)-3-aza-bicyclo[3.1.0]hex-3-yl]-methanone

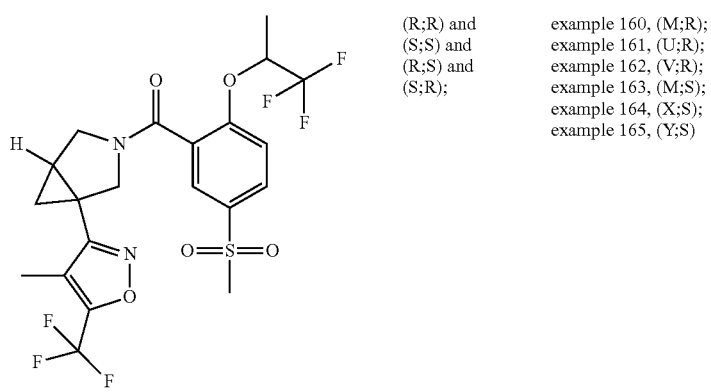

(R;R) and (S;S) and (R;S) and (S;R);

example 160, (M;R); example 161, (U;R); example 162, (V;R); example 163, (M;S); example 164, (X;S); example 165, (Y;S)

and wherever appropriate the salts, preferably pharmaceutically acceptable salts, solvates and the solvates of the salts thereof.

Preparation
The following schemes shall illustrate generally how to manufacture the compounds according to general formula (I) and the corresponding intermediate compounds by way of example. The abbreviated substituents may be as defined above if not defined otherwise within the context of the schemes.
Scheme 1
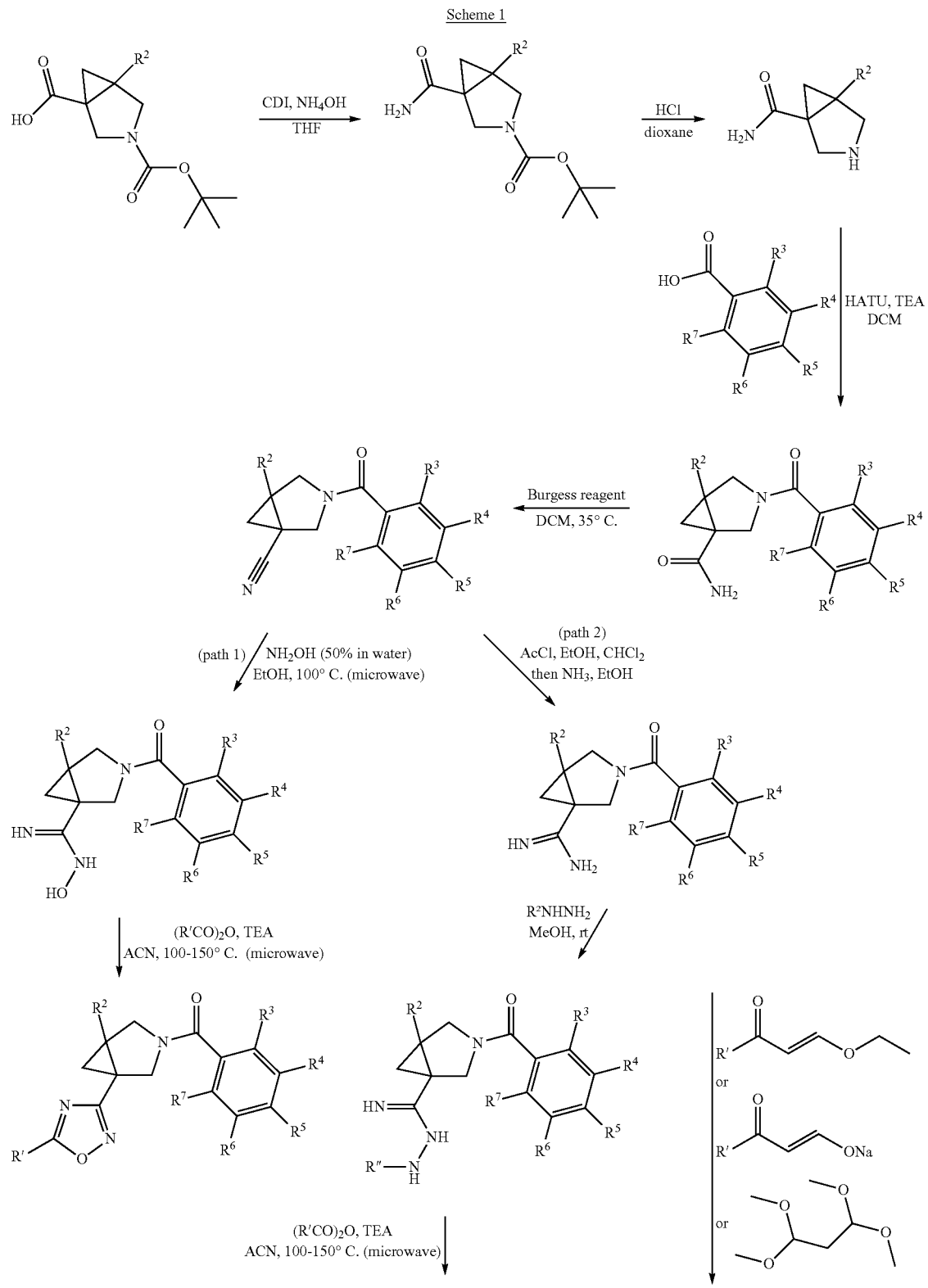

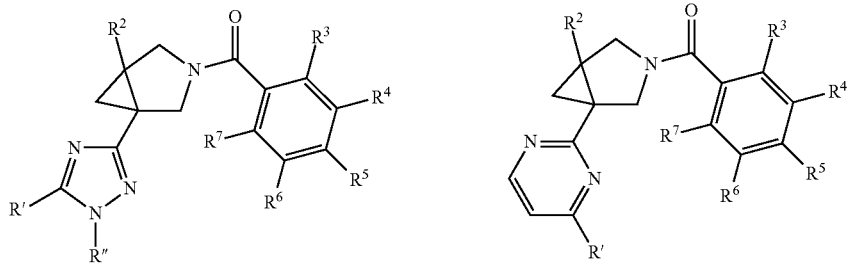

In scheme 1 all substituents $R^1$ to $R^7$ have the meaning as defined for general formula (I) and all embodiments of the invention that directly refer thereto. R' and R''=substituents as defined for $R^1$.

Scheme 1:

In a first step a derivative of 3-azabicyclo[3.1.0]hexane-1,3-dicarboxylic acid-3-tert-butyl ester is coupled with ammonium hydroxyde in the presence of 1,1'-carbonyldiimidazole in an appropriate solvent like THF. The Boc protecting group of the resulting primary amide is deprotected with hydrochloric acid in an appropriate solvent like dioxane. The resulting product is coupled with benzoic acid derivatives in an appropriate solvent like DMF and in the presence of a coupling agent (e.g. HATU or TBTU) and a base (e.g. TEA or DIPEA). The primary amide functional group of the resulting benzamide is converted into a nitrile functional group using Burgess reagent in DCM. These compounds are reacted with hydroxylamine (50% in water) in EtOH at elevated temperatures under microwave irradiation to give the corresponding amidoximes (path 1). These derivatives are then converted to 1,2,4-oxadiazole derivatives upon treatment with anhydrides, a base (e.g. TEA) and an appropriate solvent like ACN at elevated temperature under microwave irradiation. Alternatively, nitriles are converted to the corresponding amidines upon treatment with AcCl in EtOH and $CHCl_3$, followed by treatment with ammonia in EtOH (path 2). These compounds are reacted with a 1,3-dicarbonyl derivative or a synthetic equivalent (e.g. 1,1,3,3-tetramethoxypropane or 4-ethoxy-1,1,1-trifluoro-3-buten-2-one) to form the corresponding pyrimidines. Alternatively, amidines are reacted with hydrazines in MeOH to give the corresponding amidrazones. These derivatives are then converted to 1,2,4-triazole derivatives upon treatment with anhydrides, a base (e.g. TEA) and an appropriate solvent like ACN at elevated temperature under microwave irradiation.

Scheme 2

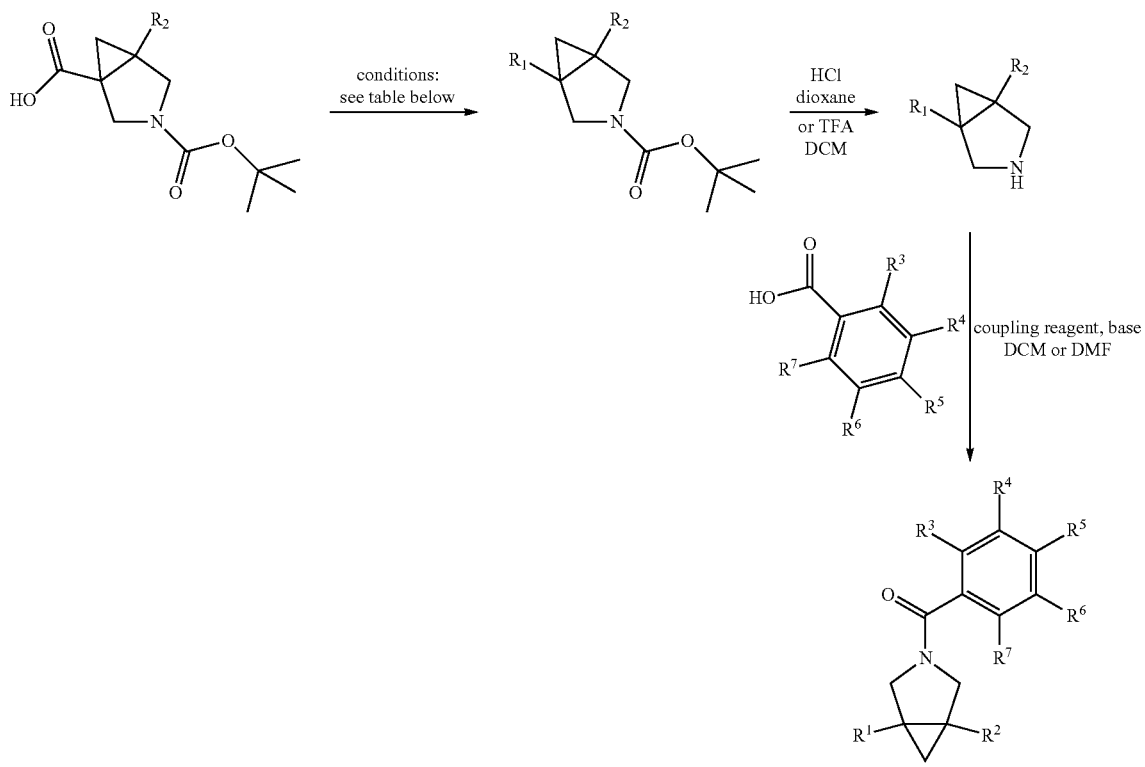

In scheme 2 all substituents $R^1$ to $R^7$ have the meaning as defined for general formula (I), all embodiments of the invention that directly refer thereto and the following table.

Scheme 2:

A derivative of 3-azabicyclo[3.1.0]hexane-1,3-dicarboxylic acid-3-tert-butyl ester is treated under conditions listed in the table below to form heteroaryl substituted 3-azabicyclo[3.1.0]hexane-3-carboxylic acid-3-tert-butyl ester. $R^a$ is a substituent of Het.

| conditions as mentioned in scheme 2 | $R^1$ | $R^a$ |
|---|---|---|
| Reaction with a coupling agent (e.g. TBTU, etc.) and a base (e.g. TEA) followed by a 2-amino-alcohol. Oxidation with Dess-Martin-Periodinane in dichloromethane or acetonitrile. Treatment with Burgess-reagent in THF at elevated temperatures. |  | H—, H₃C—, F₃C— |
| Reaction with oxalylchloride in THF followed by treatment with trimethylsilyldiazomethane followed by hydrochloric acid in dioxane. Reaction with a 2-amino-pyridine in 1,2-dimethoxyethane at elevated temperatures. | 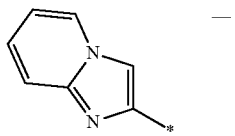 | — |
| Reaction with oxalylchloride in THF followed by treatment with trimethylsilyldiazomethane followed by hydrochloric acid in dioxane. Reaction with a thioamide in EtOH. | 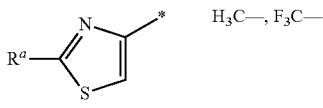 | H₃C—, F₃C— |
| Reaction with oxalylchloride in THF or DCM followed by treatment with trimethylsilydiazomethane followed by hydrochloric or hydrobromic acid. Reaction with an amide in 1-methyl-2-pyrrolidinone or EtOH at elevated temperatures | 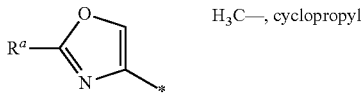 | H₃C—, cyclopropyl |
| Reaction with a coupling agent (e.g. CDI, etc.) in THF followed by ammonium hydroxyde Reaction with a haloketone in ethanol at elevated temperatures in ethanol or in dioxane optionally followed by treatment with methanesulfonylchloride and TEA in DCM |  | H₃C—, F₃C— |
| Reaction with a coupling agent (e.g. CDI, etc) in DMF followed by a N-hydroxyamidine derivative (which may be obtained from the corresponding nitrile upon treatment with hydroxylamine and potassium carbonate in water/EtOH or from the corresponding amide upon treatment with an anhydride in THF at elevated temperatures followed by hydroxylamine and potassium carbonate in MeOH) at elevated temeratures | 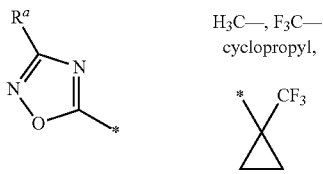 | H₃C—, F₃C—, cyclopropyl,  |
| Reaction with a coupling agent (e.g. TBTU, etc.) and a base (e.g. DIPEA) followed by a carboxylic acid hydrazide. Treatment with Burgess-reagent in 1,2-dichloroethane at elevated temperatures | 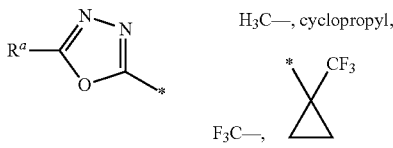 | H₃C—, cyclopropyl, 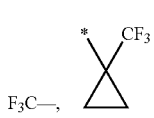 F₃C—, 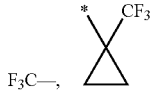 |

| conditions as mentioned in scheme 2 | R¹ | Rᵃ |
|---|---|---|
| Reaction with a coupling agent (e.g. CDI) in THF followed by ammonium hydroxyde<br>Treatment with Burgess-reagent in DCM at elevated temperatures<br>Reaction with hydroxylamine in ethanol at elevated temperatures<br>Reaction an anhydride and TEA in ACN at elevated temperatures | 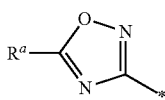 | $F_3C$—, cyclopropyl-, $CH_3$—, $CF_3C(CH_3)_2$—<br>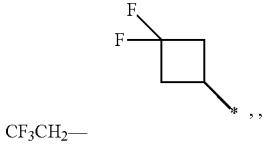,<br>$CF_3CH_2$—<br>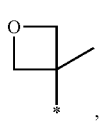, 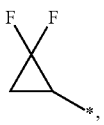,<br>, 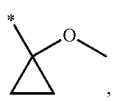,<br> |
| Reaction with CDI in DCM followed by TEA and N,O-dimethylhydroxylamine<br>Reaction with methylmagnesium bromide in THF<br>Reaction with lithium bis(trimethylsilyl)amide followed by treatment with an ester in THF<br>Reaction with hydroxylamine hydrochloride in methanol at elevated temperatures<br>Treatment with a TEA followed by a sulfonyl chloride in DCM | 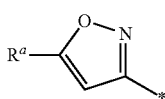 | $F_3C$— |
| a. Reaction with a coupling agent (e.g. CDI, etc.) in DCM followed by a base (e.g. TEA) and N,O-dimethylhydroxylamine<br>Reaction with ethylmagnesium bromide in THF<br>Reaction with Lithium diisopropylamide followed by treatment with an acylimidazole in THF<br>Reaction with hydroxylamine hydrochloride in methanol at elevated temperatures<br>Treatment with a TEA followed by a sulfonyl chloride in DCM; | 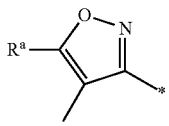 | $F_3C$— |
| Reaction with lithium aluminium hydride in THF<br>Reaction with Dess-Martin periodinane in DCM<br>Reaction with hydroxylamine hydrochloride and sodium acetate in EtOH and water<br>Reaction with N-chlorosuccinimide in DMF at 40° C.<br>Treatment with a haloalkene and TEA in DCM or CHCl₃ | 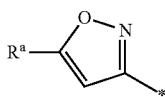 | $H_3C$—, $F_3C$— |
| Reaction with lithium aluminium hydride in THF<br>Reaction with Dess-Martin periodinane in DCM<br>Reaction with hydroxylamine hydrochloride and sodium acetate in EtOH and water<br>Reaction with N-chlorosuccinimide in DMF at 40° C.<br>Treatment with an enolether and TEA in DCM | 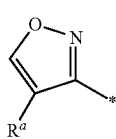 | $H_3C$—, $F_3C$— |

The resulting Het-substituted 3-azabicyclo[3.1.0]hexane-3-carboxylic acid-3-tert-butyl ester derivatives are deprotected with hydrochloric acid or TFA in an appropriate solvent like dioxane. The resulting products are coupled with benzoic acid derivatives in an appropriate solvent like DMF and in the presence of a coupling agent (e.g. HATU or TBTU) and a base (e.g. TEA or DIPEA).

tures. The resulting bromides are in turn treated with an acrylate derivative, a base (e.g. NaH) and ethanol in diethyl ether affording a cyclopropane derivative. The two ester functional groups of such compounds are converted to a diol coupled using a reducing agent (e.g. lithium aluminium hydride) in an appropriate solvent like THF. The diols are in turn converted to leaving groups such as mesylates upon

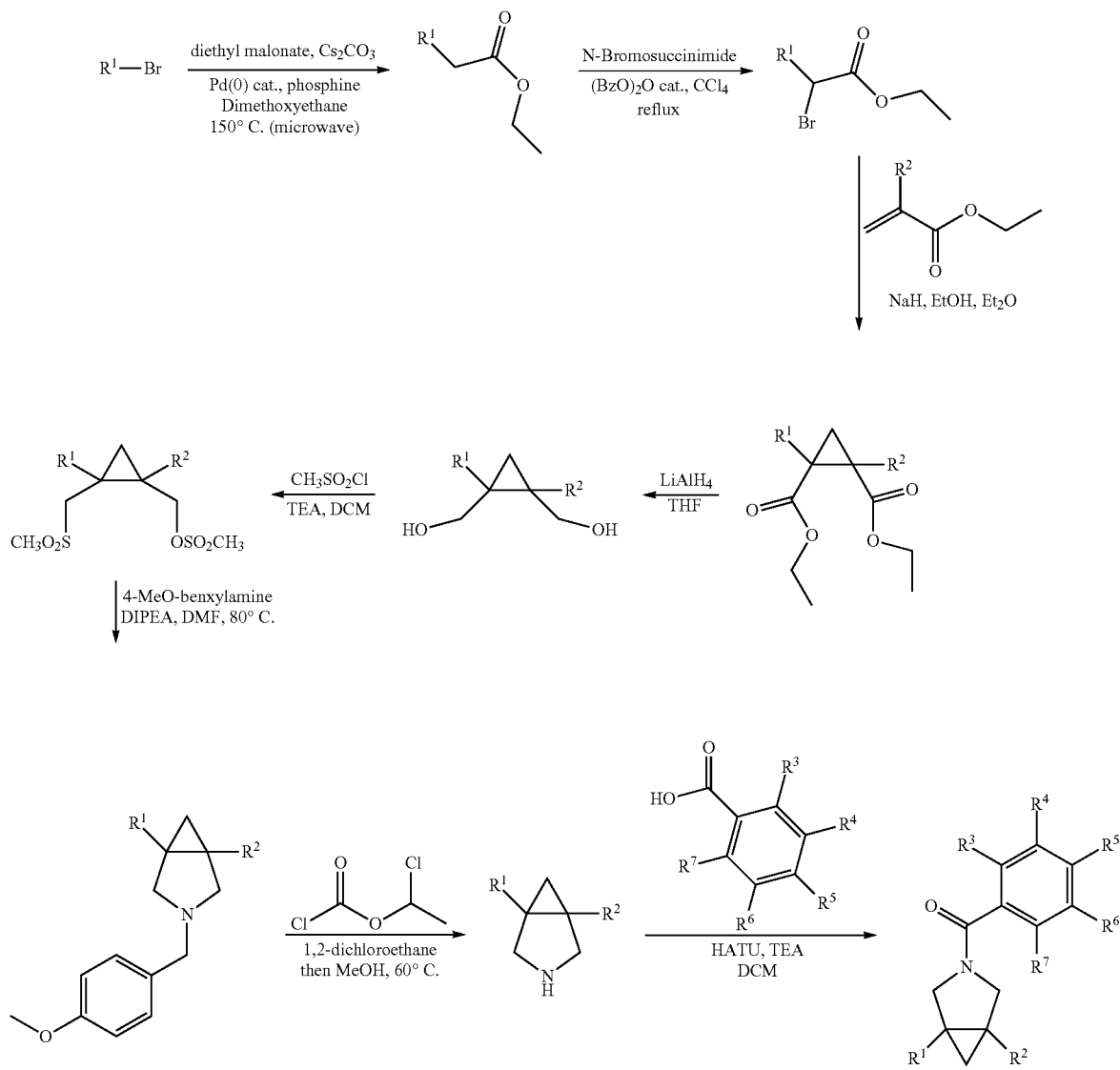

In scheme 3 all substituents $R^1$ to $R^7$ have the meaning as defined for general formula (I) and all embodiments of the invention that directly refer thereto. $R^1$—Br in the first step: the Br is attached to a carbon atom.

Scheme 3:

In a first step heteroaryl bromides are treated with a malonate derivative, a base (e.g. cesium carbonate), a Pd(O) catalyst (e.g. $Pd_2dba_3$) and a phosphine (e.g. $t-Bu_3P$) in an appropriate solvent like dimethoxyethane at elevated temperatures. The resulting acetyl-substituted derivatives are brominated with a Bromine source (e.g. N-bromosuccinimide) and a radical initiator (e.g. benzoyl peroxide) in an appropriate solvent like carbon tetrachloride at elevated temperatreatment with methanesulfonyl chloride, a base (e.g. TEA) in DCM. Ring closure to pyrrolidine derivatives is carried out employing an amine (e.g. 4-MeO-benzylamine), a base (e.g. DIPEA) in an appropriate solvent like DMF at elevated temperatures. NH-pyrrolidines are obtained by deprotection of such compounds, e.g. in the case of 4-MeO-benzyl-protection by treatment with 1-chloroethyl chloroformate in 1,2-dichloroethane followed by MeOH at elevated temperatures. The resulting products are coupled with benzoic acid derivatives in an appropriate solvent like DMF and in the presence of a coupling agent (e.g. HATU or TBTU) and a base (e.g. TEA or DIPEA).

Scheme 4

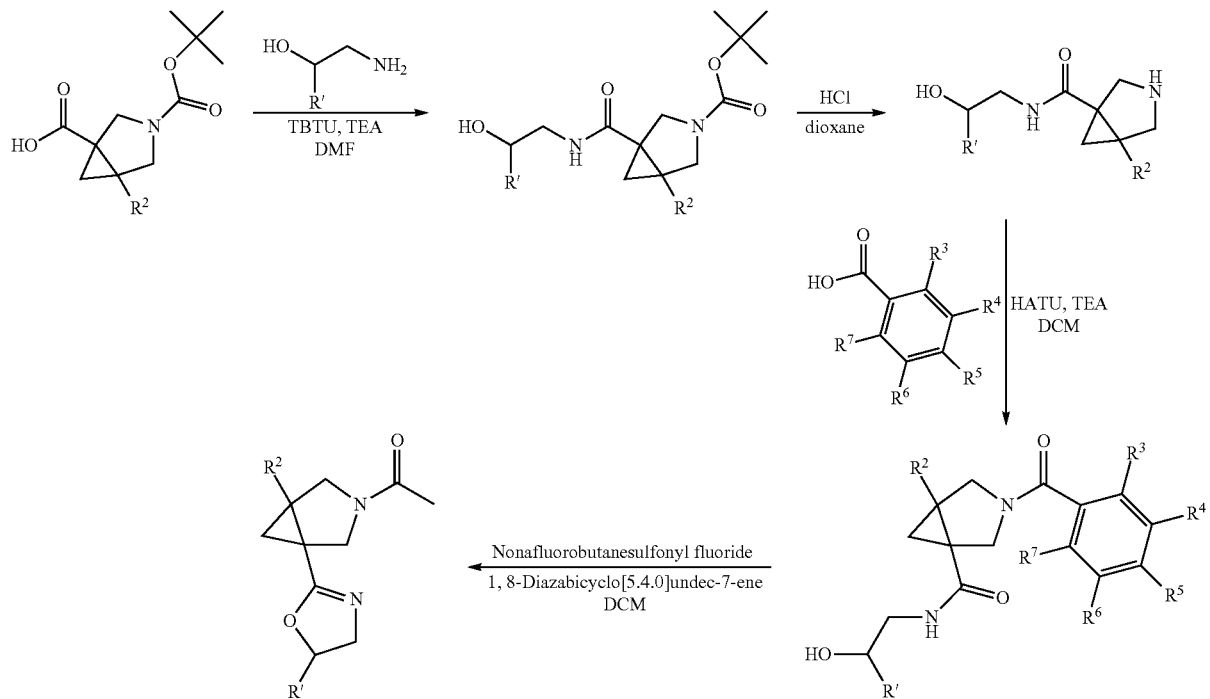

In scheme 4 all substituents $R^2$ to $R^7$ have the meaning as defined for general formula (I) and all embodiments of the invention that directly refer thereto. R'=a substituent as defined for $R^1$, e.g. —$CF_3$.

Scheme 4:

In a first step a derivative of 3-azabicyclo[3.1.0]hexane-1,3-dicarboxylic acid-3-tert-butyl ester is coupled with an amino alcohol in the presence of a coupling agent (e.g. TBTU), a base (e.g. TEA) an appropriate solvent like DMF. The Boc protecting group of the resulting amides are deprotected with hydrochloric acid in an appropriate solvent like dioxane. The resulting products are coupled with benzoic acid derivatives in an appropriate solvent like DMF and in the presence of a coupling agent (e.g. HATU or TBTU) and a base (e.g. TEA or DIPEA). The formation of the dihydro-oxazole is accomplished upon treatment with nonafluorobutanesulfonyl fluoride, a base (e.g. 1,8-diazabicyclo[5.4.0]undec-7-ene) in DCM.

Scheme 5

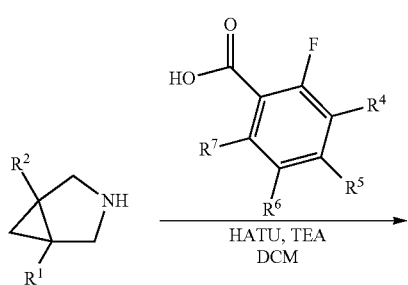

-continued

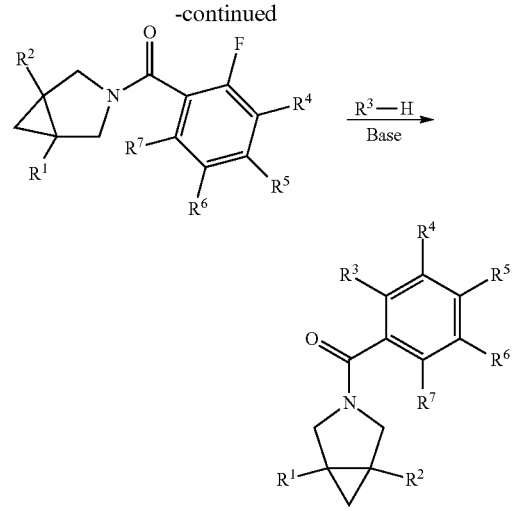

In scheme 5 all substituents $R^1$ to $R^7$ have the meaning as defined for general formula (I) and all embodiments of the invention that directly refer thereto.

Scheme 5:

In a first step a derivative of 1-heteroaryl-3-aza-bicyclo[3.1.0]hexane is coupled with fluoro-benzoic acid derivatives in an appropriate solvent like DMF and in the presence of a coupling agent (e.g. HATU) and a base (e.g. DIPEA). $R^3$ is subsequently installed by substitution of the Fluorine upon treatment with $R^3$—H and a base (e.g. NaH or KOtBu) in an appropriate solvent like THF or DMF.

3-azabicyclo[3.1.0]hexane-1,3-dicarboxylic acid-3-tert-butyl ester derivates are available from commercial vendors or, alternatively, can be synthesised following the approach described in Scheme 6.

Scheme 6

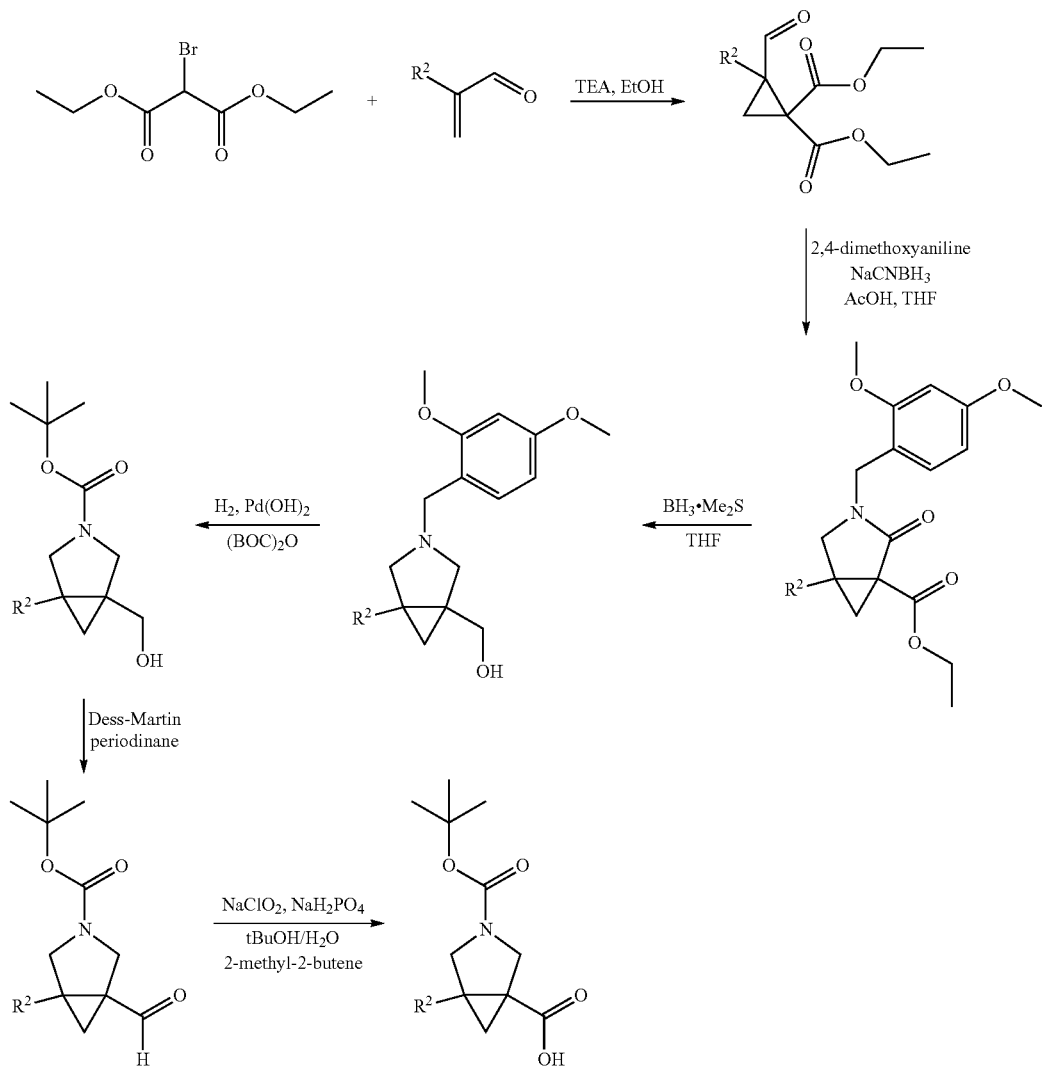

In scheme 6 substituent $R^2$ has the meaning as defined for general formula (I) and all embodiments of the invention that directly refer thereto.

Scheme 6:

In a first step a Bromo-malonate derivative is treated with an acrylate derivative, a base (e.g. TEA) in ethanol affording a cyclopropane derivative. A pyrrolidone ring is then constructed by subjecting this compound to reductive amination conditions. The pyrrolidone is in turn converted to a pyrrolidine derivative with a reducing agent (e.g. borane-dimethyl-sulfide complex). N-Boc-pyrrolidines are obtained by deprotection of such compounds, e.g. in the case of 2,4-dimethoxy-benzyl-protection by metal-catalysed hydrogenation, in the presence of di-tert-butyl dicarbonate. Derivatives of 3-azabicyclo[3.1.0]hexane-1,3-dicarboxylic acid-3-tert-butyl ester are prepared by oxydation of the corresponding alcohols, e.g. by treatment with Dess-Martin periodinane followed by Sodium chloride.

The above processes for manufacture according to schemes 1, 2, 3, 4, 5 or 6 are among other aspects of the present invention.

The intermediate compounds as outlined in the above processes for manufacture according to schemes 1, 2, 3, 4, 5 or 6 constitute another aspect of the present invention, specifically with regard to intermediate compounds according to any of the following general formulas (II), (III), (IV), (V) and (VI):

general formula (II)

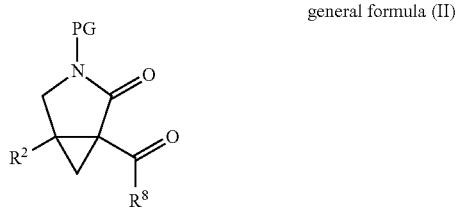

general formula (III)

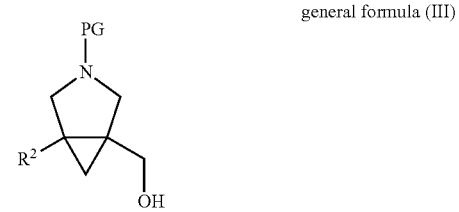

-continued general formula (IV)

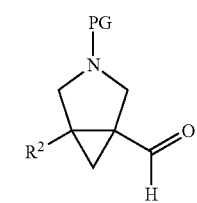

general formula (V)

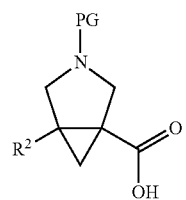

general formula (VI)

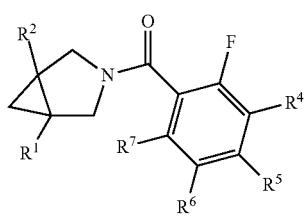

wherein in each of those independent formulas
$R^1$, $R^2$, $R^4$, $R^5$, $R^6$, and $R^7$ have the meaning as defined for general formula (I), all embodiments referring thereto and the table as outlined for scheme 2.

$R^8$ is $C_{1-4}$ alkyl-O—, optionally substituted by 1 or more substituents independently selected from each other from the group of fluoro, chloro, bromo, —CN, $C_{1-4}$ alkyl-O—, $C_{1-4}$ alkyl-, phenyl and benzyl, wherein phenyl and benzyl optionally may be substituted with one or more substituents independently selected from each other from the group of fluoro, chloro, bromo, —CN, $C_{1-4}$ alkyl-O—, $C_{1-4}$ alkyl-;

PG: is protecting group for an amino function such as outlined in: Peter G. M. Wuts, Theodora W. Greene, Greene's Protective Groups in Organic Synthesis, Wiley-Interscience; 4 edition (Oct. 30, 2006).

Preferred protecting groups are tert-butoxycarbonyl-, 9-fluorenylmethoxycarbonyl-, benzyl, 2,4-dimethoxybenzyl-.

Specifically preferred are those intermediate compounds according to general formulas (II), (III), (IV), (V) and (VI), in which any of the substituents $R^1$, $R^2$, $R^4$, $R^5$, $R^6$, and $R^7$ have the meaning according to the exemplified specific compounds of the compound families of Table 1 in combination with PG being tert-butoxycarbonyl-, 9-fluorenylmethoxycarbonyl-, benzyl-, 2,4-dimethoxybenzyl-.

Among the more preferred intermediate compounds are those according to general formulas (III), (V) and (VI).

The intermediate compounds according to general formulas (II), (III), (IV), (V) and (VI) can be made according to or in analogy to the processes outlined by schemes 1 to 6 and with respect to protecting groups for the nitrogen function of the 3-azabicyclo[3.1.0]hexane-template, by the conditions for addition of these protecting groups and removal thereof as outlined by the aforementioned book of Peter G. M. Wuts and Theodora W. Greene.

Method of Treatment

The present invention refers to compounds, which are considered effective in the treatment of diseases (active compounds according to general formula (I) and specifically the compound family classes and the members thereof). These active compounds according to the invention are effective and selective inhibitors of glycine transporter-1 (GlyT1). Thus, the medicinal concepts discussed above, specifically in the section "Background of the Invention" at the introduction part of this description, are considered of high interest as field of application for the active compounds of the present invention. The active compounds of the present invention can be used for the development of medicaments. Such medicaments shall preferably be used for the treatment of diseases in which the inhibition of GlyT1 can evolve a therapeutic, prophylactic or disease modifying effect. Preferably the medicaments shall be used to treat illnesses such as psychoses, dysfunction in memory and learning, schizophrenia (positive and negative symptoms and cognitive impairment associated with schizophrenia), dementia like Alzheimer's disease and other diseases in which cognitive processes are impaired, such as attention deficit disorders, epilepsy and/or bipolar disorder.

The medicaments are for use in a method, preferably a therapeutic method, or a method for to improve perception, concentration, cognition, learning or memory, like those occurring in particular in conditions, diseases and/or syndromes such as:

mild cognitive impairment, amnestic mild cognitive impairment, age-associated learning and memory impairments, age-associated memory losses, vascular dementia, craniocerebral trauma, stroke, dementia occurring after strokes (post stroke dementia), posttraumatic dementia, general concentration impairments, concentration impairments in children with learning and memory problems, Alzheimer's disease, prodromal Alzheimer's disease, Lewy body dementia, dementia with degeneration of the frontal lobes, including Pick's syndrome, Parkinson's disease, progressive nuclear palsy, dementia with corticobasal degeneration, amyotropic lateral sclerosis (ALS), Huntington's disease, multiple sclerosis, thalamic degeneration, Creutzfeld-Jacob dementia, HIV dementia, epilepsy, temporal lobe epilepsy, Korsakoffs psychosis or cognitive impairment associated with schizophrenia, depression, epilepsy, schizo-affective disorder or bipolar disorder.

Another aspect of the present invention concerns the treatment of a disease which is accessible by GlyT1-inhibition, in particular sleep disorders like insomnia or narcolepsy, bipolar disorder, depression, substance use disorders/abuse disorders, hearing disorders, attention deficit (hyperactive) disorder, inflammatory pain, neuropathic pain or autism spectrum disorders.

Thus the medical aspect of the present invention can be summarized in that it is considered that a compound according to formula (I) as herein defined, in particular the specifically defined species active compounds for use in or as a medicament.

Such a medicament preferably is for a therapeutic or prophylactic, preferably therapeutic method in the treatment of a CNS disease.

In an alternative use, the medicament is for the treatment of a CNS disease, the treatment of which is accessible by the inhibition of GlyT1.

In an alternative use, the medicament is for the treatment of a disease that is accessible by the inhibition of GlyT1.

In an alternative use, the medicament is for the use in a method for the treatment of Alzheimer's disease, schizophrenia (positive and negative symptoms) or cognitive impairment associated with Alzheimer's disease or associated with schizophrenia.

In a further aspect of the invention, the present invention relates to the method of treatment or prevention of a condition or disease selected from the above listed groups of conditions and diseases, wherein the method comprises the administration of a therapeutically effective amount of an active compound according to the invention in a human being in need thereof.

The dose range of an active compound of the present invention applicable per day is usually from 0.1 to 5000 mg, preferably from 0.1 to 1000 mg, preferably from 2 to 500 mg, more preferably from 5 to 250 mg, most preferably from 10 to 100 mg. A dosage unit (e.g. a tablet) preferably may contain between 2 and 250 mg, particularly preferably between 10 and 100 mg of the active compounds according to the invention.

Another aspect of the invention concerns the active compounds of the inventions for use in a therapeutic method or for use as a medicament. If indicated the therapeutic method or the medicament is preferably for the treatment of a condition or a disease selected from the group of conditions or a diseases as outlined above in this section, which is entitled "METHOD OF TREATMENT".

Pharmaceutical Composition

Suitable preparations for administering the active compounds according to the invention will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) should be in the range from 0.05 to 90 wt.-%, preferably 0.1 to 50 wt.-% of the composition as a whole.

Suitable tablets may be obtained, for example, by mixing one or more active compounds according to formula (I) with known excipients, for example inert diluents, carriers, disintegrants, adjuvants, surfactants, binders and/or lubricants. The tablets may also consist of several layers.

EXAMPLES

Examples which might illustrate possible pharmaceutical formulations, without being meant to be limiting:

The term "active substance" denotes one or more active compounds according to the invention including the salts thereof. In the case of one of the aforementioned combinations with one or more other active substances the term "active substance" may also include the additional active substances. Standard procedures should be considered for the preparation of any the herein mentioned pharmaceutical formulations

| HARD GELATINE CAPSULES | |
|---|---|
| active substance | 150.0 mg |
| lactose | 87.0 mg |
| corn starch (dried) | 80.0 mg |
| magnesium stearate | 3.0 mg |
| | 320.0 mg |

| SUPPOSITORY COMPOSITION | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2000.0 mg |

| TABLETS | | |
|---|---|---|
| active substance | 100.0 mg | 150 mg |
| lactose | 80.0 mg | 89.0 mg |
| corn starch | 34.0 mg | 40.0 mg |
| polyvinylpyrrolidone | 4.0 mg | 10 mg |
| magnesium stearate | 2.0 mg | 1.0 mg |
| | 220.0 mg | 300.0 mg |

Combination Therapy/Combination with Other Active Substances

In another aspect the present invention relates to a combination therapy in which an active compound according to the present invention is administered together with another active compound. Accordingly, the invention also refers to pharmaceutical formulations that provide such a combination of active ingredients, wherein one of which is an active compound of the present invention. Such combinations may be fixed dose combinations (the active ingredients that are to be combined are subject of the same pharmaceutical formulation) or free dose combinations (active ingredients are in separate pharmaceutical formulations).

Consequently, a further aspect of the present invention refers to a combination of each of the active compounds of the present invention, preferably at least one active compound according to the present invention, with another active compound for example selected from the group of antipsychotics such as haloperidol, clozapine, risperidone, quetiapine, aripripazole, asenapine and olanzapine; antidepressants such as selective serotonin reuptake inhibitors and dual serotonin/noradrenaline re-uptake inhibitors; mood stabilizers such as lithium valproate and lamotrigine; beta-secretase inhibitors; gamma-secretase inhibitors; gamma-secretase modulators; amyloid aggregation inhibitors such as e.g. scylloinositol; directly or indirectly acting neuroprotective and/or disease-modifying substances; anti-oxidants, such as e.g. vitamin E, ginko biloba or ginkolide; anti-inflammatory substances, such as e.g. Cox inhibitors, NSAIDs additionally or exclusively having Aβ (Abeta) lowering properties; HMG-CoA reductase inhibitors, such as statins; acetylcholine esterase inhibitors, such as donepezil, rivastigmine, tacrine, galantamine; NMDA receptor antagonists such as e.g. memantine; AMPA receptor agonists; AMPA receptor positive modulators, AMPkines, glycine transporter 1 inhibitors; monoamine receptor reuptake inhibitors; substances modulating the concentration or release of neurotransmitters; substances inducing the secretion of growth hormone such as ibutamoren mesylate and capromorelin; CB-1 receptor antagonists or inverse agonists; antibiotics such as minocyclin or rifampicin; PDE1, PDE2, PDE4, PDE5, PDE9 or PDE10 inhibitors, GABAA receptor inverse agonists; GABAA alpha5 receptor inverse agonists; GABAA receptor antagonists; nicotinic receptor agonists or partial agonists or positive modulators; alpha4beta2 nicotinic receptor agonists or partial agonists or positive modulators; alpha7 nicotinic receptor agonists or partial agonists; histamine receptor H3 antagonists; 5-HT4 receptor agonists or partial agonists; 5-HT6 receptor antagonists; alpha2-adrenoreceptor antagonists, calcium antagonists; muscarinic receptor M1 agonists or partial agonists or positive modulators; muscarinic receptor M2 antagonists; muscarinic receptor M4 antagonists; muscarinic receptor M4 positive allosteric modulators; metabotropic glutamate receptor 5 positive allosteric modulators; metabotropic glutamate receptor 2 antagonists; metabotropic glutamate receptor 2/3 agonists; metabotropic glutamate receptor 2 positive allosteric modulators and other substances that modulate receptors or enzymes in a manner such that the efficacy and/or safety of the active compounds according to the invention is increased and/or unwanted side effects are reduced.

The active compounds according to the invention may also be used in combination with immunotherapies such as e.g. active immunisation with Abeta or parts thereof or passive immunisation with humanised anti-Abeta antibodies or antibody fragments for the treatment of the above mentioned diseases and conditions.

The active compounds according to the invention also may be combined with antipsychotics like haloperidol, flupentixol, fluspirilene, chlorprothixene, prothipendyl, levomepromazine, clozapine, olanzapine, quetiapine, risperidone, paliperidone, amisulpride, ziprasidone, aripiprazol, sulpiride, zotepine, sertindole, fluphenazine, perphenazine, perazine, promazine, chlorpromazine, levomepromazine, benperidol, bromperidol, pimozid, melperone, pipamperone, iloperidone, asenapine, perospirone, blonanserin, lurasidone.

The active compounds according to the invention also may be combined with antidepressants like amitriptyline imipramine hydrochloride (TOFRANIL), imipramine maleate (SURMONTIL), lofepramine, desipramine (NORPRAMIN), doxepin (SINEQUAN, ZONALON), trimipramine (SURMONTIL).

Or the active compounds according to the invention also may be combined with serotonin (5-HT) reuptake inhibitors such as alaproclate, citalopram (CELEXA, CIPRAMIL) escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXII, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensme and tesofensine.

The combinations according to the present invention may be provided simultaneously in one and the same dosage form, i.e. in form of a combination preparation, for example the two components may be incorporated in one tablet, e. g. in different layers of said tablet. The combination may be also provided separately, in form of a free combination, i.e. the active compounds of the present invention are provided in one dosage form and one or more of the above mentioned combination partners is provided in another dosage form. These two dosage forms may be equal dosage forms, for example a co-administration of two tablets, one containing a therapeutically effective amount of the active compound of the present invention and one containing a therapeutically effective amount of the above mentioned combination partner. It is also possible to combine different administration forms, if desired. Any type of suitable administration forms may be provided.

The active compound according to the invention, or a physiologically acceptable salt thereof, in combination with another active substance may be used simultaneously or at staggered times, but particularly close together in time. If administered simultaneously, the two active substances are given to the patient together; if administered at staggered times the two active substances are given to the patient successively within a period of less than or equal to 12, particularly less than or equal to 6 hours.

The dosage or administration forms are not limited, in the frame of the present invention any suitable dosage form may be used. Exemplarily the dosage forms may be selected from solid preparations such as patches, tablets, capsules, pills, pellets, dragees, powders, troches, suppositories, liquid preparations such as solutions, suspensions, emulsions, drops, syrups, elixirs, or gaseous preparations such as aerosols, sprays and the like.

The dosage forms are advantageously formulated in dosage units, each dosage unit being adapted to supply a single dose of each active component being present. Depending from the administration route and dosage form the ingredients are selected accordingly.

The dosage for the above-mentioned combination partners may be expediently 1/5 of the normally recommended lowest dose up to 1/1 of the normally recommended dose.

The dosage forms are administered to the patient for example 1, 2, 3, or 4 times daily depending on the nature of the formulation. In case of retarding or extended release formulations or other pharmaceutical formulations, the same may be applied differently (e.g. once weekly or monthly etc.). It is preferred that the active compounds of the invention be administered either three or fewer times, more preferably once or twice daily.

Biological Assay

In-Vitro Effect:

The in-vitro effect of the active compounds of the invention can be shown with the following biological assay.

GlyT1 Assay Protocol:

Cells expressing either endogenously the GlyT1 transporter like JAR cells (human placental choriocarcinoma cells; e.g. WO 2008/002583) or SK-N-MC cells (human neuroblastoma cells; Depoortere et al., 2005. Neuropsychopharmacology 30:1963-1985) or primary neurons or cells which have been transfected with a plasmid encoding the cDNA of a functional GlyT1 transporter and stably or transiently express GlyT1 (e.g. WO 2006/08200) can be used to monitor glycine uptake in cells. Different protocols for determination of the glycine uptake into the cells described above can be applied in order to identify and rank compounds which interfere with glycine uptake in the selected cell.

Compounds outlined in the examples below were characterized using human SK-N-MC cells (ATCC number HTB-10) endogenously expressing the GlyT1 transporter which is responsible for the uptake of glycine into these cells and the uptake of glycine into these cells is monitored using the Cytostar-T assay format (GE Healthcare, RPNQ0162) which is based on the radioactive glycine taken up by the cells and brought into proximity with the scintillant contained within the base of the plate. The radioactive decay is converted to a light signal based on the integration of the scintillation matrix into the assay plate. The uptake is recorded as kinetic and the slope of the measured counts over time is used to calculate $IC_{50}$.

In detail, SK-N-MC cells are seeded into 96-well Cytostar-T assay plates at a density of 200,000 cells/well and grown for 16-18 hours to confluence in growth medium as recommended by ATCC. Before starting the assay, cells are washed once with HBSS (Hank's buffered salt solution; Sigma, H8264) cont. 5 mM alanine (referred in here as HBSS/Ala) and afterwards the following reagents are added:

1. 80 µl/well HBSS/Ala
2. 20 µl/well of HBSS/Ala containing 6× the concentration of compound in 6% DMSO
3. approx. 5-10 min incubation
4. 20 µl/well 3 µM glycine ($^3$H-glycine (Perkin Elmer, NET004001MC, specific activity: 52 Ci/mmol; diluted 1:1 with unlabelled glycine) in HBSS/Ala.

In the final assay, glycine concentration is 500 nM (250 nM derived from the $^3$H-glycine Perkin Elmer, 250 nM unlabelled glycine), DMSO concentration is 1%.

The assay plate is immediately after addition of the $^3$H-glycine placed into a Micro-Beta Counter (Perkin Elmer) and the signal is recorded over 60 min.

To calculate uptake, the slope in the linear range of the kinetics is determined using GraphPadPrism and for the different slopes at the selected concentrations $IC_{50}$ are calculated by curve fitting using the software GraphPadPrism.

Maximal glycine uptake in every experiment is determined by incubation of SK-N-MC cells with substrate but without inhibitor. Unspecific uptake of glycine by the cells is determined by incubating the cells with substrate and a reference GlyT1 inhibitor e.g. 10 μM RG-1678 (Pinard et al., 2010, J. Med. Chem. 53(12):4603-14).

Compounds are diluted from 10 mM stocks and in general, for $IC_{50}$ determination 8 compound concentrations are used.

| Example number | IC50 [nM] |
|---|---|
| 1 | 39 |
| 2 | 18 |
| 3 | 1016 |
| 4 | 9 |
| 5 | 1375 |
| 6 | 16.5 |
| 7 | 4 |
| 8 | 474 |
| 9 | 18 |
| 10 | 42 |
| 11 | 175 |
| 12 | 18 |
| 13 | 9 |
| 14 | 67 |
| 15 | 14 |
| 16 | 10 |
| 17 | 157 |
| 18 | 106 |
| 19 | 5 |
| 20 | 101 |
| 21 | 21 |
| 22 | 5 |
| 23 | 181 |
| 24 | 911 |
| 25 | 22 |
| 26 | 8 |
| 27 | 5 |
| 28 | 1438 |
| 29 | 11 |
| 30 | 5 |
| 31 | 1005 |
| 32 | 26 |
| 33 | 190 |
| 34 | 98 |
| 35 | 101 |
| 36 | 62 |
| 37 | 34 |
| 38 | 89 |
| 39 | 143 |
| 40 | 19 |
| 41 | 6 |
| 42 | 6 |
| 43 | 251 |
| 44 | 397 |
| 45 | 2 |
| 46 | 29 |
| 47 | 7 |
| 48 | 886 |
| 49 | 19 |
| 50 | 6 |
| 51 | 461 |
| 52 | 15 |
| 53 | 70 |
| 54 | 16 |
| 55 | 22 |
| 56 | 233 |
| 57 | 354 |
| 58 | 17 |
| 59 | 8 |
| 60 | 372 |
| 61 | 8 |
| 62 | 10 |
| 63 | 10 |
| 64 | 4 |
| 65 | 9 |
| 66 | 4 |
| 67 | 100 |
| 68 | 7 |
| 69 | 3 |
| 70 | 155 |
| 71 | 184 |
| 72 | 17 |
| 73 | 9 |
| 74 | 4 |
| 75 | 110 |
| 76 | 10 |
| 77 | 113 |
| 78 | 7 |
| 79 | 6 |
| 80 | 3 |
| 81 | 6 |
| 82 | 782 |
| 83 | 3 |
| 84 | 16 |
| 86 | 20 |
| 87 | 2362 |
| 88 | 168 |
| 89 | 97 |
| 90 | 2247 |
| 91 | 112 |
| 92 | 25 |
| 93 | 11 |
| 94 | 2911 |
| 95 | 131 |
| 96 | 27 |
| 97 | 8 |
| 98 | 1895 |
| 99 | 291 |
| 100 | 916 |
| 101 | 15 |
| 102 | 18 |
| 103 | 7 |
| 104 | 292 |
| 105 | 7 |
| 106 | 248 |
| 107 | 5 |
| 108 | 10 |
| 109 | 45 |
| 110 | 1134 |
| 111 | 257 |
| 113 | 216 |
| 114 | 171 |
| 116 | 10 |
| 117 | 6 |
| 118 | 700 |
| 119 | 11 |
| 120 | 6 |
| 121 | 349 |
| 122 | 21 |
| 123 | 13 |
| 124 | 503 |
| 125 | 31 |
| 126 | 16 |
| 127 | 2659 |
| 128 | 6 |
| 129 | 147 |
| 130 | 3 |
| 131 | 19 |
| 132 | 3 |
| 133 | 403 |
| 134 | 8 |
| 135 | 7 |
| 136 | 120 |
| 138 | 261 |

| Example number | IC50 [nM] |
|---|---|
| 139 | 253 |
| 140 | 3000 |
| 141 | 764 |
| 142 | 3 |
| 143 | 7 |
| 144 | 164 |
| 145 | 7 |
| 146 | 9 |
| 147 | 18 |
| 148 | 9 |
| 149 | 8 |
| 150 | 232 |
| 151 | 10 |
| 152 | 10 |
| 153 | 1200 |
| 154 | 72 |
| 155 | 36 |
| 156 | 11 |
| 157 | 147 |
| 158 | 85 |
| 159 | 953 |
| 160 | 8 |
| 161 | 9 |
| 162 | 387 |
| 163 | 16 |
| 164 | 28 |
| 165 | 394 |

Compounds with an $IC_{50}$ value of between >1 and 1000 nM are preferred, more preferred are active compounds with an $IC_{50}$ value of between >1 and 500 nM, more preferred are compounds with an $IC_{50}$ value of between >1 and 150 nM.

Compounds with an $IC_{50}$ value of between >1 and 1000 nM are preferred, more preferred are active compounds with an $IC_{50}$ value of between >1 and 500 nM, more preferred are compounds with an $IC_{50}$ value of between >1 and 150 nM.

In-Vivo Effect:

It is believed that the positive in-vitro efficacy results of the active compounds of the present invention translate in positive in-vivo efficacy.

The in-vivo effect of the active compounds of this invention can be tested regarding glycine increase in CSF according to Perry et al. 2008 (Neuropharmacology 55:743-754), in the psychostimulant-induced hyperlocomotion test according to Boulay et al. 2008 (Pharmacol. Biochem. Behav. 91:47-58) or the social recognition test according to Shimazaki et al. 2010 (Psychopharmacology 209:263-270). For further information concerning biological testing, it is also referred to these three citations.

Besides the inhibition property toward the target GlyT1 transporter, active compounds according to the present invention may provide further advantageous pharmacokinetic properties.

E.g. active compounds according to the invention may show one or more advantages in the area of safety, balanced metabolism, low risk of causing drug—drug interaction and/or balanced clearance.

Active compounds also might show one or more additional or alternative advantages in the area of bioavailability, high fraction absorbed, blood brain transport properties, a favourable (e.g. high mean) residence time (mrt), favourable exposure in the effect compartment and so on.

Chemical Manufacture
Abbreviations:
Ac Acetyl
ACN acetonitrile
APCI Atmospheric pressure chemical ionization
Boc ter-butyloxycarbony
Burgess reagent: methoxycarbonylsulfamoyl-triethyl ammonium hydroxide inner salt
CDI 1,1'-carbonyldiimidazole
d day
dba dibenzylideneacetone
DCM dichloromethane
DIPEA diisopropylethylamine
DME 1,2-dimethoxyethane
DMF dimethylformamide
ESI electrospray ionization (in MS)
EtOAc ethylacetate
EtOH ethanol
Exp. example
h hour(s)
HATU O-(7-azabenzotriazol-1-yl)-N,N,N',N'-tetramethyluronium-hexafluorophosphate
HPLC high performance liquid chromatography
HPLC-MS coupled high performance liquid chromatography-mass spectrometry
M molar (mol/L)
MeOH methanol
min minute(s)
MS mass spectrometry
NMP 1-methyl-2-pyrrolidinone
RP reverse Phase
rt room temperature
$R_t$ retention time (in HPLC)
TBTU O-(benzotriazol-1-yl)-N,N,N',N'-tetramethyluronium tetrafluoroborate
TEA triethylamine
TFA trifluoroacetic acid
THF tetrahydrofuran
TLC thin-layer chromatography
UPLC-MS ultra performance liquid chromatography—mass spectrometry
Methods:
UPLC-MS Methods:
Method 1 (Acidic Analytics)

Instrument: LC/MS Waters Acquity UPLC System DAD, SQD single quadrupole; column: HSS C18 1.8 µm 2.1×50 mm, Temp 35° C.; mobile phase: A=H$_2$O 90%+10% CH$_3$CN+CF$_3$COOH 0.1%, B=CH$_3$CN 90%+H$_2$O 10%; gradient: 0.0 min 0% B→1.20 min 100% B→1.45 min 100% B→1.55 min 0% B→1.75 min 0% B; flow rate: 0.70 mL/min; detection: UV 254 nm; detection: SQD, single quadrupole; ion source: ES+/ES−; scan range: 90-900 amu Method 2 (NH$_4$COOH)

Instrument: LC/MS Waters Acquity UPLC System DAD, SQD single quadrupole; column: BEH C18 1.7 µm 2.1×50 mm, Temp 35° C.; mobile phase: A=H$_2$O 90%+10% CH$_3$CN+NH$_4$COOH 5 mmol, B=CH$_3$CN 90%+H$_2$O 10%; gradient: 0.0 min 0% B→1.20 min 100% B→1.45 min 100% B→1.55 min 0% B→1.75 min 0% B; flow rate: 0.70 mL/min; detection: UV 254 nm; detection: SQD, single quadrupole; ion source: ES+/ES−; scan range: 90-900 amu Method 3 (QC_TFA_50 mm)

Instrument: LC/MS Waters Acquity UPLC System DAD, ELSD detector, SQD single quadrupole; column: HSS C18 1.8 µm 2.1×50 mm, Temp 35° C.; mobile phase: A=H$_2$O 90%+10% CH$_3$CN+CF$_3$COOH 0.1%, B=CH$_3$CN 90%+H$_2$O 10%; gradient: 0.0 min 0% B→2.40 min 100% B→2.70 min 100% B→2.80 min 0% B→3.00 min 0% B; flow rate: 0.70 mL/min; detection: UV 254 nm; detection: ELSD detector; detection: SQD, single quadrupole; ion source: ES+/ES−; scan range: 90-900 amu Method 4 (QC_NH$_4$COOH_50 mm)

Instrument: LC/MS Waters Acquity UPLC System DAD, ELSD detector, SQD single quadrupole; column: HSS C18 1.8 μm 2.1×50 mm, Temp 35° C.; mobile phase: A=H$_2$O 90%+10% CH$_3$CN+NH$_4$COOH 5 mmol, B=CH$_3$CN 90%+ H$_2$O 10%; gradient: 0.0 min 0% B→2.40 min 100% B→2.70 min 100% B→2.80 min 0% B→3.00 min 0% B; flow rate: 0.70 mL/min; detection: UV 254 nm; detection: ELSD detector; detection: SQD, single quadrupole; ion source: ES+/ES−; scan range: 90-900 amu HPLC-MS Methods:

Method 5 (1Eh)

Instrument: LC/MS ThermoFinnigan. Hplc Surveyor DAD, MSQ Quadrupole; column: Synergi Hydro-RP80A, 4 um, 4.60×100 mm; eluent A: 90% water+10% ACN+ammonium formate 10 mM; eluent B=ACN 90%+10% H$_2$O+ NH$_4$COOH 10 mM; gradient: A (100) for 1.5 min, then to B (100) in 10 min for 1.5 min; flow rate: 1.2 mL/min; UV Detection: 254 nm; Ion source: APCI.

Method 6 (2FF)

Instrument: LC/MS ThermoFinnigan HPLC Surveyor DAD, LCQ Fleet Ion Trap; column: Simmetry Shield RP8, 5 μm, 4.6×150 mm; eluent A: 90% water+10% ACN+HCOOH 0.1%; eluent B=ACN 90%+10% H$_2$O+HCOOH 0.1%; gradient: 0.0 min 5% B→1.5 min 5% B→11.5 min 95% B→13.0 min 95% B→13.3 min 5% B→15.0 min 5% B; flow rate: 1.0 mL/min; UV Detection: 254 nm; Detection: Finnigan Fleet, Ion Trap; ion source: ES+; scan range: 100-900 amu Method 7 (2LF)

Instrument: LC/MS ThermoFinnigan. Hplc Surveyor DAD, MSQ Quadrupole; column: Synergi Hydro-RP8, 4 urn, 4.60×100 mm; eluent A: 90% water+10% ACN+ammonium formate 10 mM; eluent B=ACN 90%+10% H$_2$O+NH$_4$COOH 10 mM; gradient: 0.0 min 30% B→1.50 min 50% B 8.50 min 100% B→13.50 min 100% B→14.00 min 30% B→15.00 min 30% B; flow rate: 0.85 mL/min; UV Detection: 254 nm; Ion source: ES+.

Method 7a

Instrument: LC/MS ThermoFinnigan. Hplc Surveyor DAD, MSQ Quadrupole; column: Synergi Hydro RP100A, 2.5 urn, 3×50 mm; eluent A: 90% water+10% ACN+ammonium formate 10 mM; eluent B=ACN 90%+10% H$_2$O+ NH$_4$COOH 10 mM; gradient: 0.0 min 0% B→1.50 min 0% B→8.00 min 100% B→10.00 min 100% B→11.00 min 0% B→12.00 min 0% B; flow rate: 0.7 mL/min; UV Detection: 254 nm; Ion source: APCI+.

Method 7b

Instrument: LC/MS ThermoFinnigan. Hplc Surveyor DAD, MSQ Quadrupole; column: Synergi Hydro RP100A, 2.5 um, 3×50 mm; eluent A: 90% water+10% ACN+ammonium formate 10 mM; eluent B=ACN 90%+10% H$_2$O+ NH$_4$COOH 10 mM; gradient: 0.0 min 0% B→4.00 min 100% B→5.30 min 100% B→5.50 min 0% B→6.00 mM 0% B; flow rate: 1.2 mL/min; UV Detection: 254 nm; Ion source: APCI+.

GC-MS Methods:

Method 8 (3A.2)

Instrument: GC/MS Thermo Scientific TRACE GC ULTRA, DSQ II MS single quadrupole; column: Agilent DB-5MS, 25 m×0.2 5 mmol×0.25 μm; carrier gas: Helium, 1 mL/min constant flow; oven program: 50° C., to 100° C. in 10° C./min, to 200° C. in 20° C./min, to 320° C. in 30° C./min (hold 10 min); detection: DSQ II MS single quadrupole; ion source: EI; scan range: 50-450 amu Chiral HPLC Methods:

Method 9:

HPLC apparatus type: Agilent 1100; column: Daicel chiralpack AD-H, 5.0 μm, 250 mm×10 mm; method: eluent hexane/IPA 70:30; flow rate: 1 mL/min, Temperature: 25° C.; UV Detection: 210 nm Method 10:

HPLC apparatus type: Agilent 1100; column: Daicel chiralpack AD-H, 5.0 μm, 250 mm×10 mm; method: eluent hexane/IPA 70:30; flow rate: 1 mL/min, Temperature: 25° C.; UV Detection: 230 nm Method 11:

HPLC apparatus type: Agilent 1100; column: Daicel chiralpack AD-H, 5.0 μm, 250 mm×4.6 mm; method: eluent hexane/IPA 75:25; flow rate: 1 mL/min, Temperature: 25° C.; UV Detection: 230 nm Method 12:

HPLC apparatus type: Agilent 1100; column: Daicel chiralpack AD-H, 5.0 μm, 250 mm×4.6 mm; method: eluent hexane/IPA 70:30; flow rate: 1 mL/min, Temperature: 25° C.; UV Detection: 230 nm Method 13:

HPLC apparatus type: Agilent 1100; column: Daicel chiralpack AD-H, 5.0 μm, 250 mm×4.6 mm; method: eluent hexane/IPA 80:20; flow rate: 1 mL/min, Temperature: 25° C.; UV Detection: 230 nm Method 14:

HPLC apparatus type: Agilent 1100; column: Daicel chiralpack AS-H, 5.0 μm, 250 mm×4.6 mm; method: eluent hexane/IPA 70:30; flow rate: 0.8 mL/min, Temperature: 25° C.; UV Detection: 230 nm Method 15:

HPLC apparatus type: Agilent 1100; column: Daicel chiralpack AS-H, 5.0 μm, 250 mm×4.6 mm; method: eluent hexane/EtOH 70:30; flow rate: 0.8 mL/min, Temperature: 25° C.; UV Detection: 230 nm Method 16:

HPLC apparatus type: Agilent 1100; column: Daicel chiralpack AD-H, 5.0 μm, 250 mm×4.6 mm; method: eluent hexane/IPA 95:5; flow rate: 1 mL/min, Temperature: 25° C.; UV Detection: 210 nm Method 17:

HPLC apparatus type: Agilent 1100; column: Daicel chiralpack AS-H, 5.0 μm, 250 mm×4.6 mm; method: eluent hexane/IPA 75:25; flow rate: 0.9 mL/min, Temperature: 25° C.; UV Detection: 230 nm Method 18:

HPLC apparatus type: Agilent 1100; column: Daicel chiralpack AS-H, 5.0 μm, 250 mm×4.6 mm; method: eluent hexane/IPA 80:20; flow rate: 1 mL/min, Temperature: 25° C.; UV Detection: 230 nm Method 19:

HPLC apparatus type: Agilent 1100; column: Daicel chiralpack AS-H, 5.0 μm, 250 mm×4.6 mm; method: eluent hexane/IPA 90:10; flow rate: 1 mL/min, Temperature: 25° C.; UV Detection: 230 nm Method 20:

HPLC apparatus type: Agilent 1100; column: Daicel chiralpack AD-H, 5.0 μm, 250 mm×4.6 mm; method: eluent hexane/IPA 85:15; flow rate: 1 mL/min, Temperature: 25° C.; UV Detection: 230 nm Method 21:

HPLC apparatus type: Agilent 1100; column: Daicel chiralpack OJ-H, 5.0 μm, 250 mm×4.6 mm; method: eluent hexane/IPA 80:20; flow rate: 1 mL/min, Temperature: 25° C.; UV Detection: 230 nm Method 22:

HPLC apparatus type: Agilent 1100; column: Daicel chiralpack IA, 5.0 μm, 250 mm×4.6 mm; method: eluent hexane/IPA 80:20; flow rate: 1 mL/min, Temperature: 25° C.; UV Detection: 230 nm Method 23:

HPLC apparatus type: Agilent 1100; column: Daicel chiralpack IA, 5.0 μm, 250 mm×4.6 mm; method: eluent hexane/IPA 70:30; flow rate: 1 mL/min, Temperature: 25° C.; UV Detection: 230 nm Method 24:

HPLC apparatus type: Agilent 1100; column: Daicel chiralpack IA, 5.0 μm, 250 mm×4.6 mm; method: eluent hexane/IPA 75:25; flow rate: 1 mL/min, Temperature: 25° C.; UV Detection: 230 nm Method 25:

HPLC apparatus type: Agilent 1100; column: Daicel chiralpack IA, 5.0 μm, 250 mm×4.6 mm; method: eluent hexane/IPA 85:15; flow rate: 1 mL/min, Temperature: 25° C.; UV Detection: 230 nm Microwave Heating:

Discover® CEM instruments, equipped with 10 and 35 mL vessels;

General Comment Concerning the Presentation of the Structures

Some active compounds have stereogenic center(s). The structures depicted in the experimental examples will not necessarily show all the possible stereochemical possibilities of said compounds but only one.

For $R^1$, only the relative configuration with respect to $R^2$ is known: their relative configuration is always syn.

The structural presentations of the compounds of the present inventions will not show a stereochemical bond with regard to the bond of the scaffold to $R^1$ but a plain one plus an additional comment, that indicates if the described compound is a mixture of diastereisomers, a mixture of enantiomers, a specific diastereomer or a specific enantiomer of which the absolute configuration at said $R^1$ bond is not determined. The position of R1 is the bridgehead position.

EXPERIMENTAL

Example 1a

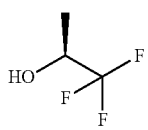

1,1,1-Trifluoroacetone (25 g, 216.419 mmol) in ethyl ether (20 mL) is added dropwise to (−)-beta-chlorodiisopinocampheylborane (81 g, 252.53 mmol) in ethyl ether (125 mL) cooled to −24° C. Stirring is continued at −24° C. for 5 d. 3-Phenyl propionaldehyde (35.4 mL, 259.7 mmol) is added dropwise and the reaction mixture is warmed to room temperature. After 24 h, the reaction mixture is cooled to 0° C. and 4N NaOH is added dropwise until pH>10. The reaction mixture is warmed to room temperature and stirred at that temperature for 30 min. $KH_2PO_4$, is added until pH=7/8. The layers are separated and the aqueous layer is extracted twice with ethyl ether. The combined organic layers are dried over $Na_2SO_4$ and distilled twice to obtain the title compound (b.p. 30-75° C., 18.3 g, content 65%, 48%).

Example 2a

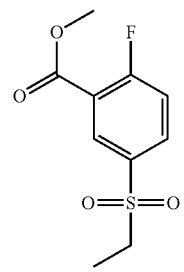 [SMILES: CCS(=O)(=O)c1ccc(F)c(C(=O)OC)c1]

Trimethylsilyldiazomethane in hexanes (2M, 2.153 mL, 4.3 mmol) is added dropwise to 5-(ethanesulfonyl)-2-fluorobenzoic acid (500 mg, 2.15 mmol) in DCM (5 mL) and MeOH (2.5 mL) cooled to 0° C. Stirring is continued for 120 min, then the reaction mixture is washed with saturated $NaHCO_3$. The organic layer is separated, dried and evaporated under reduced pressure to furnish the title compound (420 mg, 79%).

GC-MS (Method 8): $R_t$=11.36 min

MS (EI pos): m/z=246 $(M)^+$

Example 2b

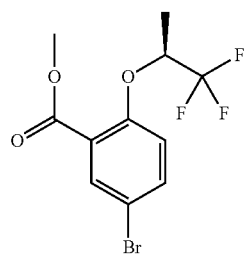 [SMILES: COC(=O)c1cc(Br)ccc1O[C@@H](C)C(F)(F)F]

Example 1a (1748 mg, 77% content, 11.80 mmol) is added to sodium hydride (60% suspension in mineral oil, 472 mg, 11.80 mmol) in THF (5 mL). Stirring is continued at room temperature for 45 min. Methyl 5-bromo-2-fluorobenzoate (1100 mg, 4.72 mmol) in THF (5 mL) is added and stirring is continued at room temperature overnight. Example 1a (65 mg, 75% content, 0.43 mmol) is added to sodium hydride (60% suspension in mineral oil, 17 mg, 0.43 mmol) in THF (1 mL) and the resulting mixture added to the reaction mixture and stirring is continued at room temperature overnight. The reaction mixture is diluted with DCM, washed with saturated $NH_4Cl$, dried and concentrated under reduced pressure giving a residue. Trimethylsilyldiazomethane in hexanes (2M, 2.153 mL, 4.3 mmol) is added dropwise to the residue in DCM (5 mL) and MeOH (2.5 mL) cooled to 0° C. Stirring is continued for 120 min, then the reaction mixture is evaporated under reduced pressure to furnish the title compound (200 mg, 50% content, 7%).

HPLC-MS (Method 2): $R_t$=1.38 min

MS (ESI pos): m/z=327 $(M+H)^+$

Example 3a

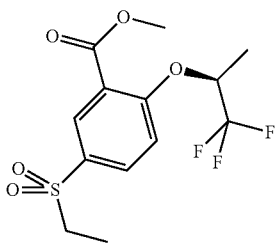 [SMILES: CCS(=O)(=O)c1ccc(O[C@@H](C)C(F)(F)F)c(C(=O)OC)c1]

Example 1a (278 mg, 75% content, 1.83 mmol) is added to sodium hydride (60% suspension in mineral oil, 62 mg, 1.54 mmol) in THF (1 mL). Stirring is continued at room temperature for 45 min. Example 2a (150 mg, 0.61 mmol) in THF (1 mL) is added and stirring is continued at room temperature overnight. Example 1a (65 mg, 75% content, 0.43 mmol) is added to sodium hydride (60% suspension in mineral oil, 17 mg, 0.43 mmol) in THF (1 mL) and the resulting mixture added to the reaction mixture and stirring is continued at room temperature overnight. Volatiles are evaporated under reduced pressure and the residue treated with DCM, washed with saturated $NH_4Cl$, dried with a phase separator cartridge, filtered and concentrated under reduced pressure giving a residue that is purified by flash chromatography (eluent 80-100% DCM/cyclohexane) to furnish the title compound (130 mg, 63%).

HPLC-MS (Method 6): $R_t$=11.04 min

MS (ESI posy: m/z=341 $(M+H)^+$

Example 3b

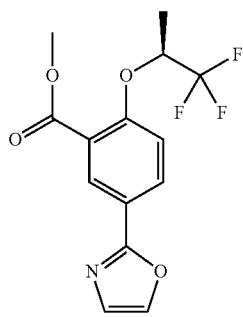 [SMILES: COC(=O)c1cc(-c2ncco2)ccc1O[C@@H](C)C(F)(F)F]

Example 2b (200 mg, 50% content, 0.31 mmol), 2-(tri-n-butylstannyl)-oxazole (806 µl, 3.82 mmol) and tetrakis(triphenylphosphine)palladium(0) (106 mg, 0.09 mmol) in toluene (4 mL) are degassed with a flow of nitrogen for 5 minutes and then heated to 130° C. in a microwave oven for 1 hour. Volatiles are evaporated under reduced pressure, the resulting residue redissolved in dichloromethane, washed with water, dried using a phase separator cartridge, and concentrated under reduced pressure. The resulting residue is purified by flash chromatography (eluent 20% ethyl acetate/cyclohexane) to furnish the title compound (30 mg, 31%).

HPLC-MS (Method 2): $R_t$=1.25 min

MS (ESI posy: m/z=316 $(M+H)^+$

| Examples | | Structure | Literature Reference |
|---|---|---|---|
| 4a | 5-Methanesulfonyl-2-((S)-2,2,2-trifluoro-1-methyl-ethoxy)-benzoic acid | 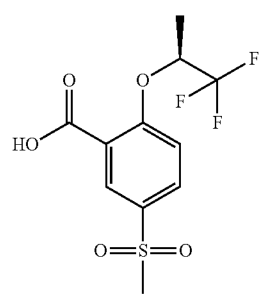 [SMILES: C[C@H](Oc1ccc(S(C)(=O)=O)cc1C(=O)O)C(F)(F)F] | WO2008/107334 (using example 1a) |
| 4b | 5-Methanesulfonyl-2-((R)-2,2,2-trifluoro-1-methyl-ethoxy)-benzoic acid | 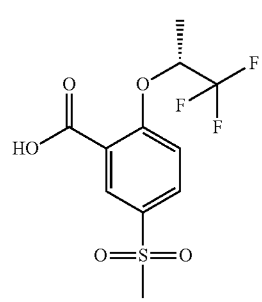 [SMILES: C[C@@H](Oc1ccc(S(C)(=O)=O)cc1C(=O)O)C(F)(F)F] | US2006/160788 [using (R)-1,1,1-trifluoro-propan-2-ol] |

| Examples | | Structure | Literature Reference |
|---|---|---|---|
| 4c | 5-Methanesulfonyl-2-(2,2,2-trifluoro-1-methyl-ethoxy)-benzoic acid | 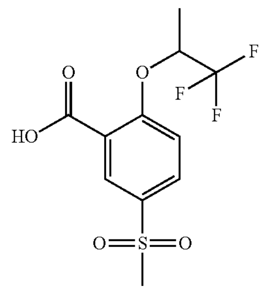 [SMILES: CC(Oc1ccc(S(C)(=O)=O)cc1C(=O)O)C(F)(F)F] | US2005/209241 |

Example 4d

Racemic Mixture

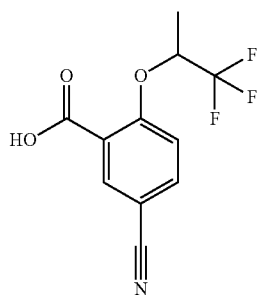 [SMILES: CC(Oc1ccc(C#N)cc1C(=O)O)C(F)(F)F]

Potassium tert-butoxide (0.666 g, 5.93 mmol) followed by 5-cyano-2-fluorobenzoic acid (700 mg, 4.24 mmol) are added portionwise to 1,1,1-trifluoro-2-propanol (0.594 mL, 6.36 mmol) in THF (15 mL). Stirring is continued for 3 h at room temperature followed by 1 h at reflux. The reaction mixture is diluted with THF (5 mL) and DMF (5 mL), and stirred at room temperature overnight. Potassium tert-butoxide (0.666 g, 5.93 mmol) is added to 1,1,1-trifluoro-2-propanol (0.594 mL, 6.36 mmol) in THF (5 mL) and the resulting mixture added to the reaction mixture dropwise. Stirring is continued for 6 h at 80° C. Volatiles are removed under reduced pressure and the resulting residue partitioned between 10% citric acid and DCM. The organic layer is separated, washed with brine and evaporated under reduced pressure to give a residue which is triturated with petroleum ether to furnish the title compound (0.95 g, 87%).

HPLC-MS (Method 7): $R_t$=6.41 min
MS (ESI posy): m/z=260 (M+H)$^+$

Example 4e

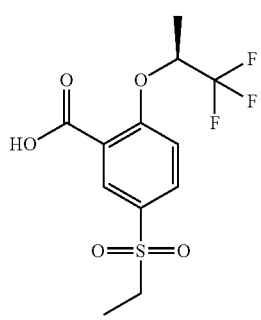 [SMILES: CCS(=O)(=O)c1ccc(O[C@@H](C)C(F)(F)F)c(C(=O)O)c1]

Lithium hydroxide monohydrate (48 mg, 1.15 mmol) is added to example 3a (130 mg, 0.38 mmol) in THF (5 mL) and water (5 mL). Stirring is continued at rt overnight, then the reaction mixture is diluted with EtOAc and water. The aqueous layer is separated and the organic layer extracted with 5% NaHCO$_3$. The combined aqueous layers are acidified to pH=3 with 1N HCl and extracted with EtOAc. The organic layer is separated, dried and evaporated under reduced pressure to furnish the title compound (112 mg, 90%).

HPLC-MS (Method 2): $R_t$=0.81 min
MS (ESI pos): m/z=327 (M+H)$^+$

Example 4f

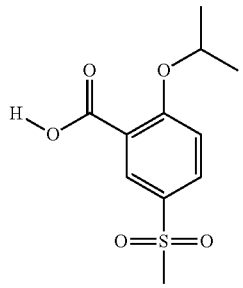 [SMILES: CC(C)Oc1ccc(S(C)(=O)=O)cc1C(=O)O]

Cesium carbonate (2.240 g, 6.87 mmol) is added to 2-fluoro-5-methanesulfonyl-benzoic acid (500 mg, 2.29 mmol) in 2-propanol (15 mL). Stirring is continued for 72 h at 80° C. Volatiles are removed under reduced pressure and the resulting residue partitioned between 4N HCl and DCM. The organic layer is separated, dried using a phase separator cartridge and evaporated under vacuum to furnish the title compound (0.60 g, 80% content, 81%).

HPLC-MS (Method 2): $R_t$=0.52 min
MS (ESI pos): m/z=259 (M+H)$^+$

Example 4g

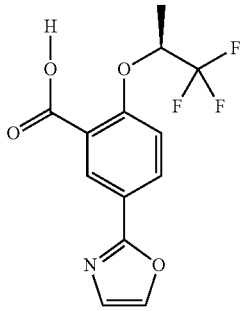 [SMILES: C[C@H](Oc1ccc(-c2ncco2)cc1C(=O)O)C(F)(F)F]

Potassium hydroxide (27 mg, 0.48 mmol) is added to example 3b (30 mg, 0.09 mmol) in EtOH (20 mL). The reaction mixture is acidified with 4N HCl and extracted with DCM.

The organic layer is separated and evaporated under reduced pressure to furnish the title compound (20 mg, 70%).

HPLC-MS (Method 2): $R_t$=0.88 min

MS (ESI neg): m/z=320 (M−H)⁻

The following examples are synthesized in analogy to the preparation of example 4d:

| Example | Structure | Reactant(s) | $R_t$ [min], method | MS (ESI pos, m/z) |
|---|---|---|---|---|
| 4h | 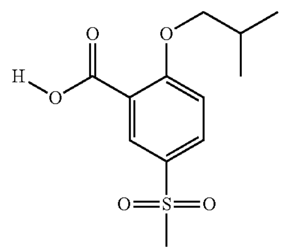 [SMILES: CC(C)COc1ccc(S(C)(=O)=O)cc1C(=O)O] | 2-methyl-1-propanol (326 µl, 3.53 mmol); 2-fluoro-5-methanesulfonyl-benzoic acid (700 mg, 3.21 mmol) | 9.27, method 6 | 273 (M + H)⁺ |
| 4i | 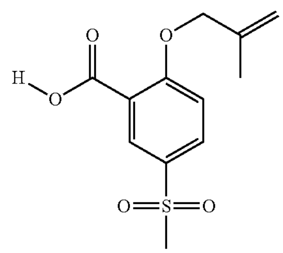 [SMILES: C=C(C)COc1ccc(S(C)(=O)=O)cc1C(=O)O] | 2-methyl-2-propen-1-ol (1283 µl, 15.12 mmol); 2-fluoro-5-methanesulfonyl-benzoic acid (3000 mg, 13.75 mmol) | 0.97, method 1 | 271 (M + H)⁺ |
| 4j | 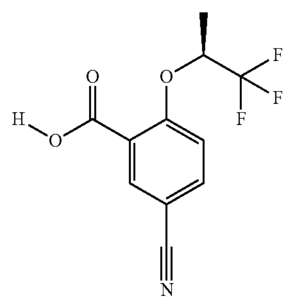 [SMILES: C[C@H](Oc1ccc(C#N)cc1C(=O)O)C(F)(F)F] | 1a (2.159 g, 64% content, 12.11 mmol); 5-cyano-2-fluorobenzoic acid (500 mg, 3.03 mmol) | 1.03, method 1 | 260 (M + H)⁺ |
| 4k | 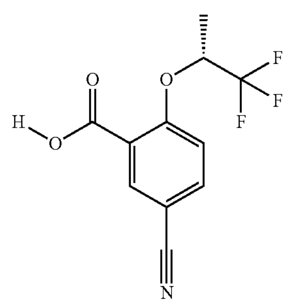 [SMILES: C[C@@H](Oc1ccc(C#N)cc1C(=O)O)C(F)(F)F] | (R)-1,1,1-trifluoro-propan-2-ol (1.842 g, 75% content, 12.11 mmol); 5-cyano-2-fluorobenzoic acid (500 mg, 3.03 mmol) | 1.04, method 1 | 260 (M + H)⁺ |
| 4l | 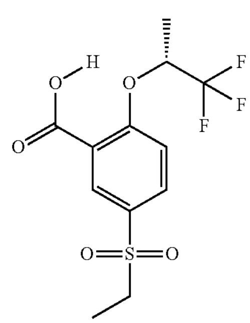 [SMILES: CCS(=O)(=O)c1ccc(O[C@H](C)C(F)(F)F)c(C(=O)O)c1] | (R)-1,1,1-trifluoro-propan-2-ol, (216 mg, 75% content, 1.42 mmol); 5-(ethanesulfonyl)-2-fluorobenzoic acid (300 mg, 1.29 mmol) | 1.00, method 1 | 326 (M + H)⁺ |

-continued

| Example | Structure | Reactant(s) | R$_t$ [min], method | MS (ESI pos, m/z) |
|---|---|---|---|---|
| 4m | 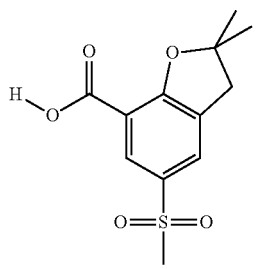 | 2-Fluoro-5-methanesulfonyl-benzoic acid (350 mg, 1.60 mmol); (R)-(−)-3-hydroxytetrahydro-furan (145 µL, 1.76 mmol) | 6.91, method 6 | 287 (M + H)$^+$ |

Example 4n

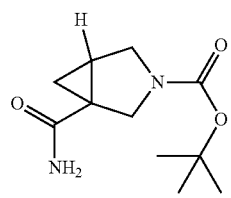 [SMILES: CC(C)(C)OC(=O)N1CC2CC2(C(N)=O)C1]

Example 4i (500 mg, 1.85 mmol) is heated in NMP for 3 h at 175° C. followed by 3 h at 210° C. The reaction mixture is cooled to room temperature and diluted with aq. NH$_4$Cl and DCM. The organic layer is separated and extracted with 1N NaOH. The aqueous layer is acidified with 1N HCl and extracted with DCM. The resulting organic layer is separated, The organic layer is separated, dried and evaporated under reduced pressure to furnish a residue that is purified by preparative HPLC (stationary phase: Sunfire C18 ODB 5 µm 19×100 mm. Mobile phase: ACN/H$_2$O+NH$_4$COOH 5 mmol). Fractions containing the title compound are combined and freeze dried to furnish the title compound (120 mg, 24%).

HPLC-MS (Method 1): R$_t$=0.95 min
MS (ESI pos): m/z=271 (M+H)$^+$

Example 5a

Racemic Mixture

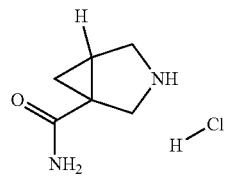

To a solution of racemic 3-azabicyclo[3.1.0]hexane-1,3-dicarboxylic acid-3-tert-butyl ester (600 mg, 2.64 mmol) in dry THF (12 mL), CDI (471 mg, 2.90 mmol) is added. Mixture is stirred at room temperature for 1.5 h, then ammonium hydroxide (6 mL of a 30% solution in water) is added and the mixture stirred for additional 15 min. Solvents are evaporated, crude dissolved in EtOAc, washed with 0.1 N hydrochloric acid, sat. NaHCO$_3$ and brine. Organic phases are separated, dried and evaporated under vacuum to obtain the title compound (505 mg, 85%) used in the next step without any further purification.

HPLC-MS (Method 5): R$_t$=6.43 min
MS (APCI): m/z=127 (M−tBuOCO+H)$^+$

Example 6a

Racemic Mixture

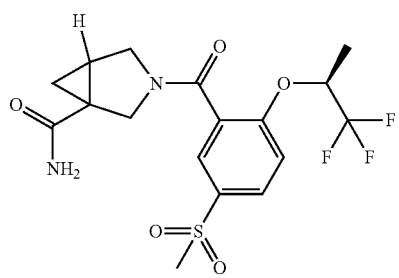 [SMILES: C[C@H](Oc1ccc(S(C)(=O)=O)cc1C(=O)N1CC2CC2(C(N)=O)C1)C(F)(F)F]

Example 5a (505 mg, 2.23 mmol) is dissolved in 14.4 mL of hydrochloric acid (4M solution in dioxane) cooled to 0° C. Stirring is continued for 2 h at rt. Solvent is removed under vacuum to obtain the title compound (260 mg, 72%) used in the next step without any further purification.

HPLC-MS (Method 5): R$_t$=1.74 min
MS (APCI): m/z=127 (M+H)$^+$

Example 7a

Diastereomeric Mixture

To a solution of example 6a (210 mg, 1.29 mmol) in dry DCM (12 mL), HATU (638 mg, 1.68 mmol) and dry TEA (0.540 mL, 3.874 mmol) are added. Mixture is stirred at room temperature for 10 min, then example 4a (403 mg, 1.29 mmol) is added and the mixture stirred at room temperature for additional 2 h. 0.1 N hydrochloric acid and DCM are added, organic phase is separated, washed with brine, dried using a phase separator cartridge and evaporated under vacuum. The crude is purified by flash cromatography (eluent 0-5% MeOH/DCM) to obtain the title compound as a white solid (370 mg, 68%)

HPLC-MS (Method 2): $R_t$=0.72 min
MS (ESI pos): m/z=421 (M+H)$^+$

Example 7b

Diastereomeric Mixture

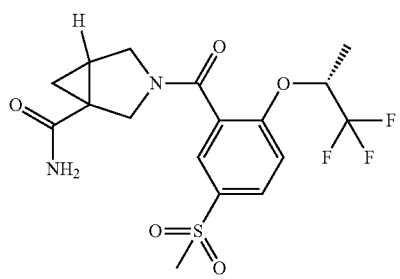 [SMILES: C[C@@H](Oc1ccc(S(C)(=O)=O)cc1C(=O)N1CC2CC2(C(N)=O)C1)C(F)(F)F]

The title compound is prepared as described for example 7a, using example 4b (90 mg, 0.29 mmol).
HPLC-MS (Method 2): $R_t$=0.69 min
MS (ESI pos): m/z=421 (M+H)$^+$ Example 8a Diastereomeric Mixture

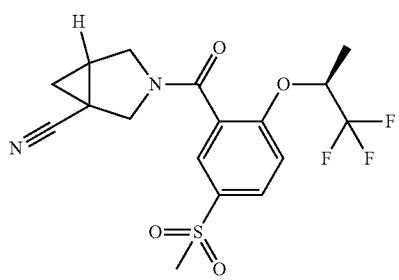 [SMILES: C[C@H](Oc1ccc(S(C)(=O)=O)cc1C(=O)N1CC2CC2(C#N)C1)C(F)(F)F]

To a solution of example 7a (370 mg, 0.88 mmol) in dry DCM (12 mL), Burgess reagent (294 mg, 1.23 mmol) is added and the mixture stirred at 35° C. for 3 h. Burgess reagent (50 mg, 0.21 mmol) is added and the mixture stirred at 35° C. for 2 h. A diluted solution of HCl (0.2 M) is added, organics separated, washed with brine, dried using a phase separator cartridge and evaporated under vacuum. The crude is purified by flash cromatography (eluent 50-70% AcOEt/cyclohexane) to obtain the title compound (253 mg, 71%)

HPLC-MS (Method 6): $R_t$=9.72 min
MS (ESI pos): m/z=403 (M+H)$^+$

Example 8b

Diastereomeric Mixture

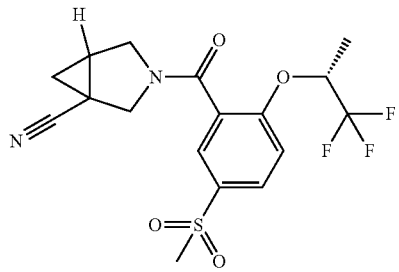 [SMILES: C[C@@H](Oc1ccc(S(C)(=O)=O)cc1C(=O)N1CC2CC2(C#N)C1)C(F)(F)F]

The title compound is prepared as described above for example 8a, starting from example 7b (82 mg, 0.19 mmol).
HPLC-MS (Method 2): $R_t$=0.91 min
MS (ESI pos): m/z=403 (M+H)$^+$ Example 9a Diastereomeric Mixture

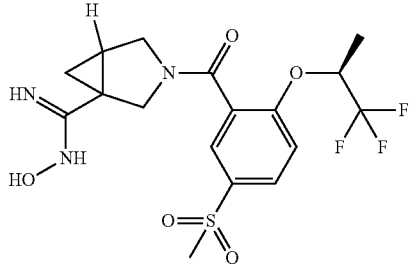 [SMILES: C[C@H](Oc1ccc(S(C)(=O)=O)cc1C(=O)N1CC2CC2(C(=N)NO)C1)C(F)(F)F]

To a solution of example 8a (0.16 g, 0.4 mmol) in EtOH (3 mL), hydroxylamine (49 μl of a 50% solution in water, 0.79 mmol) is added and the mixture stirred under microwave irradation for 30 min at 100° C. After evaporation of the solvent, the title compound (0.17 g, 98%) is used in the next step without any further purification.
HPLC-MS (Method 2): $R_t$=0.73 min
MS (ESI pos): m/z=436 (M+H)$^+$ Example 9b Diastereomeric Mixture

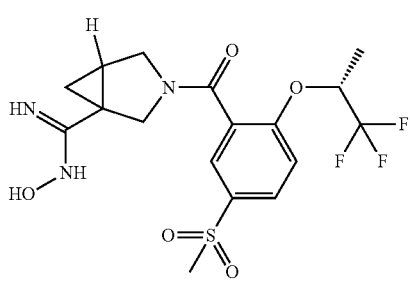 [SMILES: C[C@@H](Oc1ccc(S(C)(=O)=O)cc1C(=O)N1CC2CC2(C(=N)NO)C1)C(F)(F)F]

The title compound is prepared as described above for example 9a using example 8h (60 mg, 0.15 mmol).

HPLC-MS (Method 1): $R_t$=0.73 min
MS (ESI pos): m/z=436 (M+H)$^+$

Example 10a

Diastereomeric Mixture

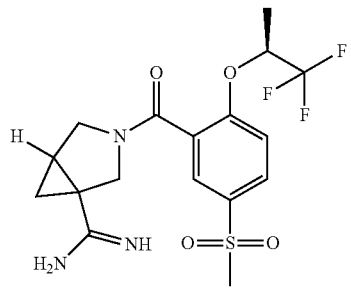 [SMILES: C[C@H](Oc1ccc(S(C)(=O)=O)cc1C(=O)N1CC2CC2(C(=N)N)C1)C(F)(F)F]

Acetyl chloride (1.082 mL, 14.91 mmol) is added to EtOH (1.5 mL) and chloroform (2.0 mL) cooled to 0° C. After 20 min a solution of example 8a (200 mg, 0.49 mmol) in chloroform (2.0 mL) is added and the mixture warmed to room temperature overnight. Volatiles are evaporated under reduced pressure and ammonia solution (7N in MeOH, 2.13 mL, 14.91 mmol) is added to resulting residue redissolved in EtOH (2.0 mL). The reaction mixture is warmed to room temperature and stirring continued overnight. After evaporation of the solvent, the title compound (208 mg, 100%) is used in the next step without any further purification.

HPLC-MS (Method 2): $R_t$=0.87 min
MS (ESI pos): m/z=420 (M+H)$^+$

Example 10b

Diastereomeric Mixture

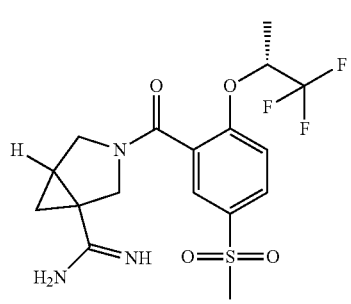 [SMILES: C[C@@H](Oc1ccc(S(C)(=O)=O)cc1C(=O)N1CC2CC2(C(=N)N)C1)C(F)(F)F]

Example 10b is prepared as described for example 10a using example 8b (145 mg, 0.36 mmol).

HPLC-MS (Method 2): $R_t$=0.85 min
MS (ESI pos): m/z=420 (M+H)$^+$

Example 11a

Racemic Mixture

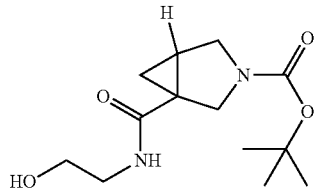 [SMILES: CC(C)(C)OC(=O)N1CC2CC2(C(=O)NCCO)C1]

To a solution of racemic 3-azabicyclo[3.1.0]hexane-1,3-dicarboxylic acid-3-tert-butyl ester (0.1 g, 0.44 mmol) in dry DMF (3 mL), TBTU (0.17 g, 0.52 mmol) and dry TEA (0.079 mL, 0.57 mmol) are added. Mixture is stirred at room temperature for 1 h, then ethanolamine (0.03 mL, 0.48 mmol) is added and the mixture stirred for additional 30 min. Solvents are evaporated, crude dissolved in EtOAc, washed with a saturated solution of sodium bicarbonate and brine. Organic phases are separated, dried and evaporated under vacuum to obtain the title compound (55 mg) used in the next step without any further purification.

HPLC-MS (Method 1): $R_t$=6.34 min
MS (ESI pos): m/z=269 (M+H–tBu)$^+$

Example 11b

Diastereomeric Mixture

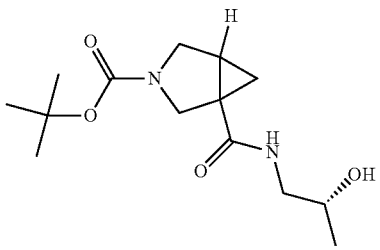 [SMILES: C[C@@H](O)CNC(=O)C12CC1CN(C(=O)OC(C)(C)C)C2]

Example 11 b is prepared as described for example 11a, using racemic 3-azabicyclo[3.1.0]hexane-1,3-dicarboxylic acid-3-tert-butyl ester (200 mg, 0.88 mmol) and (R)-(–)-1-amino-2-propanol (73 mg, 0.968 mmol).

HPLC-MS (Method 2): $R_t$=0.77 min
MS (ESI pos): m/z=285 (M+H)$^+$

Example 12a

Racemic Mixture

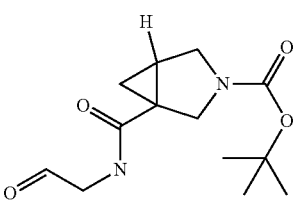 [SMILES: CC(C)(C)OC(=O)N1CC2CC2(C(=O)NCC=O)C1]

To a solution of example 11a (55 mg) in dry DCM (2 mL) Dess-Martin periodinane (0.95 g) is added and the mixture stirred at room temperature for 1 h. A saturated solution of NaHCO$_3$ is added, mixture is diluted with DCM, organic phases are separated, dried and evaporated under vacuum to obtain the title compound (53 mg) used in the next step without any further purification.

HPLC-MS (Method 2): R$_t$=0.72 min
MS (ESI pos): m/z=269 (M+H)$^+$

Example 12b

Racemic Mixture

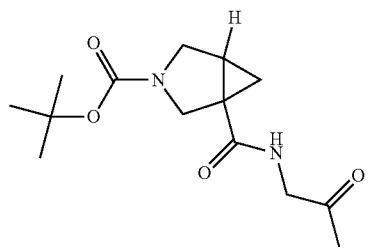 [SMILES: CC(=O)CNC(=O)C12CC1CN(C(=O)OC(C)(C)C)C2]

Example 12b is prepared as described for example 12a using example 11b (224 mg, 80% content, 0.630 mmol).

HPLC-MS (Method 2): R$_t$=0.83 min
MS (ESI pos): m/z=283 (M+H)$^+$

Example 13a

Racemic Mixture

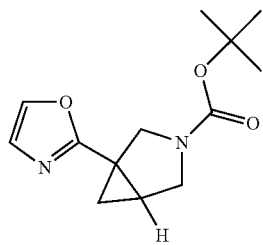 [SMILES: CC(C)(C)OC(=O)N1CC2CC2(c2ncco2)C1]

To a solution of example 12a (0.053 g) in dry THF (0.5 mL) Burgess reagent (0.05 g, 0.24 mmol) is added. Mixture is heated under microwave irradation for 1 min at 110° C. Burgess reagent (0.024 g, 0.10 mmol) is added. Mixture is heated under microwave irradation for 1 min at 110° C. Solvent is evaporated, crude dissolved in DCM, organics washed with water and brine, dried and evaporated under vacuum. The crude is purified by flash cromatography (cyclohexane/EtOAc from 50:50 to 0:100) to obtain the title compound (0.015 g, purity 50%).

HPLC-MS (Method 2): R$_t$=1.05 min
MS (ESI pos): m/z=195 (M−tBu+H)$^+$

Example 13b

Racemic Mixture

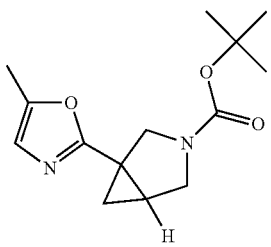 [SMILES: Cc1cnc(C23CC2CN(C(=O)OC(C)(C)C)C3)o1]

Example 13b is prepared as described for example 13a using example 12b (176 mg).

HPLC-MS (Method 6): R$_t$=10.91 min
MS (ESI pos): m/z=265 (M+H)$^+$

Example 14a

Racemic Mixture

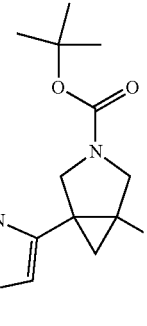

DMF (1 drop) and oxalyl chloride (82 µl, 0.97 mmol) are added to a solution of racemic 3-azabicyclo[3.1.0]hexane-1,3-dicarboxylic acid-3-tert-butyl ester (200 mg, 0.88 mmol) in THF (2.5 mL) cooled to 0° C. After stirring for 2 h at 0° C., ACN (2.5 mL) and trimethylsilyldiazomethane in hexanes (2M, 880 µl, 1.76 mmol) are added and the reaction mixture stirred at 0° C. for 2 h. Hydrochloric acid in dioxane (4M, 440 µl, 1.76 mmol) is added and the reaction mixture warmed to room temperature. After stirring for 15 min at room temperature, the reaction mixture is diluted with EtOAc and washed with saturated NaHCO$_3$ and brine, dried over Na$_2$SO$_4$. After evaporation of the solvent, the resulting residue is dissovled in DME (2.5 mL) and 2-aminopyridine (145 mg, 1.54 mmol) is added. The reaction mixture is heated at 90° C. for 2 h and volatiles are evaporated under reduced pressure. The resulting residue is redissolved in DCM, washed twice with water and brine and dried over Na$_2$SO$_4$. After evaporation of the solvent, the title compound (172 mg, 65%) is used in the next step without any further purification.

HPLC-MS (Method 2): R$_t$=1.03 min
MS (ESI pos): m/z=300 (M+H)$^+$

Example 14b

Racemic Mixture

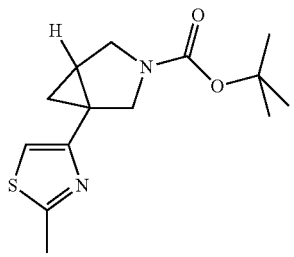 [SMILES: Cc1nc(C23CC2CN(C(=O)OC(C)(C)C)C3)cs1]

DMF (1 drop) and oxalyl chloride (41 μl, 0.48 mmol) are added to a solution of racemic 3-azabicyclo[3.1.0]hexane-1,3-dicarboxylic acid-3-tert-butyl ester (100 mg, 0.44 mmol) in THF (1.25 mL) cooled to 0° C. After stirring for 2 h at 0° C., ACN (1.25 mL) and trimethylsilyldiazomethane in hexanes (2M, 440 μl, 0.88 mmol) are added and the reaction mixture stirred at 0° C. for 2 h. Hydrochloric acid in dioxane (4M, 220 μl, 0.88 mmol) is added and the reaction mixture warmed to room temperature. After stirring for 15 min at room temperature, the reaction mixture is diluted with EtOAc and washed with saturated NaHCO$_3$ and brine, dried over Na$_2$SO$_4$. After evaporation of the solvent, the resulting residue is dissolved in absolute EtOH (2 mL) and thioacetamide (52 mg, 0.69 mmol) is added. Mixture stirred at room temperature overnight. Solvent evaporated, crude purified by flash cromatography (0-50% EtOAc:cyclohexane) to obtain 0.044 g of the title compound.

HPLC-MS (Method 6): R$_t$=11.50 min
MS (ESI pos): m/z=281 (M+H)$^+$

Example 14c

Racemic Mixture

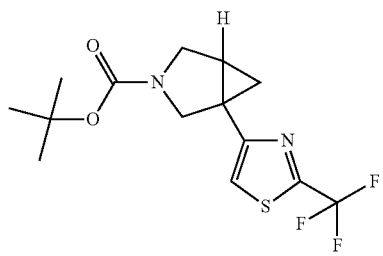 [SMILES: CC(C)(C)OC(=O)N1CC2CC2(c2csc(C(F)(F)F)n2)C1]

Oxalyl chloride (410 μl, 4.84 mmol) and a drop of DMF are added to racemic 3-azabicyclo[3.1.0]hexane-1,3-dicarboxylic acid-3-tert-butyl ester (1000 mg, 4.40 mmol) in DCM (12 mL) cooled to 0° C. After stirring at that temperature for 2 h, ACN (12 mL) followed by trimethylsilyldiazomethane in hexanes (2M, 4.4 mL, 8.80 mmol) are added dropwise. The reaction mixture is stirred at 0° C. for 2 h and then at room temperature overnight. The reaction mixture is then cooled to 0° C., hydrobromic acid (48%, 989 μl, 8.80 mmol) is added dropwise and stirring is continued at rt for 10 min. Solid NaHCO$_3$ is added until basic pH and stirring is continued for 5 min. The reaction mixture is diluted with EtOAc, washed with water and saturated NaHCO$_3$, brine, dried over Na$_2$SO$_4$ and evaporated under reduced pressure to obtain a residue, 980 mg. 200 mg of such residue are mixed with 2,2,2-trifluoroethanethioamide (170 mg, 1.31 mmol) in EtOH (1 mL) and heated at 70° C. overnight. Volatiles are evaporated under reduced pressure and the resulting residue purified by flash chromatography (eluent 10% EtOAc/cyclohexane) to furnish the title compound (146 mg, 49%).

HPLC-MS (Method 2): R$_t$=1.48 min
MS (ESI pos): m/z=279 (M−tBu+H)$^+$

Example 14d

Racemic Mixture

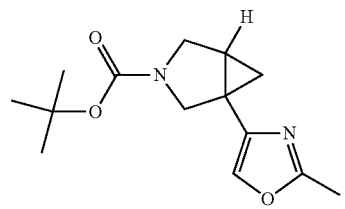 [SMILES: Cc1nc(C23CC2CN(C(=O)OC(C)(C)C)C3)co1]

DMF (1 drop) and oxalyl chloride (410 μl, 4.84 mmol) are added to a solution of racemic 3-azabicyclo[3.1.0]hexane-1,3-dicarboxylic acid-3-tert-butyl ester (1000 mg, 4.40 mmol) in THF (12.5 mL) cooled to 0° C. After stirring for 2 h at 0° C., ACN (12.5 mL) and trimethylsilyldiazomethane in hexanes (2M, 4.4 mL, 8.80 mmol) are added. After stirring for 2 h at 0° C., hydrochloric acid in dioxane (4M, 2.2 mL, 8.80 mmol) is added and the reaction mixture warmed to room temperature. After stirring for 15 min at room temperature, the reaction mixture is diluted with EtOAc and washed with saturated NaHCO$_3$ and brine, dried over Na$_2$SO$_4$. 200 mg out of the 1200 mg obtained after evaporation of the solvent are dissolved in NMP (4 mL) and acetamide (80 mg, 1.35 mmol) is added. The reaction mixture stirred at 100° C. for 34 h and then diluted with EtOAc, washed with water, brine, dried over Na$_2$SO$_4$, filtered and concentrated under reduced pressure giving a residue that is purified by flash chromatography (eluent 0-30% EtOAc/cyclohexane) to furnish the title compound (9 mg, 13%).

HPLC-MS (Method 5): R$_t$=9.02 min
MS (APCI): m/z=165 (M−CO$_2$tBu+H)$^+$

Example 14e

Racemic Mixture

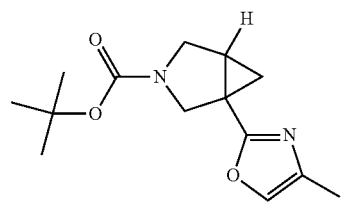 [SMILES: Cc1coc(C23CC2CN(C(=O)OC(C)(C)C)C3)n1]

Example 5a (100 mg, 0.442 mmol) and chloroacetone (106 μl, 1.32 mmol) in EtOH (2 mL) are stirred at 70° C. for 2.5 d. Volatiles are evaporated under reduced pressure to furnish the title compound that is used as such (70 mg, 44% content, 27%).

HPLC-MS (Method 2): R$_t$=1.22 min
MS (ESI pos): m/z=209 (M–tBu+H)$^+$

Example 14f

Racemic Mixture

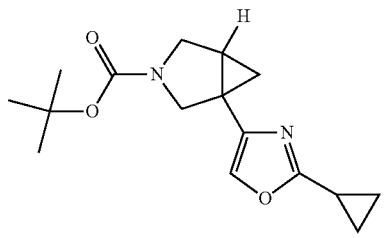 [SMILES: CC(C)(C)OC(=O)N1CC2CC2(c2coc(C3CC3)n2)C1]

DMF (1 drop) and oxalyl chloride (696 µl, 8.23 mmol) are added to a solution of racemic 3-azabicyclo[3.1.0]hexane-1,3-dicarboxylic acid-3-tert-butyl ester (1700 mg, 7.48 mmol) in DCM (20 mL) cooled to 0° C. After stirring for 2 h at 0° C., ACN (20 mL) and trimethylsilyldiazomethane in hexanes (2M, 7.5 mL, 14.96 mmol) are added. After stirring for 2 h at 0° C. and overnight at room temperature, hydrobromic acid (1.7 mL, 48%, 14.96 mmol) is added and the reaction mixture warmed to room temperature. After stirring for 20 min at room temperature, the reaction mixture is diluted with EtOAc and washed with saturated NaHCO$_3$ and brine, dried over Na$_2$SO$_4$. The residue obtained after evaporation of volatiles, 1370 mg, is split in two equal aliquots and each of them dissolved in EtOH (3 mL) and cyclopropanecarboxamide (372 mg, 4.37 mmol) is added. The reaction mixture stirred at 70° C. for 32 h and then diluted with EtOAc, washed with saturated NaHCO$_3$, brine, dried using a phase separator cartridge and concentrated under reduced pressure giving a residue that is purified by flash chromatography (eluent 0-25% EtOAc/cyclohexane) to furnish the title compound (163 mg, 13%).

HPLC-MS (Method 2): R$_t$=1.20 min
MS (ESI pos): m/z=291 (M+H)$^+$

Example 14g

Racemic Mixture

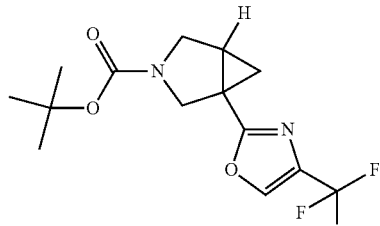

Example 5a (980 mg, 4.33 mmol) and 3-bromo-1,1,1-trifluoroacetone (1.38 ml, 13.00 mmol) in anhydrous dioxan (10 mL) are stirred at 100° C. for 3 hours and volatiles are evaporated under reduced pressure. The residue is dissolved in anhydrous DCM (5 ml), cooled at 0° C., a solution of methansulfonylchloride (0.50 ml, 6.50 mmol) in 1 ml of anhydrous DCM is added and the reaction mixture is then stirred overnight at room temperature then purified by Si flash chromatography (eluent 5-10% EtOAc/cyclohexane) to furnish the title compound (515 mg, content 95%, 35%).

GC-MS (Method 8): R$_t$=10.59 min
MS (ESI pos): m/z=318 (M)$^+$

Example 15a

Racemic Mixture

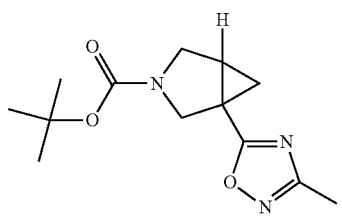 [SMILES: Cc1noc(C23CC2CN(C(=O)OC(C)(C)C)C3)n1]

Racemic 3-azabicyclo[3.1.0]hexane-1,3-dicarboxylic acid-3-tert-butyl ester (200 mg, 0.88 mmol) and CDI (214 mg, 1.320 mmol) in DMF (5 mL) are stirred at rt for 45 min; N-hydroxyacetamidine (93 mg, 1.258 mmol) is then added to the reaction mixture and stirring is continued over weekend. The reaction mixture is then heated under microwave irradation (100° C.) for 20 min. Volatiles are evaporated under reduced pressure and the resulting residue partitioned between EtOAc and water. The organic layer is separated, washed with brine, dried using a phase separator cartridge and concentrated under reduced pressure to give a residue that is purified by flash chromatography (eluent 0-30% EtOAc/petroleum ether) to furnish the title compound (169 mg, 72%).

HPLC-MS (Method 5): R$_t$=8.51 min
MS (APCI): m/z=166 (M–CO$_2$tBu+H)$^+$

Example 15b

Racemic Mixture

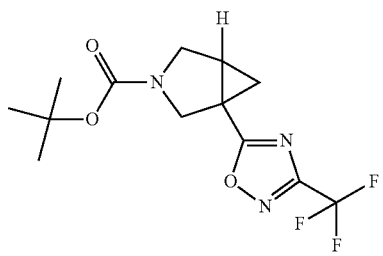 [SMILES: CC(C)(C)OC(=O)N1CC2CC2(c2nc(C(F)(F)F)no2)C1]

Racemic 3-azabicyclo[3.1.0]hexane-1,3-dicarboxylic acid-3-tert-butyl ester (200 mg, 0.88 mmol) and CDI (214 mg, 1.32 mmol) in DMF (5 mL) are stirred at room temperature for 45 min. 2,2,2-Trifluoro-N'-hydroxy-acetamidine (161 mg, 1.26 mmol) is then added and the reaction mixture stirred at room temperature overnight and then heated to 110° C. in a microwave oven for 4 hours and 40 min. Volatiles are removed under reduced pressure and the residue redissolved in EtOAc, washed with water and brine. The organic layer is then concentrated under reduced pressure and the resulting residue purified by flash chromatography (eluent 0-30% EtOAc/cyclohexane) to furnish the title compound (202 mg, 72%).

HPLC-MS (Method 5): $R_t$=10.28 min
MS (APCI): m/z=220 (M–CO$_2$tBu+H)$^+$

Example 15c

Racemic Mixture

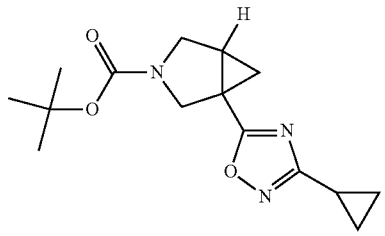 [SMILES: CC(C)(C)OC(=O)N1CC2CC2(c2nc(C3CC3)no2)C1]

The title compound is prepared in analogy to example 15b starting from N'-Hydroxycyclopropanecarboximidamide (207.3 mg, 1.76 mmol) in place of 2,2,2-Trifluoro-N'-hydroxy-acetamidine and heating, after the intermediate formation, into a microwave oven at 110° C. for 2 hours to obtain 150 mg of product (58%)
HPLC-MS (Method 7): $R_t$=7.78 min
MS (ESI pos): m/z=236 (M–tBu+H)$^+$ Example 15d Racemic Mixture

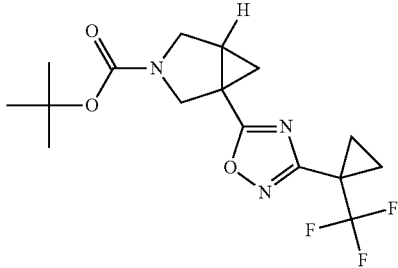 [SMILES: CC(C)(C)OC(=O)N1CC2CC2(c2nc(C3(C(F)(F)F)CC3)no2)C1]

1,1-carbonyldiimidazole (1.26 g, 7.79 mmol) is added to a solution of 1-trifluoromethylcyclopropane-1-carboxylic acid (1.00 g, 6.49 mmol) in 10 ml of anhydrous ACN and stirred at room temperature for 2 hours. 30% aqueous ammonium hydroxide solution (6 ml, 46.22 mmol) is added and the reaction mixture is stirred overnight. EtOAc and brine are added, organic layer is separated, washed with 1N aqueous HCl solution, dried over Na$_2$SO$_4$ and concentrated under reduced pressure to obtain 0.81 g of primary amide. 400 mg of this amide are dissolved, under nitrogen atmosphere, in 5 ml of THF, trifluoroacetic anhydride (1.82 ml, 13.06 mmol) is added and the reaction mixture is heated overnight at 60° C.; after cooling to room temperature potassium carbonate (3.25 g, 23.51 mmol), hydroxylamine hydrochloride (556 mg, 7.84 mmol) and MeOH (30 ml) are added and the reaction mixture is heated at 65° C. and stirred overnight.
The cooled mixture is filtered and concentrated under reduced pressure, the residue is suspended in EtOH and stirred cooling with an ice-water bath. A precipitate is filtered out over a celite pad then the filtrate is concentrated under reduced pressure. The obtained residue is added, after 1 h hour stirring, to a solution of racemic 3-azabicyclo[3.1.0] hexane1,3-dicarboxylic acid-3-tert-butyl ester (227 mg, 1.00 mmol) and 1,1-carbonyldiimidazole (176 mg, 1.08 mmol) in DMF (2 ml) and the reaction mixture is stirred overnight at room temperature then heated under microwave irradation (110° C.) for 30 minutes. Solvent is concentrated under reduced pressure, residue is partitioned between DCM and 10% aqueous citric acid solution, organic layer is separated, washed with saturated aqueous NaHCO$_3$ solution and brine then concentrated under reduced pressure to obtain the title compound (240 mg, 51%).
HPLC-MS (Method 2): $R_t$=1.39 min
MS (ESI pos): m/z=377 (M+NH$_4$)$^+$ Example 16a Racemic Mixture

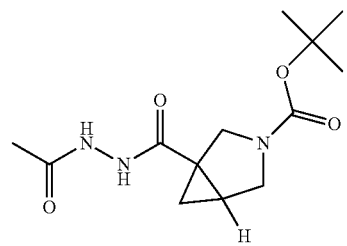 [SMILES: CC(=O)NNC(=O)C12CC1CN(C(=O)OC(C)(C)C)C2]

Racemic 3-azabicyclo[3.1.0]hexane-1,3-dicarboxylic acid-3-tert-butyl ester (300 mg, 1.32 mmol), TBTU (636 mg, 1.980 mmol) and DIPEA (1.15 mL, 6.60 mmol) in DMF (4 mL) are stirred at rt for 10 min; acetic hydrazide (196 mg, 2.64 mmol) is then added to the reaction mixture and stirring is continued for 4 h. Volatiles are evaporated under reduced pressure and the resulting residue partitioned between EtOAc and saturated NaHCO$_3$. The organic layer is separated, washed with 10% citric acid and brine, dried over Na$_2$SO$_4$ and concentrated under reduced pressure to give a residue that is purified by flash chromatography (eluent 0-5% MeOH/DCM) to furnish the title compound (72 mg, 19%).
HPLC-MS (Method 5): $R_t$=5.97 min
MS (APCI): m/z=184 (M–CO$_2$tBu+H)$^+$ Example 17a Racemic Mixture

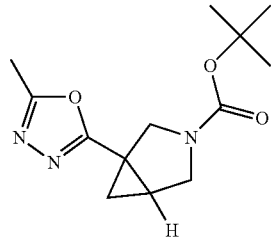 [SMILES: Cc1nnc(C23CC2CN(C(=O)OC(C)(C)C)C3)o1]

Burgess reagent (335 mg, 1.40 mmol) is added to example 16a (100 mg, 0.35 mmol) in 1,2-dichlomethane (2.5 mL) and the reaction mixture is then heated under microwave irradiation (120° C.) for 20 min. Volatiles are evaporated under reduced pressure and the resulting residue partitioned between EtOAc and water. The organic layer is separated, washed with brine, dried over Na₂SO₄ and concentrated under reduced pressure to give a residue that is purified by flash chromatography (eluent 20-50% EtOAc/cyclohexane) to furnish the title compound (77 mg).

HPLC-MS (Method 5): $R_t$=7.86 min
MS (APCI): m/z=266 (M+H)⁺

Example 18a

Racemic Mixture

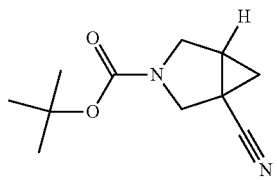

Burgess reagent (2.890 g, 12.13 mmol) is added to example 5a (1.960 g, 90% content, 7.79 mmol) in DCM (28 mL) and the reaction mixture is stirred at 35° C. for 3 h. The reaction mixture is diluted with DCM, washed with 0.N HCl and brine, dried using a phase separator cartridge. The organic layer is then concentrated under reduced pressure and the resulting residue purified by flash chromatography (eluent 0-20% EtOAc/cyclohexane) to furnish the title compound (1.590 g, 98%).

HPLC-MS (Method 2): $R_t$=1.09 min
MS (ESI pos): m/z=209 (M+H)⁺

The enantiomers of the title compound are separated by HPLC using a chiral stationary phase.

Method for Separation:

HPLC apparatus type: Agilent 1100; column: Daicel chiralpack AD-H, 5.0 μm, 250 mm×20 mm; method: eluent hexane/IPA 95:5; flow rate: 15 mL/min, Temperature: 25° C.; UV Detection: 210 nm

| Example | structure | Chiral HPLC $R_t$ [min] |
|---|---|---|
| Exp. 18b Enantiomer 1 Unknown absolute stereochemistry at bridgehead | 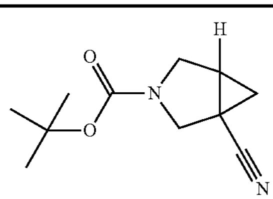 | 6.353 (Method 16) |
| Exp. 18c Enantiomer 2 Unknown absolute stereochemistry at bridgehead | 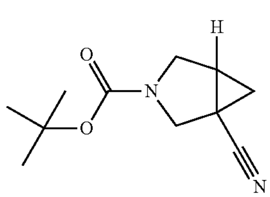 | 7.199 (Method 16) |

Example 19a

Racemic Mixture

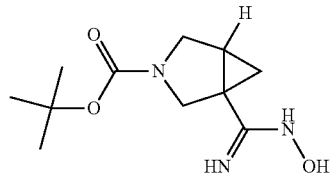 [SMILES: CC(C)(C)OC(=O)N1CC2CC2(C(=N)NO)C1]

To a solution of example 18a (300 mg, 1.44 mmol) in EtOH (2 mL), hydroxylamine (177 μl, 50% solution in water, 2.88 mmol) is added and the mixture stirred under microwave irradation for 30 min at 100° C. After evaporation of the solvent, the title compound (340 mg, 98%) is used in the next step without any further purification.

HPLC-MS (Method 2): $R_t$=0.90 min
MS (ESI pos): m/z=242 (M+H)⁺

Example 19b

Single Enantiomer, Unknown Absolute Stereochemistry at Bridgehead

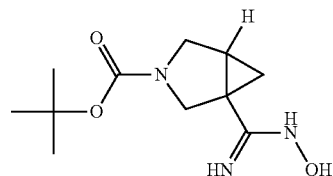 [SMILES: CC(C)(C)OC(=O)N1CC2CC2(C(=N)NO)C1]

The title compound is prepared as described for example 19a, starting from example 18b (45 mg, 0.21 mmol).

HPLC-MS (Method 2): $R_t$=0.92 min
MS (ESI pos): m/z=242 (M+H)⁺

Example 19c

Single Enantiomer, Unknown Absolute Stereochemistry at Bridgehead

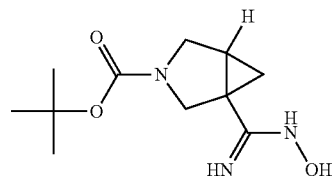 [SMILES: CC(C)(C)OC(=O)N1CC2CC2(C(=N)NO)C1]

The title compound is prepared as described for example 19a, starting from example 18c (45 mg, 0.21 mmol).

HPLC-MS (Method 2): $R_t$=0.95 min
MS (ESI pos): m/z=242 (M+H)⁺

Example 20a

Racemic Mixture

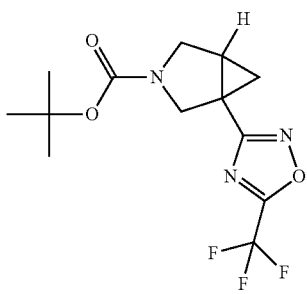 [SMILES: CC(C)(C)OC(=O)N1CC2CC2(c2noc(C(F)(F)F)n2)C1]

Example 19a (1.160 g, 4.81 mmol), is dissolved in ACN (10 mL) in a microwave vessel and trifluoroacetic anhydride (2.005 mL, 14.42 mmol) and dry TEA (2.680 mL, 19.23 mmol) are added. The reaction mixture is heated under microwave irradation for two cycles at 100° C. for 30 min. Volatiles are evaporated under reduced pressure and the residue purified by flash chromatography (eluent 7-60% EtOAc/cyclohexane) to furnish the title compound (1.000 g, 65%).

HPLC-MS (Method 2): $R_t$=1.43 min

MS (ESI pos): m/z=320 (M+H)$^+$

Example 20b

Racemic Mixture

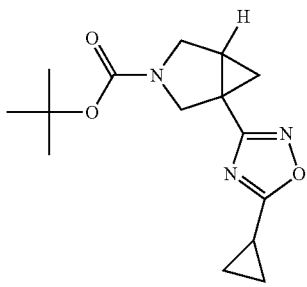 [SMILES: CC(C)(C)OC(=O)N1CC2CC2(c2noc(C3CC3)n2)C1]

To a solution of example 19a (350 mg, 1.45 mmol) in dry ACN (2.5 mL) dicyclopropyl anhydride (1.240 g, 75% content, 6.03 mmol; prepared as described in J. Org. Chem., 67, 5226-5231; 2002) and dry TEA (1.415 mL, 10.15 mmol) are added and the mixture heated under microwaves irradiation (100° C.) for 20 min and then heated at 150° C. for additional 30 min. Solvents are evaporated under reduced pressure and the resulting residue is purified by flash chromatography (eluent 0-20% EtOAc/cyclohexane) to furnish the title compound (353 mg, 84%).

HPLC-MS (Method 5): $R_t$=9.60 min

MS (APCI): m/z=192 (M-CO$_2$tBu+H)$^+$

Example 20c

Racemic Mixture

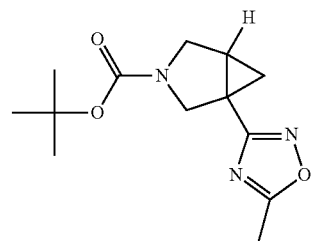 [SMILES: Cc1nc(C23CC2CN(C(=O)OC(C)(C)C)C3)no1]

The title compound is prepared as described for example 20a, starting from example 19a (340 mg, 1.409 mmol) using acetic anhydride (200 µl, 2.11 mmol) HPLC-MS (Method 2): $R_t$=1.17 min MS (ESI pos): m/z=266 (M+H)$^+$

Example 20d

Single Enantiomer, Unknown Absolute Stereochemistry at Bridgehead

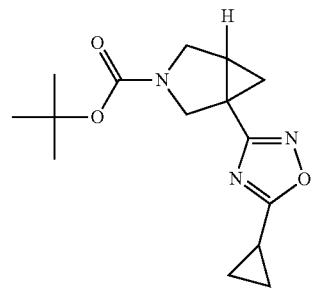 [SMILES: CC(C)(C)OC(=O)N1CC2CC2(c2noc(C3CC3)n2)C1]

The title compound is prepared as described for example 20b, starting from example 19b (46 mg, 0.19 mmol).

HPLC-MS (Method 2): $R_t$=1.34 min

MS (ESI pos): m/z=236 (M-tBu+H)$^+$

Example 20e

Single Enantiomer, Unknown Absolute Stereochemistry at Bridgehead

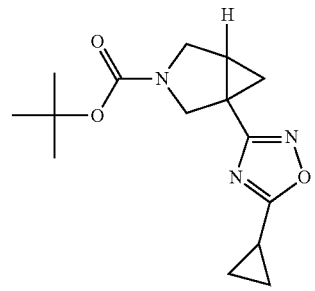 [SMILES: CC(C)(C)OC(=O)N1CC2CC2(c2noc(C3CC3)n2)C1]

The title compound is prepared as described for example 20b, starting from example 19c (45 mg, 0.18 mmol).

HPLC-MS (Method 2): $R_t$=1.33 min

MS (ESI pos): m/z=236 (M–tBu+H)$^+$

Example 20f

Single Enantiomer, Unknown Absolute Stereochemistry at Bridgehead

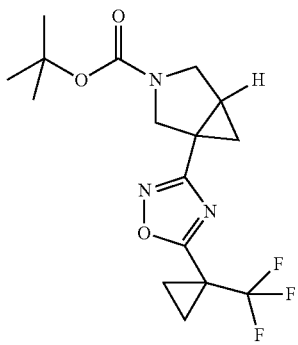 [SMILES: CC(C)(C)OC(=O)N1CC2CC2(c2noc(C3(C(F)(F)F)CC3)n2)C1]

The title compound is prepared as described for example 20b starting from example 19c (60.3 mg, 0.25 mmol), 1-trifluoromethylcyclopropane-1-carboxylic acid anhydride (250 mg, prepared following the procedure described in J. Org. Chem., 67, 5226-5231; 2002 starting from 1-trifluoromethylcyclopropane-1-carboxylic acid) and 0-40% EtOAc/cyclohexane as purification eluent to give 70 mg (78%) of product.

HPLC-MS (Method 2): $R_t$=1.41 min

MS (ESI pos): m/z=377 (M+NH$_4$)$^+$

Example 21a

Racemic Mixture

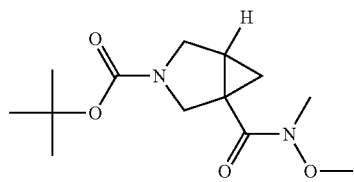 [SMILES: CON(C)C(=O)C12CC1CN(C(=O)OC(C)(C)C)C2]

CDI (313 mg, 1.93 mmol) is added to racemic 3-azabicyclo[3.1.0]hexane-1,3-dicarboxylic acid-3-tert-butyl ester (337 mg, 1.48 mmol) dissolved in DCM (5 mL) under stirring at room temperature. TEA (0.289 mL, 2.07 mmol) followed by N,O-dimethylhydroxylamine hydrochloride (203 mg, 2.076 mmol) are added to the reaction mixture after 1 hour. After 2 hours the reaction mixture is diluted with DCM, washed with 0.2 M HCl, saturated NaHCO$_3$ and brine and then dried over Na$_2$SO$_4$ before being evaporated to furnish the title compound (373 mg, 93%), that is used as such.

HPLC-MS (Method 5): $R_t$=7.64 min

MS (APCI): m/z=171 (M–CO$_2$tBu+H)$^+$

Example 22a

Racemic Mixture

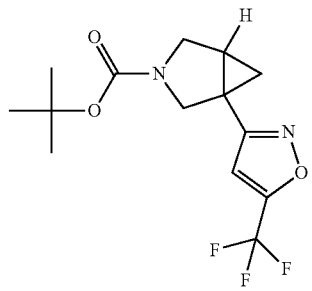 [SMILES: CC(C)(C)OC(=O)N1CC2CC2(c2cc(C(F)(F)F)on2)C1]

Methylmagnesium bromide (3M in ethyl ether, 920 μL, 2.76 mmol) is added dropwise to example 21a (373 mg, 1.38 mmol) dissolved in THF (5 mL) cooled to 0° C. Stirring is continued at 0° C. for 15 min followed by 2 h at room temperature. The reaction mixture is cooled to 0° C. and methylmagnesium bromide (3M in ethyl ether, 920 μL, 2.76 mmol) is added dropwise. Stirring is continued at 0° C. for 15 min followed by overnight at room temperature. The reaction mixture is cooled to 0° C., 1N HCl (6 mL) is added dropwise and stirring is continued for 15 min. EtOAc is added, the organic layer separated, washed with brine, dried over Na$_2$SO$_4$ and concentrated under reduced pressure to furnish a residue. Lithium bis(trimethylsilyl)amide (1M in THF, 1.25 mL, 1.27 mmol) is added dropwise to such residue dissolved in THF (8 mL) and cooled to −78° C. Stirring is continued at −20° C. for 1 h. The reaction mixture is cooled to −60° C. and ethyl trifluoroacetate (273 μL, 2.28 mmol) is added. Stirring is continued at room temperature overnight. Water and EtOAc are added, the organic layer separated, dried over Na$_2$SO$_4$ and concentrated under reduced pressure to furnish a residue. Hydroxylamine hydrochloride (1.048 g, 15.00 mmol) is added to such residue dissolved in MeOH (40 mL) and the reaction mixture refluxed for 2 h. Volatiles are evaporated under reduced pressure, the residue partitioned between EtOAc and saturated NaHCO$_3$, the organic layer separated, washed with saturated NaHCO$_3$, dried over Na$_2$SO$_4$ and concentrated under reduced pressure to furnish a residue. TEA (147 μL, 1.057 mmol) followed by methanesulfonyl chloride (76 μL, 0.98 mmol) are added to such residue dissolved in DCM (11 mL) and cooled to 0° C. Stirring is continued for 5 h at room temperature. Water and DCM are added, the aqueous layer further extracted with DCM, the organic layers combined, dried using a phase separator cartridge and concentrated under reduced pressure. The resulting residue is purified by flash chromatography (eluent 0-10% EtOAc/cyclohexane) to furnish the title compound (195 mg, 44%).

HPLC-MS (Method 5): $R_t$=10.41 min

MS (APCI): m/z=219 (M–CO$_2$tBu+H)$^+$

Example 22a (Racemic Mixture), Alternative Procedure

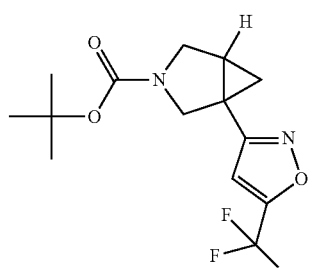

N-Chlorosuccinimide (212 mg, 1.59 mmol) is added to example 23a (vide infra) (360 mg, 1.59 mmol) in DMF (8 mL) cooled to 0° C. Stirring is continued overnight. The reaction mixture is partitioned between water and AcOEt. The organic layer is washed with brine, dried over $Na_2SO_4$ and evaporated under reduced pressure to furnish a residue (386 mg). 100 mg of such residue are dissolved in anhydrous chloroform (5 mL) and cooled to 0° C. 2-Bromo-3,3,3-trifluoropropene (671 mg, 3.84 mmol) followed by TEA (160 μl, 1.15 mmol) are added to the reaction mixture and stirring is continued 3 hours. The reaction mixture is partitioned between water and DCM. The organic layer is washed with brine, dried over $Na_2SO_4$ and evaporated under reduced pressure to give residue, which is purified by Si-flash chromatography, using Cyclohexan/EtOAc 85:15 as eluent, to obtain 76 mg (62%) of product.

HPLC-MS (Method 7b): $R_t$=3.67 min
MS (APCI pos): m/z=219 (M−Boc+H)$^+$

Example 22b

Racemic Mixture

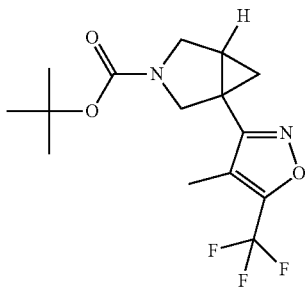 [SMILES: Cc1c(C23CC2CN(C(=O)OC(C)(C)C)C3)noc1C(F)(F)F]

Ethylmagnesium bromide (3M in ethyl ether, 3.95 ml, 11.84 mmol) is added dropwise to example 21a (1.6 g, 5.92 mmol) dissolved in anhydrous THF (20 mL) cooled to 0° C. Stirring is continued at 0° C. for 15 min then overnight at room temperature. The reaction mixture is cooled to 0° C. and methylmagnesium bromide (3M in ethyl ether, 1.97 ml, 5.92 mmol) is added dropwise. Stirring is continued at 0° C. for 15 min followed by 2 h at room temperature. The reaction mixture is cooled to 0° C., aqueous $NH_4Cl$ is added dropwise and stirring is continued for 5 min. EtOAc is added, the organic layer separated, washed with brine, dried over $Na_2SO_4$ and concentrated under reduced pressure to furnish 1.37 g of crude ketone. Lithium bis(trimethylsilyl)amide (1.8M, 1.03 mL, 1.86 mmol) is added dropwise to the crude ketone (370 mg, 1.55 mmol) dissolved in anhydrous THF (10 mL) and cooled to −78° C. Stirring is continued at −20° C. for 1 h. The reaction mixture is cooled to −78° C. and 1-(trifluoroacetyl)imidazole (0.70 ml, 6.18 mmol) is added. Stirring is continued 3 h at room temperature. Aqueous $NH_4Cl$ solution and EtOAc are added, the organic layer is separated, dried over a phase-separator cartridge and concentrated under reduced pressure to furnish a residue that is purified by Si flash chromatography (5-40% EtOAc/Hexane as eluent) to obtain 190 mg of intermediate. Hydroxylamine hydrochloride (512 mg, 7.37 mmol) is added to such product dissolved in MeOH (20 mL) and the reaction mixture refluxed for 2 h. Volatiles are evaporated under reduced pressure, the residue is partitioned between EtOAc and saturated $NaHCO_3$, the organic layer is separated, washed with saturated $NaHCO_3$, dried over phase separator cartridge and concentrated under reduced pressure to furnish a 90 mg of residue. TEA (50 μL, 0.36 mmol) followed by methanesulfonyl chloride (26 μL, 0.33 mmol) are added to such residue dissolved in DCM (10 mL) and cooled to 0° C. Stirring is continued at room temperature then further TEA (50 μL, 0.36 mmol) and methanesulfonyl chloride (26 μL, 0.33 mmol) are added and stirring is continued for 2 h. Water and DCM are added, the aqueous layer is further extracted with DCM, the organic layers are combined, dried over a phase-separator cartridge and concentrated under reduced pressure. The resulting residue is purified by flash chromatography (eluent 0-10% EtOAc/hexane) to furnish the title compound (20 mg, 23% on the last step).

Example 23a

Racemic Mixture

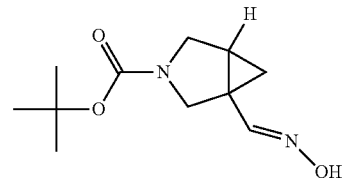 [SMILES: CC(C)(C)OC(=O)N1CC2CC2(/C=N/O)C1]

Lithium aluminium hydride (50 mg, 1.30 mmol) is added portionwise to racemic 3-azabicyclo[3.1.0]hexane-1,3-dicarboxylic acid-3-tert-butyl ester (315 mg, 1.30 mmol) in THF (6 mL) cooled to 0° C. Stirring is continued for 10 min at 0° C. followed by 1 h at rt. The reaction mixture is cooled to 0° C. and water (100 μL), 1M NaOH (100 μL) and water (300 μL) are added. Stirring is continued for 15 min at rt. Solids are filtered away on celite and the filtrate dried over $Na_2SO_4$ before being evaporated to furnish a residue that is dissolved in DCM (7 mL), cooled to 0° C. and treated with Dess-Martin periodinane (679 mg, 1.60 mmol) portionwise. Stirring is continued for 3 h at rt. Saturated $NaHCO_3$ and sodium thiosulphate (2 g in 5 mL of water) are added and stirring is continued for 30 min. The organic layer is separated, dried using a phase separator cartridge and evaporated under reduced pressure. The resulting residue is dissolved in EtOH (13 mL) and added to hydroxylamine hydrochloride (387 mg, 5.56 mmol) and sodium acetate (730 mg, 8.9 mmol) in water (5 mL). After stirring overnight at room temperature the reaction mixture is partitioned between water and AcOEt. The organic layer is washed with brine, dried over $Na_2SO_4$ and evaporated under reduced pressure to furnish the title compound (265 mg, 90% content, 79%) that is used as such.

HPLC-MS (Method 2): $R_t$=1.05 min
MS (ESI pos): m/z=227 (M+H)$^+$

Example 24a

Racemic Mixture

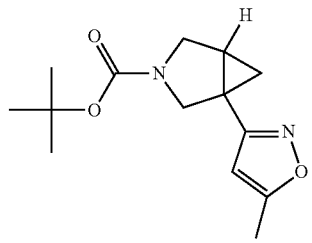 [SMILES: Cc1cc(C23CC2CN(C(=O)OC(C)(C)C)C3)no1]

N-Chlorosuccinimide (148 mg, 1.10 mmol) is added to example 23a (265 mg, 90% content, 1.05 mmol) in DMF (5 mL) cooled to 0° C. Stirring is continued for 2 h at 40° C. N-Chlorosuccinimide (72 mg, 0.538 mmol) is added to the reaction mixture and stirring is continued for 1 h at 40° C. The reaction mixture is partitioned between water and AcOEt. The organic layer is washed with brine, dried over Na₂SO₄ and evaporated under reduced pressure to furnish a residue (270 mg). 135 mg of such residue are dissolved in DCM (5 mL) and cooled to 0° C. 2-Chloropropene (1 mL, 11.75 mmol) followed by TEA (217 µl, 1.553 mmol) are added to the reaction mixture and stirring is continued overnight. The reaction mixture is partitioned between water and DCM. The organic layer is washed with brine, dried over Na₂SO₄ and evaporated under reduced pressure to give residue, which is purified by flash chromatography (eluent 0-10% EtOAc/cyclohexane) to furnish the title compound (69 mg, 50%).

HPLC-MS (Method 6): $R_t$=11.20 min

MS (ESI pos): m/z=265 (M+H)⁺

Example 24b

Racemic Mixture

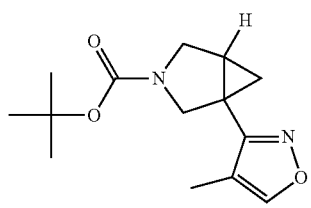 [SMILES: Cc1conc1C12CC1CN(C(=O)OC(C)(C)C)C2]

N-Chlorosuccinimide (148 mg, 1.10 mmol) is added to example 23a (265 mg, 90% content, 1.05 mmol) in DMF (5 mL) cooled to 0° C. Stirring is continued for 2 h at 40° C. N-Chlorosuccinimide (72 mg, 0.538 mmol) is added to the reaction mixture and stirring is continued for 1 h at 40° C. The reaction mixture is partitioned between water and AcOEt. The organic layer is washed with brine, dried over Na₂SO₄ and evaporated under reduced pressure to furnish a residue (270 mg). 67 mg of such residue are dissolved in DCM (2.5 mL) and cooled to 0° C. Ethyl propenyl ether (0.654 mL, 5.91 mmol) followed by TEA (72 µl, 0.51 mmol) are added to the reaction mixture and stirring is continued overnight at room temperature. The reaction mixture is partitioned between water and DCM. The organic layer is washed with brine, dried over Na₂SO₄ and evaporated under reduced pressure to give residue, which is purified by flash chromatography (eluent 5-30% EtOAc/cyclohexane) to furnish the title compound (68 mg).

HPLC-MS (Method 8): $R_t$=6.82 min

MS (ESI pos): m/z=165 (M−CO₂tBu+H)⁺

Example 24c

Racemic Mixture

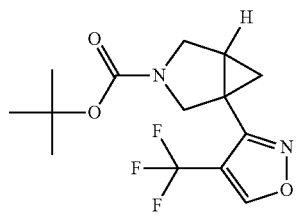 [SMILES: CC(C)(C)OC(=O)N1CC2CC2(c2nocc2C(F)(F)F)C1]

N-Chlorosuccinimide (148 mg, 1.10 mmol) is added to example 23a (265 mg, 90% content, 1.05 mmol) in DMF (5 mL) cooled to 0° C. Stirring is continued for 2 h at 40° C. N-Chlorosuccinimide (72 mg, 0.54 mmol) is added to the reaction mixture and stirring is continued for 1 h at 40° C. The reaction mixture is partitioned between water and AcOEt. The organic layer is washed with brine, dried over Na₂SO₄ and evaporated under reduced pressure to furnish a residue (270 mg). 67 mg of such residue are dissolved in DCM (2.5 mL) and cooled to 0° C. (E)-1-Methoxy-3,3,3-trifluoropropene (746 mg, 5.91 mmol) followed by TEA (72 µl, 0.51 mmol) are added to the reaction mixture and stirring is continued overnight at room temperature.

The reaction mixture is partitioned between water and DCM. The organic layer is washed with brine, dried over Na₂SO₄ and evaporated under reduced pressure to give residue, which is purified by flash chromatography (eluent 0-20% EtOAc/cyclohexane) to furnish the title compound (41 mg).

HPLC-MS (Method 8): $R_t$=10.41 min

MS (ESI pos): m/z=219 (M−CO₂tBu+H)⁺

Example 25a

Racemic Mixture

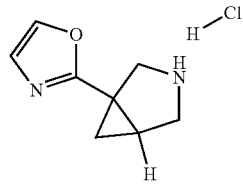

Example 13a (0.015 mg, purity 50%) is dissolved in dry 1,4-dioxane (0.5 mL) and hydrochloric acid (1 mL of a 4N solution in dioxane) is added. Mixture is stirred at room temperature for 1 h, solvent evaporated to obtain the title compound (15 mg) used in the next step without any further purification.

HPLC-MS (Method 2): $R_t$=0.28 min

MS (ESI pos): m/z=150 (M+H)⁺

The following examples are synthesized in analogy to the preparation of example 25a:

| Example | Structure | Reactant, amount | $R_t$ [min], method | MS (ESI pos or APCI, m/z) |
|---|---|---|---|---|
| 25b (racemic mixture) | 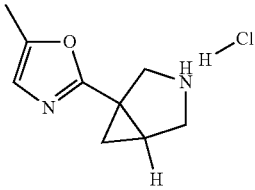 | 13b, 115 mg | 7.35, method 5 | 165 (M + H)⁺ |
| 25c (racemic mixture) | 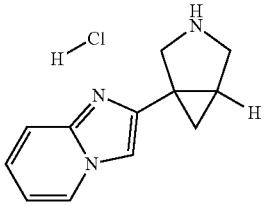 | 14a, 172 mg | 7.88, method 5 | 200 (M + H)⁺ |
| 25d (racemic mixture) | 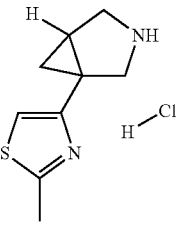 | 14b, 44 mg | 1.42, Method 6 | 181 (M + H)⁺ |
| 25e (racemic mixture) | 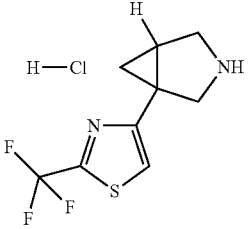 | 14c, 155 mg | 8.53, method 5 | 235 (M + H)⁺ |
| 25f (racemic mixture) | 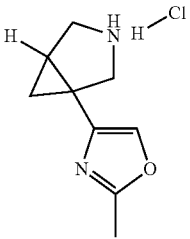 | 14d, 17 mg | 0.39, Method 2 | 165 (M + H)⁺ |
| 25g (racemic mixture) | 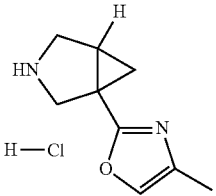 | 14e, 76 mg, 48% content | 0.81, Method 2 | 165 (M + H)⁺ |

-continued

| Example | Structure | Reactant, amount | R$_t$ [min], method | MS (ESI pos or APCI, m/z) |
|---|---|---|---|---|
| 25h (racemic mixture) | 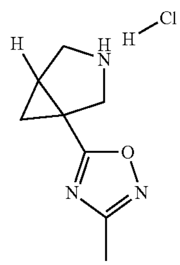 | 15a, 167 mg | 0.34, Method 2 | 166 (M + H)$^+$ |
| 25i (racemic mixture) | 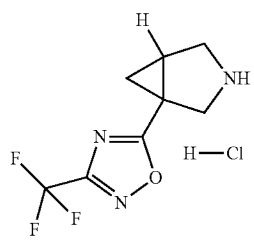 | 15b, 200 mg | 7.77, Method 5 | 220 (M + H)$^+$ |
| 25j (racemic mixture) | 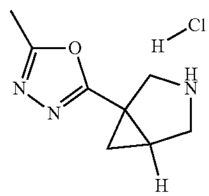 | 17a, 77 mg | 5.15, Method 5 | 166 (M + H)$^+$ |
| 25k (racemic mixture) | 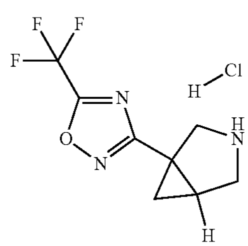 | 20a, 1000 mg | 0.96, Method 2 | 220 (M + H)$^+$ |
| 25l (racemic mixture) | 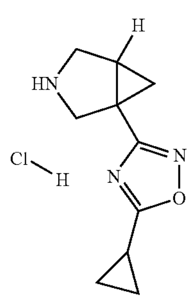 | 20b, 353 mg | 6.81, Method 5 | 192 (M + H)$^+$ |
| 25m (racemic mixture) | 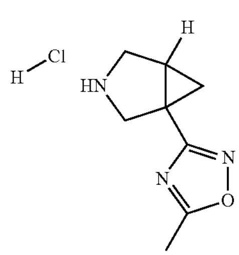 | 20c, 296 mg (90% content) | 0.34, Method 2 | 165 (M + H)$^+$ |

-continued

| Example | Structure | Reactant, amount | $R_t$ [min], method | MS (ESI pos or APCI, m/z) |
|---|---|---|---|---|
| 25n (single enantiomer, Unknown absolute stereochemistry at bridgehead) | 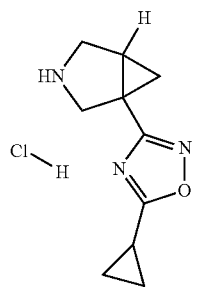 | 20d, 48 mg | 0.86, Method 2 | 192 (M + H)+ |
| 25o (single enantiomer, Unknown absolute stereochemistry at bridgehead) | 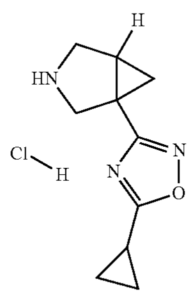 | 20e, 48 mg | 0.86, Method 2 | 192 (M + H)+ |
| 25p (racemic mixture) | 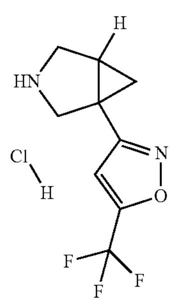 | 22a, 190 mg | 7.96, Method 5 | 219 (M + H)+ |
| 25q (racemic mixture) | 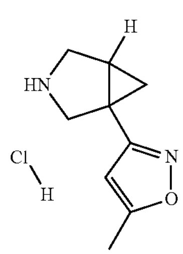 | 24a, 69 mg | 0.69, Method 2 | 165 (M + H)+ |
| 25r (racemic mixture) | 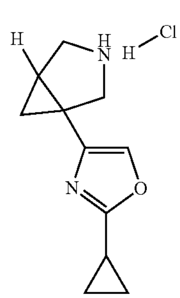 | 14f, 163 mg | 0.57, method 2 | 191 (M + H)+ |

-continued

| Example | Structure | Reactant, amount | R$_t$ [min], method | MS (ESI pos or APCI, m/z) |
|---|---|---|---|---|
| 25u (racemic mixture) | 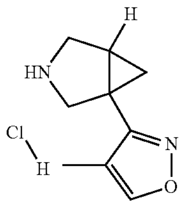 | 24b, 68 mg | 0.38 and 0.58, method 2 | 165 (M + H)+ |
| 25v (racemic mixture) | 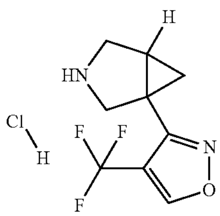 | 24c, 41 mg | 0.88, method 2 | 219 (M + H)+ |
| 25w (racemic mixture) | 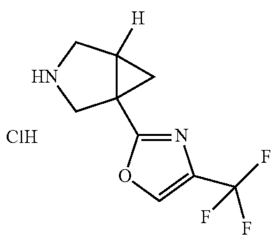 [SMILES: Cl ; FC(F)(F)c1coc(C23CNCC2C3)n1] | 14g, 515 mg, content 95 | Rt = 4.54 min; Method 7a | 219 (M + H)+ |
| 25x (single enantiomer, Unknown absolute stereochemistry at bridgehead) | 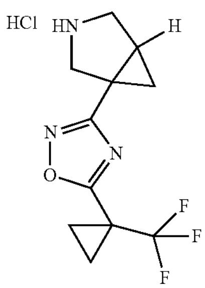 [SMILES: Cl ; FC(F)(F)C1(c2nc(C34CNCC3C4)no2)CC1] | 20f, 70 mg | Rt = 0.77 min; method 2 | 260 (M + H)+ |
| 25y (racemic mixture) | 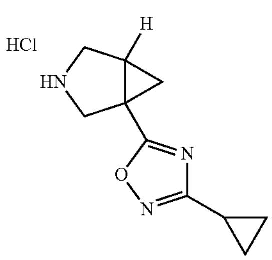 [SMILES: Cl ; C1CC1c1noc(C23CNCC2C3)n1] | 15c, 150 mg | Rt = 4.00 min; Method 7a | 192 (M + H)+ |
| 25z (racemic mixture) | 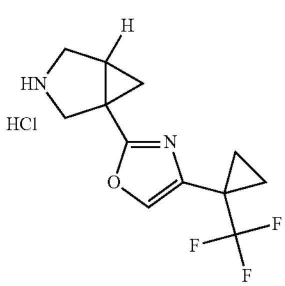 [SMILES: Cl ; FC(F)(F)C1(c2coc(C34CNCC3C4)n2)CC1] | 15d, 240 mg | Rt = 0.85 min; method 2 | 260 (M + H)+ |

| Example | Structure | Reactant, amount | R_t [min], method | MS (ESI pos or APCI, m/z) |
|---|---|---|---|---|
| 25za (racemic mixture) | 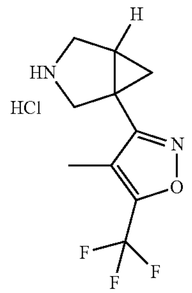 [SMILES: Cl ; Cc1c(C23CNCC2C3)noc1C(F)(F)F] | 22b, 30 mg | Rt = 5.27 min; method 7a | 233 (M + H)+ |

Example 26a

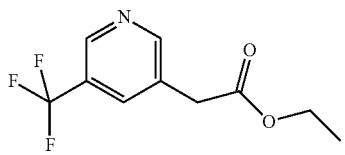 [SMILES: CCOC(=O)Cc1cncc(C(F)(F)F)c1]

3-Bromo-5-(trifluoromethyl)pyridine (6.0 g, 26.55 mmol), diethyl malonate (4.8 mL, 0.032 mol) and cesium carbonate (11.2 g, 0.035 mol) in DME (30 mL) are degassed with a flow of nitrogen for 5 min. Tris(dibenzylideneacetone)dipalladium(0) (486 mg, 0.531 mmol) and tri-tert-butylphosphine (644 µl, 2.65 mmol) are the added and the reaction mixture split in six equal portions. Each portion is heated to 150° C. in a microwave oven for 1 hour. The combined portions are mixed with saturated NH₄Cl and extracted three times with ethyl ether. The combined organic layers are dried using a phase separator cartridge, and concentrated under reduced pressure to give a residue that is purified by flash chromatography (eluent 0-25% EtOAc/petroleum ether) to furnish the title compound (2.63 g, 43%).

HPLC-MS (Method 2): R_t=1.02 min
MS (ESI pos): m/z=233 (M+H)+

Example 27a

Racemic Mixture

Benzoyl peroxide (24 mg, 0.1 mmol) and N-bromosuccinimide (0.885 g, 4.97 mmol) are added to example 26a (1.160 g, 4.97 mmol) in carbon tetrachloride (30 mL) and the reaction mixture is refluxed overnight. The reaction mixture is cooled to room temperature, undissolved material is filtered away and washed with EtOAc. The filtrate and the EtOAc washings are evaporated under reduced pressure to give a residue that is purified by flash chromatography (eluent 0-10% EtOAc/petroleum ether) to furnish the title compound (1.000 g, 64%).

HPLC-MS (Method 2): R_t=1.18 min
MS (ESI pos): m/z=312 (M+H)+

Example 27b

Racemic Mixture

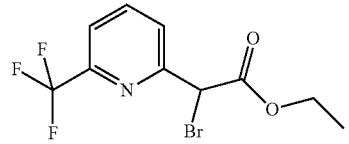 [SMILES: CCOC(=O)C(Br)c1cccc(C(F)(F)F)n1]

The title compound is prepared as described for example 27a, using 2-pyridineacetic acid, 6-(trifluoromethyl)-, ethyl ester (3.000 g, 88% content, 11.32 mmol, prepared as described in WO2009/121919).

HPLC-MS (Method 2): R_t=1.24 min
MS (ESI pos): m/z=312 (M+H)+

Example 28a

Diastereomeric Mixture

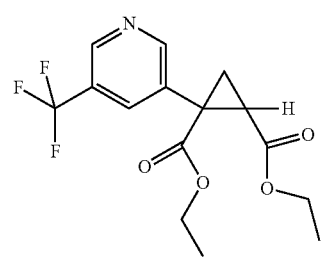 [SMILES: CCOC(=O)C1CC1(C(=O)OCC)c1cncc(C(F)(F)F)c1]

EtOH (416 µl) followed by a solution of example 27a (1.000 g, 3.20 mmol) in ethyl acrylate (662 µl, 6.09 mmol) and EtOH (125 µl) are added to sodium hydride (60% suspension in mineral oil, 128 mg, 3.20 mmol) in diethyl ether (12 mL) cooled to 0° C. Stirring is continued at room temperature over weekend. EtOH (5 mL), ethyl ether (50 mL) and water are added and the organic layer separated, dried using a phase separator cartridge and concentrated under reduced pressure to give a residue that is purified by flash chromatography (eluent 0-20% EtOAc/petroleum ether) to furnish the title compound (0.96 g, 90%).

HPLC-MS (Method 7): $R_t$=7.33-7.52 min
MS (ESI pos): m/z=332 (M+H)$^+$

Example 28b

Diastereomeric Mixture

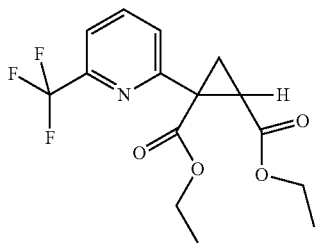 [SMILES: CCOC(=O)C1CC1(C(=O)OCC)c1cccc(C(F)(F)F)n1]

The title compound is prepared as described for example 28a, using example 27b (1.780 g, 5.70 mmol).

GC-MS (Method 8): $R_t$=10.76 min
MS (EI pos): m/z=331 (M)$^+$

Example 29a

Syn: Racemic Mixture

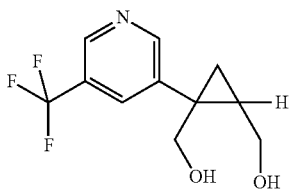 [SMILES: OCC1CC1(CO)c1cncc(C(F)(F)F)c1]

Lithium aluminum hydride (149 mg, 3.92 mmol) is added portionwise to example 28a (1000 mg, 3.02 mmol) in THF cooled to 0° C. Stirring is continued for 10 min at 0° C. and then for 1 h at room temperature. Lithium aluminum hydride (22 mg, 0.58 mmol) is added and stirring is continued overnight. Lithium aluminum hydride (23 mg, 0.60 mmol) is added and stirring is continued for 3 h. Water (194 µl), 1M NaOH (194 µl) and water (582 µl) are added to the reaction mixture cooled to 0° C. and stirring is continued for 40 min at room temperature. Solids are filtered away on celite and washed with EtOAc. The filtrate and the EtOAc washings are evaporated under reduced pressure to give a residue that is purified by flash chromatography (eluent 0-10% MeOH/DCM) to furnish the title compound (209 mg, 28%).

HPLC-MS (Method 6): $R_t$=7.18 min
MS (ESI pos): m/z=248 (M+H)$^+$

Example 29b

Diastereomeric Mixture

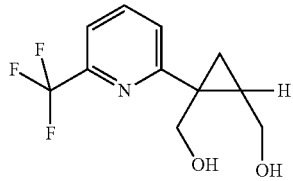

The title compound is prepared as described for example 29a, using example 28b (200 mg, 0.60 mmol).

HPLC-MS (Method 5): $R_t$=7.18 min
MS (APCI): m/z=248 (M+H)$^+$

Example 30a

Syn; Racemic Mixture

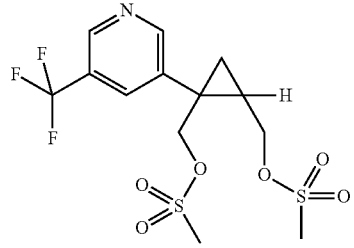 [SMILES: CS(=O)(=O)OCC1CC1(COS(C)(=O)=O)c1cncc(C(F)(F)F)c1]

TEA (280 µl, 2.01 mmol) followed by methanesulfonyl chloride (143 µl, 1.84 mmol) are added to example 29a (207 mg, 0.84 mmol) in DCM (5 mL) at 0° C. After stirring for 30 min at room temperature the reaction mixture is diluted with DCM, washed with sat. NaHCO$_3$ and brine, dried using a phase separator cartridge and concentrated under reduced pressure to furnish the title compound (319 mg, 94%) that is used as such.

HPLC-MS (Method 6): $R_t$=9.84 min
MS (ESI pos): m/z=404 (M+H)$^+$

Example 30b

Diastereomeric Mixture

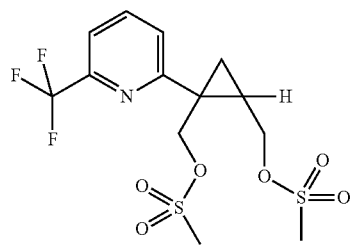 [SMILES: CS(=O)(=O)OCC1CC1(COS(C)(=O)=O)c1cccc(C(F)(F)F)n1]

The title compound is prepared as described for example 30a, using example 29b (213 mg, 0.86 mmol).

HPLC-MS (Method 2): $R_t$=1.07 min
MS (ESI pos): m/z=404 (M+H)$^+$

Example 31a

Racemic Mixture

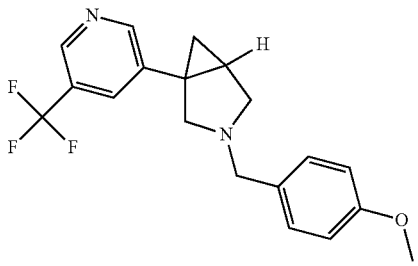 [SMILES: COc1ccc(CN2CC3CC3(c3cncc(C(F)(F)F)c3)C2)cc1]

Example 30a (318 mg, 0.788 mmol), 4-methoxybenzylamine (206 µl, 1.58 mmol) and DIPEA (343 µl, 1.97 mmol) in DMF (5 mL) are stirred at 80° C. for 2.5 h. The reaction mixture is cooled to room temperature, volatiles are evaporated under reduced pressure and the resulting residue partitioned between EtOAc and water. The organic layer is separated, washed with NaHCO$_3$ and brine, dried using a phase separator cartridge and concentrated under reduced pressure to give a residue that is purified by flash chromatography (eluent 0-30% EtOAc/petroleum ether) to furnish the title compound (182 mg, 66%).
HPLC-MS (Method 6): R$_t$=6.41 min
MS (ESI pos): m/z=349 (M+H)$^+$ Example 31b Racemic Mixture

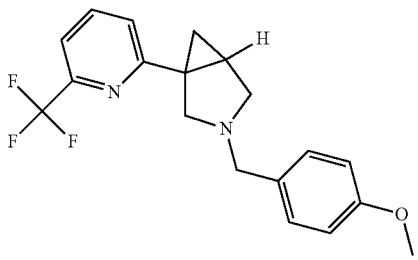 [SMILES: COc1ccc(CN2CC3CC3(c3cccc(C(F)(F)F)n3)C2)cc1]

The title compound is prepared as described for example 31a, using example 30b (345 mg, 0.85 mmol).
HPLC-MS (Method 5): R$_t$=10.09 min
MS (APCI): m/z=349 (M+H)$^+$ Example 32a Racemic Mixture

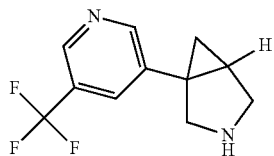

1-Chloroethyl chloroformate (68 µl, 0.62 mmol) is added to example 31a (180 mg, 0.52 mmol) in 1,2-dichloroethane (3.3 mL) cooled to 0° C. Stirring is continued for 2.5 h at room temperature. 1-Chloroethyl chloroformate (25 µl, 0.23 mmol) is added to the reaction mixture and stirring is continued for 1 h. MeOH (6.6 mL) is added to the reaction mixture and stirring is continued for 1 h at 60° C. The reaction mixture is cooled to room temperature and concentrated under reduced pressure to give a residue that is purified by flash chromatography (eluent 5% MeOH in DCM+0.5% of NH$_3$) to furnish the title compound (113 mg, 96%).
HPLC-MS (Method 5): R$_t$=8.22 min
MS (APCI): m/z=229 (M+H)$^+$ Example 32b Racemic Mixture

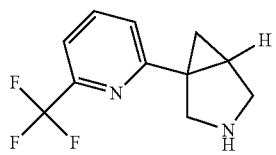 [SMILES: FC(F)(F)c1cccc(C23CNCC2C3)n1]

The title compound is prepared as described for Example 32a, using example 31b (165 mg, 0.47 mmol).
HPLC-MS (Method 5): R$_t$=8.81 min
MS (APCI): m/z=229 (M+H)$^+$ Example 33a Racemic Mixture

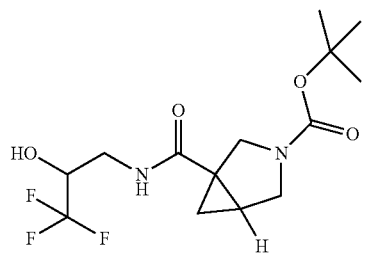 [SMILES: CC(C)(C)OC(=O)N1CC2CC2(C(=O)NCC(O)C(F)(F)F)C1]

To a solution of racemic 3-azabicyclo[3.1.0]hexane-1,3-dicarboxylic acid-3-tert-butyl ester (200 mg, 0.88 mmol) in DMF (5 mL), TBTU (339 mg, 1.056 mmol) and TEA (160 µL, 1.14 mmol) are added. Mixture is stirred at room temperature for 10 min, then racemic 3-amino-1,1,1-trifluoro-2-propanol (125 mg, 0.97 mmol) is added and the mixture stirred at room temperature overnight. AcOEt and saturated NaHCO$_3$ are added, the organic phases separated and washed with 10% citric acid and brine. The organic layer is then dried using a phase separator cartridge and evaporated under reduced pressure to furnish the title compound (330 mg, 90% content, 100%), that is used as such.
HPLC-MS (Method 2): R$_t$=0.94 min
MS (ESI pos): m/z=339 (M+H)$^+$

Example 34a

Racemic Mixture

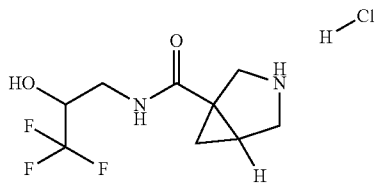 [SMILES: Cl ; O=C(NCC(O)C(F)(F)F)C12CNCC1C2]

Example 33a (310 mg, 94% content, 0.86 mmol) is dissolved in dry 1,4-dioxane (5 mL) and hydrochloric acid (5 mL of a 4N solution in dioxane) is added. Mixture is stirred at room temperature for 2.5 h, solvent evaporated to obtain the title compound (310 mg, 64% content, 84%) used in the next step without any further purification.

HPLC-MS (Method 2): $R_t$=0.35 min
MS (ESI pos): m/z=239 (M+H)$^+$

Example 35a

Racemic Mixture

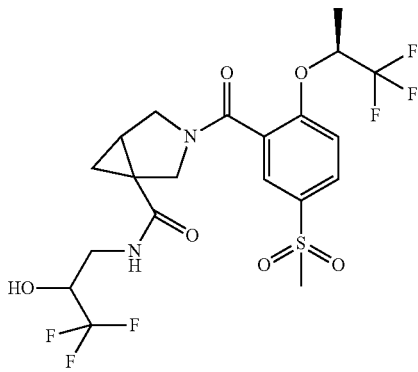 [SMILES: C[C@H](Oc1ccc(S(C)(=O)=O)cc1C(=O)N1CC2CC2(C(=O)NCC(O)C(F)(F)F)C1)C(F)(F)F]

To a solution of example 34a (310 mg, 64% content, 0.72 mmol) in DMF (5 mL), example 4a (226 mg, 0.72 mmol), TBTU (255 mg, 0.79 mmol) and DIPEA (618 μL, 3.61 mmol) are added. Stirring is continued at room temperature overnight. AcOEt and saturated NaHCO$_3$ are added, the organic phases separated and washed with brine, dried and evaporated under reduced pressure. The resulting residue is purified by flash chromatography (eluent 0-5% MeOH/DCM) to furnish the title compound (270 mg, 70%).

HPLC-MS (Method 5): $R_t$=7.08 min
MS (APCI): m/z=533 (M+H)$^+$

Example 36a

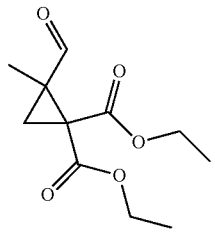 [SMILES: CCOC(=O)C1(C(=O)OCC)CC1(C)C=O]

To a solution of methacrolein (2.61 mL, 30 mmol) in dry EtOH (40 mL), dry TEA (3.47 mL, 25 mmol) and diethlybromomalonate (4.63 mL, 25 mmol) are added at room temperature. The resulting clear solution is stirred at room temperature for 20 h. A white precipitate is formed. Solvent is reduced under vacuum. The white solid suspended in pentane/diethylether 90:10 and the suspension filtered under vacuum. The solution is evaporated to give 5.5 g of colorless oil. Crude is purified by flash cromatography (eluent from pentane/diethylether 90:10 to 75:25) to furnish the title compound (3.49 g, purity 60%, 36.7% yield) as colorless oil.

GC-MS (Method 8): m/z=8.99 min

Example 37a

Racemic Mixture, Syn

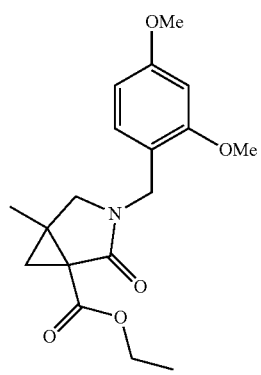 [SMILES: CCOC(=O)C12CC1(C)CN(Cc1ccc(OC)cc1OC)C2=O]

To a solution of Example 36a (2.8 g, 60% purity, 7.36 mmol) in dry THF (30 mL), 2,4-dimethoxybenzylamine (1.24 mL, 8.1 mmol) is added followed by AcOH (0.49 mL, 8.1 mmol). The mixture is stirred at room temperature for 20 min, then cooled at 0° C. and sodium cianoborohydride (0.54 g, 8.1 mmol) is added. After 30 min, the ice bath is removed and reaction mixture left under stirring overnight. A saturated solution of NaHCO$_3$ is added, mixture extracted with Et$_2$O, phases separated and organics washed with brine and dried over sodium sulphate. Evaporation of the solvent give a yellow oil purified by flash cromatagraphy (eluent from 7% to 63% Acetone/Cyclohexane) to furnish the title compound as colorless oil (0.89 g, 36%)

HPLC-MS (Method 2): $R_t$=1.15 min
MS (ESI pos): m/z=334 (M+H)$^+$

Example 38a

Racemic Mixture, Syn

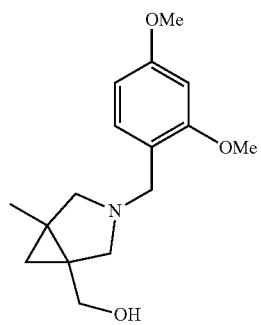 [SMILES: COc1ccc(CN2CC3(C)CC3(CO)C2)c(OC)c1]

To a solution of Example 37a (0.87 g, 2.61 mmol) in dry THF (20 mL) under reflux, borane dimethlysulfide complex (2M solution in THF, 5.22 mL, 10.44 mmol) is added dropwise. After 1 h, mixture is cooled at 0° C. and 5 mL of a solution of MeOH/HCl 36% (9:1) are added dropwise and mixture then refluxed overnight. Solvents are evaporated, the residue is loaded on SCX cartridge and ammonia fractions are evaporated to furnish the title compound as colorless oil (0.63 g, 87%)

HPLC-MS (Method 2): $R_t$=0.91 min
MS (ESI pos): m/z=278 (M+H)$^+$

Example 39a

Racemic Mixture, Syn

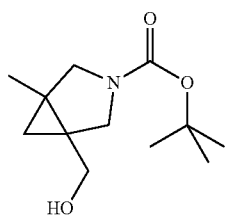 [SMILES: CC(C)(C)OC(=O)N1CC2(C)CC2(CO)C1]

To a solution of Example 38a (0.42 g, 1.51 mmol) in absolute EtOH (20 mL), di-tert-buthyldicarbonate (0.33 g, 1.51 mmol) and palladium hydroxide (0.06 g, 0.03 mmol) are added and the mixture hydrogenated at 20 psi for 20 h. Catalyst is removed by filtration, solvent evaporated and the crude is purified by flash cromatography (eluent gradient from 0% to 100% Cyclohexane in AcOEt) to furnish the title compound as colorless oil (0.19 g, 55%)

GC-MS (Method 8): $R_t$=10.19 min

Example 40a

Racemic Mixture, Syn

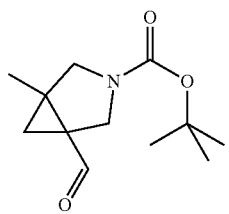 [SMILES: CC(C)(C)OC(=O)N1CC2(C)CC2(C=O)C1]

To a solution of Example 39a (0.095 g, 0.42 mmol) in dry DCM (5 mL) at 0° C., Dess-Martin periodinane (0.25 g, 0.59 mmol) is added and the mixture then stirred for 3 h at room temperature. A saturated solution of NaHCO$_3$ is added followed by 2.5 mL of a 5% solution of Na$_2$S$_2$O$_3$ and the mixture stirred at room temperature for 30 min. Phases are separated, organics dried over sodium sulphate and evaporated to furnish the title compound, used in the next steo without further purification. (0.08 g, 85%)

GC-MS (Method 8): $R_t$=9.85 min

Example 41a

Racemic Mixture, Syn

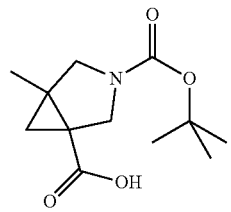 [SMILES: CC(C)(C)OC(=O)N1CC2(C)CC2(C(=O)O)C1]

To a solution of Example 40a (0.08 g, 0.36 mmol) in t-BuOH (2 mL) and 2-methyl-2-butene (0.65 mL of a 2N solution in THF) at room temperature sodiumhydrogenphosphate (0.133 g, 0.96 mmol) in water (1.5 mL) is added followed by sodiumchlorite (0.112 g, 0.99 mmol) and the mixture then stirred at room temperature for 5 hrs, then a solution of citric acid (5% in water) is added. Mixture is extracted with DCM, phased separated, dried over sodium sulphate and evaporated to furnish the title compound (0.065 g, 76%)

GC-MS (Method 8): $R_t$=10.66 min
MS (EI pos): m/z=241 (M)$^+$

Example 42a

Racemic Mixture

Example 18a (550 mg, 2.64 mmol) is dissolved in dry 1,4-dioxane (2 mL) and hydrochloric acid (1 mL of a 4N solution in dioxane) is added. Mixture is stirred at room temperature for 3 h, solvent evaporated to obtain the title compound (380 mg, 100%) used in the next step without any further purification.

HPLC-MS (Method 2): $R_t$=0.24 min
MS (ESI pos): m/z=109 (M+H)$^+$

Example 43a

Diastereomeric Mixture

To a solution of example 4e (210 mg, 0.64 mmol) in dry DMF (5 mL), HATU (318 mg, 0.84 mmol) and dry TEA (269 µl, 1.93 mmol) are added. Mixture is stirred at room temperature for 20 min, then example 42a (93 mg, 0.64 mmol) is added and the mixture stirred at room temperature for additional 2 h. The reaction mixture is treated with basic alumina and volatiles are evaporated under reduced pressure. The residue is dissolved in EtOAc, washed with 10% citric acid and then with brine, dried using a phase separator cartridge and evaporated under vacuum. The crude is purified by flash cromatography (eluent 50-70% EtOAc/Cyclohexane) to obtain the title compound as a white solid (235 mg, 88%)

HPLC-MS (method 2): $R_t$=0.93 min
MS (ESI pos): m/z=417 (M+H)$^+$

Example 43b

Diastereomeric Mixture

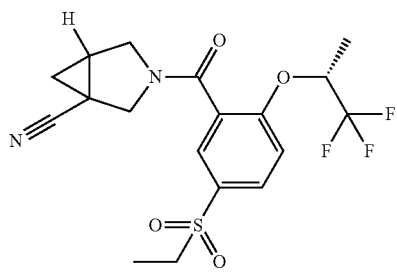 [SMILES: CCS(=O)(=O)c1ccc(O[C@H](C)C(F)(F)F)c(C(=O)N2CC3CC3(C#N)C2)c1]

The title compound is prepared as described above for example 43a, starting from example 42a (53 mg, 0.36 mmol) and example 41(118 mg, 0.36 mmol)

HPLC-MS (method 2): $R_t$=1.07 min
MS (ESI pos): m/z=417 (M+H)$^+$

Example 45a

Diastereomeric Mixture

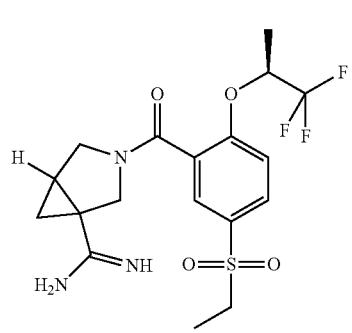 [SMILES: CCS(=O)(=O)c1ccc(O[C@@H](C)C(F)(F)F)c(C(=O)N2CC3CC3(C(=N)N)C2)c1]

Example 45a is prepared as described for example 10a using example 43a (235 mg, 0.56 mmol).

HPLC-MS (method 2): $R_t$=0.68 min
MS (ESI pos): m/z=434 (M+H)$^+$

Example 45b

Diastereomeric Mixture

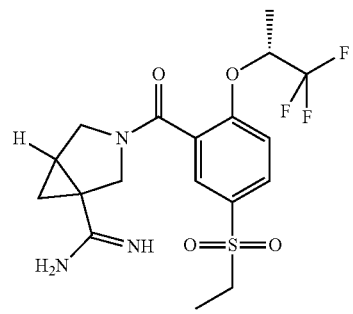 [SMILES: CCS(=O)(=O)c1ccc(O[C@H](C)C(F)(F)F)c(C(=O)N2CC3CC3(C(=N)N)C2)c1]

Example 45b is prepared as described for example 10a using example 43b (121 mg, 0.26 mmol).

HPLC-MS (method 2): $R_t$=0.87 min
MS (ESI pos): m/z=434 (M+H)$^+$

Example 46a

Diastereomeric Mixture

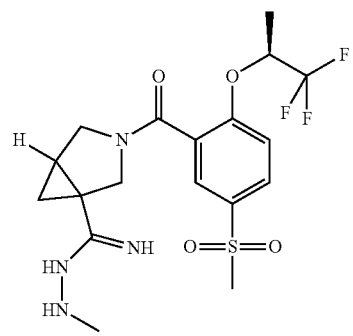 [SMILES: CNNC(=N)C12CC1CN(C(=O)c1cc(S(C)(=O)=O)ccc1O[C@@H](C)C(F)(F)F)C2]

Methylhydrazine (29 µl, 0.55 mmol) is added to example 10a (208 mg, 0.50 mmol) in MeOH (2 mL) cooled to 0° C. Stirring is continued for 2.5 days at room temperature followed by 1 h at 40° C. After evaporation of volatiles, the title compound (244 mg, 85% content, 93%) is used in the next step without any further purification.

HPLC-MS (Method 2): $R_t$=0.87 min
MS (ESI pos): m/z=449 (M+H)$^+$

Example 47a

Racemic Mixture

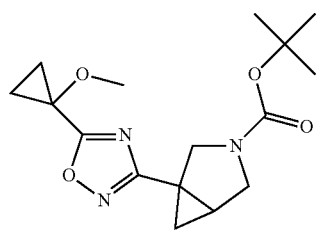 [SMILES: COC1(c2nc(C34CC3CN(C(=O)OC(C)(C)C)C4)no2)CC1]

A solution of 1-methoxycyclopropane-1-carboxylic acid (750 mg, 6.46 mmol) and N,N'-dicyclohexylcarbodiimide (670.2 mg, 3.25 mmol) is stirred under nitrogen atmosphere for 20 hours then Et$_2$O is added to the mixture, the solid is filtered out and solvent is removed under reduced pressure. The obtained anhydride is added to a solution of example 19a (490 mg, 2.03 mmol) and TEA (1.4 ml, 10.06 mmol) in ACN (4 ml) and heated under microwaves irradation (100° C.) for 30 min and then at 150° C. for additional 30 min. Solvents are evaporated under reduced pressure, the residue is partitioned between EtOAc and water, the organic layer is separated, dried over $Na_2SO_4$ and concentrated under reduced pressure. The crude is purified by Si-flash chromatography (eluent n-Hexane/EtOAc 8:2) to obtain the title compound (450 mg, content 90%, 69%).

HPLC-MS (Method 2): $R_t$=1.26 min
MS (ESI pos): m/z=322 (M+H)$^+$

Example 47b

Racemic Mixture

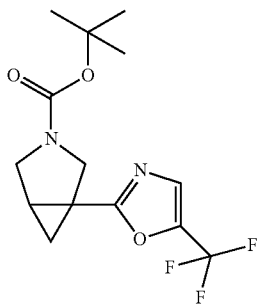 [SMILES: CC(C)(C)OC(=O)N1CC2CC2(c2ncc(C(F)(F)F)o2)C1]

Dess-Martin periodinane (2.63 g, 6.20 mmol) is added to a solution of example 33a (1.50 g, 4.43 mmol) in ACN and stirred for 6 hours at room temperature. The reaction mixture is poured into 10% $NaHCO_3$+5% $Na_2SO_3$ aqueous solution and extracted with EtOAc, organic layer is separated, washed with water, dried over $Na_2SO_4$ and concentrated under reduced pressure. An aliquote of crude ketone (900 mg, 2.68 mmol) is dissolved into anhydrous THF, Burgess reagent (2.50 g, 10.49 mmol) is added and the reaction mixture is then heated under microwave irradiation (120° C.) for 30 min. EtOAc is added to the reaction mixture and the organic layer is washed with water, dried over $Na_2SO_4$, concentrated under reduced pressure to give a residue that is purified by Si flash chromatography (eluent EtOAc/cyclohexane 2:8) to furnish the title compound (140 mg, 16%).

HPLC-MS (Method 2): $R_t$=0.93 min
MS (ESI pos): m/z=319 (M+H)$^+$

Example 47c

Racemic Mixture

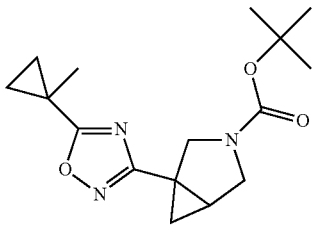 [SMILES: CC(C)(C)OC(=O)N1CC2CC2(c2noc(C3(C)CC3)n2)C1]

The title compound is prepared in analogy to example 47a starting from 1-methylcyclopropane-1-Carboxylic acid (550 mg, 5.49 mmol) in place of 1-methoxycyclopropane-1-carboxylic acid to obtain 340 mg (84% on the last step) of product.

HPLC-MS (Method 2): $R_t$=1.40 min
MS (ESI pos): m/z=306 (M+H)$^+$

Example 48a

Racemic Mixture

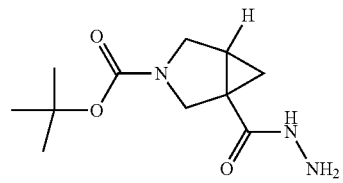 [SMILES: CC(C)(C)OC(=O)N1CC2CC2(C(=O)NN)C1]

Trimethylsilyldiazomethane (3.63 ml, 7.26 mmol) is added dropwise into a stirred solution of racemic 3-azabicyclo[3.1.0]hexane-1,3-dicarboxylic acid-3-tert-butyl ester (1.50 g, 6.60 mmol) dissolved in anhydrous Toluene/anhydrous MeOH mixture at 0° C. under nitrogen atmosphere then the reaction mixture is stirred at room temperature for 2 hours. A small amount of glacial acetic acid is added, solvent is removed under reduced pressure and the residue is partitioned between water and EtOAc. Organic layer is separated, washed with water, dried over $Na_2SO_4$ and concentrated under reduced pressure. The obtained ester is dissolved in anhydrous MeOH and hydrazine hydrate (6.00 ml, 123.45 mmol) is added; the reaction mixture is refluxed for 16 hours, solvent is removed and the residue is partitioned between water and DCM. Organic layer is separated, dried over $Na_2SO_4$ and concentrated under reduced pressure to obtain the title compound (1.40 g, 87%).

HPLC-MS (Method 2): $R_t$=0.74 min
MS (ESI pos): m/z=242 (M+H)$^+$

Example 49a

Racemic Mixture

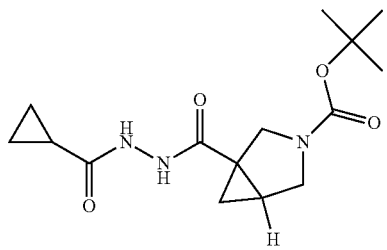 [SMILES: CC(C)(C)OC(=O)N1CC2CC2(C(=O)NNC(=O)C2CC2)C1]

Racemic 3-azabicyclo[3.1.0]hexane-1,3-dicarboxylic acid-3-tert-butyl ester (300 mg, 1.32 mmol), HATU (552 mg, 1.45 mmol) and DIPEA (0.25 mL, 1.45 mmol) in DMF (15 mL) are stirred at rt for 15 min; cyclopropyl hydrazide hydrochloride (198 mg, 1.45 mmol) followed by DIPEA (0.25 ml, 1.45 mmol) is then added to the reaction mixture and stirring is continued for 1 h. 100 ml of water are added, the reaction mixture is extracted with $Et_2O$ (2×100 ml), EtOAc/$Et_2O$ (1:1 mixture, 2×100 ml), EtOAc (1×50 ml) then the collected organic phases are washed with 0.5N HCl, 10% aqueous $NaHCO_3$, dried over a phase-separator cartridge and concentrated under reduced pressure to furnish the title compound (290 mg, 70%) used for the following step without further purification HPLC-MS (Method 1): $R_t$=0.79 min
MS (ESI pos): m/z=254 (M−tBu+H)$^+$ Example 49b Racemic Mixture

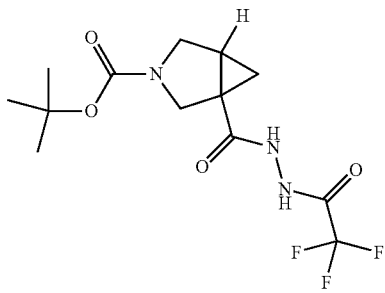 [SMILES: CC(C)(C)OC(=O)N1CC2CC2(C(=O)NNC(=O)C(F)(F)F)C1]

Trifluoroacetic anhydride (0.20 ml, 1.41 mmol) is added dropwise into a solution of example 48a (340 mg, 1.41 mmol) and DIPEA (0.27 ml, 1.55 mmol) in ACN at 0° C. then the reaction mixture is stirred at room temperature for 2 hours. Solvent is eliminated under reduced pressure and the residue is partitioned between water and EtOAc, organic layer is separated, washed with water, dried over Na$_2$SO$_4$ and concentrated under reduced pressure to obtain the title compound (450 mg, 95%)

HPLC-MS (Method 2): $R_t$=0.79 min
MS (ESI pos): m/z=355 (M+NH$_4$)$^+$

Example 49c

Racemic Mixture

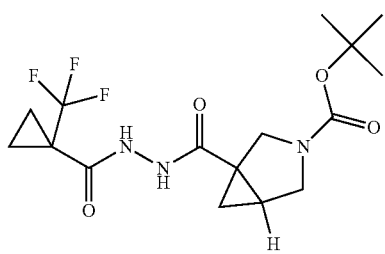 [SMILES: CC(C)(C)OC(=O)N1CC2CC2(C(=O)NNC(=O)C2(C(F)(F)F)CC2)C1]

HATU (997 mg, 2.62 mmol) and DIPEA (450 µl, 2.62 mmol) are added into a solution of 1-Trifluomethylcyclopropane-1-carboxylic acid (404 mg, 2.62 mmol) in 20 ml of anhydrous DMF and the reaction mixture is stirred for 30 minutes; Tert-butyl carbazate (315 mg, 2.38 mmol) is added and the resulting mixture is stirred 3 hours. Water and Et$_2$O are added and phases are separated; organic layer is washed with 0.5M HCl, 10% aqueous NaHCO$_3$, dried over phase-separator cartridge and concentrated under reduced pressure. The residue is dissolved in 5 ml of 1,4-dioxane, 4M HCl dioxane solution (9.7 ml, 38.8 mmol) is slowly added and the reaction mixture is stirred overnight. Solvent is removed under reduced pressure to obtain 403 mg of 1-Trifluoromethyl-cyclopropanecarboxylic acid hydrazide hydrochloride.

Title compound is then prepared in analogy to example 49a using 410 mg (1.80 mmol) of racemic 3-azabicyclo[3.1.0] hexane-1,3-dicarboxylic acid-3-tert-butyl ester, DIPEA (0.68 ml, 3.97 mmol), HATU (754 mg, 1.98 mmol), 1-Trifluoromethyl-cyclopropanecarboxylic acid hydrazide hydrochloride (403 mg, 1.97 mmol) to obtain 637 mg (94%) of product.

HPLC-MS (Method 2): $R_t$=0.94 min
MS (ESI pos): m/z=395 (M+NH$_4$)$^+$

Example 50a

Racemic Mixture

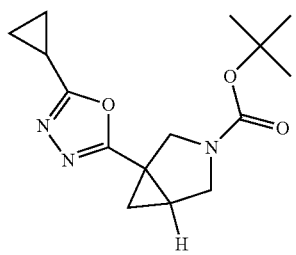 [SMILES: CC(C)(C)OC(=O)N1CC2CC2(c2nnc(C3CC3)o2)C1]

Burgess reagent (894 mg, 3.75 mmol) is added to example 49a (290 mg, 0.94 mmol) in anhydrous THF (5 mL) and the reaction mixture is then heated under microwave irradation (120° C.) for 25 min. EtOAc is added to the reaction mixture and the organic layer is washed with water, brine, dried over phase separator cartridge and concentrated under reduced pressure to give a residue that is purified by Si flash chromatography (eluent 25-100% EtOAc/cyclohexane) to furnish the title compound (162 mg, 59%).

HPLC-MS (Method 1): $R_t$=1.08 min
MS (ESI pos): m/z=292 (M+H)$^+$

Example 50b

Racemic Mixture

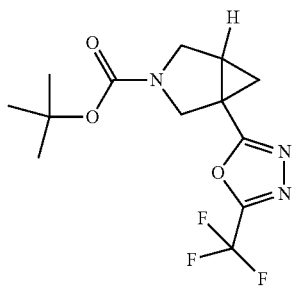 [SMILES: CC(C)(C)OC(=O)N1CC2CC2(c2nnc(C(F)(F)F)o2)C1]

The title compound is prepared in analogy to example 50a, starting from example 49b (100 mg, 0.30 mmol) in place of example 49a to obtain 50 mg of product (53%)

HPLC-MS (Method 2): $R_t$=1.25 min
MS (ESI pos): m/z=337 (M+NH$_4$)$^+$

Example 50c

Racemic Mixture

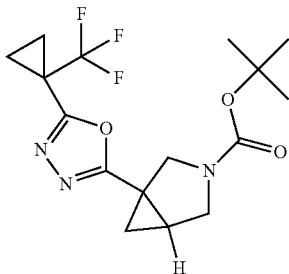 [SMILES: CC(C)(C)OC(=O)N1CC2CC2(c2nnc(C3(C(F)(F)F)CC3)o2)C1]

Title compound is prepared in analogy to example 50a starting from example 49c (637 mg, 1.69 mmol) in place of example 49a to obtain 546 mg (94%) of product.
HPLC-MS (Method 2): $R_t$=1.23 min
MS (ESI pos): m/z=360 (M+H)$^+$

Example 51a

Racemic Mixture, Syn

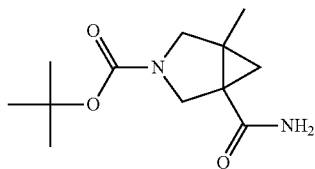 [SMILES: CC(C)(C)OC(=O)N1CC2(C)CC2(C(N)=O)C1]

Title compound is prepared in analogy to example 5a starting from example 41a (185.0 mg, 0.77 mmol) in place of racemic 3-azabicyclo[3.1.0]hexane-1,3-dicarboxylic acid-3-tert-butyl ester to obtain 130 mg (71%) of product.
HPLC-MS (Method 8): $R_t$=11.34 min
MS (ESI pos): m/z=184 (M−tBu)$^+$

Example 52a

Racemic Mixture, Syn

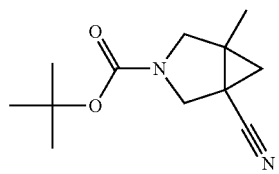 [SMILES: CC(C)(C)OC(=O)N1CC2(C)CC2(C#N)C1]

Title compound is prepared in analogy to example 8a starting from example 51a (128 mg, 0.53 mmol) in place of example 7a, using 10% citric acid aqueous solution in place of aqueous HCl to obtain 138 mg (content 80%, 93%) of product used without further purification.
HPLC-MS (Method 8): $R_t$=9.71 min
MS (ESI pos): m/z=166 (M−tBu)$^+$

Example 53a

Racemic Mixture, Syn

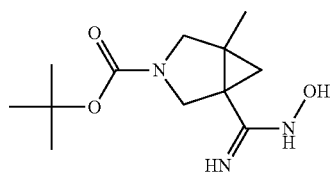 [SMILES: CC(C)(C)OC(=O)N1CC2(C)CC2(C(=N)NO)C1]

Title compound is prepared in analogy to example 19a starting from example 52a (138 mg, content 80%, 0.50 mmol) in place of example 18a to obtain 127 mg (100%) of product.
HPLC-MS (Method 6): $R_t$=2.00 min
MS (ESI pos): m/z=200 (M−tBu+H)$^+$

Example 54a

Racemic Mixture, Syn

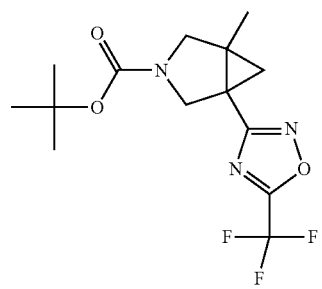 [SMILES: CC(C)(C)OC(=O)N1CC2(C)CC2(c2noc(C(F)(F)F)n2)C1]

Title compound is prepared in analogy to example 20a starting from example 53a (125 mg, 0.49 mmol) in place of example 19a and using 0-40% EtOAc/Cyclohexan as purification eluent to obtain 100 mg (61%) of product.
HPLC-MS (Method 8): $R_t$=9.76 min
MS (ESI pos): m/z=277 (M−tBu)$^+$

Example 55a

Racemic Mixture

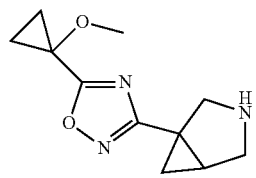 [SMILES: COC1(c2nc(C34CNCC3C4)no2)CC1]

Title compound is prepared in analogy to example 25a, starting from example 47a (450 mg, content 90%, 1.26 mmol) in place of 13a. After basic work-up the free amine is obtained (230 mg, 82%).
HPLC-MS (Method 1): $R_t$=0.59 min
MS (ESI pos): m/z=222 (M+H)$^+$

Example 55b

Racemic Mixture

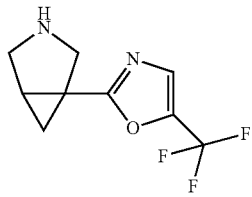 [SMILES: FC(F)(F)c1cnc(C23CNCC2C3)o1]

The title compound is prepared in analogy to example 55a starting from example 47b (310 mg, 0.97 mmol) in place of example 47a to obtain 130 mg (61%) of product.

HPLC-MS (Method 2): $R_t$=0.70 min
MS (ESI pos): m/z=219 (M+H)$^+$

Example 55c

Racemic Mixture

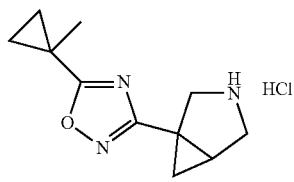

Title compound is prepared in analogy to example 25a, starting from example 47c (340 mg, content 90%, 1.0 mmol) in place of example 13a to obtain (190 mg, 80%).

HPLC-MS (Method 1): $R_t$=0.73 min
MS (ESI pos): m/z=206 (M+H)$^+$

Example 55d

Racemic Mixture

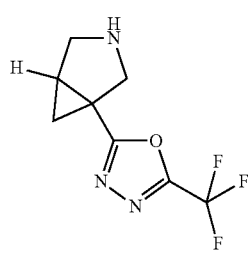 [SMILES: FC(F)(F)c1nnc(C23CNCC2C3)o1]

The title compound is prepared in analogy to example 55a starting from example 50b (330 mg, 1.03 mmol) in place of example 47a to obtain 200 mg (88%) of product.

HPLC-MS (Method 1): $R_t$=0.61 min
MS (ESI pos): m/z=220 (M+H)$^+$

Example 55e

Racemic Mixture

Example 50a (162 mg, 0.56 mmol) is dissolved in dichloromethane (5 mL) and trifluomacetic acid (0.5 mL) is added. Mixture is stirred overnight at room temperature, solvent is evaporated and the crude is first purified over SCX cartridge then by RP chromatography (eluent 5-40% ACN/Water) to furnish the title compound (100 mg, 94%).

HPLC-MS (Method 2): $R_t$=0.49 min, broad
MS (ESI pos): m/z=192 (M+H)$^+$

Example 55f

Racemic Mixture

Title compound is prepared in analogy to example 25a, starting from example 50c (546 mg, 1.52 mmol) to obtain 450 mg (100%) of product.

HPLC-MS (Method 1): $R_t$=0.65 min
MS (ESI pos): m/z=260 (M+H)$^+$

Example 55g

Racemic Mixture, Syn

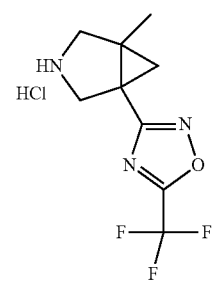 [SMILES: Cl ; CC12CNCC1(c1noc(C(F)(F)F)n1)C2]

Title compound is prepared in analogy to example 25a starting from example 54a (100 mg, 0.30 mmol) in place of example 13a to obtain 90 mg (81%) of product.

HPLC-MS (Method 6): $R_t$=2.01 min
MS (ESI pos): m/z=234 (M+H)$^+$

Example 56a

Racemic Mixture

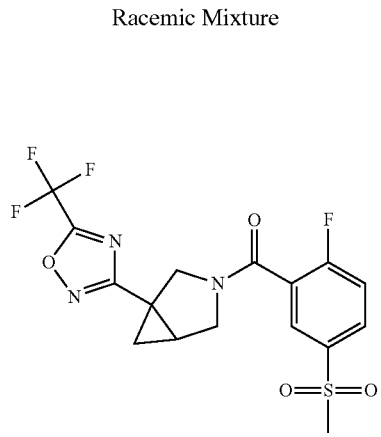

2-Fluoro-5-methanesulfonyl-benzoic acid (563.0 mg, 2.58 mmol), HATU (1064 mg, 2.80 mmol) and DIPEA (1.12 ml, 6.45 mmol) are added to example 25k (550.0 mg, 2.15 mmol) in DMF (10 mL). The reaction mixture is stirred at room temperature overnight. Volatiles are evaporated under reduced pressure and the resulting residue partitioned between DCM and saturated NaHCO₃. The organic layer is washed with brine, concentrated under reduced pressure giving a residue that is purified by flash chromatography (eluent 12-100% EtOAc/cyclohexane) to furnish the title compound (690 mg, 77%).

HPLC-MS (Method 6): $R_t$=10.69 min
MS (ESI pos): m/z=420 (M+H)$^+$

Exemplary Embodiments of Active Compounds

Example 1

Diastereomeric Mixture

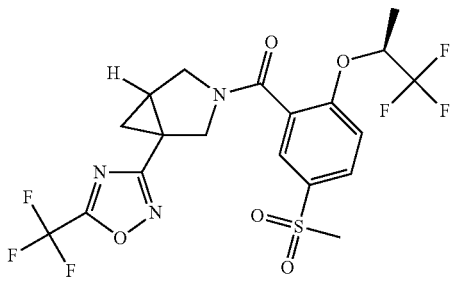 [SMILES: C[C@H](Oc1ccc(S(C)(=O)=O)cc1C(=O)N1CC2CC2(c2noc(C(F)(F)F)n2)C1)C(F)(F)F]

Example 9a (54 mg, 0.12 mmol), is dissolved in ACN (2 mL) in a microwave vessel and trifluoroacetic anhydride (23 µl, 0.16 mmol) and dry TEA (52 µl, 0.37 mmol) are added. Mixture is heated under microwave irradation at 100° C. for 20 min. Trifluoroacetic anhydride (100 µl, 0.70 mmol) is added and the mixture is heated under microwave irradation at 100° C. for 30 min. Solvents are evaporated and the crude purified by flash chromatography (eluent DCM/MeOH 98:2) to obtain the title compound (54 mg, 85%).

HPLC-MS (Method 5): $R_t$=9.72 min
MS (APCI): m/z=514 (M+H)$^+$

The diastereoisomers of the title compound are separated by HPLC using a chiral stationary phase.
Method for Separation:
HPLC apparatus type: Agilent 1100; column: Daicel chiralpack AD-H, 5.0 µm, 250 mm×20 mm; method: eluent hexane/IPA 70:30; flow rate: 12 mL/min, temperature: 25° C.; UV Detection: 230 nm
Example of Separation by Chiral HPLC:
Submitted to separation: 78 mg of Example 1;
Obtained: 27 mg of Diastereoisomer 1 (Exp. 2) and 42 mg of Diastereoisomer 2 (Exp. 3)

| Example 2: Diastereoisomer 1 | Example 3: Diastereoisomer 2 |
|---|---|
| Unknown absolute stereochemistry at bridgehead | Unknown absolute stereochemistry at bridgehead |// 
| 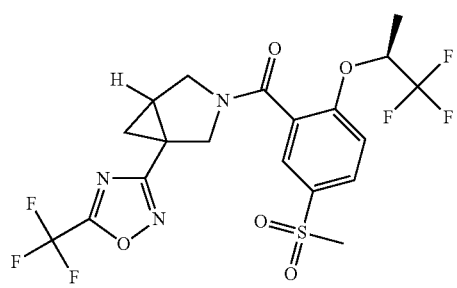 [SMILES: C[C@H](Oc1ccc(S(C)(=O)=O)cc1C(=O)N1CC2CC2(c2noc(C(F)(F)F)n2)C1)C(F)(F)F] | 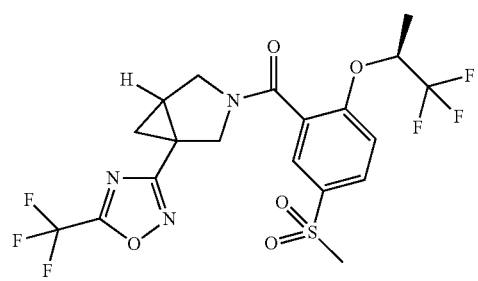 [SMILES: C[C@H](Oc1ccc(S(C)(=O)=O)cc1C(=O)N1CC2CC2(c2noc(C(F)(F)F)n2)C1)C(F)(F)F] |

| Example | Chiral HPLC $R_t$ [min] | HPLC-MS (Method 6): $R_t$ [min] | MS (ESI pos): m/z |
|---|---|---|---|
| Exp. 2 | 6.146 (Method 9) | 11.64 | 514 |
| Exp. 3 | 8.218 (Method 9) | 11.65 | 514 |

Example 4 (Diastereoisomer 1, Unknown Absolute Stereochemistry at Bridgehead) and Example 5 (Diastereoisomer 2, Unknown Absolute Stereochemistry at Bridgehead)

The mixture of the title compounds is prepared as described for example 1, starting from example 9b (73 mg, 0.17 mmol); Obtained: 54 mg of diatereomeric mixture (62%). The title compounds are obtained by separation of such mixture by HPLC using a chiral stationary phase.
Method for Separation:

HPLC apparatus type: Agilent 1100; column: Daicel chiralpack AD-H, 5.0 μm, 250 mm×20 mm; method: eluent hexane/IPA 70:30; flow rate: 12 mL/min, temperature: 25° C.; UV Detection: 230 nm
Example of Separation by Chiral HPLC:

Submitted to separation: 54 mg of Diastereomeric mixture;
Obtained: 23 mg of Diastereoisomer 1 (exp. 4) and 23 mg of Diastereoisomer 2 (Exp. 5)

Example 9a (54 mg, 0.12 mmol) is dissolved in ACN (2 mL) in a microwave vessel and acetic anhydride (15 μl, 0.16 mmol) and dry TEA (52 μl, 0.37 mmol) are added. The reaction mixture is heated under microwave irradation at 100° C. for 20 min. Dry TEA (100 μl, 0.71 mmol) is added and the reaction mixture is heated under microwave irradation at 150° C. for 30 min. Solvents are evaporated and the crude purified by flash cromatography (eluent DCM/MeOH 98:2) to obtain the title compound (38 mg, 67%)
HPLC-MS (Method 5): $R_t$=7.97 min
MS (APCI): m/z=460 (M+H)$^+$ The diastereoisomers of the title compound are separated by HPLC using a chiral stationary phase.

Method for Separation:

HPLC apparatus type: Agilent 1100; column: Daicel chiralpack AD-H, 5.0 μm, 250 mm×20 mm; method: eluent hexane/IPA 70:30; flow rate: 10 mL/min, Temperature: 25° C.; UV Detection: 230 nm

| Example 4: Diastereoisomer 1 Unknown absolute stereochemistry at bridgehead | Example 5: Diastereoisomer 2 Unknown absolute stereochemistry at bridgehead |
|---|---|
| 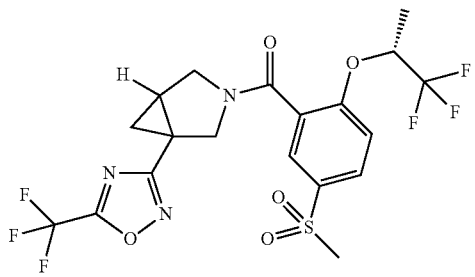 [SMILES: C[C@@H](Oc1ccc(S(C)(=O)=O)cc1C(=O)N1CC2CC2(c2noc(C(F)(F)F)n2)C1)C(F)(F)F] | 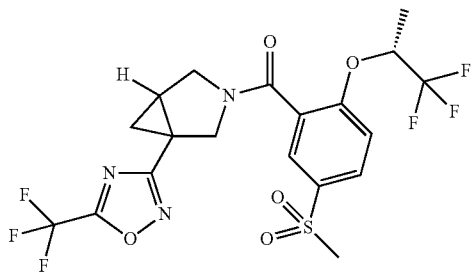 [SMILES: C[C@@H](Oc1ccc(S(C)(=O)=O)cc1C(=O)N1CC2CC2(c2noc(C(F)(F)F)n2)C1)C(F)(F)F] |

| Example | Chiral HPLC $R_t$ [min] | HPLC-MS (Method 6): $R_t$ [min] | MS (ESI pos): m/z |
|---|---|---|---|
| Exp. 4 | 6.868 (Method 9) | 11.62 | 514 |
| Exp. 5 | 8.214 (Method 9) | 11.63 | 514 |

Example 6

Diastereomeric Mixture

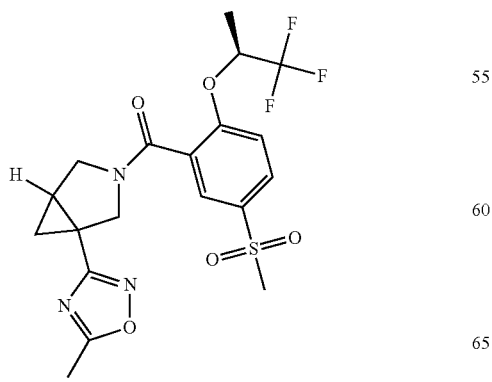

Example of Separation by Chiral HPLC:
Submitted to separation: 200 mg of Example 6;
Obtained: 61 mg of Diastereoisomer 1 (Exp. 7) and 75 mg of Diastereoisomer 2 (Exp. 8)

| | Example 7: Diastereoisomer 1 Unknown absolute stereochemistry at bridgehead | Example 8: Diastereoisomer 2 Unknown absolute stereochemistry at bridgehead | |
|---|---|---|---|
| | 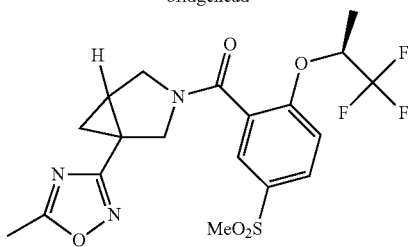 | 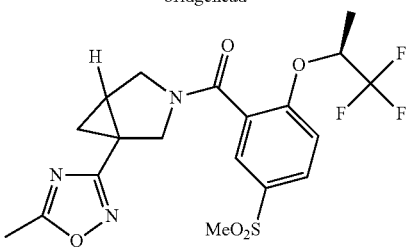 | |
| Example | Chiral HPLC R$_t$ [min] | HPLC-MS (Method 5): R$_t$ [min] | MS (APCI pos): m/z |
| Exp. 7 | 11.561 (Method 12) | 7.55 | 460 |
| Exp. 8 | 16.154 (Method 12) | 7.57 | 460 |

Example 9

Diastereomeric Mixture

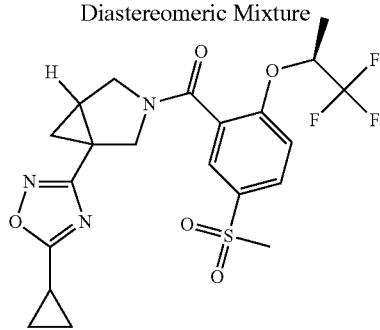

To a solution of example 9a (0.055 g, 0.12 mmol) in dry ACN (2 mL), dicyclopropyl anhydride (0.075 g, 90% content, 0.44 mmol, prepared as described in J. Org. Chem., 67, 5226-5231; 2002) and dry TEA (0.088 mL, 0.62 mmol) are added and the mixture heated under microwaves irradation (100° C.) for 50 min and then heated at 150° C. for additional 30 min. Solvents evaporated, crude purified by flash cromatography (cyclohexane/EtOAc from 50:50 to 20:80) to obtain the title compound (0.033 g, 54%).

HPLC-MS (Method 6): R$_t$=10.80 min
MS (ESI pos): m/z=486 (M+H)$^+$

The diastereoisomers of the title compound are separated by HPLC using a chiral stationary phase.

Method for Separation:
HPLC apparatus type: Agilent 1100; column: Daicel chiralpack AS-H, 5.0 μm, 250 mm×20 mm; method: eluent hexane/EtOH 70:30; flow rate: 15 mL/min, Temperature: 25° C.; UV Detection: 230 nm Example of Separation by Chiral HPLC:
Submitted to separation: 200 mg of Example 9
Obtained: 84 mg of Diastereoisomer 1 (Exp. 10) and 78 mg of Diastereoisomer 2 (Exp. 11)

| | Example 10: Diastereoisomer 1 Unknown absolute stereochemistry at bridgehead | Example 11: Diastereoisomer 2 Unknown absolute stereochemistry at bridgehead | |
|---|---|---|---|
| | 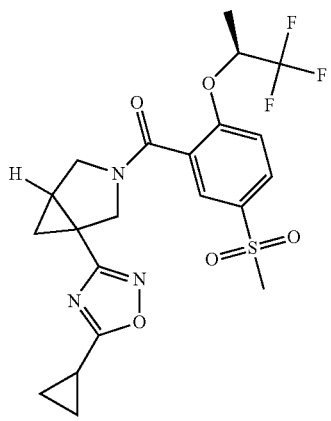 [SMILES: C[C@H](Oc1ccc(S(C)(=O)=O)cc1C(=O)N1CC2CC2(c2noc(C3CC3)n2)C1)C(F)(F)F] | 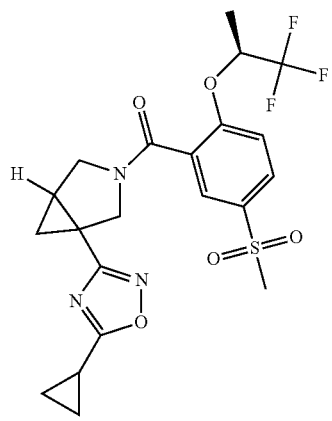 [SMILES: C[C@H](Oc1ccc(S(C)(=O)=O)cc1C(=O)N1CC2CC2(c2noc(C3CC3)n2)C1)C(F)(F)F] | |
| Example | Chiral HPLC R$_t$ [min] | HPLC-MS (Method 5): R$_t$ [min] | MS (APCI pos): m/z |
| Exp. 10 | 10.736 (Method 15) | 8.29 | 486 |

-continued

| Exp. 11 | 12.824 (Method 15) | 8.29 | 486 |

Example 12

Diastereomeric Mixture

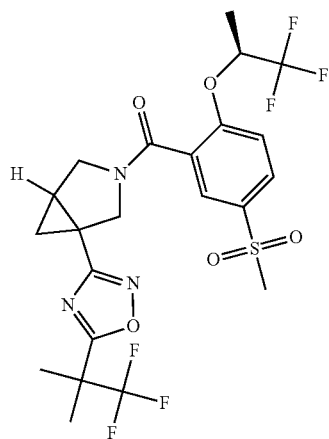 [SMILES: C[C@H](Oc1ccc(S(C)(=O)=O)cc1C(=O)N1CC2CC2(c2noc(C(C)(C)C(F)(F)F)n2)C1)C(F)(F)F]

N,N'-Dicyclohexylcarbodiimide (330 mg, 1.60 mmol) is added to 3,3,3-trifluoro-2,2-dimethylpropionic acid (500 mg, 3.20 mmol) in DCM and stirring is continued for 2 d at room temperature. Volatiles are evaporated under reduced pressure and the resulting residue, example 9a (100 mg, 0.23 mmol) and TEA (160 µl, 0.15 mmol) in ACN (2 mL) are heated under microwave irradiation (100° C.) for two 30 min cycles. Solvents are evaporated under reduced pressure and the resulting residue purified by flash cromatography (cyclohexane/EtOAc from 100:0 to 20:80) followed by preparative HPLC (stationary phase: Xterra C18 5 µm 30×100 mm. Mobile phase: ACN/H$_2$O+NH$_4$COOH 5 mmol). Fractions containing the title compound are combined and freeze dried to furnish the title compound (35 mg, 27%).
HPLC-MS (Method 5): R$_t$=9.63 min
MS (APCI): m/z=556 (M+H)$^+$

Example 13

Diastereomeric Mixture

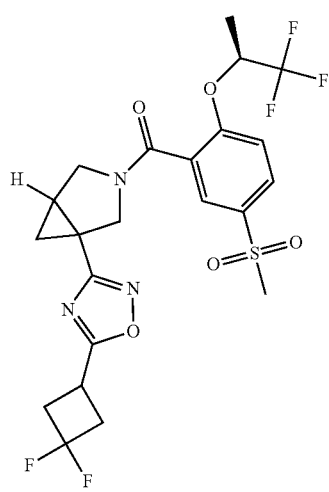 [SMILES: C[C@H](Oc1ccc(S(C)(=O)=O)cc1C(=O)N1CC2CC2(c2noc(C3CC(F)(F)C3)n2)C1)C(F)(F)F]

The title compound is prepared as described for example 12, employing example 9a (100 mg, 96% content, 0.22 mmol) and 3,3-difluorocyclobutanecarboxylic acid (142 mg, 1.04 mmol) in the place of 3,3,3-trifluoro-2,2-dimethylpropionic acid. Obtained: 80 mg (70%).
HPLC-MS (Method 6): R$_t$=11.15 min
MS (ESI pos): m/z=536 (M+H)$^+$

Example 14

Diastereomeric Mixture

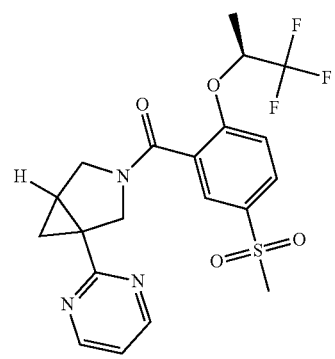 [SMILES: C[C@H](Oc1ccc(S(C)(=O)=O)cc1C(=O)N1CC2CC2(c2ncccn2)C1)C(F)(F)F]

Example 10a (150 mg, 83% content, 0.3 mmol) and 1,1,3,3-tetramethoxypropane (1.5 mL) are heated to 175° C. in a microwave oven for 1 hour. Water and DCM are added to the reaction mixture and the organic layer dried over Na$_2$SO$_4$, filtered and concentrated under reduced pressure giving a residue that is purified by flash chromatography (eluent 70-100% EtOAc/petroleum ether) to furnish the title compound (44 mg, 33%).
HPLC-MS (Method 5): R$_t$=9.35 min
MS (APCI): m/z=456 (M+H)$^+$

Example 15

Diastereomeric Mixture

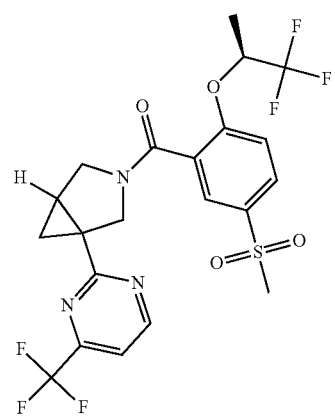 [SMILES: C[C@H](Oc1ccc(S(C)(=O)=O)cc1C(=O)N1CC2CC2(c2nccc(C(F)(F)F)n2)C1)C(F)(F)F]

Example 10a (95 mg, 0.23 mmol) in 4-ethoxy-1,1,1-trifluoro-3-buten-2-one (3.0 mL) is heated under microwave irradation at 70° C. for 5 min and then at 110° C. for 5 min. Volatiles are evaporated under reduced pressure and the resulting residue purified by flash chromatography (eluent 50-80% cyclohexane/EtOAc) to furnish the title compound (100 mg, 84%)

HPLC-MS (Method 6): $R_t$=11.56 min
MS (ESI pos): m/z=524 (M+H)$^+$

The diastereoisomers of the title compound are separated by HPLC using a chiral stationary phase.

Method for Separation:
HPLC apparatus type: Agilent 1100; column: Daicel chiralpack AS-H, 5.0 μm, 250 mm×20 mm; method: eluent hexane/IPA 75:25; flow rate: 15 mL/min, Temperature: 25° C.; UV Detection: 230 nm Example of Separation by Chiral HPLC:
Submitted to separation: 100 mg of Example 15;
Obtained: 45 mg of Diastereoisomer 1 (Exp. 16) and 48 mg of Diastereoisomer 2 (Exp. 17)

Example 18 (Diastereoisomer 1, Unknown Absolute Stereochemistry at Bridgehead) and Example 19 (Diastereoisomer 2, Unknown Absolute Stereochemistry at Bridgehead)

The mixture of the title compounds is prepared as described for example 15, starting from example 10b (95 mg, 0.23 mmol); obtained 75 mg of the diastereomeric mixture (59%). The title compounds are obtained by separation of such mixture by HPLC using a chiral stationary phase.

Method for Separation:
HPLC apparatus type: Agilent 1100; column: Daicel chiralpack AS-H, 5.0 μm, 250 mm×20 mm; method: eluent hexane/EtOH 75:25; flow rate: 15 mL/min, Temperature: 25° C.; UV Detection: 230 nm Example of Separation by Chiral HPLC:
Submitted to separation: 70 mg of Diastereomeric mixture;
Obtained: 33 mg of Diastereoisomer 1 (exp. 18) and 33 mg of Diastereoisomer 2 (Exp. 19)

| Example 16: Diastereoisomer 1 Unknown absolute stereochemistry at bridgehead | Example 17: Diastereoisomer 2 Unknown absolute stereochemistry at bridgehead |
|---|---|
| 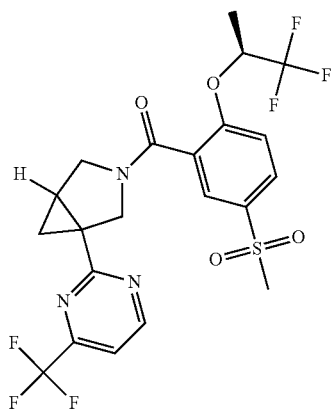 [SMILES: C[C@H](Oc1ccc(S(C)(=O)=O)cc1C(=O)N1CC2CC2(c2nccc(C(F)(F)F)n2)C1)C(F)(F)F] | 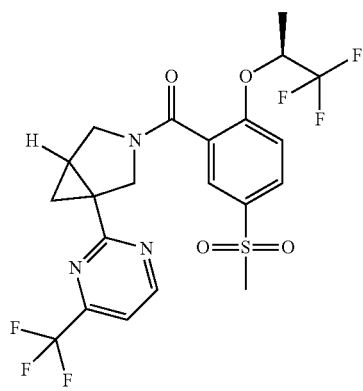 [SMILES: C[C@H](Oc1ccc(S(C)(=O)=O)cc1C(=O)N1CC2CC2(c2nccc(C(F)(F)F)n2)C1)C(F)(F)F] |

| Example | Chiral HPLC $R_t$ [min] | HPLC-MS (Method 5): $R_t$ [min] | MS (APCIpos): m/z |
|---|---|---|---|
| Exp. 16 | 9.185 (Method 14) | 8.96 | 524 |
| Exp. 17 | 10.943 (Method 14) | 8.90 | 524 |

| | Example 18: Diastereoisomer 1 Unknown absolute stereochemistry at bridgehead | Example 19: Diastereoisomer 2 Unknown absolute stereochemistry at bridgehead | |
|---|---|---|---|
| | 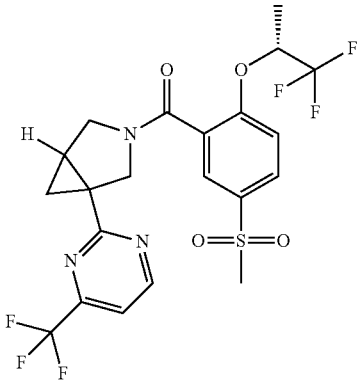 [SMILES: C[C@@H](Oc1ccc(S(C)(=O)=O)cc1C(=O)N1CC2CC2(c2nccc(C(F)(F)F)n2)C1)C(F)(F)F] | 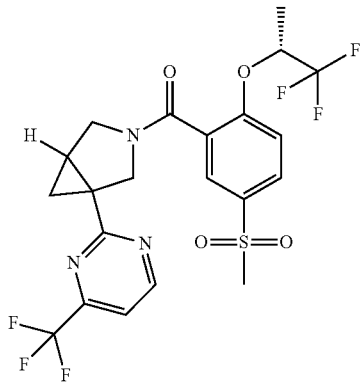 [SMILES: C[C@@H](Oc1ccc(S(C)(=O)=O)cc1C(=O)N1CC2CC2(c2nccc(C(F)(F)F)n2)C1)C(F)(F)F] | |
| Example | Chiral HPLC $R_t$ [min] | HPLC-MS (Method 5): $R_t$ [min] | MS (APCI): m/z |
| Exp. 18 | 9.45 (Method 13) | 8.96 | 524 |
| Exp. 19 | 10.602 (Method 13) | 8.94 | 524 |

Example 20

Diastereomeric Mixture

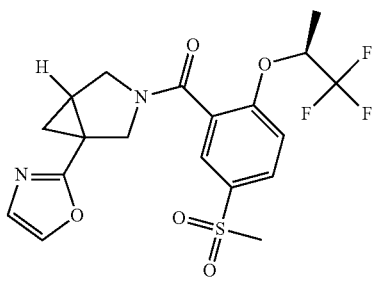 [SMILES: C[C@H](Oc1ccc(S(C)(=O)=O)cc1C(=O)N1CC2CC2(c2ncco2)C1)C(F)(F)F]

Example 4a (19 mg, 0.061 mmol), HATU (27 mg, 0.072 mmol) and TEA (39 µl, 0.266 mmol) are added to example 25a (15 mg) in DMF (1 mL). The reaction mixture is stirred at room temperature overnight. Volatiles are evaporated under reduced pressure and the resulting residue partitioned between EtOAc and saturated NaHCO$_3$. The organic layer is washed with brine, dried over Na$_2$SO$_4$, filtered and concentrated under reduced pressure giving a residue that is purified by flash chromatography (eluent 50-100% EtOAc/cyclohexane) to furnish the title compound (8 mg).

HPLC-MS (Method 5): $R_t$=7.75 min

MS (APCI): m/z=445 (M+H)$^+$

Example 21

Diastereomeric Mixture

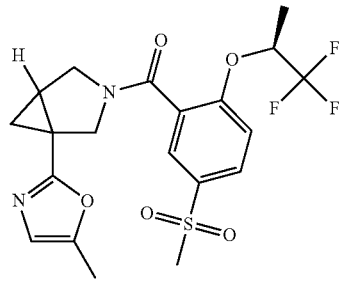 [SMILES: Cc1cnc(C23CC2CN(C(=O)c2cc(S(C)(=O)=O)ccc2O[C@@H](C)C(F)(F)F)C3)o1]

The title compound is prepared in analogy to example 20, starting from example 25b (87 mg, 95% content, 0.41 mmol) and employing TBTU (146 mg, 0.45 mmol) in the place of HATU and DIPEA (354 µl, 2.067 mmol) in the place of TEA. Obtained: 140 mg (73%).

HPLC-MS (Method 5): $R_t$=7.98 min

MS (APCI): m/z=459 (M+H)$^+$

The diastereoisomers of the title compound are separated by HPLC using a chiral stationary phase.

Method for Separation:

HPLC apparatus type: Waters 600 Pump; column: Daicel Chiralpack AD-H, 5.0 µm, 250 mm×20 mm; method: eluent hexane/IPA 75:25; flow rate: 10 mL/min, Temperature: 25° C.; UV Detection: 230 nm Example of Separation by Chiral HPLC:

Submitted to separation: 110 mg of Example 21 prepared as described above;

Obtained: 43 mg of Diastereoisomer 1 (Exp. 22) and 47 mg of Diastereoisomer 2 (Exp. 23)

| | Example 22: Diastereoisomer 1 Unknown absolute stereochemistry at bridgehead | Example 23: Diastereoisomer 2 Unknown absolute stereochemistry at bridgehead |
|---|---|---|
| | 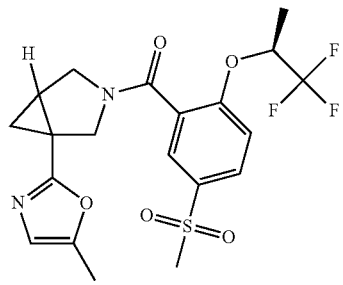 [SMILES: Cc1cnc(C23CC2CN(C(=O)c2cc(S(C)(=O)=O)ccc2O[C@@H](C)C(F)(F)F)C3)o1] | 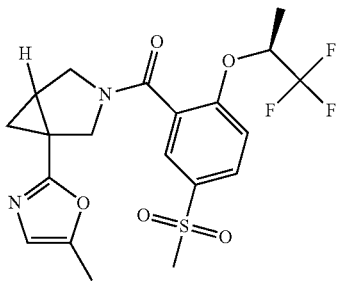 [SMILES: Cc1cnc(C23CC2CN(C(=O)c2cc(S(C)(=O)=O)ccc2O[C@@H](C)C(F)(F)F)C3)o1] |

| Example | Chiral HPLC $R_t$ [min] | HPLC-MS (Method 5): $R_t$ [min] | MS (APCI): m/z |
|---|---|---|---|
| Exp. 22 | 12.002 (Method 11) | 7.88 | 459 |
| Exp. 23 | 16.017 (Method 11) | 7.92 | 459 |

Example 24

Diastereomeric Mixture

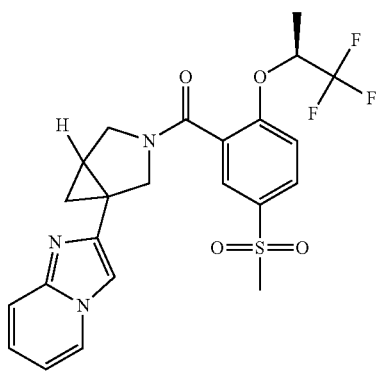 [SMILES: C[C@H](Oc1ccc(S(C)(=O)=O)cc1C(=O)N1CC2CC2(c2cn3ccccc3n2)C1)C(F)(F)F]

The title compound is prepared as described for example 20, starting from example 25c (180 mg, 75% content, 0.57 mmol). Obtained: 180 mg (63%).

HPLC-MS (Method 5): $R_t$=7.77 min MS (APCI): m/z=494 (M+H)⁺

Example 25

Diastereomeric Mixture

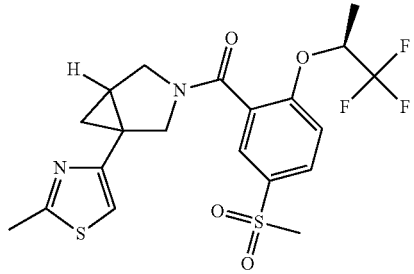 [SMILES: Cc1nc(C23CC2CN(C(=O)c2cc(S(C)(=O)=O)ccc2O[C@@H](C)C(F)(F)F)C3)cs1]

The title compound is prepared as described for example 20, starting from example 25d (33 mg, 0.15 mmol). Obtained: 52 mg (72%)

HPLC-MS (Method 5): $R_t$=8.48 min
MS (APCI): m/z=475 (M+H)⁺

Example 26

Diastereomeric Mixture

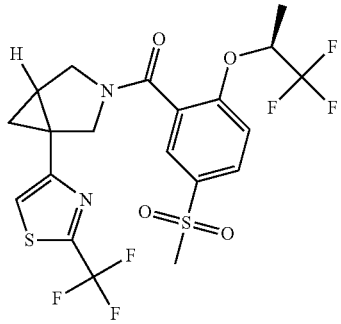 [SMILES: C[C@H](Oc1ccc(S(C)(=O)=O)cc1C(=O)N1CC2CC2(c2csc(C(F)(F)F)n2)C1)C(F)(F)F]

The title compound is prepared in analogy to example 20, starting from example 25e (87 mg, 0.32 mmol) and employing TBFU (114 mg, 0.35 mmol) in the place of HATU and DIPEA (275 µl, 1.607 mmol) in the place of TEA. Obtained: 102 mg (70%).

HPLC-MS (Method 6): $R_t$=12.00 min
MS (ESI): m/z=529 (M+H)⁺

The diastereoisomers of the title compound are separated by HPLC using a chiral stationary phase.
Method for Separation:
HPLC apparatus type: Waters 600 Pump; column: Daicel Chiralpack AD-H, 5.0 µm, 250 mm×20 mm; method: eluent hexane/IPA 70:30; flow rate: 15 mL/min, Temperature: 25° C.; UV Detection: 230 nm
Example of Separation by Chiral HPLC:
Submitted to separation: 100 mg of Example 26 prepared as described above;
Obtained: 40 mg of Diastereoisomer 1 (Exp. 27) and 43 mg of Diastereoisomer 2 (Exp. 28)

| Example 27: Diastereoisomer 1 Unknown absolute stereochemistry at bridgehead | Example 28: Diastereoisomer 2 Unknown absolute stereochemistry at bridgehead |
|---|---|
| 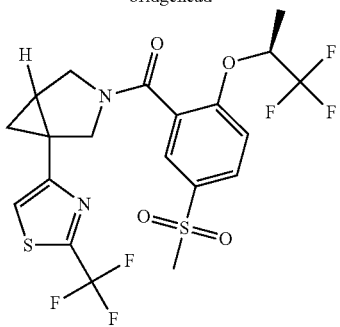 | 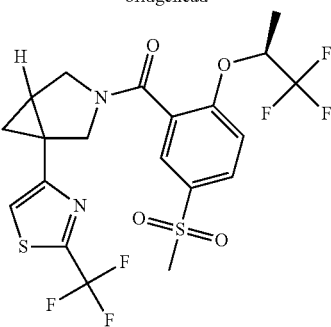 |

| Example | Chiral HPLC $R_t$ [min] | HPLC-MS (Method 5): $R_t$ [min] | MS (APCI): m/z |
|---|---|---|---|
| Exp. 27 | 7.217 (Method 10) | 9.37 | 529 |
| Exp. 28 | 13.157 (Method 10) | 9.33 | 529 |

Example 29

Diastereomeric Mixture

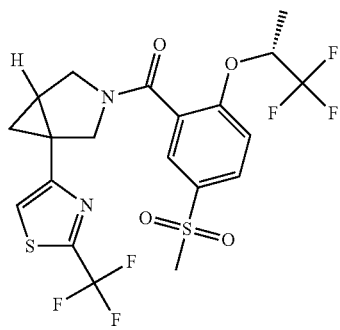 [SMILES: C[C@@H](Oc1ccc(S(C)(=O)=O)cc1C(=O)N1CC2CC2(c2csc(C(F)(F)F)n2)C1)C(F)(F)F]

The title compound is prepared as described for example 20, starting from example 25e (87 mg, 0.32 mmol) and employing example 4b (110 mg, 0.35 mmol) in the place of example 4a, TBTU (114 mg, 0.35 mmol) in the place of HATU and DIPEA (275 µl, 1.607 mmol) in the place of TEA. Obtained: 104 mg (60%).

HPLC-MS (Method 6): $R_t$=12.01 min

MS (ESI): m/z=529 (M+H)$^+$

The diastereoisomers of the title compound are separated by HPLC using a chiral stationary phase.

Method for Separation:

HPLC apparatus type: Waters 600 Pump; column: Daicel Chiralpack AD-H, 5.0 µm, 250 mm×20 mm; method: eluent hexane/IPA 70:30; flow rate: 12 mL/min, Temperature: 25° C.; UV Detection: 210 nm Example of Separation by Chiral HPLC:

Submitted to separation: 100 mg of Example 29 prepared as described above;

Obtained: 37 mg of Diastereoisomer 1 (Exp. 30) and 52 mg of Diastereoisomer 2 (Exp. 31)

| Example 30: Diastereoisomer 1 Unknown absolute stereochemistry at bridgehead | Example 31: Diastereoisomer 2 Unknown absolute stereochemistry at bridgehead |
|---|---|
| 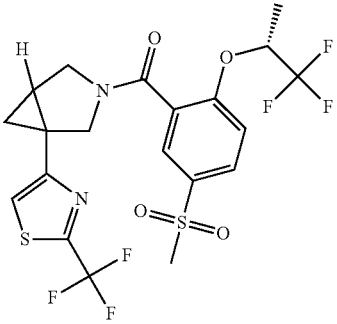 [SMILES: C[C@@H](Oc1ccc(S(C)(=O)=O)cc1C(=O)N1CC2CC2(c2csc(C(F)(F)F)n2)C1)C(F)(F)F] | 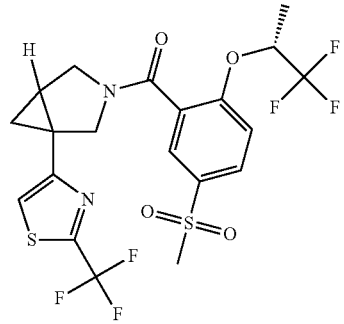 [SMILES: C[C@@H](Oc1ccc(S(C)(=O)=O)cc1C(=O)N1CC2CC2(c2csc(C(F)(F)F)n2)C1)C(F)(F)F] |

| Example | Chiral HPLC $R_t$ [min] | HPLC-MS (Method 6): $R_t$ [min] | MS (ESI): m/z |
|---|---|---|---|
| Exp. 30 | 9.033 (Method 10) | 11.83 | 529 |

| Exp. 31 | 16.773 (Method 10) | 11.83 | 529 |

Example 32

Diastereomeric Mixture

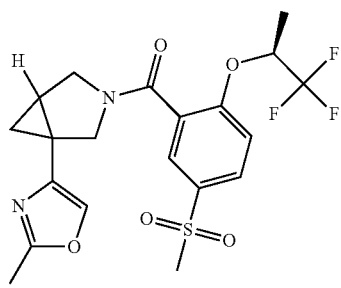 [SMILES: Cc1nc(C23CC2CN(C(=O)c2cc(S(C)(=O)=O)ccc2O[C@@H](C)C(F)(F)F)C3)co1]

The title compound is prepared in analogy to example 20, starting from example 25f (13 mg, 0.063 mmol) and employing TBTU (22 mg, 0.070 mmol) in the place of HATU and DIPEA (54 µl, 0.316 mmol) in the place of TEA. Obtained: 17 mg (58%).

HPLC-MS (Method 5): $R_t$=7.70 min

MS (APCI): m/z=459 (M+H)$^+$

Example 33

Diastereomeric Mixture

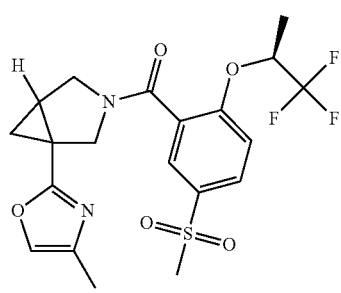 [SMILES: Cc1coc(C23CC2CN(C(=O)c2cc(S(C)(=O)=O)ccc2O[C@@H](C)C(F)(F)F)C3)n1]

The title compound is prepared in analogy to example 20, starting from example 25g (34 mg, 82% content, 0.14 mmol) and employing TBTU (49 mg, 0.15 mmol) as coupling agent and DIPEA (119 µl, 0.69 mmol) as base. Obtained: 21 mg (33%).

HPLC-MS (Method 6): $R_t$=10.06 min

MS (ESI pos): m/z=459 (M+H)$^+$

Example 34

Diastereomeric Mixture

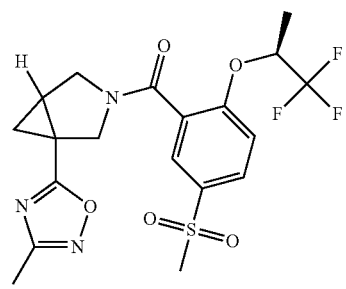 [SMILES: Cc1noc(C23CC2CN(C(=O)c2cc(S(C)(=O)=O)ccc2O[C@@H](C)C(F)(F)F)C3)n1]

The title compound is prepared in analogy to example 20, starting from example 25h (64 mg, 0.31 mmol) and employing TBTU (111 mg, 0.35 mmol) as coupling agent and DIPEA (270 µl, 1.574 mmol) as base. Obtained: 124 mg (85%).

HPLC-MS (Method 5): $R_t$=7.65 min

MS (APCI): m/z=460 (M+H)$^+$

Example 35

Diastereomeric Mixture

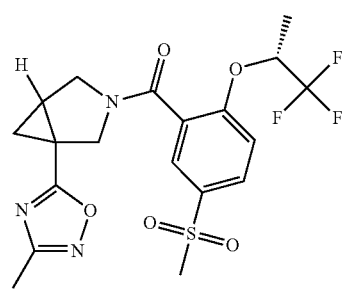 [SMILES: Cc1noc(C23CC2CN(C(=O)c2cc(S(C)(=O)=O)ccc2O[C@H](C)C(F)(F)F)C3)n1]

The title compound is prepared in analogy to example 20, starting from example 25h (64 mg, 0.31 mmol) and employing example 4b (103 mg, 0.33 mmol) in the place of example 4a, TBTU (111 mg, 0.35 mmol) as coupling agent and DIPEA (270 µl, 1.574 mmol) as base. Obtained: 90 mg (62%).

HPLC-MS (Method 5): $R_t$=7.63 min

MS (APCI): m/z=460 (M+H)$^+$

Example 36

Diastereomeric Mixture

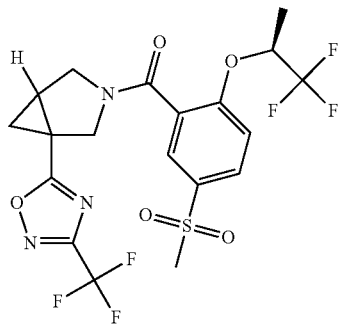 [SMILES: C[C@H](Oc1ccc(S(C)(=O)=O)cc1C(=O)N1CC2CC2(c2nc(C(F)(F)F)no2)C1)C(F)(F)F]

The title compound is prepared in analogy to example 20, starting from example 25i (80 mg, 0.31 mmol) and employing TBTU (111 mg, 0.35 mmol) as coupling agent and DIPEA (268 μl, 1.565 mmol) as base. Obtained: 102 mg (63%).

HPLC-MS (Method 5): $R_t$=9.14 min

MS (APCI): m/z=514 (M+H)$^+$

Example 37

Diastereomeric Mixture

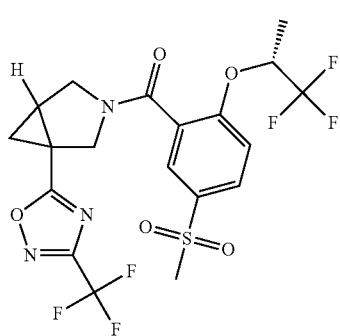 [SMILES: C[C@@H](Oc1ccc(S(C)(=O)=O)cc1C(=O)N1CC2CC2(c2nc(C(F)(F)F)no2)C1)C(F)(F)F]

The title compound is prepared in analogy to example 20, starting from example 25i (80 mg, 0.313 mmol) and employing example 4b (98 mg, 0.31 mmol) in the place of example 4a, TBTU (111 mg, 0.35 mmol as coupling agent and DIPEA (268 μl, 1.56 mmol) as base. Obtained: 120 mg (74%).

HPLC-MS (Method 5): $R_t$=9.14 min

MS (APCI): m/z=514 (M+H)$^+$

Example 38

Diastereomeric Mixture

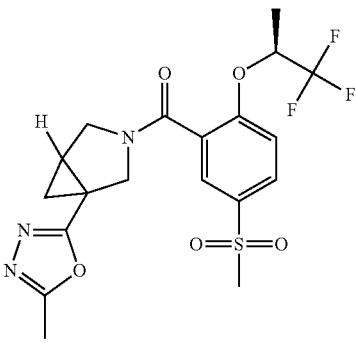 [SMILES: Cc1nnc(C23CC2CN(C(=O)c2cc(S(C)(=O)=O)ccc2O[C@@H](C)C(F)(F)F)C3)o1]

The title compound is prepared as described for example 20, starting from example 25j (58 mg, 0.29 mmol). Obtained: 11 mg (8%).

HPLC-MS (Method 5): $R_t$=7.14 min

MS (APCI): m/z=460 (M+H)$^+$

Example 39

Diastereomeric Mixture

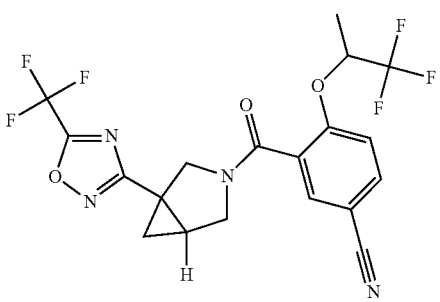 [SMILES: CC(Oc1ccc(C#N)cc1C(=O)N1CC2CC2(c2noc(C(F)(F)F)n2)C1)C(F)(F)F]

The title compound is prepared in analogy to example 20, starting from example 25k (50 mg, 0.19 mmol) and employing example 4d (61 mg, 0.23 mmol) in the place of example 4a and DIPEA (234 μl, 1.37 mmol) as base. Obtained: 71 mg (78%).

HPLC-MS (Method 5): $R_t$=9.76 min

MS (APCI): m/z=461 (M+H)$^+$

Example 40

Diastereomeric Mixture

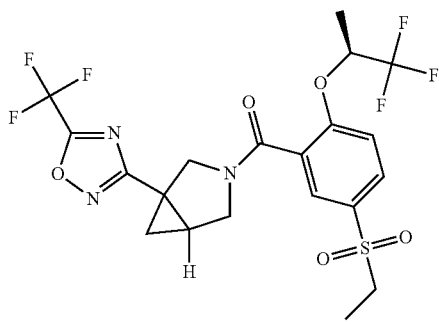 [SMILES: CCS(=O)(=O)c1ccc(O[C@@H](C)C(F)(F)F)c(C(=O)N2CC3CC3(c3noc(C(F)(F)F)n3)C2)c1]

The title compound is prepared in analogy to example 20, starting from example 25k (50 mg, 0.19 mmol) and employing example 4e (77 mg, 0.235 mmol) in the place of example 4a and DIPEA (268 µl, 1.565 mmol) as base. Obtained: 75 mg (73%)

HPLC-MS (Method 6): $R_t$=11.77 min

MS (ESI pos): m/z=528 (M+H)$^+$

Example 41

Diastereomeric Mixture

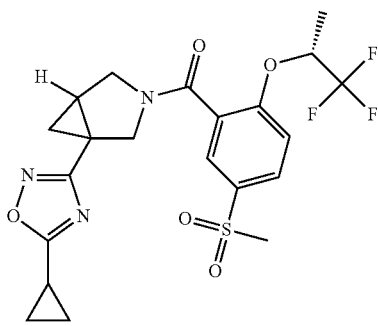 [SMILES: C[C@@H](Oc1ccc(S(C)(=O)=O)cc1C(=O)N1CC2CC2(c2noc(C3CC3)n2)C1)C(F)(F)F]

The title compound is prepared as described for example 20, starting from example 25l (135 mg, 0.59 mmol) and employing example 4b (185 mg, 0.59 mmol) in the place of example 4a. Obtained: 190 mg (66%).

HPLC-MS (Method 5): $R_t$=8.31 min

MS (APCI): m/z=486 (M+H)$^+$

Example 42 (Diastereoisomer 1, Unknown Absolute Stereochemistry at Bridgehead) and Example 43 (Diastereoisomer 2, Unknown Absolute Stereochemistry at Bridgehead)

The mixture of the title compounds is prepared as described for example 20, starting from example 25m (100 mg) and employing example 4b (207 mg, 75% content, 0.498 mmol) in the place of example 4a; obtained 145 mg. The single diastereoisomers are obtained by separation of such mixture by HPLC using a chiral stationary phase.

Method for Separation:

HPLC apparatus type: Agilent 1100; column: Daicel chiralpack AD-H, 5.0 µm, 250 mm×20 mm; method: eluent hexane/IPA 80:20; flow rate: 15 mL/min, Temperature: 25° C.; UV Detection: 230 nm Example of Separation by Chiral HPLC:

Submitted to separation: 145 mg of the mixture;

Obtained: 55 mg of Diastereoisomer 1 (Exp. 42) and 60 mg of Diastereoisomer 2 (Exp. 43)

| Example 42: Diastereoisomer 1 Unknown absolute stereochemistry at bridgehead | Example 43: Diastereoisomer 2 Unknown absolute stereochemistry at bridgehead |
|---|---|
| 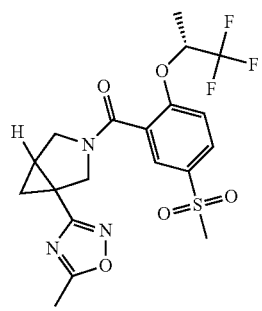 [SMILES: Cc1nc(C23CC2CN(C(=O)c2cc(S(C)(=O)=O)ccc2O[C@H](C)C(F)(F)F)C3)no1] | 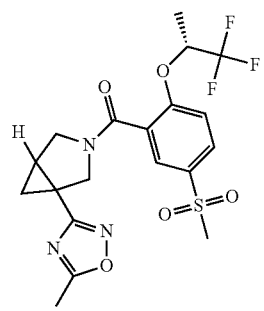 [SMILES: Cc1nc(C23CC2CN(C(=O)c2cc(S(C)(=O)=O)ccc2O[C@H](C)C(F)(F)F)C3)no1] |

| Example | Chiral HPLC: $R_t$ [min] | HPLC-MS (Method 5): $R_t$ [min] | MS (APCI): m/z |
|---|---|---|---|
| Exp. 42 | 26.709 (Method 13) | 7.57 | 460 |
| Exp. 43 | 30.798 (Method 13) | 7.51 | 460 |

Example 44

Single Stereoisomer, Unknown Absolute Stereochemistry at Bridgehead

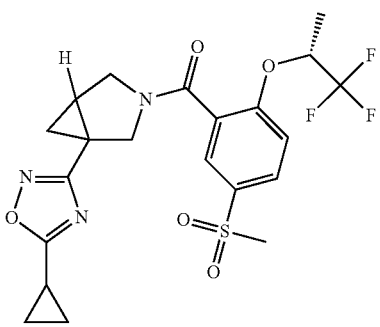 [SMILES: C[C@@H](Oc1ccc(S(C)(=O)=O)cc1C(=O)N1CC2CC2(c2noc(C3CC3)n2)C1)C(F)(F)F]

The title compound is prepared in analogy to example 20, starting from example 25n (35 mg, 94% content, 0.14 mmol) and employing example 4h (48 mg, 0.15 mmol) in the place of example 4a and HATU (76 mg, 0.20 mmol) as coupling agent. Obtained: 26 mg (37%).

HPLC-MS (Method 6): $R_t$=10.74 min

MS (ESI pos): m/z=486 (M+H)$^+$

HPLC (chiral stationary phase, Method 10): $R_t$=13.704 min

Example 45

Single Stereoisomer, Unknown Absolute Stereochemistry at Bridgehead

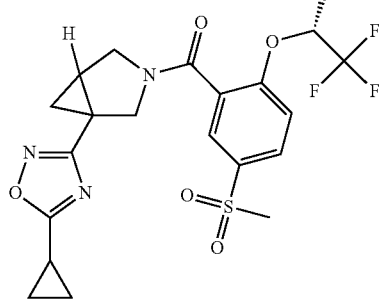

The title compound is prepared in analogy to example 20, starting from example 25o (35 mg, 88% content, 0.13 mmol) and employing example 4b (42 mg, 0.13 mmol) in the place of example 4a and HATU (67 mg, 0.17 mmol) as coupling agent. Obtained: 15 mg (22%):

HPLC-MS (Method 6): $R_t$=10.71 min

MS (ESI pos): m/z=486 (M+H)$^+$

HPLC (chiral stationary phase, Method 10): $R_t$=13.665 min

Example 46

Diastereomeric Mixture

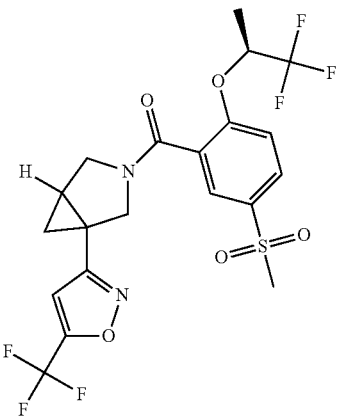 [SMILES: C[C@H](Oc1ccc(S(C)(=O)=O)cc1C(=O)N1CC2CC2(c2cc(C(F)(F)F)on2)C1)C(F)(F)F]

The title compound is prepared as described for example 20, starting from example 25p (83 mg, 90% content, 0.29 mmol). Obtained: 102 mg (68%).

HPLC-MS (Method 5): $R_t$=9.22 min

MS (APCI): m/z=513 (M+H)$^+$

The single diastereoisomers were obtained by HPLC separation using a chiral stationary phase.

Method for Separation:

HPLC apparatus type: Agilent 1100; column: Daicel chiralpack AD-H, 5.0 μm, 250 mm×20 mm; method: eluent hexane/IPA 70:30; flow rate: 15 mL/min, Temperature: 25° C.; UV Detection: 230 nm Example of Separation by Chiral HPLC:

Submitted to separation: 72 mg of the Example 46;

Obtained: 25 mg of Diastereoisomer 1 (Exp. 47) and 30 mg of Diastereoisomer 2 (Exp. 48)

| | Example 47: Diastereoisomer 1<br>Unknown absolute stereochemistry at bridgehead | Example 48: Diastereoisomer 2<br>Unknown absolute stereochemistry at bridgehead |
|---|---|---|
| | 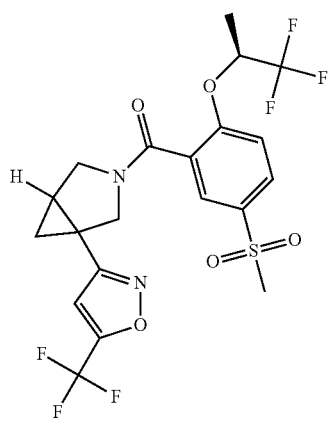 [SMILES: C[C@H](Oc1ccc(S(C)(=O)=O)cc1C(=O)N1CC2CC2(c2cc(C(F)(F)F)on2)C1)C(F)(F)F] | 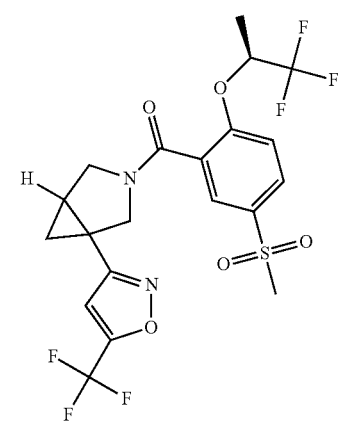 [SMILES: C[C@H](Oc1ccc(S(C)(=O)=O)cc1C(=O)N1CC2CC2(c2cc(C(F)(F)F)on2)C1)C(F)(F)F] |
| Example | Chiral HPLC:<br>$R_t$ [min] | HPLC-MS<br>(Method 6): $R_t$ [min] | MS (ESI): m/z |
| Exp. 47 | 6.301<br>(Method 12) | 11.76 | 513 |
| Exp. 48 | 9.619<br>(Method 12) | 11.76 | 513 |

Example 49

Diastereomeric Mixture

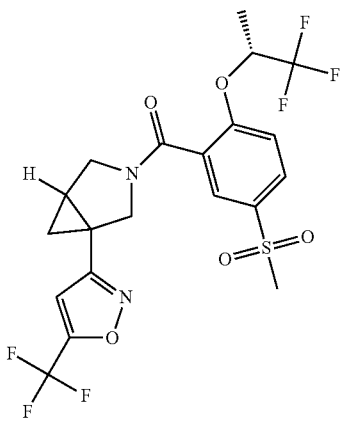 [SMILES: C[C@@H](Oc1ccc(S(C)(=O)=O)cc1C(=O)N1CC2CC2(c2cc(C(F)(F)F)on2)C1)C(F)(F)F]

The title compound is prepared as described for example 20, starting from example 25p (83 mg, 90% content, 0.29 mmol) and employing example 4b (91 mg, 0.29 mmol) in the place of example 4a. Obtained: 130 mg (87%).

HPLC-MS (Method 6): $R_t$=11.76 min

MS (ESI pos): m/z=513 (M+H)$^+$

Method for Separation:

HPLC apparatus type: Agilent 1100; column: Daicel chiralpack AD-H, 5.0 µm, 250 mm×20 mm; method: eluent hexane/IPA 70:30; flow rate: 15 mL/min, Temperature: 25° C.; UV Detection: 230 nm Example of Separation by Chiral HPLC:

Submitted to separation: 100 mg of the Example 49;
Obtained: 40 mg of Diastereoisomer 1 (Exp. 50) and 35 mg of Diastereoisomer 2 (Exp. 51)

Example 52

Diastereomeric Mixture

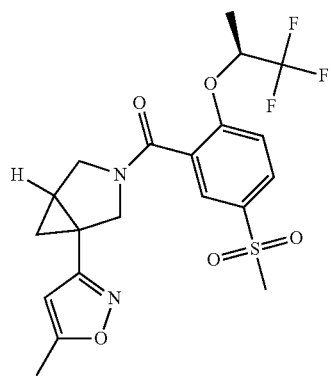

The title compound is prepared in analogy to example 20, starting from example 25q (50 mg, 90% content, 0.22 mmol) and employing HATU (111 mg, 0.29 mmol) as coupling agent. Obtained: 82 mg (79%).

HPLC-MS (Method 6): $R_t$=10.28 min

MS (ESI pos): m/z=459 (M+H)$^+$

| Example 50: Diastereoisomer 1 Unknown absolute stereochemistry at bridgehead | Example 51: Diastereoisomer 2 Unknown absolute stereochemistry at bridgehead |
|---|---|
| 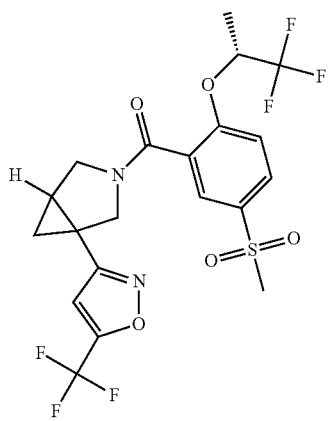 [SMILES: C[C@@H](Oc1ccc(S(C)(=O)=O)cc1C(=O)N1CC2CC2(c2cc(C(F)(F)F)on2)C1)C(F)(F)F] | 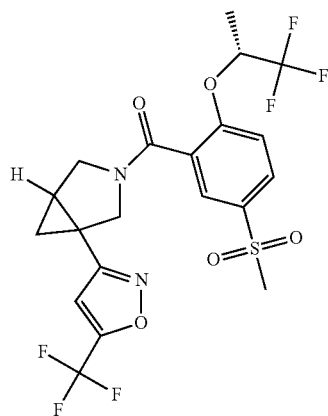 |

| Example | Chiral HPLC: $R_t$ [min] | HPLC-MS (Method 6): $R_t$ [min] | MS (ESI): m/z |
|---|---|---|---|
| Exp. 50 | 8.004 (Method 12) | 11.77 | 513 |
| Exp. 51 | 9.898 (Method 12) | 11.77 | 513 |

Example 53

Diastereomeric Mixture

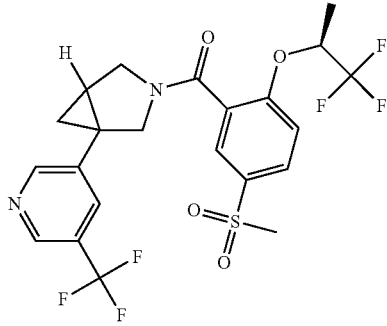 [SMILES: C[C@H](Oc1ccc(S(C)(=O)=O)cc1C(=O)N1CC2CC2(c2cncc(C(F)(F)F)c2)C1)C(F)(F)F]

The title compound is prepared in analogy to example 20, starting from example 32a (150 mg, 0.48 mmol) and employing TBTU (164 mg, 0.51 mmol) as coupling agent and DIPEA (419 µl, 2.402 mmol) as base. Obtained: 161 mg (64%).

HPLC-MS (Method 5): $R_t$=8.92 min
MS (APCI): m/z=523 (M+H)$^+$

Example 54

Diastereomeric Mixture

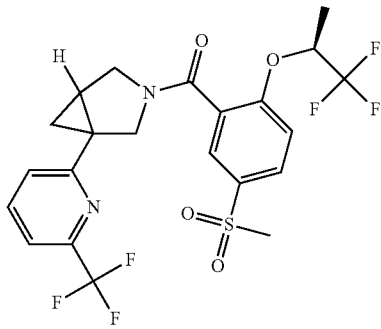 [SMILES: C[C@H](Oc1ccc(S(C)(=O)=O)cc1C(=O)N1CC2CC2(c2cccc(C(F)(F)F)n2)C1)C(F)(F)F]

The title compound is prepared in analogy to example 20, starting from example 32h (97 mg, 0.31 mmol) and employing TBTU (106 mg, 0.33 mmol) as coupling agent and DIPEA (271 µl, 1.553 mmol) as base. Obtained: 108 mg (66%).

HPLC-MS (Method 7): $R_t$=7.96 min
MS (ESI pos): m/z=523 (M+H)$^+$

The diastereoisomers of the title compound are separated by HPLC using a chiral stationary phase.

Method for Separation:
HPLC apparatus type: Agilent 1100; column: Daicel chiralpack AD-H, 5.0 µm, 250 mm×20 mm; method: eluent hexane/IPA 70:30; flow rate: 12 mL/min, Temperature: 25° C.; UV Detection: 228 nm Example of Separation by Chiral HPLC:
Submitted to separation: 78 mg of the Example 54;
Obtained: 31 mg of Diastereoisomer 1 (Exp. 55) and 33 mg of Diastereoisomer 2 (Exp. 56)

| | Example 55: Diastereoisomer 1 Unknown absolute stereochemistry at bridgehead | Example 56: Diastereoisomer 2 Unknown absolute stereochemistry at bridgehead | |
|---|---|---|---|
| | 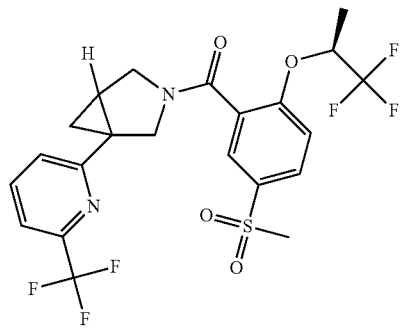 [SMILES: C[C@H](Oc1ccc(S(C)(=O)=O)cc1C(=O)N1CC2CC2(c2cccc(C(F)(F)F)n2)C1)C(F)(F)F] | 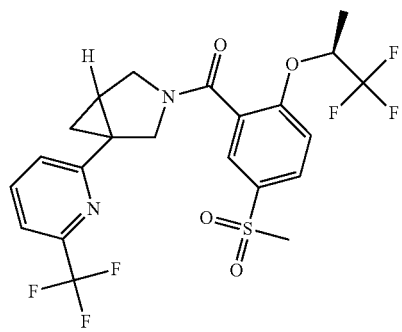 [SMILES: C[C@H](Oc1ccc(S(C)(=O)=O)cc1C(=O)N1CC2CC2(c2cccc(C(F)(F)F)n2)C1)C(F)(F)F] | |
| Example | Chiral HPLC: $R_t$ [min] | HPLC-MS (Method 6): $R_t$ [min] | MS (ESI): m/z |
| Exp. 55 | 8.87 (Method 9) | 11.95 | 523 |
| Exp. 56 | 13.428 (Method 9) | 11.95 | 523 |

Example 57

Diastereomeric Mixture

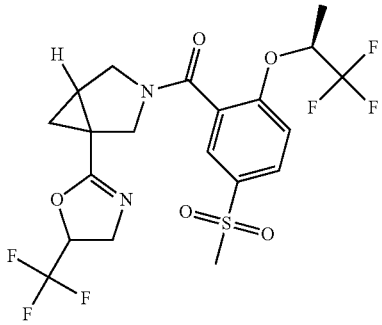 [SMILES: C[C@H](Oc1ccc(S(C)(=O)=O)cc1C(=O)N1CC2CC2(C2=NCC(C(F)(F)F)O2)C1)C(F)(F)F]

Nonafluorobutanesulfonyl fluoride (136 mg, 0.45 mmol) and 1,8-diazabicyclo[5.4.0]undec-7-ene (135 µL, 0.90 mmol) are added to example 35a (160 mg, 0.300 mmol) in DCM (1 mL). Stirring is continued for 1 h at rt. Volatiles are evaporated under reduced pressure to give a residue, which is purified by flash chromatography (eluent 60-90% EtOAc/cyclohexane) to furnish the title compound (90 mg, 58%).

HPLC-MS (Method 5): $R_t$=8.29 min
MS (APCI): m/z=515 (M+H)⁺

Example 58

Diastereomeric Mixture

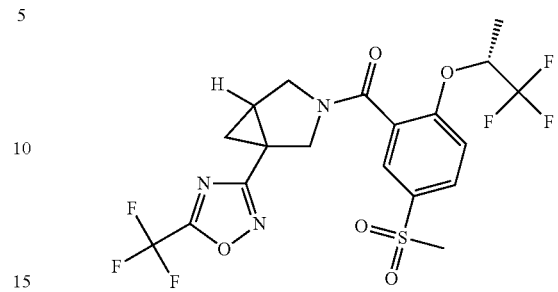

The title compounds is prepared as described for example 1, starting from example 9b (73 mg, 0.17 mmol); Obtained: 54 mg (63%).

HPLC-MS (Method 2): $R_t$=1.19 min
MS (ESI pos): m/z=514 (M+H)⁺

Example 59 (Diastereoisomer 1, Unknown Absolute Stereochemistry at Bridgehead) and Example 60 (Diastereoisomer 2, Unknown Absolute Stereochemistry at Bridgehead)

The diastereoisomers of example 13 are separated by HPLC using a chiral stationary phase.
Method for Separation:
HPLC apparatus type: Agilent 1100; column: Daicel chiralpack AS-H, 5.0 µm, 250 mm×20 mm; method: eluent hexane/IPA 75:15; flow rate: 15 mL/min, temperature: 25° C.; UV Detection: 230 nm
Example of Separation by Chiral HPLC:
Submitted to separation: 60 mg of Example 13
Obtained: 21 mg of Diastereoisomer 1 (Exp. 59) and 23 mg of Diastereoisomer 2 (Exp. 60)

| | Example 59: Diastereoisomer 1 Unknown absolute stereochemistry at bridgehead | Example 60: Diastereoisomer 2 Unknown absolute stereochemistry at bridgehead |
|---|---|---|

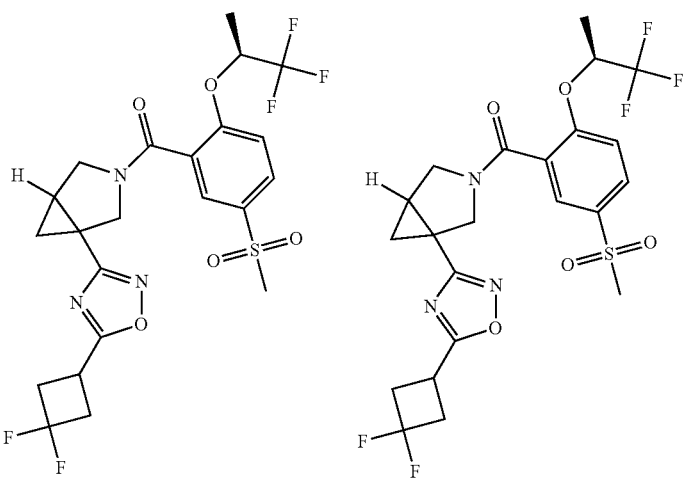

| Example | Chiral HPLC $R_t$ [min] | HPLC-MS (Method 7): $R_t$ [min] | MS (ESI pos): m/z |
|---|---|---|---|
| Exp. 59 | 14.180 (Method 17) | 7.12 | 536 |
| Exp. 60 | 18.345 (Method 17) | 7.11 | 536 |

Example 61

Diastereomeric Mixture

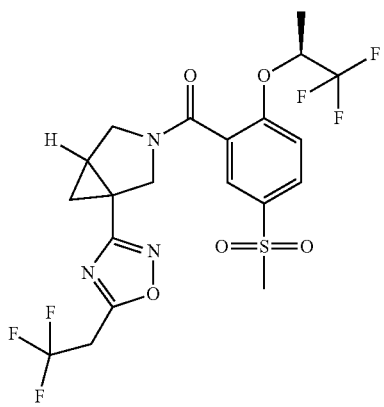 [SMILES: C[C@H](Oc1ccc(S(C)(=O)=O)cc1C(=O)N1CC2CC2(c2noc(CC(F)(F)F)n2)C1)C(F)(F)F]

The title compound is prepared as described for example 12, employing example 9a (150 mg, 98% content, 0.34 mmol) and 3,3,3-trifluoropropionic anhydride (198 mg, content 81%, 0.68 mmol) coming from a crude anhydride batch of 830 mg synthesized from 3,3,3-trifluoropropionic acid (500 µl, 5.66 mmol) in the place of 3,3,3-trifluoro-2,2-dimethyl-propionic acid. Obtained: 38 mg (21%).

HPLC-MS (Method 7): $R_t$=6.81 min

MS (ESI pos): m/z=528 (M+H)$^+$

Example 62

Diastereomeric Mixture

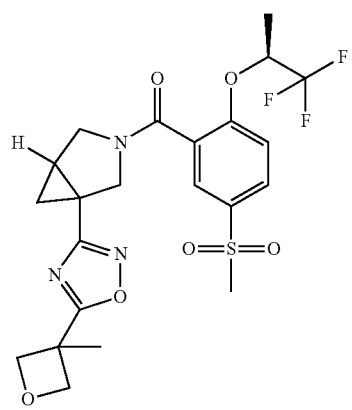 [SMILES: C[C@H](Oc1ccc(S(C)(=O)=O)cc1C(=O)N1CC2CC2(c2noc(C3(C)COC3)n2)C1)C(F)(F)F]

The title compound is prepared as described for example 12, employing example 9a (122 mg, 98% content, 0.28 mmol) and 3-methyloxetane-3-carboxylic acid anhydride (300 mg of a 450 mg crude anhydride batch) synthesized from 3-methyloxetane-3-carboxylic acid (300 mg, 2.58 mmol) in the place of 3,3,3-trifluoro-2,2-dimethylpropionic acid. Obtained: 91 mg (64%).

HPLC-MS (Method 7): $R_t$=5.82 min

MS (ESI pos): m/z=516 (M+H)$^+$

Example 63

Diastereomeric Mixture

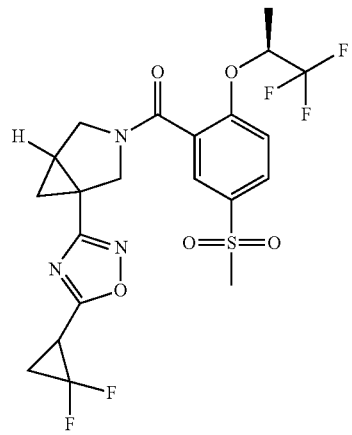 [SMILES: C[C@H](Oc1ccc(S(C)(=O)=O)cc1C(=O)N1CC2CC2(c2noc(C3CC3(F)F)n2)C1)C(F)(F)F]

The title compound is prepared as described for example 12, employing example 9a (180 mg, 96% content, 0.40 mmol) and 2,2-difluorocyclopropanecarboxylic acid anhydride (46% of a batch obtained from 544 mg, 4.46 mmol of 2,2-difluorocyclopropanecarboxylic acid) in the place of 3,3,3-trifluoro-2,2-dimethylpropionic acid. Obtained: 76 mg (37%).

HPLC-MS (Method 7): $R_t$=6.64 min

MS (ESI pos): m/z=522 (M+H)$^+$

Example 64

Diastereomeric Mixture

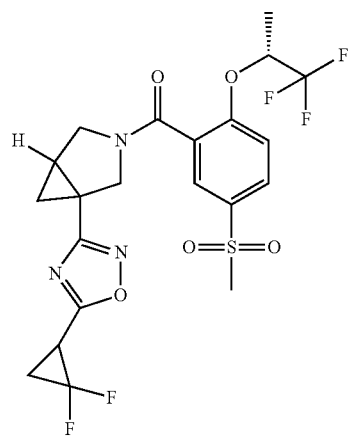 [SMILES: C[C@@H](Oc1ccc(S(C)(=O)=O)cc1C(=O)N1CC2CC2(c2noc(C3CC3(F)F)n2)C1)C(F)(F)F]

The title compound is prepared as described for example 12, employing example 9b (260 mg, 93% content, 0.55 mmol) and 2,2-difluorocyclopropanecarboxylic acid anhydride (88% of a batch obtained from 700 mg, 5.73 mmol, of 2,2-difluorocyclopropanecarboxylic acid) in the place of 3,3,3-trifluoro-2,2-dimethylpropionic acid. Obtained: 160 mg (55%).

HPLC-MS (Method 7a): $R_t$=6.14 min

MS (APCI pos): m/z=522 (M+H)$^+$

Example 65

Diastereomeric Mixture

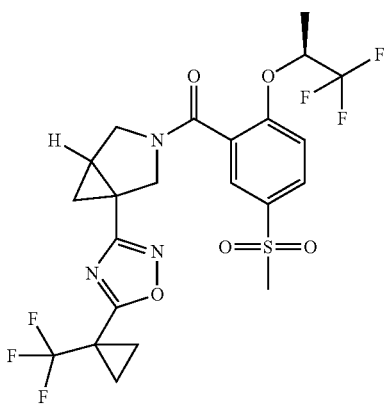 [SMILES: C[C@H](Oc1ccc(S(C)(=O)=O)cc1C(=O)N1CC2CC2(c2noc(C3(C(F)(F)F)CC3)n2)C1)C(F)(F)F]

The title compound is prepared as described for example 12, employing example 9a (120 mg, 0.28 mmol) and 1-(Trifluoromethyl)cyclopropane-1-carboxylic acid anhydride (67% of a batch obtained from 500 mg, 3.24 mmol, of 1-(Trifluoromethyl)cyclopropane-1-carboxylic acid) in the place of 3,3,3-trifluoro-2,2-dimethylpropionic acid. Obtained: 71 mg (47%).

HPLC-MS (Method 7): $R_t$=7.56 min
MS (ESI pos): m/z=554 (M+H)$^+$

The diastereoisomers of the title compound are separated by HPLC using a chiral stationary phase.

Method for Separation:
HPLC apparatus type: Agilent 1100; column: Daicel chiralpack AD-H, 5.0 μm, 250 mm×20 mm; method: eluent hexane/IPA 73:27; flow rate: 15 mL/min, temperature: 25° C.; UV Detection: 230 nm Example of Separation by Chiral HPLC:
Submitted to separation: 65 mg of Example 65;
Obtained: 21 mg of Diastereoisomer 1 (Exp. 66) and 31 mg of Diastereoisomer 2 (Exp. 67)

Example 68

Diastereomeric Mixture

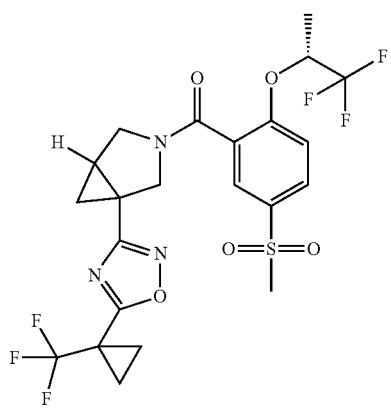

The title compound is prepared as described for example 12, employing example 9b (173 mg, 93% content, 0.37 mmol) and 1-(Trifluoromethyl)cyclopropane-1-carboxylic acid anhydride (89% of a batch obtained from 500 mg, 3.24 mmol, of 1-(Trifluoromethyl)cyclopropane-1-carboxylic acid) in the place of 3,3,3-trifluoro-2,2-dimethylpropionic acid. Obtained: 85 mg (42%).

HPLC-MS (Method 7a): $R_t$=6.71 min
MS (APCI pos): m/z=554 (M+H)$^+$

The diastereoisomers of the title compound are separated by HPLC using a chiral stationary phase.

Method for Separation:
HPLC apparatus type: Agilent 1100; column: Daicel chiralpack AD-H, 5.0 μm, 250 mm×20 mm; method: eluent hexane/IPA 70:30; flow rate: 15 mL/min, temperature: 25° C.; UV Detection: 230 nm Example of Separation by Chiral HPLC:
Submitted to separation: 64 mg of Example 68;
Obtained: 27 mg of Diastereoisomer 1 (Exp. 69) and 22 mg of Diastereoisomer 2 (Exp. 70)

| Example 66: Diastereoisomer 1 Unknown absolute stereochemistry at bridgehead | Example 67: Diastereoisomer 2 Unknown absolute stereochemistry at bridgehead |
|---|---|
| 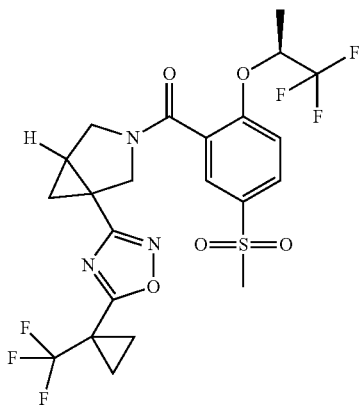 [SMILES: C[C@H](Oc1ccc(S(C)(=O)=O)cc1C(=O)N1CC2CC2(c2noc(C3(C(F)(F)F)CC3)n2)C1)C(F)(F)F] | 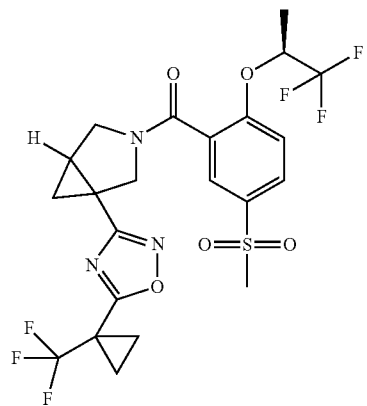 [SMILES: C[C@H](Oc1ccc(S(C)(=O)=O)cc1C(=O)N1CC2CC2(c2noc(C3(C(F)(F)F)CC3)n2)C1)C(F)(F)F] |

| Example | Chiral HPLC $R_t$ [min] | HPLC-MS (Method 7): $R_t$ [min] | MS (ESI pos): m/z |
|---|---|---|---|
| Exp. 66 | 9.516 (Method 9) | 6.82 | 554 |
| Exp. 67 | 10.452 (Method 9) | 6.81 | 554 |

| | Example 69: Diastereoisomer 1 Unknown absolute stereochemistry at bridgehead | Example 70: Diastereoisomer 2 Unknown absolute stereochemistry at bridgehead |
|---|---|---|
| | 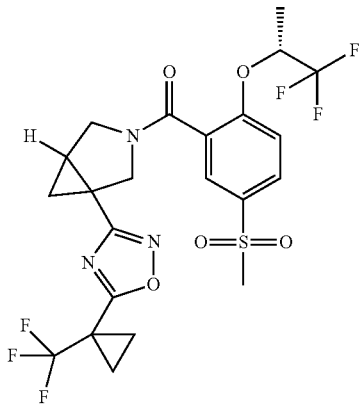 [SMILES: C[C@@H](Oc1ccc(S(C)(=O)=O)cc1C(=O)N1CC2CC2(c2noc(C3(C(F)(F)F)CC3)n2)C1)C(F)(F)F] | 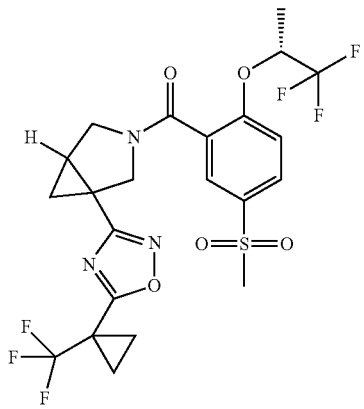 |

| Example | Chiral HPLC R$_t$ [min] | HPLC-MS (Method 7a): R$_t$ [min] | MS (APCI pos): m/z |
|---|---|---|---|
| Exp. 69 | 9.785 (Method 9) | 6.73 | 554 |
| Exp. 70 | 11.430 (Method 9) | 6.71 | 554 |

Example 71

Diastereomeric Mixture

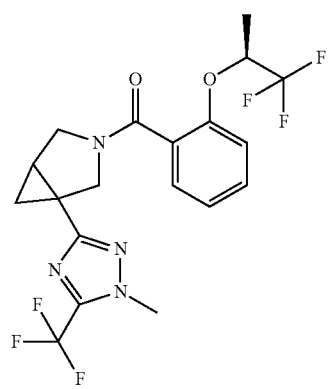 [SMILES: C[C@H](Oc1ccccc1C(=O)N1CC2CC2(c2nc(C(F)(F)F)n(C)n2)C1)C(F)(F)F]

Example 46a (110 mg, 85% content, 0.21 mmol), is dissolved in ACN (2 mL) in a microwave vessel and trifluoroacetic anhydride (59 μl, 0.42 mmol) and dry TEA (87 μl, 0.62 mmol) are added. Mixture is heated under microwave irradation at 100° C. for 20 min. Solvents are evaporated and the crude purified by flash cromatography (eluent 60-90% EtOAc/Cyclohexane) then by preparative HPLC (stationary phase: Xbridge C18 5 μm 19×100 mm. Mobile phase: ACN/ H$_2$O+NH$_4$COOH 5 mmol). to obtain the title compound (11 mg, 10%).

HPLC-MS (Method 5): R$_t$=9.72 min
MS (APCI): m/z=514 (M+H)$^+$

Example 72

Diastereomeric Mixture

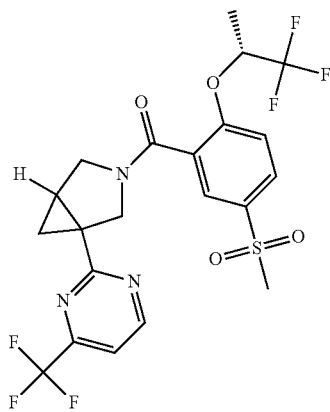 [SMILES: C[C@@H](Oc1ccc(S(C)(=O)=O)cc1C(=O)N1CC2CC2(c2nccc(C(F)(F)F)n2)C1)C(F)(F)F]

Example 10b (95 mg, 0.23 mmol) in 4-ethoxy-1,1,1-trifluoro-3-buten-2-one (6.0 mL) is heated under microwave irradation at 120° C. for 60 min. Volatiles are evaporated under reduced pressure and the resulting residue purified by flash chromatography (eluent 50-80% cyclohexane/EtOAc) to furnish the title compound (70 mg, 59%)

HPLC-MS (Method 6): R$_t$=11.56 min
MS (ESI pos): m/z=524 (M+H)$^+$

Example 73

Diastereomeric Mixture

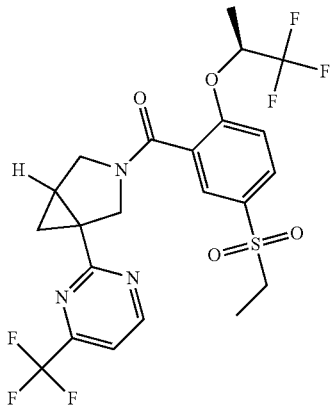 [SMILES: CCS(=O)(=O)c1ccc(O[C@@H](C)C(F)(F)F)c(C(=O)N2CC3CC3(c3nccc(C(F)(F)F)n3)C2)c1]

The title compound is prepared as described for example 15, employing example 45a (240 mg, 0.55 mmol) in the place of example 10a. Obtained: 160 mg (54%).

HPLC-MS (Method 7a): $R_t$=6.79 min
MS (APCI pos): m/z=538 (M+H)$^+$

The diastereoisomers of the title compound are separated by HPLC using a chiral stationary phase.
Method for Separation:
HPLC apparatus type: Agilent 1100; column: Daicel chiralpack AD-H, 5.0 μm, 250 mm×20 mm; method: eluent hexane/IPA 70:30; flow rate: 12 mL/min, Temperature: 25° C.; UV Detection: 230 nm
Example of Separation by Chiral HPLC:
Submitted to separation: 137 mg of Example 73;
Obtained: 53 mg of Diastereoisomer 1 (Exp. 74) and 59 mg of Diastereoisomer 2 (Exp. 75)

Example 76

Diastereomeric Mixture

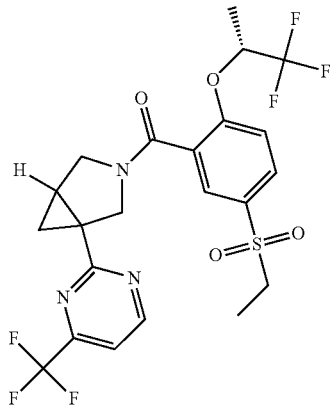

The title compound is prepared as described for example 15, employing example 45b (125 mg, 76% content, 0.22 mmol) in the place of example 10a. Obtained: 53 mg (45%).

HPLC-MS (Method 7a): $R_t$=6.79 min
MS (APCI pos): m/z=538 (M+H)$^+$

The diastereoisomers of the title compound are separated by HPLC using a chiral stationary phase.
Method for Separation:
HPLC apparatus type: Agilent 1100; column: Daicel chiralpack AS-H, 5.0 μm, 250 mm×20 mm; method: eluent hexane/IPA 80:20; flow rate: 15 mL/min, Temperature: 25° C.; UV Detection: 230 nm
Example of Separation by Chiral HPLC:
Submitted to separation: 45 mg of Example 76;
Obtained: 21 mg of Diastereoisomer 1 (Exp. 77) and 20 mg of Diastereoisomer 2 (Exp. 78)

| Example 74: Diastereoisomer 1 Unknown absolute stereochemistry at bridgehead | Example 75: Diastereoisomer 2 Unknown absolute stereochemistry at bridgehead |
|---|---|
| 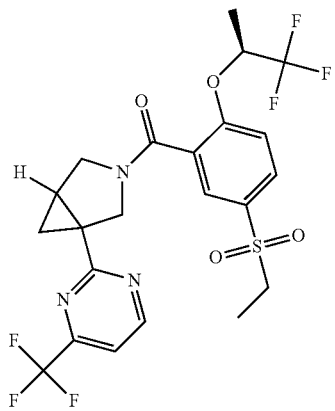 [SMILES: CCS(=O)(=O)c1ccc(O[C@@H](C)C(F)(F)F)c(C(=O)N2CC3CC3(c3nccc(C(F)(F)F)n3)C2)c1] | 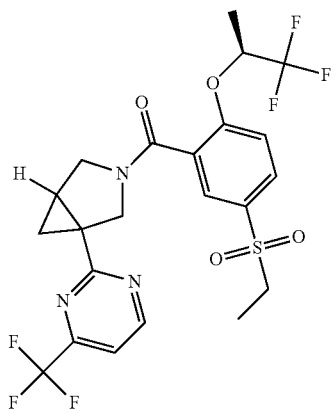 [SMILES: CCS(=O)(=O)c1ccc(O[C@@H](C)C(F)(F)F)c(C(=O)N2CC3CC3(c3nccc(C(F)(F)F)n3)C2)c1] |

| Example | Chiral HPLC $R_t$ [min] | HPLC-MS (Method 7): $R_t$ [min] | MS (ESIpos): m/z |
|---|---|---|---|
| Exp. 74 | 9.737 (Method 9) | 7.62 | 538 |
| Exp. 75 | 12.472 (Method 9) | 7.58 | 538 |

| | Example 77: Diastereoisomer 1 Unknown absolute stereochemistry at bridgehead | Example 78: Diastereoisomer 2 Unknown absolute stereochemistry at bridgehead | |
|---|---|---|---|
| Example | Chiral HPLC R$_t$ [min] | HPLC-MS (Method 7): R$_t$ [min] | MS (ESI pos): m/z |
| Exp. 77 | 9.835 (Method 18) | 7.59 | 538 |
| Exp. 78 | 14.885 (Method 18) | 7.60 | 538 |

Example 79

Diastereomeric Mixture

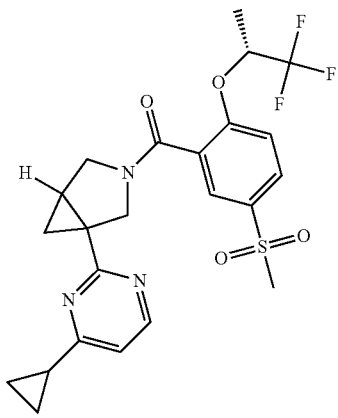 [SMILES: C[C@@H](Oc1ccc(S(C)(=O)=O)cc1C(=O)N1CC2CC2(c2nccc(C3CC3)n2)C1)C(F)(F)F]

Example 10b (450 mg, 93% content, 1.00 mmol) and sodium 3-cyclopropyl-3-oxoprop-1-en-1-olate (700 mg, 5.22 mmol) in EtOH (9.0 mL) is heated under microwave irradation at 120° C. for 2 h. Volatiles are evaporated under reduced pressure and the resulting residue partitioned between ethyl acetate and sat. NaHCO$_3$. The organic layer is washed with brine dried and evaporated under reduced pressure to furnish a residue that is purified by preparative HPLC (stationary phase: Xbridge C18 5 µm 19×100 mm. Mobile phase: ACN/ H$_2$O+NH$_4$COOH 5 mmol). Fractions containing the title compound are combined and freeze dried to furnish a residue that is further purified by flash chromatography (eluent 70% cyclohexane/EtOAc) to afford the title compound (22 mg, 4%)

HPLC-MS (Method 7a): R$_t$=6.54 min
MS (APCI pos): m/z=496 (M+H)$^+$

Example 80

Diastereomeric Mixture

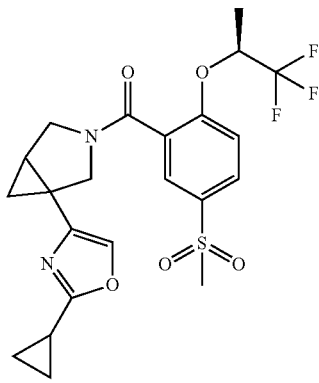 [SMILES: C[C@H](Oc1ccc(S(C)(=O)=O)cc1C(=O)N1CC2CC2(c2coc(C3CC3)n2)C1)C(F)(F)F]

The title compound is prepared in analogy to example 20, starting from example 25r (30 mg, 0.13 mmol). Obtained: 45 mg (71%).
HPLC-MS (Method 7): R$_t$=6.50 min
MS (ESI pos): m/z=485 (M+H)$^+$

Example 81

Diastereomeric Mixture

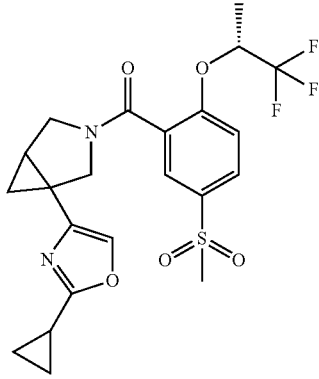 [SMILES: C[C@@H](Oc1ccc(S(C)(=O)=O)cc1C(=O)N1CC2CC2(c2coc(C3CC3)n2)C1)C(F)(F)F]

The title compound is prepared in analogy to example 20, starting from example 25r (42 mg, 0.18 mmol) and example 4b (64 mg, 90% content, 0.18 mmol). Obtained: 53 mg (59%).

HPLC-MS (Method 7a): $R_t$=6.23 min

MS (APCI): m/z=485 (M+H)$^+$

The diastereoisomers of the title compound are separated by HPLC using a chiral stationary phase.

Method for Separation:

HPLC apparatus type: Agilent 1100; column: Daicel chiralpack AS-H, 5.0 μm, 250 mm×20 mm; method: eluent hexane/IPA 90:10; flow rate: 15 mL/min, Temperature: 25° C.; UV Detection: 230 nm Example of Separation by Chiral HPLC:

Submitted to separation: 51 mg of Example 81;

Obtained: 9 mg of Diastereoisomer 1 (Exp. 82) and 11 mg of Diastereoisomer 2 (Exp. 83)

Example 84 (Diastereoisomer 1, Unknown Absolute Stereochemistry at Bridgehead) and Example 85 (Diastereoisomer 2, Unknown Absolute Stereochemistry at Bridgehead)

The diastereoisomers of example 36 are separated by HPLC using a chiral stationary phase.

Method for Separation:

HPLC apparatus type: Agilent 1100; column: Daicel chiralpack AD-H, 5.0 μm, 250 mm×20 mm; method: eluent hexane/IPA 70:30; flow rate: 15 mL/min, Temperature: 25° C.; UV Detection: 230 nm Example of Separation by Chiral HPLC:

Submitted to separation: 68 mg of Example 36;

Obtained: 24 mg of Diastereoisomer 1 (Exp. 84) and 29 mg of Diastereoisomer 2 (Exp. 85)

| Example 82: Diastereoisomer 1 Unknown absolute stereochemistry at bridgehead | Example 83: Diastereoisomer 2 Unknown absolute stereochemistry at bridgehead |
|---|---|

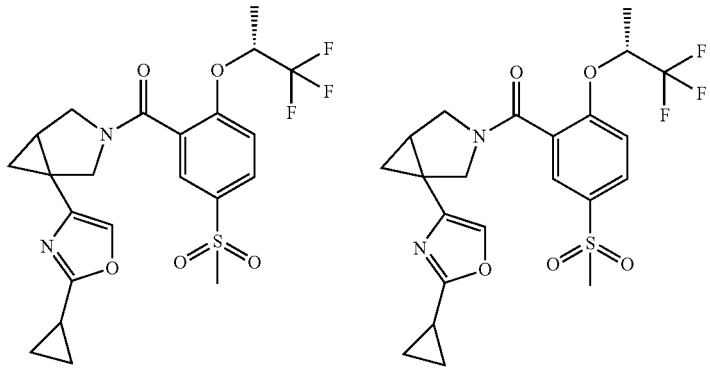

| Example | Chiral HPLC $R_t$ [min] | HPLC-MS (Method 7a): $R_t$ [min] | MS (APCIpos): m/z |
|---|---|---|---|
| Exp. 82 | 24.984 (Method 19) | 6.06 | 485 |
| Exp. 83 | 28.913 (Method 19) | 6.10 | 485 |

| | Example 84: Diastereoisomer 1 Unknown absolute stereochemistry at bridgehead | Example 85: Diastereoisomer 2 Unknown absolute stereochemistry at bridgehead |
|---|---|---|
| | 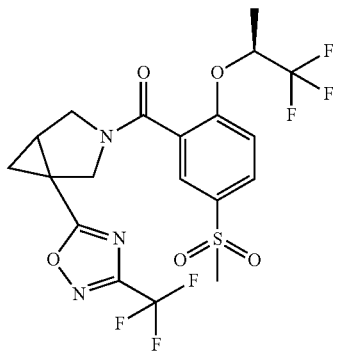 [SMILES: C[C@H](Oc1ccc(S(C)(=O)=O)cc1C(=O)N1CC2CC2(c2nc(C(F)(F)F)no2)C1)C(F)(F)F] | 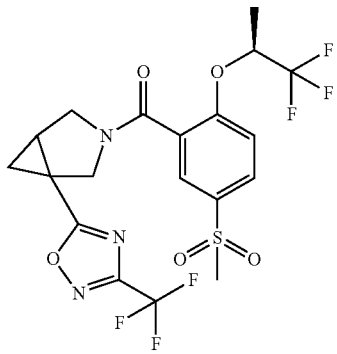 [SMILES: C[C@H](Oc1ccc(S(C)(=O)=O)cc1C(=O)N1CC2CC2(c2nc(C(F)(F)F)no2)C1)C(F)(F)F] |

| Example | Chiral HPLC $R_t$ [min] | HPLC-MS (Method 7): $R_t$ [min] | MS (ESI pos): m/z |
|---|---|---|---|
| Exp. 84 | 6.669 (Method 9) | 7.27 | 514 |
| Exp. 85 | 8.505 (Method 9) | 7.27 | 514 |

Example 86 (Diastereoisomer 1, Unknown Absolute Stereochemistry at Bridgehead) and Example 87 (Diastereoisomer 2, Unknown Absolute Stereochemistry at Bridgehead)

The diastereoisomers of example 37 are separated by HPLC using a chiral stationary phase.
Method for Separation:
HPLC apparatus type: Agilent 1100; column: Daicel chiralpack AD-H, 5.0 μm, 250 mm×20 mm; method: eluent hexane/IPA 70:30; flow rate: 15 mL/min, Temperature: 25° C.; UV Detection: 230 nm Example of Separation by Chiral HPLC:

Submitted to separation: 84 mg of Example 37;

Obtained: 36 mg of Diastereoisomer 1 (Exp. 86) and 31 mg of Diastereoisomer 2 (Exp. 87)

| | Example 86: Diastereoisomer 1 Unknown absolute stereochemistry at bridgehead | Example 87: Diastereoisomer 2 Unknown absolute stereochemistry at bridgehead |
|---|---|---|
| | 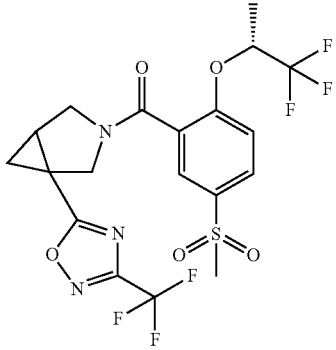 [SMILES: C[C@@H](Oc1ccc(S(C)(=O)=O)cc1C(=O)N1CC2CC2(c2nc(C(F)(F)F)no2)C1)C(F)(F)F] | 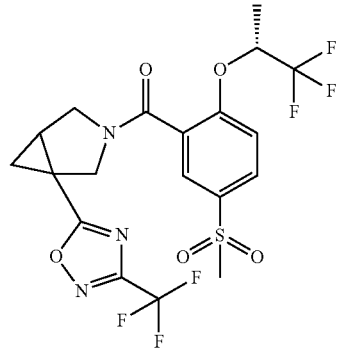 [SMILES: C[C@@H](Oc1ccc(S(C)(=O)=O)cc1C(=O)N1CC2CC2(c2nc(C(F)(F)F)no2)C1)C(F)(F)F] |

| Example | Chiral HPLC $R_t$ [min] | HPLC-MS (Method 7): $R_t$ [min] | MS (ESI pos): m/z |
|---|---|---|---|
| Exp. 86 | 7.362 (Method 9) | 7.27 | 514 |
| Exp. 87 | 9.002 (Method 9) | 7.27 | 514 |

Example 88

Diastereomeric Mixture

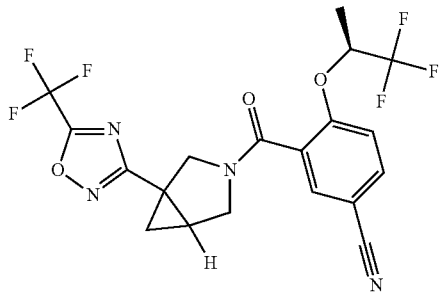 [SMILES: C[C@H](Oc1ccc(C#N)cc1C(=O)N1CC2CC2(c2noc(C(F)(F)F)n2)C1)C(F)(F)F]

The title compound is prepared in analogy to example 20, starting from example 25k (80 mg, 0.31 mmol) and employing example 4j, 97 mg, 0.38 mmol) in the place of example 4a, DIPEA (429 µl, 2.50 mmol) as base and TBTU (151 mg, 0.47 mmol) as coupling agent. Obtained: 32 mg (22%).
HPLC-MS (Method 6): $R_t$=12.11 min
MS (ESI pos): m/z=461 (M+H)$^+$ The diastereoisomers of the title compound are separated by HPLC using a chiral stationary phase.

Method for Separation:
HPLC apparatus type: Agilent 1100; column: Daicel chiralpack AD-H, 5.0 µm, 250 mm×20 mm; method: eluent hexane/IPA 70:30; flow rate: 12 mL/min, Temperature: 25° C.; UV Detection: 230 nm Example of Separation by Chiral HPLC:
Submitted to separation: 160 mg of Example 88;
Obtained: 55 mg of Diastereoisomer 1 (Exp. 89) and 62 mg of Diastereoisomer 2 (Exp. 90)

Example 91

Diastereomeric Mixture

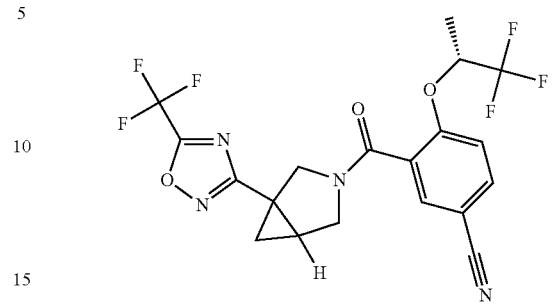

The title compound is prepared in analogy to example 20, starting from example 25k (80 mg, 0.31 mmol) and employing example 4k (97 mg, 0.38 mmol) in the place of example 4a, DIPEA (429 µl, 2.50 mmol) as base and TBTU (151 mg, 0.47 mmol) as coupling agent. Obtained: 56 mg (39%).
HPLC-MS (Method 6): $R_t$=12.12 min
MS (ESI pos): m/z=461 (M+H)$^+$

Example 92

Diastereomeric Mixture

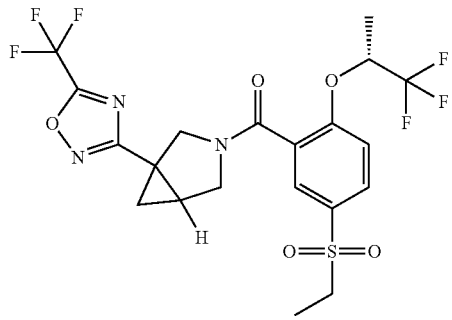 [SMILES: CCS(=O)(=O)c1ccc(O[C@H](C)C(F)(F)F)c(C(=O)N2CC3CC3(c3noc(C(F)(F)F)n3)C2)c1]

| Example | Chiral HPLC $R_t$ [min] | HPLC-MS (Method 7): $R_t$ [min] | MS (ESI pos): m/z |
|---|---|---|---|
| Exp. 89 | 7.300 (Method 20) | 8.17 | 461 |
| Exp. 90 | 8.356 (Method 20) | 8.18 | 461 |

Example 89: Diastereoisomer 1
Unknown absolute stereochemistry at bridgehead

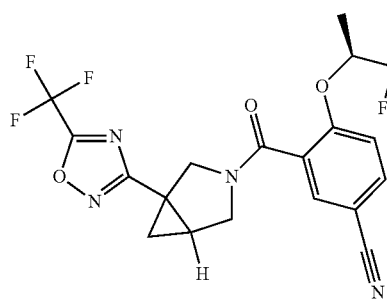

Example 90: Diastereoisomer 2
Unknown absolute stereochemistry at bridgehead

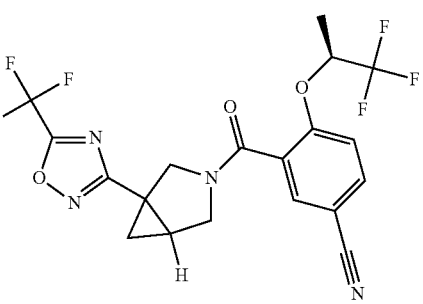

The title compound is prepared in analogy to example 20, starting from example 25k (90 mg, 0.35 mmol) and employing example 41(138 mg, 0.42 mmol) in the place of example 4a, DIPEA (482 µl, 2.82 mmol) as base and TBTU (170 mg, 0.53 mmol) as coupling agent. Obtained: 59 mg (32%).

HPLC-MS (Method 6): $R_t$=11.81 min
MS (ESI pos): m/z=528 (M+H)$^+$

The diastereoisomers of the title compound are separated by HPLC using a chiral stationary phase.

Method for Separation:

HPLC apparatus type: Agilent 1100; column: Daicel chiralpack AD-H, 5.0 µm, 250 mm×20 mm; method: eluent hexane/IPA 70:30; flow rate: 12 mL/min, Temperature: 25° C.; UV Detection: 230 nm Example of Separation by Chiral HPLC:

Submitted to separation: 54 mg of Example 92;
Obtained: 25 mg of Diastereoisomer 1 (Exp. 93) and 35 mg of Diastereoisomer 2 (Exp. 94)

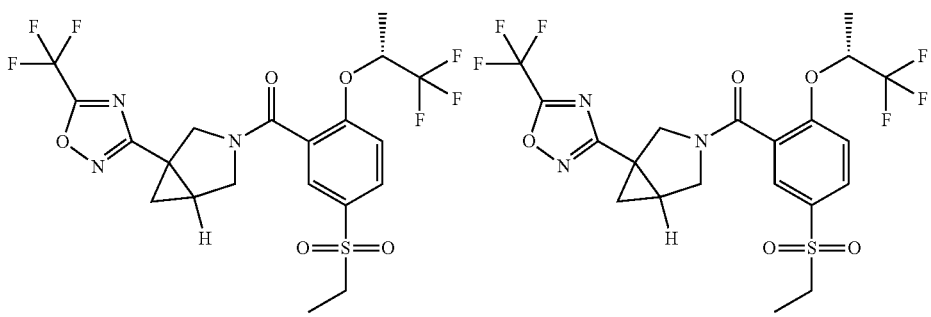

| Example | Chiral HPLC $R_t$ [min] | HPLC-MS (Method 7): $R_t$ [min] | MS (ESI pos): m/z |
|---|---|---|---|
| Exp. 93 | 7.024 (Method 9) | 7.75 | 528 |
| Exp. 94 | 8.841 (Method 9) | 7.75 | 528 |

Example 95

Racemic Mixture

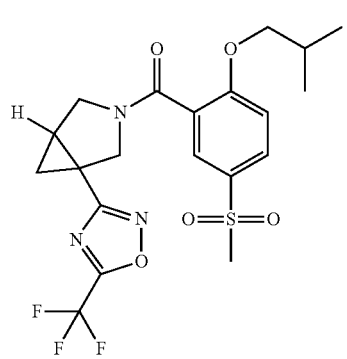 [SMILES: CC(C)COc1ccc(S(C)(=O)=O)cc1C(=O)N1CC2CC2(c2noc(C(F)(F)F)n2)C1]

The title compound is prepared in analogy to example 20, starting from example 25k (70 mg, 0.27 mmol) and employing example 4h (75 mg, 0.27 mmol) in the place of example 4a. Obtained: 110 mg (85%).

HPLC-MS (Method 7): $R_t$=7.54 min
MS (ESI pos): m/z=474 (M+H)$^+$

Example 96

Racemic Mixture

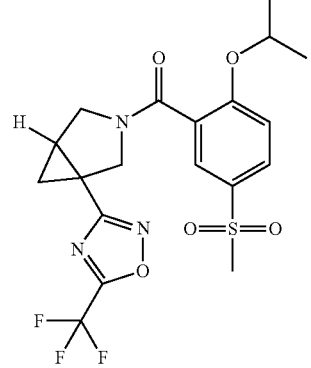

The title compound is prepared in analogy to example 20, starting from example 25k (100 mg, 0.39 mmol) and employing example 4f (126 mg, 80% content, 0.39 mmol) in the place of example 4a and DIPEA (204 µl, 1.17 mmol) as base. Obtained: 116 mg (65%).

HPLC-MS (Method 6): $R_t$=6.85 min
MS (ESI pos): m/z=460 (M+H)$^+$

The enantiomers of the title compound are separated by HPLC using a chiral stationary phase.

Method for Separation:

HPLC apparatus type: Agilent 1100; column: Daicel chiralpack AD-H, 5.0 µm, 250 mm×20 mm; method: eluent hexane/IPA 70:30; flow rate: 15 mL/min, Temperature: 25° C.; UV Detection: 230 nm Example of Separation by Chiral HPLC:

Submitted to separation: 116 mg of Example 96;
Obtained: 46 mg of enantiomer 1 (Exp. 97) and 44 mg of enantiomer 2 (Exp. 98)

Example 97: Enantiomer 1
Unknown absolute stereochemistry at bridgehead

Example 98: Enantiomer 2
Unknown absolute stereochemistry at bridgehead

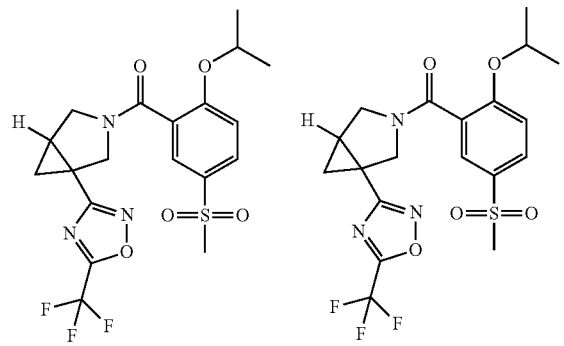

| Example | Chiral HPLC $R_t$ [min] | HPLC-MS (Method 7): $R_t$ [min] | MS (ESI pos): m/z |
|---|---|---|---|
| Exp. 97 | 6.850 (Method 9) | 7.02 | 460 |
| Exp. 98 | 9.112 (Method 9) | 7.03 | 460 |

Example 99

Racemic Mixture

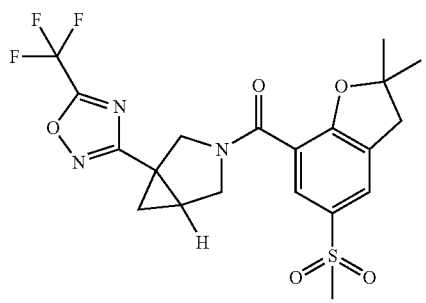 [SMILES: CC1(C)Cc2cc(S(C)(=O)=O)cc(C(=O)N3CC4CC4(c4noc(C(F)(F)F)n4)C3)c2O1]

The title compound is prepared in analogy to example 20, starting from example 25k (80 mg, 0.31 mmol) and employing example 4n (97 mg, 0.38 mmol) in the place of example 4a, DIPEA (429 µl, 2.50 mmol) as base and TBTU (151 mg, 0.47 mmol) as coupling agent. Obtained: 23 mg (16%).

HPLC-MS (Method 6): $R_t$=11.27 min

MS (ESI pos): m/z=472 (M+H)$^+$

Example 100

Diastereomeric Mixture

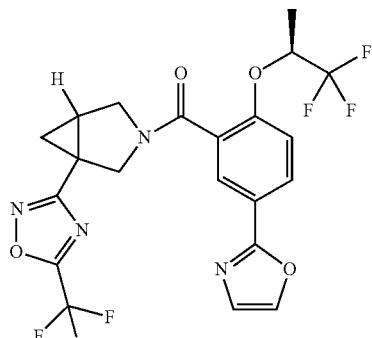

The title compound is prepared in analogy to example 20, starting from example 25k (18 mg, 0.07 mmol) and employing example 4g (20 mg, 0.07 mmol) in the place of example 4a, DIPEA (73 mg, 0.56 mmol) as base and TBTU (29 mg, 0.09 mmol) as coupling agent. Obtained: 12 mg (34%).

HPLC-MS (Method 7): $R_t$=8.21 min

MS (ESI pos): m/z=503 (M+H)$^+$

Example 101

Diastereomeric Mixture

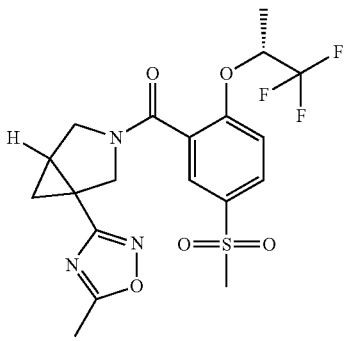 [SMILES: Cc1nc(C23CC2CN(C(=O)c2cc(S(C)(=O)=O)ccc2O[C@H](C)C(F)(F)F)C3)no1]

The title compound is prepared in analogy to example 20, starting from example 25m (100 mg, 0.50 mmol) and employing example 4b (207 mg, 75% content, 0.50 mmol) in the place of example 4a. Obtained: 145 mg (64%).

HPLC-MS (Method 5): $R_t$=7.60 min

MS (APCI): m/z=460 (M+H)$^+$

Example 102

Diastereomeric Mixture

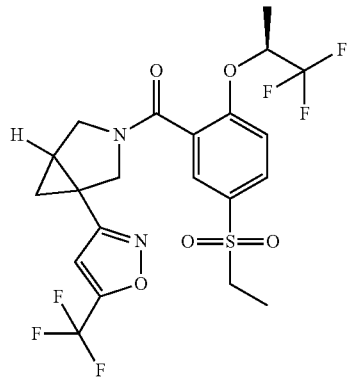 [SMILES: CCS(=O)(=O)c1ccc(O[C@@H](C)C(F)(F)F)c(C(=O)N2CC3CC3(c3cc(C(F)(F)F)on3)C2)c1]

The title compound is prepared in analogy to example 20, starting from example 25p (16 mg, 0.46 mmol) and employing example 4e (149 mg, 0.46 mmol) in the place of example 4a. Obtained: 208 mg (87%).

HPLC-MS (Method 7): $R_t$=7.79 min
MS (ESI pos): m/z=527 (M+H)$^+$

The diastereoisomers of the title compound are separated by HPLC using a chiral stationary phase.
Method for Separation:

HPLC apparatus type: Agilent 1100; column: Daicel chiralpack AD-H, 5.0 μm, 250 mm×20 mm; method: eluent hexane/IPA 70:30; flow rate: 15 mL/min, Temperature: 25° C.; UV Detection: 230 nm
Example of Separation by Chiral HPLC:

Submitted to separation: 62 mg of Example 102;
Obtained: 20 mg of Diastereoisomer 1 (Exp. 103) and 30 mg of Diastereoisomer 2 (Exp. 104)

Example 105

Diastereomeric Mixture

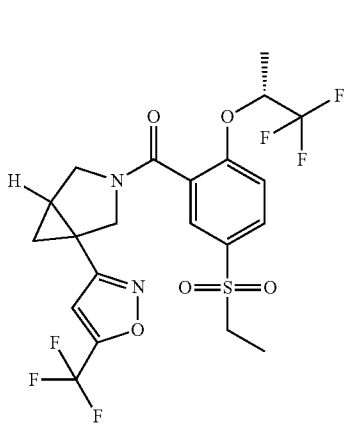

The title compound is prepared in analogy to example 20, starting from example 25p (70 mg, 0.27 mmol) and employing example 41 (87 mg, 0.27 mmol) in the place of example 4a. Obtained: 71 mg (49%).

HPLC-MS (Method 7): $R_t$=7.82 min
MS (ESI pos): m/z=527 (M+11)$^+$

The diastereoisomers of the title compound are separated by HPLC using a chiral stationary phase.
Method for Separation:

HPLC apparatus type: Agilent 1100; column: Daicel chiralpack OJ-H, 5.0 μm, 250 mm×20 mm; method: eluent hexane/IPA 80:20; flow rate: 12 mL/min, Temperature: 25° C.; UV Detection: 230 nm
Example of Separation by Chiral HPLC:

Submitted to separation: 60 mg of Example 105;
Obtained: 24 mg of Diastereoisomer 1 (Exp. 106) and 27 mg of Diastereoisomer 2 (Exp. 107)

| Example 103: Diastereoisomer 1 Unknown absolute stereochemistry at bridgehead | Example 104: Diastereoisomer 2 Unknown absolute stereochemistry at bridgehead |
|---|---|
| 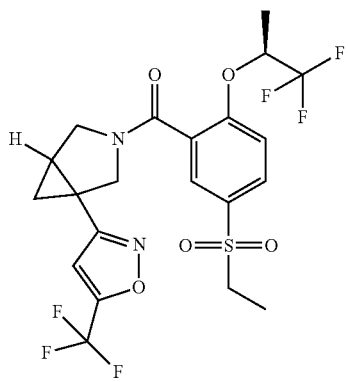 [SMILES: CCS(=O)(=O)c1ccc(O[C@@H](C)C(F)(F)F)c(C(=O)N2CC3CC3(c3cc(C(F)(F)F)on3)C2)c1] | 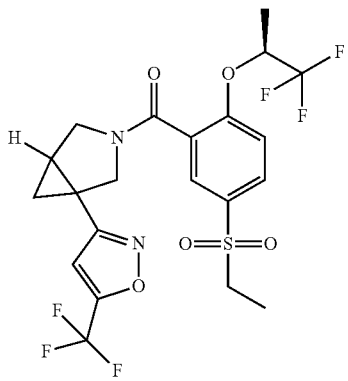 [SMILES: CCS(=O)(=O)c1ccc(O[C@@H](C)C(F)(F)F)c(C(=O)N2CC3CC3(c3cc(C(F)(F)F)on3)C2)c1] |

| Example | Chiral HPLC $R_t$ [min] | HPLC-MS (Method 7a): $R_t$ [min] | MS (APCI pos): m/z |
|---|---|---|---|
| Exp. 103 | 6.574 (Method 9) | 6.86 | 527 |
| Exp. 104 | 9.550 (Method 9) | 6.86 | 527 |

| | Example 106: Diastereoisomer 1 Unknown absolute stereochemistry at bridgehead | Example 107: Diastereoisomer 2 Unknown absolute stereochemistry at bridgehead |
|---|---|---|
| | 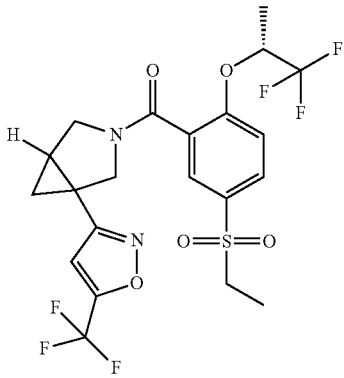 [SMILES: CCS(=O)(=O)c1ccc(O[C@H](C)C(F)(F)F)c(C(=O)N2CC3CC3(c3cc(C(F)(F)F)on3)C2)c1] | 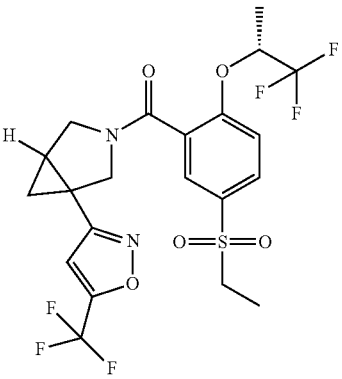 [SMILES: CCS(=O)(=O)c1ccc(O[C@H](C)C(F)(F)F)c(C(=O)N2CC3CC3(c3cc(C(F)(F)F)on3)C2)c1] |

| Example | Chiral HPLC $R_t$ [min] | HPLC-MS (Method 7): $R_t$ [min] | MS (ESI pos): m/z |
|---|---|---|---|
| Exp. 106 | 15.151 (Method 21) | 7.78 | 527 |
| Exp. 107 | 18.365 (Method 21) | 7.77 | 527 |

Example 108

Diastereomeric Mixture

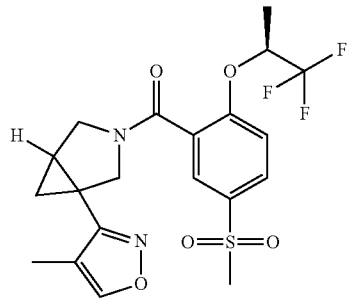 [SMILES: Cc1conc1C12CC1CN(C(=O)c1cc(S(C)(=O)=O)ccc1O[C@@H](C)C(F)(F)F)C2]

The title compound is prepared in analogy to example 20, starting from example 25u (50 mg, 0.25 mmol) and employing example 4a (78 mg, 0.25 mmol). Obtained: 6 mg (5%).
HPLC-MS (Method 7): $R_t$=5.86 min
MS (ESI pos): m/z=459 (M+H)$^+$ Example 109

Diastereomeric Mixture

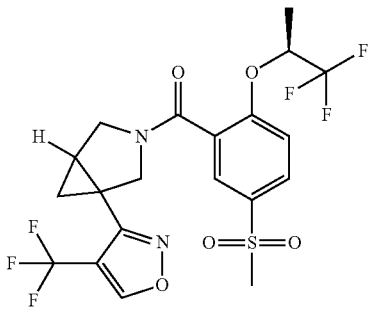 [SMILES: C[C@H](Oc1ccc(S(C)(=O)=O)cc1C(=O)N1CC2CC2(c2nocc2C(F)(F)F)C1)C(F)(F)F]

The title compound is prepared in analogy to example 20, starting from example 25v (30 mg, 0.12 mmol) and employing example 4a (37 mg, 0.12 mmol). Obtained: 57 mg (94%).
HPLC-MS (Method 7): $R_t$=6.86 min
MS (ESI pos): m/z=513 (M+H)$^+$ Example 110

Racemic Mixture

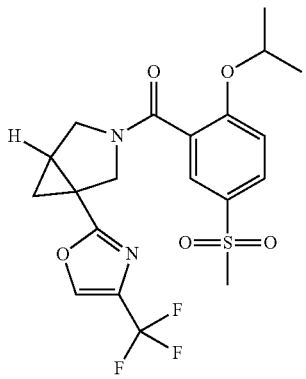 [SMILES: CC(C)Oc1ccc(S(C)(=O)=O)cc1C(=O)N1CC2CC2(c2nc(C(F)(F)F)co2)C1]

TEA (70 µL, 0.53 mmol) is added to a suspension of example 25w (90 mg, 0.35 mmol) in anhydrous DCM (4 ml); after 30 minutes stirring example 4f (100 mg, 0.39 mmol), N-(3-dimethylaminopropyl)-N'-ethylcarbodiimidehydrochloride (74.5 mg, 0.39 mmol) and 1-s Hydroxybenzotriazole (4.78 mg, 0.04 mmol) are added and the mixture is stirred overnight. Water is added, phases are separated then the organic layer is washed with 10% aqueous NaHCO$_3$, dried over phase-separator cartridge and solvent is eliminated under reduced pressure. Crude product is purified by preparative HPLC (stationary phase: Xterra C18 5 µm 30×100 mm.

Mobile phase: ACN/H$_2$O+NH$_4$COOH 5 mmol) to obtain 71 mg (43%) of product.

HPLC-MS (Method 7a): R$_t$=6.42 min
MS (APCI pos): m/z=459 (M+H)$^+$

The enantiomers of the title compound are separated by HPLC using a chiral stationary phase.

Method for Separation:

HPLC apparatus type: Waters 600 Pump; column: Daicel Chiralpack IA, 5.0 µm, 250 mm×20 mm; method: eluent hexane/IPA 70:30; flow rate: 15 mL/min, Temperature: 25° C.; UV Detection: 230 nm Example of Separation by Chiral HPLC:

Submitted to separation: 56 mg of Example 110 prepared as described above;

Obtained: 25 mg of enantiomer 1 (Exp. 111) and 24 mg of enantiomer 2 (Exp. 112)

| Example 111: Enantiomer 1 Unknown absolute stereochemistry at bridgehead | Example 112: Enantiomer 2 Unknown absolute stereochemistry at bridgehead |
|---|---|
| 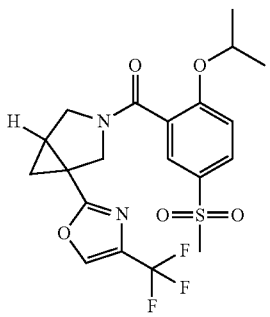 | 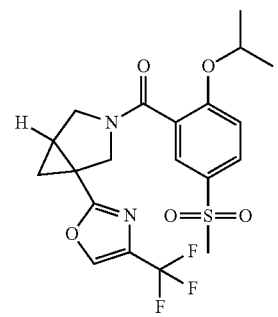 [SMILES: CC(C)Oc1ccc(S(C)(=O)=O)cc1C(=O)N1CC2CC2(c2nc(C(F)(F)F)co2)C1] |

| Example | Chiral HPLC R$_t$ [min] | HPLC-MS (Method 7b): R$_t$ [min] | MS (APCI): m/z |
|---|---|---|---|
| Exp. 111 | 10.07 (Method 23) | 2.74 | 459 |
| Exp. 112 | 15.26 (Method 23) | 2.76 | 459 |

Example 113

Diasteromeric Mixture

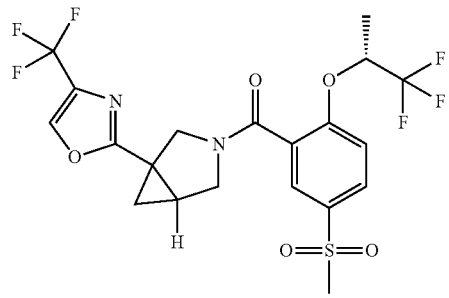 [SMILES: C[C@@H](Oc1ccc(S(C)(=O)=O)cc1C(=O)N1CC2CC2(c2nc(C(F)(F)F)co2)C1)C(F)(F)F]

Title compound is prepared in analogy to example 110, starting from example 4b (81 mg, 0.26 mmol) in place of example 4f to obtain the title compound (59 mg, 48%).

HPLC-MS (Method 7a): R$_t$=6.63 min
MS (APCI pos): m/z=513 (M+H)$^+$

The diasteromers of the title compound are separated by HPLC using a chiral stationary phase.

Method for Separation:

HPLC apparatus type: Waters 600 Pump; column: Daicel Chiralpack IA, 5.0 µm, 250 mm×20 mm; method: eluent hexane/IPA 80:20; flow rate: 15 mL/min, Temperature: 25° C.; UV Detection: 230 nm Example of Separation by Chiral HPLC:

Submitted to separation: 40 mg of Example 113 prepared as described above;

Obtained: 17 mg of Diastereoisomer 1 (Exp. 114) and 19 mg of Diastereoisomer 2 (Exp. 115)

| Example 114: Diastereoisomer 1 Unknown absolute stereochemistry at bridgehead | Example 115: Diastereoisomer 2 Unknown absolute stereochemistry at bridgehead |
|---|---|
| 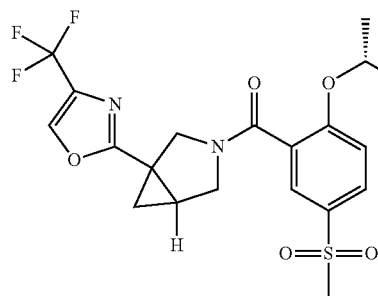 | 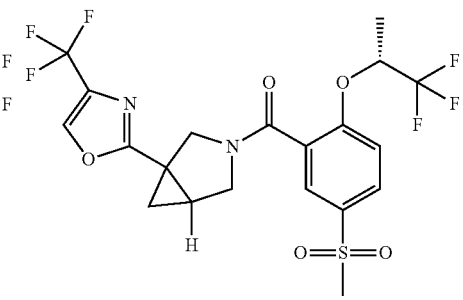 |

| Example | Chiral HPLC R$_t$ [min] | HPLC-MS (Method 7b): R$_t$ [min] | MS (APCI): m/z |
|---|---|---|---|
| Exp. 114 | 17.00 (Method 24) | 6.68 | 513 |
| Exp. 115 | 21.92 (Method 24) | 6.66 | 513 |

Example 116

Diasteromeric Mixture

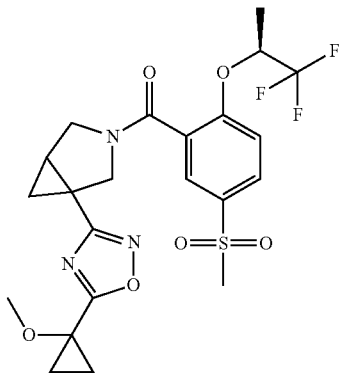 [SMILES: COC1(c2nc(C34CC3CN(C(=O)c3cc(S(C)(=O)=O)ccc3O[C@@H](C)C(F)(F)F)C4)no2)CC1]

N-(3-dimethylaminopropyl)-N'-ethylcarbodiimidehydrochloride (110 mg, 0.57 mmol) is added to a stirred mixture of example 55a (110 mg, 0.50 mmol), example 4a (159 mg, 0.51 mmol) and 1-Hydroxybenzotriazole (10 mg, 0.07 mmol) in THF/DMF mixture. After stirring 18 hours the mixture is poured in water and extracted with EtOAc. Organic layer is separated, washed with 5% aqueous NaHCO$_3$ solution, dried over Na$_2$SO$_4$ and concentrated under reduced pressure. The residue is purified by Si flash chromatography (Fluent EtOAc/n-Hexane/MeOH 80:20:1) to obtain the title compound (200 mg, 78%).

HPLC-MS (Method 6): R$_t$=11.00 min

MS (ESI posy: m/z=516 (M+H)$^+$

The diasteromers of the title compound are separated by HPLC using a chiral stationary phase.

Method for Separation:

HPLC apparatus type: Waters 600 Pump; column: Daicel Chiralpack IA, 5.0 μm, 250 mm×20 mm; method: eluent hexane/IPA 80:20; flow rate: 15 mL/min, Temperature: 25° C.; UV Detection: 230 nm Example of Separation by Chiral HPLC:

Submitted to separation: 120 mg of Example 116 prepared as described above;

Obtained: 50 mg of Diastereoisomer 1 (Exp. 117) and 54 mg of Diastereoisomer 2 (Exp. 118)

| Example 117: Diastereoisomer 1 Unknown absolute stereochemistry at bridgehead | Example 118: Diastereoisomer 2 Unknown absolute stereochemistry at bridgehead |
|---|---|
| 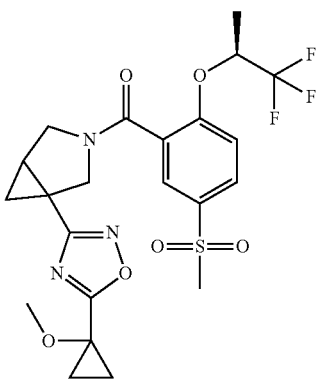 [SMILES: COC1(c2nc(C34CC3CN(C(=O)c3cc(S(C)(=O)=O)ccc3O[C@@H](C)C(F)(F)F)C4)no2)CC1] | 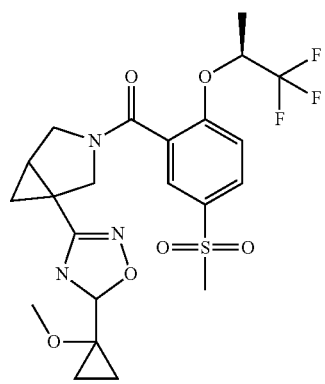 [SMILES: COC1(C2NC(C34CC3CN(C(=O)c3cc(S(C)(=O)=O)ccc3O[C@@H](C)C(F)(F)F)C4)=NO2)CC1] |

| Example | Chiral HPLC R$_t$ [min] | HPLC-MS (Method 7a): R$_t$ [min] | MS (APCI): m/z |
|---|---|---|---|
| Exp. 117 | 16.56 (Method 22) | 6.08 | 516 |
| Exp. 118 | 29.55 (Method 22) | 6.08 | 516 |

Example 119

Diasteromeric Mixture

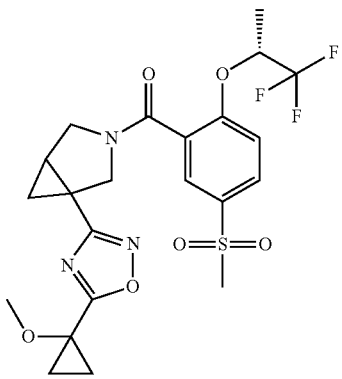 [SMILES: COC1(c2nc(C34CC3CN(C(=O)c3cc(S(C)(=O)=O)ccc3O[C@H](C)C(F)(F)F)C4)no2)CC1]

Title compound is prepared in analogy to example 116 starting from example 4b (158.7 mg, 0.51 mmol) in place of example 4a to obtain 180 mg (70%) of product.

HPLC-MS (Method 7a): $R_t$=6.23 min

MS (APCI pos): m/z=516 (M+H)$^+$

The diasteromers of the title compound are separated by HPLC using a chiral stationary phase.

Method for Separation:

HPLC apparatus type: Waters 600 Pump; column: Daicel Chiralpack IA, 5.0 μm, 250 mm×20 mm; method: eluent hexane/IPA 80:20; flow rate: 15 mL/min, Temperature: 25° C.; UV Detection: 230 nm Example of Separation by Chiral HPLC:

Submitted to separation: 70 mg of Example 119 prepared as described above;

Obtained: 31 mg of Diastereoisomer 1 (Exp. 120) and 29 mg of Diastereoisomer 2 (Exp. 121)

The title compound is prepared in analogy to example 116 starting from example 55d (90 mg, 0.41 mmol) in place of example 55a and example 4b (131 mg, 0.42 mmol) in place of example 4a and EtOAc/n-Hexane/MeOH 70:30:1 as eluent for the Si-flash chromatography to obtain 150 mg (71%) of product.

HPLC-MS (Method 7a): $R_t$=6.20 min

MS (APCI pos): m/z=514 (M+H)$^+$

The diasteromers of the title compound are separated by HPLC using a chiral stationary phase.

| Example 120: Diastereoisomer 1 Unknown absolute stereochemistry at bridgehead | Example 121: Diastereoisomer 2 Unknown absolute stereochemistry at bridgehead |
|---|---|
| 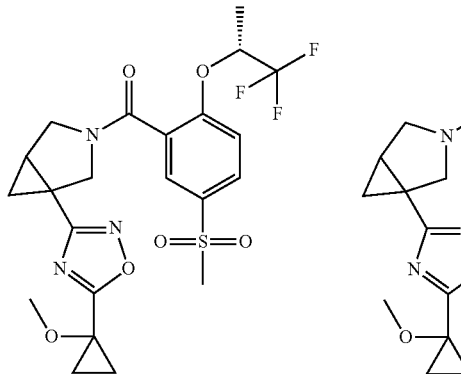 | 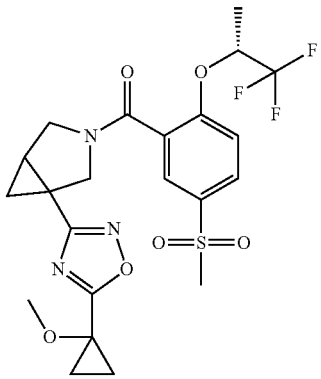 [SMILES: COC1(c2nc(C34CC3CN(C(=O)c3cc(S(C)(=O)=O)ccc3O[C@H](C)C(F)(F)F)C4)no2)CC1] |

| Example | Chiral HPLC $R_t$ [min] | HPLC-MS (Method 7a): $R_t$ [min] | MS (APCI): m/z |
|---|---|---|---|
| Exp. 120 | 16.51 (Method 22) | 6.08 | 516 |
| Exp. 121 | 23.06 (Method 22) | 6.08 | 516 |

Example 122

Diasteromeric Mixture

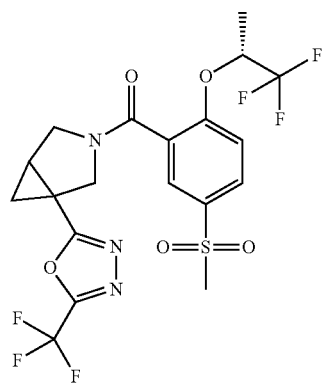 [SMILES: C[C@@H](Oc1ccc(S(C)(=O)=O)cc1C(=O)N1CC2CC2(c2nnc(C(F)(F)F)o2)C1)C(F)(F)F]

Method for Separation:

HPLC apparatus type: Waters 600 Pump; column: Daicel Chiralpack IA, 5.0 μm, 250 mm×20 mm; method: eluent hexane/IPA 75:25; flow rate: 15 mL/min, Temperature: 25° C.; UV Detection: 230 nm Example of Separation by Chiral HPLC:

Submitted to separation: 110 mg of Example 122 prepared as described above;

Obtained: 49 mg of Diastereoisomer 1 (Exp. 123) and 50 mg of Diastereoisomer 2 (Exp. 124)

Example 123: Diastereoisomer 1
Unknown absolute stereochemistry at bridgehead

Example 124: Diastereoisomer 2
Unknown absolute stereochemistry at bridgehead

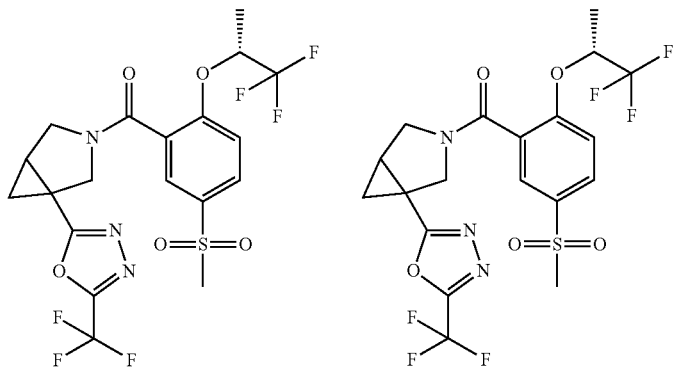

1.1.2.1

| Example | Chiral HPLC $R_t$ [min] | HPLC-MS (Method 7a): $R_t$ [min] | MS (APCI): m/z |
|---|---|---|---|
| Exp. 123 | 8.21 (Method 23) | 6.35 | 514 |
| Exp. 124 | 11.49 (Method 23) | 6.33 | 514 |

Example 125

Diasteromeric Mixture

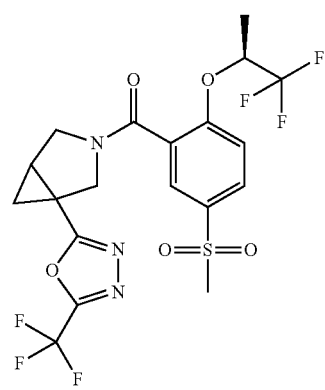 [SMILES: C[C@H](Oc1ccc(S(C)(=O)=O)cc1C(=O)N1CC2CC2(c2nnc(C(F)(F)F)o2)C1)C(F)(F)F]

The title compound is prepared in analogy to example 116 starting from example 55d (90 mg, 0.41 mmol) in place of example 55a and EtOAc/n-Hexane/MeOH 70:30:1 as eluent for the Si-flash chromatography to obtain 140 mg (66%) of product.

HPLC-MS (Method 7a): $R_t$=6.22 min

MS (APCI pos): m/z=514 (M+H)$^+$

The diasteromers of the title compound are separated by HPLC using a chiral stationary phase.

Method for Separation:

HPLC apparatus type: Waters 600 Pump; column: Daicel Chiralpack IA, 5.0 μm, 250 mm×20 mm; method: eluent hexane/IPA 70:30; flow rate: 15 mL/min, Temperature: 25° C.; UV Detection: 230 nm Example of Separation by Chiral HPLC:

Submitted to separation: 100 mg of Example 125 prepared as described above;

Obtained: 39 mg of Diastereoisomer 1 (Exp. 126) and 45 mg of Diastereoisomer 2 (Exp. 127)

Example 126: Diastereoisomer 1
Unknown absolute stereochemistry at bridgehead

Example 127: Diastereoisomer 2
Unknown absolute stereochemistry at bridgehead

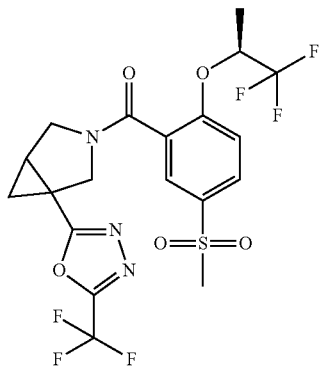 [SMILES: C[C@H](Oc1ccc(S(C)(=O)=O)cc1C(=O)N1CC2CC2(c2nnc(C(F)(F)F)o2)C1)C(F)(F)F]
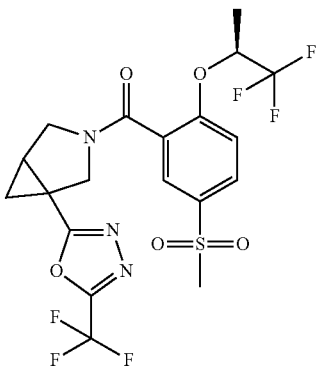 [SMILES: C[C@H](Oc1ccc(S(C)(=O)=O)cc1C(=O)N1CC2CC2(c2nnc(C(F)(F)F)o2)C1)C(F)(F)F]

| Example | Chiral HPLC $R_t$ [min] | HPLC-MS (Method 7a): $R_t$ [min] | MS (APCI): m/z |
| --- | --- | --- | --- |
| Exp. 126 | 8.23 (Method 23) | 6.43 | 514 |
| Exp. 127 | 13.65 (Method 23) | 6.40 | 514 |

Example 128

Diasteromeric Mixture

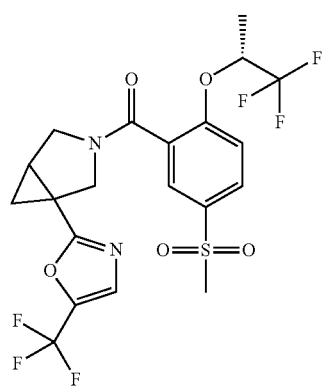 [SMILES: C[C@@H](Oc1ccc(S(C)(=O)=O)cc1C(=O)N1CC2CC2(c2ncc(C(F)(F)F)o2)C1)C(F)(F)F]

The title compound is prepared in analogy to example 116 starting from example 55b (50 mg, 0.23 mmol) in place of example 55a, example 4b (73.2 mg, 0.23 mmol) in place of example 4a and EtOAc/n-Hexane/MeOH 70:30:1 as eluent for the Si-flash chromatography to obtain 90 mg (77%) of product.

HPLC-MS (Method 7a): $R_t$=6.68 min

MS (APCI pos): m/z=513 (M+H)$^+$

The diasteromers of the title compound are separated by HPLC using a chiral stationary phase.

Method for Separation:

HPLC apparatus type: Waters 600 Pump; column: Daicel Chiralpack AD-H, 5.0 μm, 250 mm×20 mm; method: eluent hexane/IPA 70:30; flow rate: 15 mL/min, Temperature: 25° C.; UV Detection: 230 nm Example of Separation by Chiral HPLC:

Submitted to separation: 70 mg of Example 128 prepared as described above;

Obtained: 28 mg of Diastereoisomer 1 (Exp. 129) and 24 mg of Diastereoisomer 2 (Exp. 130)

Example 129: Diastereoisomer 1
Unknown absolute stereochemistry at bridgehead

Example 130: Diastereoisomer 2
Unknown absolute stereochemistry at bridgehead

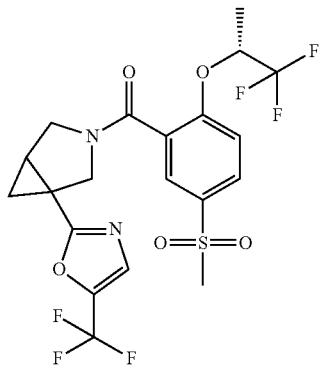
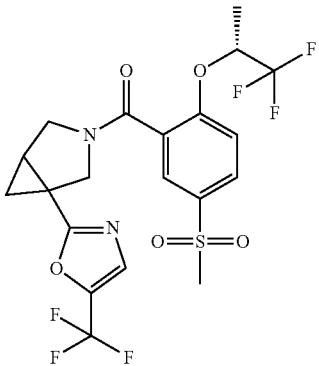 [SMILES: C[C@@H](Oc1ccc(S(C)(=O)=O)cc1C(=O)N1CC2CC2(c2ncc(C(F)(F)F)o2)C1)C(F)(F)F]

| Example | Chiral HPLC $R_t$ [min] | HPLC-MS (Method 7a): $R_t$ [min] | MS (APCI): m/z |
|---|---|---|---|
| Exp. 129 | 8.20 (Method 12) | 6.69 | 513 |
| Exp. 130 | 10.65 (Method 12) | 6.69 | 513 |

Example 131

Diasteromeric Mixture

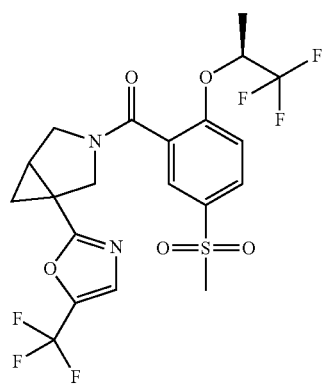 [SMILES: C[C@H](Oc1ccc(S(C)(=O)=O)cc1C(=O)N1CC2CC2(c2ncc(C(F)(F)F)o2)C1)C(F)(F)F]

The title compound is prepared in analogy to example 116 starting from example 55b (50 mg, 0.23 mmol) in place of example 55a and EtOAc/n-Hexane/MeOH 70:30:1 as eluent for the Si-flash chromatography to obtain 75 mg (64%) of product.

HPLC-MS (Method 2): $R_t$=1.14 min

MS (ESI pos): m/z=513 (M+H)$^+$

The diasteromers of the title compound are separated by HPLC using a chiral stationary phase.

Method for Separation:

HPLC apparatus type: Waters 600 Pump; column: Daicel Chiralpack IA, 5.0 μm, 250 mm×20 mm; method: eluent hexane/IPA 80:20; flow rate: 15 mL/min, Temperature: 25° C.; UV Detection: 230 nm Example of Separation by Chiral HPLC:
Submitted to separation: 75 mg of Example 131 prepared as described above;
Obtained: 32 mg of Diastereoisomer 1 (Exp. 132) and 30 mg of Diastereoisomer 2 (Exp. 133)

Example 132: Diastereoisomer 1
Unknown absolute stereochemistry at bridgehead

Example 133: Diastereoisomer 2
Unknown absolute stereochemistry at bridgehead

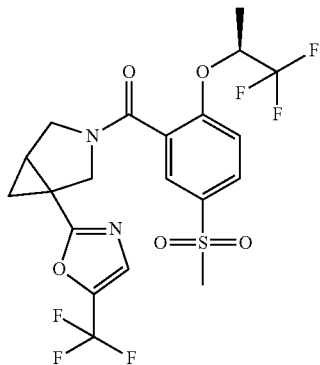 [SMILES: C[C@H](Oc1ccc(S(C)(=O)=O)cc1C(=O)N1CC2CC2(c2ncc(C(F)(F)F)o2)C1)C(F)(F)F]
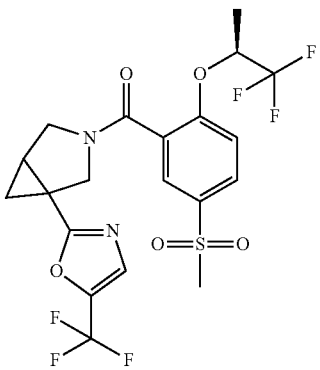 [SMILES: C[C@H](Oc1ccc(S(C)(=O)=O)cc1C(=O)N1CC2CC2(c2ncc(C(F)(F)F)o2)C1)C(F)(F)F]

| Example | Chiral HPLC $R_t$ [min] | HPLC-MS (Method 7a): $R_t$ [min] | MS (APCI): m/z |
|---|---|---|---|
| Exp. 132 | 14.50 (Method 22) | 6.69 | 513 |
| Exp. 133 | 22.28 (Method 22) | 6.69 | 513 |

Example 134

Diasteromeric Mixture

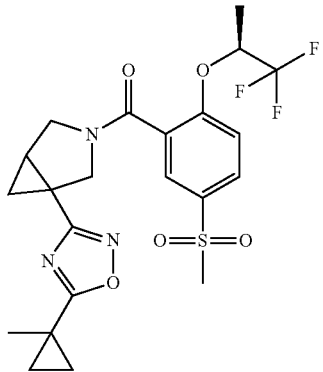 [SMILES: C[C@H](Oc1ccc(S(C)(=O)=O)cc1C(=O)N1CC2CC2(c2noc(C3(C)CC3)n2)C1)C(F)(F)F]

DIPEA (0.15 ml, 0.88 mmol) is added to a stirred solution of example 55c (90 mg, 0.37 mmol) and example 4a (140 mg, 0.45 mmol) in DMF; after 10 minutes HATU (190 mg, 0.50 mmol) is added and the reaction is stirred for 18 hours. The reaction mixture is poured into water and extracted with EtOAc, organic layer is separated, washed with 5% NaHCO$_3$ aqueous solution, dried over Na$_2$SO$_4$ and concentrated under reduced pressure. The crude is purified by flash chromatography using EtOAc/n-Hexane/MeOH 60:40:1 as eluent to obtain the title compound (130 mg, 70%)

HPLC-MS (Method 7a): $R_t$=6.19 min
MS (APCI pos): m/z=500 (M+H)$^+$

Example 135

Diastereomeric Mixture

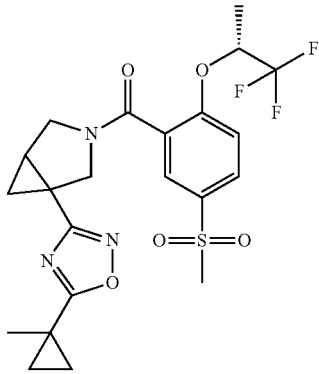 [SMILES: C[C@@H](Oc1ccc(S(C)(=O)=O)cc1C(=O)N1CC2CC2(c2noc(C3(C)CC3)n2)C1)C(F)(F)F]

The title compound is prepared in analogy to example 134 starting from example 4b (140 mg, 0.45 mmol) in place of example 4a to obtain 140 mg (76%) of product.

HPLC-MS (Method 7a): $R_t$=6.17 min
MS (APCI pos): m/z=500 (M+H)$^+$

Example 136 (Diastereoisomer 1, Unknown Absolute Stereochemistry at Bridgehead) and Example 137 (Diastereoisomer 2, Unknown Absolute Stereochemistry at Bridgehead)

The mixture of the title compounds is prepared in analogy to example 110, starting from example 4a (81 mg, 0.26 mmol) in place of example 4f and example 25w (60 mg, 0.24 mmol) to obtain the title compound (45 mg, 37%).

HPLC-MS (Method 7a): $R_t$=6.63 min
MS (APCI pos): m/z=513 (M+H)$^+$

The diasteromers are separated by HPLC using a chiral stationary phase.

Method for Separation:
HPLC apparatus type: Waters 600 Pump; column: Daicel Chiralpack IA, 5.0 μm, 250 mm×20 mm; method: eluent hexane/IPA 75:25; flow rate: 15 mL/min, Temperature: 25° C.; UV Detection: 230 nm
Example of Separation by Chiral HPLC:
Submitted to separation: 38 mg of diastereomeric mixture prepared as described above;
Obtained: 17 mg of Diastereoisomer 1 (Exp. 136) and 18 mg of Diastereoisomer 2 (Exp. 137)

The title compound is prepared in analogy to example 20 starting from example 4m (121.0 mg, 0.42 mmol) in place of example 4a, example 25k (80.0 mg, 0.31 mmol) in place of example 25a and DIPEA (0.18 ml, 1.06 mmol) in place of TEA to obtain 118 mg (77%) of product.

HPLC-MS (Method 6): $R_t$=10.15 min

MS (ESI pos): m/z=488 (M+H)$^+$

The diasteromers of the title compound are separated by HPLC using a chiral stationary phase.

Example 136: Diastereoisomer 1
Unknown absolute stereochemistry at bridgehead

Example 137: Diastereoisomer 2
Unknown absolute stereochemistry at bridgehead

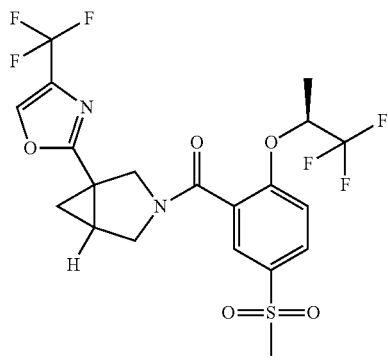 [SMILES: C[C@H](Oc1ccc(S(C)(=O)=O)cc1C(=O)N1CC2CC2(c2nc(C(F)(F)F)co2)C1)C(F)(F)F]
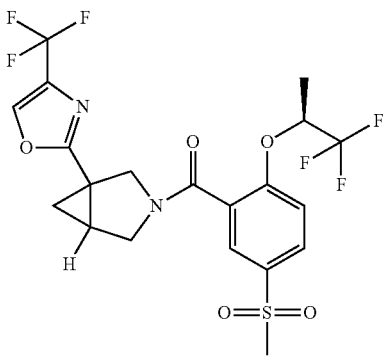 [SMILES: C[C@H](Oc1ccc(S(C)(=O)=O)cc1C(=O)N1CC2CC2(c2nc(C(F)(F)F)co2)C1)C(F)(F)F]

| Example | Chiral HPLC $R_t$ [min] | HPLC-MS (Method 7a): $R_t$ [min] | MS (APCI): m/z |
|---|---|---|---|
| Exp. 136 | 10.94 (Method 24) | 6.64 | 513 |
| Exp. 137 | 19.70 (Method 24) | 6.64 | 513 |

Example 138

Diasteromeric Mixture

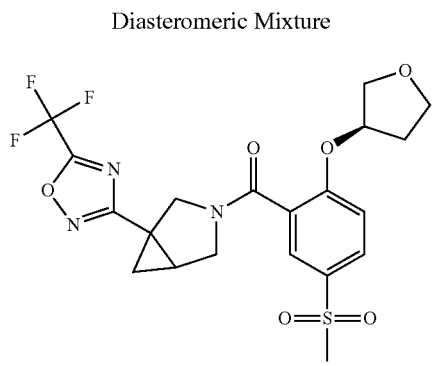

Method for Separation:

HPLC apparatus type: Waters 600 Pump; column: Daicel Chiralpack AD-H, 5.0 μm, 250 mm×20 mm; method: eluent hexane/IPA 70:30; flow rate: 15 mL/min, Temperature: 25° C.; UV Detection: 230 nm Example of Separation by Chiral HPLC:

Submitted to separation: 110 mg of Example 138 prepared as described above;

Obtained: 53 mg of Diastereoisomer 1 (Exp. 139) and 54 mg of Diastereoisomer 2 (Exp. 140)

| | Example 139: Diastereoisomer 1 Unknown absolute stereochemistry at bridgehead | Example 140: Diastereoisomer 2 Unknown absolute stereochemistry at bridgehead |
|---|---|---|
| | 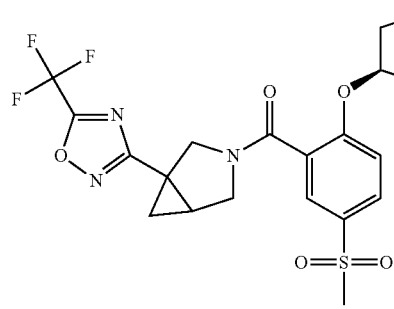 | 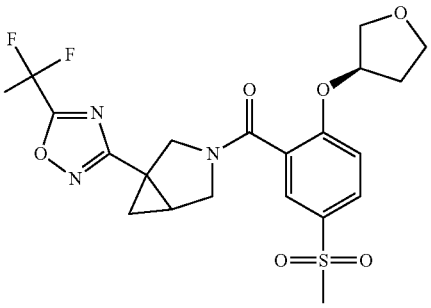 |
| Example | Chiral HPLC $R_t$ [min] | HPLC-MS (Method 7a): $R_t$ [min] | MS (APCI): m/z |
| Exp. 139 | 10.38 (Method 12) | 5.97 | 488 |
| Exp. 140 | 13.32 (Method 12) | 5.97 | 488 |

Example 141

Racemic Mixture

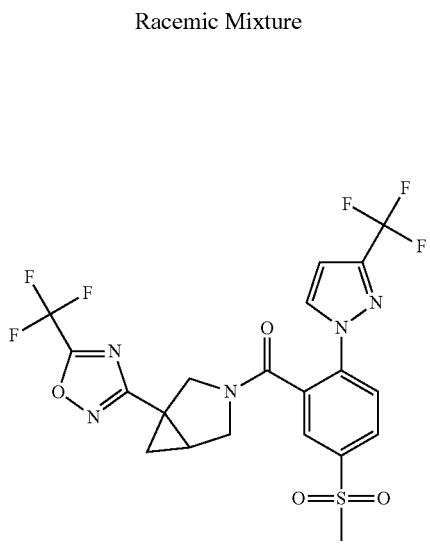

Potassium tert-butoxide (44.2 mg, 0.39 mmol) is added, under nitrogen atmosphere, to a solution of example 56a (150 mg, 0.36 mmol) and 1-(3-trifluoromethyl)pyrazole (58.4 mg, 0.43 mmol) in anhydrous THF (2 ml) then the reaction mixture is stirred overnight at room temperature. Solvent is concentrated under reduced pressure then the residue is partitioned between DCM and 10% citric acid aqueous solution, organic layer is separated over a phase-separator cartridge and concentrated under reduced pressure.

The crude is purified by RP-flash chromatography using ACN/water 20-100% as eluent to obtain the title product (87 mg, 45%)

HPLC-MS (Method 7): $R_t$=7.88 min

MS (ESI pos): m/z=536 (M+H)$^+$

Example 142

Single Enantiomer, Unknown Absolute Stereochemistry at Bridgehead

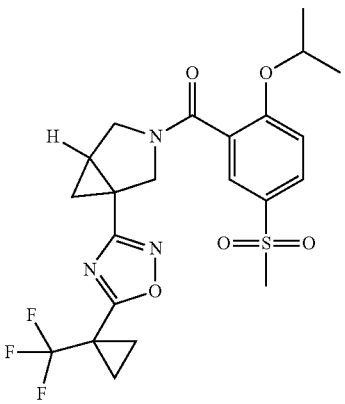 [SMILES: CC(C)Oc1ccc(S(C)(=O)=O)cc1C(=O)N1CC2CC2(c2noc(C3(C(F)(F)F)CC3)n2)C1]

The title compound is prepared in analogy to example 20 starting from example 25x (54 mg, 0.18 mmol) in place of example 25a, example 4f (65 mg, content 80%, 0.20 mmol) in place of example 4a and 10-100% EtOAc/Cyclohexane as purification eluent to obtain 60 mg (66%) of product.

HPLC-MS (Method 7a): $R_t$=6.21 min

MS (APCI pos): m/z=500 (M+H)$^+$

Example 143 (Diastereoisomer 1, Unknown Absolute Stereochemistry at Bridgehead) and Example 144 (Diastereoisomer 2, Unknown Absolute Stereochemistry at Bridgehead)

The mixture of the title compounds is prepared in analogy to example 20 starting from example 4a (75.0 mg, 0.24 mmol), example 25y (55.0 mg, 0.24 mmol) in place of example 25a and DIPEA (0.21 ml, 1.20 mmol) in place of TEA to obtain 85 mg (content 88%, 64%) of product.

The diasteromers are separated by HPLC using a chiral stationary phase.

Method for Separation:
HPLC apparatus type: Waters 600 Pump; column: Daicel Chiralpack AD-H, 5.0 μm, 250 mm×20 mm; method: eluent hexane/IPA 70:30; flow rate: 15 mL/min, Temperature: 25° C.; UV Detection: 230 nm Example of Separation by Chiral HPLC:
Submitted to separation: 85 mg of the diastereomic mixture prepared as described above;
Obtained: 28 mg of Diastereoisomer 1 (Exp. 143) and 34 mg of Diastereoisomer 2 (Exp. 144)

| Example 143: Diastereoisomer 1 Unknown absolute stereochemistry at bridgehead | Example 144: Diastereoisomer 2 Unknown absolute stereochemistry at bridgehead |
|---|---|
| 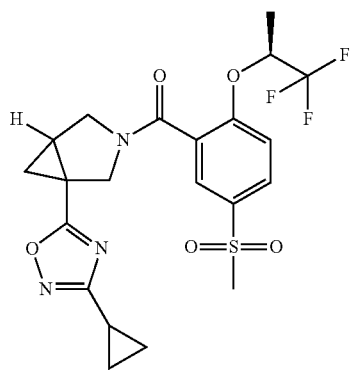 [SMILES: C[C@H](Oc1ccc(S(C)(=O)=O)cc1C(=O)N1CC2CC2(c2nc(C3CC3)no2)C1)C(F)(F)F] | 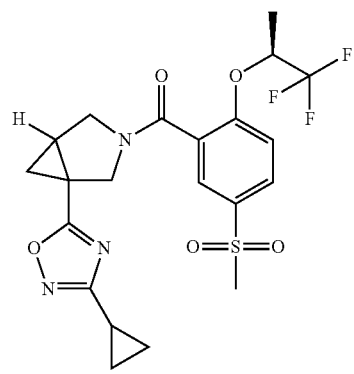 |

| Example | Chiral HPLC $R_t$ [min] | HPLC-MS (Method 7): $R_t$ [min] | MS (ESI pos): m/z |
|---|---|---|---|
| Exp. 143 | 10.95 (Method 12) | 6.52 | 486 |
| Exp. 144 | 13.35 (Method 12) | 6.52 | 486 |

Example 145

Diastereomeric Mixture

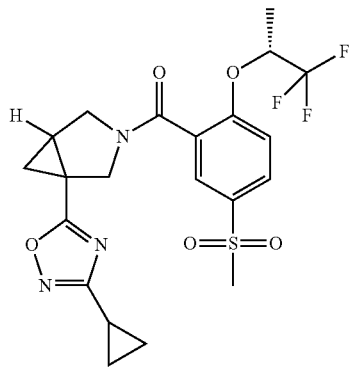 [SMILES: C[C@@H](Oc1ccc(S(C)(=O)=O)cc1C(=O)N1CC2CC2(c2nc(C3CC3)no2)C1)C(F)(F)F]

The title compound is prepared in analogy to example 20 starting from example 4b (75.0 mg, 0.24 mmol) in place of example 4a, example 25y (55.0 mg, 0.24 mmol) in place of example 25a and DIPEA (0.21 ml, 1.20 mmol) in place of TEA to obtain 68 mg (58%) of product.

HPLC-MS (Method 7): $R_t$=6.58 min

MS (ESI pos): m/z=486 (M+H)$^+$

Example 146

Diasteromeric Mixture

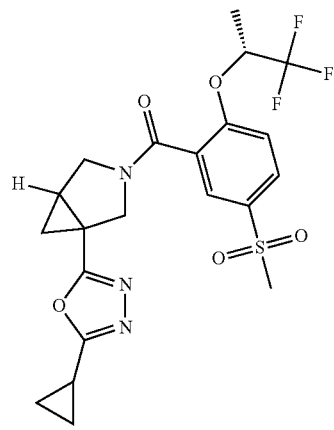 [SMILES: C[C@@H](Oc1ccc(S(C)(=O)=O)cc1C(=O)N1CC2CC2(c2nnc(C3CC3)o2)C1)C(F)(F)F]

HATU (109 mg, 0.29 mmol) and DIPEA (49 lA, 0.29 mmol) are added into a solution of example 4b (90 mg, 0.29 mmol) in 3 ml of anhydrous DMF and the reaction mixture is stirred for 30 minutes; example 55e (50 mg, 0.26 mmol) dissolved into 3 ml of anhydrous DMF is added and the resulting mixture is stirred overnight. EtOAc and water are added, phases are separated then the organic layer is washed with 0.5M HCl, 10% aqueous NaHCO$_3$, brine, dried over a phase-separator cartridge and concentrated under reduced pressure. Residue is purified by Si flash chromatography (eluent 20-100% EtOAc/cyclohexane) to furnish the title compound (36.5 mg, 29%).

HPLC-MS (Method 7a): $R_t$=5.28 min

MS (APCI pos): m/z=486 (M+H)$^+$

Example 147

Diasteromeric Mixture

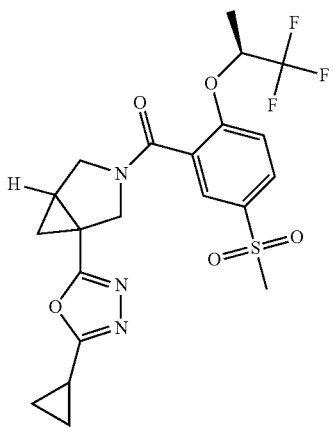 [SMILES: C[C@H](Oc1ccc(S(C)(=O)=O)cc1C(=O)N1CC2CC2(c2nnc(C3CC3)o2)C1)C(F)(F)F]

The title compound is prepared in analogy to example 146, starting from example 4a (90 mg, 0.29 mmol) in place of example 4b to obtain 41 mg of product (32%)

HPLC-MS (Method 7a): $R_t$=5.28 min

MS (APCI pos): m/z=486 (M+H)$^+$

Example 148

Diasteromeric Mixture

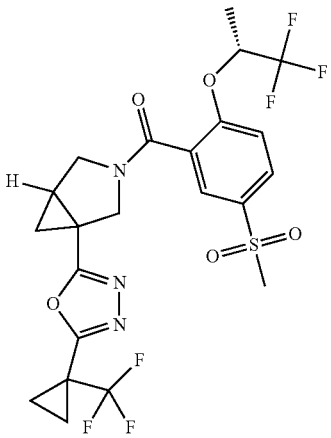 [SMILES: C[C@@H](Oc1ccc(S(C)(=O)=O)cc1C(=O)N1CC2CC2(c2nnc(C3(C(F)(F)F)CC3)o2)C1)C(F)(F)F]

The title compound is prepared in analogy to example 146, starting from example 4b (80 mg, 0.28 mmol), example 55f (83 mg, 0.28 mmol) in place of example 55e, DIPEA (0.096 ml, 0.56 mmol), HATU (107 mg, 0.28 mmol) to obtain 102 mg of product (72%).

HPLC-MS (Method 7a): $R_t$=6.05 min

MS (APCI pos): m/z=554 (M+H)$^+$

The diastereoisomers of the title compound are separated by HPLC using a chiral stationary phase.

Method for Separation:

HPLC apparatus type: Waters 600 Pump; column: Daicel Chiralpack IA, 5.0 µm, 250 mm×20 mm; method: eluent hexane/IPA 75:25; flow rate: 15 mL/min, Temperature: 25° C.; UV Detection: 230 nm Example of Separation by Chiral HPLC:

Submitted to separation: 75 mg of Example 148 prepared as described above;

Obtained: 33 mg of Diastereoisomer 1 (Exp. 149) and 35 mg of Diastereoisomer 2 (Exp. 150)

| Example 149: Diastereoisomer 1 Unknown absolute stereochemistry at bridgehead | Example 150: Diastereoisomer 2 Unknown absolute stereochemistry at bridgehead |
|---|---|
| 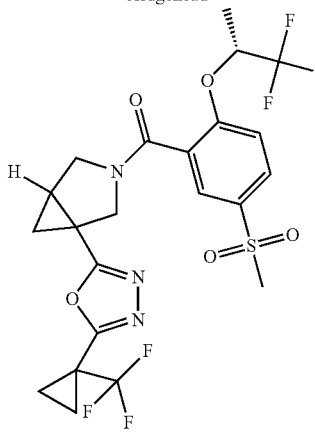 | 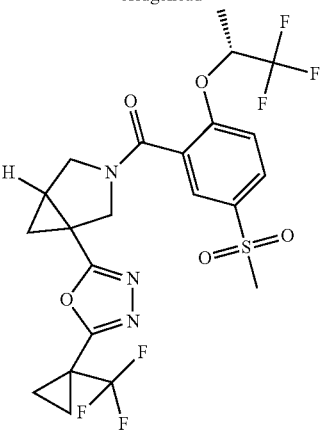 |

| Example | Chiral HPLC $R_t$ [min] | HPLC-MS (Method 6): $R_t$ [min] | MS (ESI pos): m/z |
|---|---|---|---|
| Exp. 149 | 20.50 (Method 22) | 6.17 | 554 |
| Exp. 150 | 24.51 (Method 22) | 6.17 | 554 |

Example 151
Diasteromeric Mixture

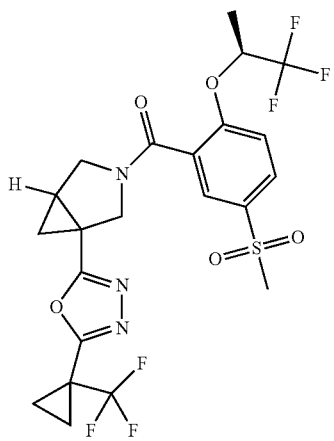 [SMILES: C[C@H](Oc1ccc(S(C)(=O)=O)cc1C(=O)N1CC2CC2(c2nnc(C3(C(F)(F)F)CC3)o2)C1)C(F)(F)F]

The title compound is prepared in analogy to example 148, starting from example 4a (80 mg, 0.28 mmol) in place of example 4b to obtain 100 mg of product (71%).

HPLC-MS (Method 7a): $R_t$=6.03 min
MS (APCI pos): m/z=554 (M+H)$^+$

The diastereoisomers of the title compound are separated by HPLC using a chiral stationary phase.
Method for Separation:

HPLC apparatus type: Waters 600 Pump; column: Daicel Chiralpack IA, 5.0 µm, 250 mm×20 mm; method: eluent hexane/IPA 75:25; flow rate: 15 mL/min, Temperature: 25° C.; UV Detection: 230 nm
Example of Separation by Chiral HPLC:

Submitted to separation: 75 mg of Example 151 prepared as described above;

Obtained: 30 mg of Diastereoisomer 1 (Exp. 152) and 34 mg of Diastereoisomer 2 (Exp. 153)

Example 154
Racemic Mixture

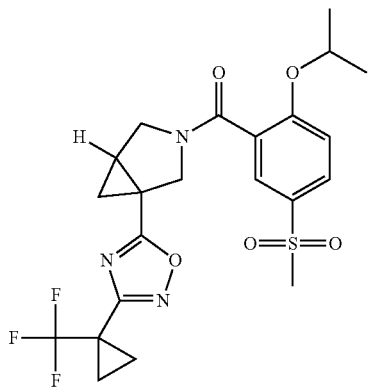

Title compound is prepared in analogy to example 20 starting from example 4f (58 mg, 0.22 mmol) in place of example 4a, example 25z (63 mg, 0.21 mmol) in place of example 25a and anhydrous ACN (2 ml) in place of DMF. The crude is purified by RP-flash chromatography using 20-100% ACN/water as eluent then by Si-flash chromatography using 20-100% EtOAc/Cyclohexan as eluent to obtain 15 mg (14%) of product.

HPLC-MS (Method 7a): $R_t$=6.50 min
MS (APCI pos): m/z=500 (M+H)$^+$

| Example 152: Diastereoisomer 1 Unknown absolute stereochemistry at bridgehead | Example 153: Diastereoisomer 2 Unknown absolute stereochemistry at bridgehead |
|---|---|
| 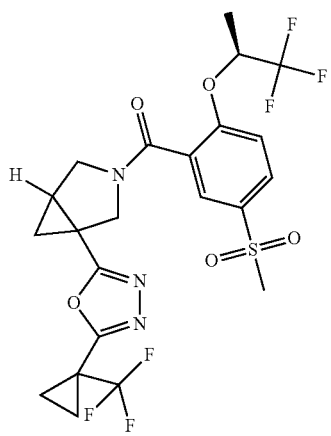 | 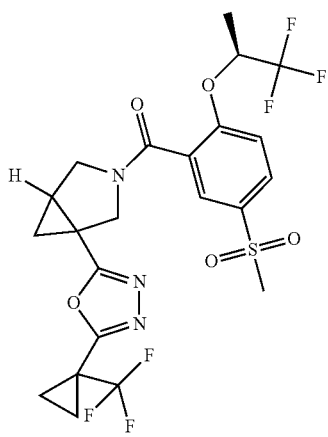 [SMILES: C[C@H](Oc1ccc(S(C)(=O)=O)cc1C(=O)N1CC2CC2(c2nnc(C3(C(F)(F)F)CC3)o2)C1)C(F)(F)F] |

| Example | Chiral HPLC $R_t$ [min] | HPLC-MS (Method 6): $R_t$ [min] | MS (ESI pos): m/z |
|---|---|---|---|
| Exp. 152 | 19.00 (Method 22) | 11.03 | 554 |
| Exp. 153 | 33.02 (Method 22) | 11.03 | 554 |

Example 155

Diasteromeric Mixture

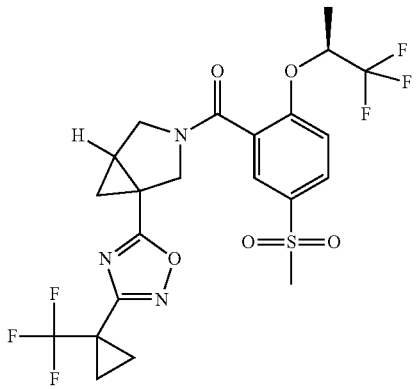 [SMILES: C[C@H](Oc1ccc(S(C)(=O)=O)cc1C(=O)N1CC2CC2(c2nc(C3(C(F)(F)F)CC3)no2)C1)C(F)(F)F]

Title compound is prepared in analogy to example 20 starting from example 4a (70 mg, 0.22 mmol), example 25z (63 mg, 0.21 mmol) in place of example 25a and anhydrous ACN (2 ml) in place of DMF. The crude is purified by RP-flash chromatography using 20-100% ACN/water as eluent then by Si-flash chromatography using 20-100% EtOAc/Cyclohexan as eluent to obtain 30 mg (25%) of product.

HPLC-MS (Method 6): $R_t$=11.91 min
MS (ESI pos): m/z=554 (M+1-1)$^+$

Example 156

Diasteromeric Mixture

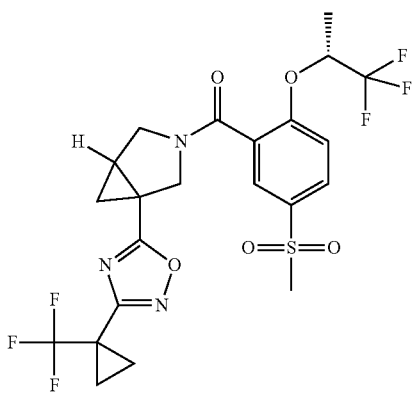 [SMILES: C[C@@H](Oc1ccc(S(C)(=O)=O)cc1C(=O)N1CC2CC2(c2nc(C3(C(F)(F)F)CC3)no2)C1)C(F)(F)F]

Title compound is prepared in analogy to example 20 starting from example 4b (70 mg, 0.22 mmol) in place of example 4a, example 25z (63 mg, 0.21 mmol) in place of example 25a and anhydrous ACN (2 ml) in place of DMF. The crude is purified by RP-flash chromatography using 20-100% ACN/water as eluent then by Si-flash chromatography using 20-100% EtOAc/Cyclohexan as eluent to obtain 26 mg (22%) of product.

HPLC-MS (Method 7a): $R_t$=6.67 min
MS (APCI pos): m/z=554 (M+H)$^+$

Example 157

Diasteromeric Mixture

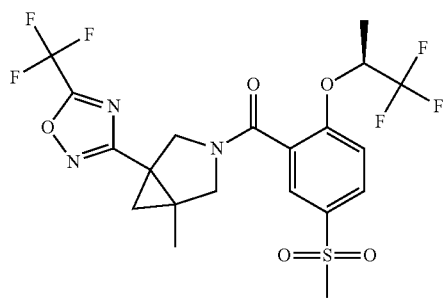 [SMILES: C[C@H](Oc1ccc(S(C)(=O)=O)cc1C(=O)N1CC2(C)CC2(c2noc(C(F)(F)F)n2)C1)C(F)(F)F]

The title compound is prepared in analogy to example 20 starting from example 4a (110 mg, 0.35 mmol), example 55g (79 mg, 0.29 mmol) in place of example 25a, DIPEA (153 µl, 0.88 mmol) in place of TEA and purifying by RP-flash chromatography using 20-100% ACN/water as eluent to obtain 115 mg (74%) of product.

HPLC-MS (Method 7a): $R_t$=7.07 min
MS (APCI pos): m/z=528 (M+H)$^+$

The diasteromers of the title compound are separated by HPLC using a chiral stationary phase.

Method for Separation:
HPLC apparatus type: Waters 600 Pump; column: Daicel Chiralpack AD-H, 5.0 µm, 250 mm×20 mm; method: eluent hexane/IPA 75:25; flow rate: 15 mL/min, Temperature: 25° C.; UV Detection: 230 nm Example of Separation by Chiral HPLC:
Submitted to separation: 110 mg of Example 157 prepared as described above;
Obtained: 50 mg of Diastereoisomer 1 (Exp. 158) and 53 mg of Diastereoisomer 2 (Exp. 159)

| | Example 158: Diastereoisomer 1 Unknown absolute stereochemistry at bridgehead | Example 159: Diastereoisomer 2 Unknown absolute stereochemistry at bridgehead | |
|---|---|---|---|
| Example | Chiral HPLC $R_t$ [min] | HPLC-MS (Method 7): $R_t$ [min] | MS (ESI pos): m/z |
| Exp. 158 | 7.43 (Method 11) | 7.89 | 528 |
| Exp. 159 | 7.46 (Method 11) | 7.86 | 528 |

Example 160

Diastereomeric Mixture

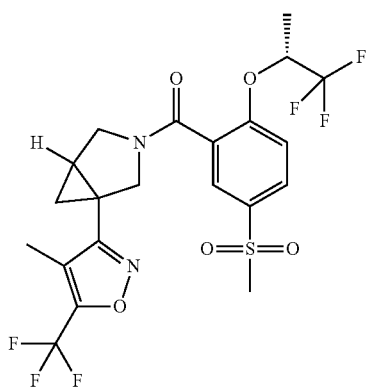 [SMILES: Cc1c(C23CC2CN(C(=O)c2cc(S(C)(=O)=O)ccc2O[C@H](C)C(F)(F)F)C3)noc1C(F)(F)F]

The title compound is prepared as described for example 20, starting from example 25za (22 mg, 0.08 mmol) in place of example 25a and example 4b (25.6 mg, 0.08 mmol) in place of example 4a to obtain 4.5 mg (10%).

HPLC-MS (Method 7a): $R_t$=6.88 min

MS (APCI): m/z=527 (M+H)$^+$

The diastereomers of the title compound are separated by HPLC using a chiral stationary phase.

Method for Separation:

HPLC apparatus type: Waters 600 Pump; column: Daicel Chiralpack AD-H, 5.0 μm, 250 mm×20 mm; method: eluent hexane/IPA 85:15; flow rate: 15 mL/min, Temperature: 25° C.; UV Detection: 210 nm Example of Separation by Chiral HPLC:

Submitted to separation: 60 mg of example 160 prepared as described above;

Obtained: 19 mg of Diastereoisomer 1 (Exp. 161) and 17 mg of Diastereoisomer 2 (Exp. 162)

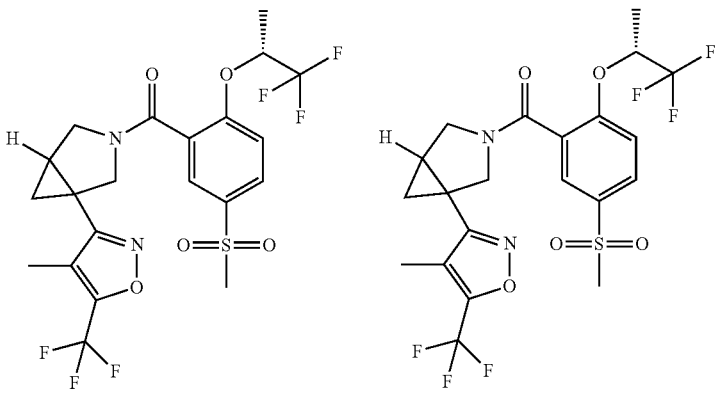

| | Example 161: Diastereoisomer 1 Unknown absolute stereochemistry at bridgehead | Example 162: Diastereoisomer 2 Unknown absolute stereochemistry at bridgehead | |
|---|---|---|---|
| Example | Chiral HPLC $R_t$ [min] | HPLC-MS (Method 7a): $R_t$ [min] | MS (APCI): m/z |
| Exp. 161 | 19.58 (Method 20) | 6.82 | 527 |

| Exp. 162 | 24.15 (Method 20) | 6.82 | 527 |

Example 163

Diastereomeric Mixture

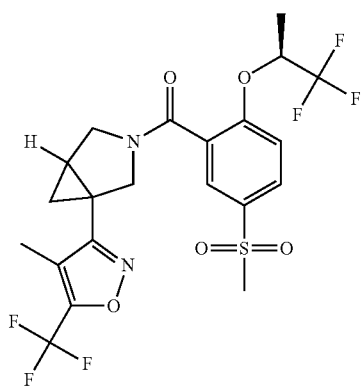 [SMILES: Cc1c(C23CC2CN(C(=O)c2cc(S(C)(=O)=O)ccc2O[C@@H](C)C(F)(F)F)C3)noc1C(F)(F)F]

HATU (100 mg, 0.26 mmol) and DIPEA (120 ill, 0.69 mmol) are added into a solution of example 4a (80 mg, 0.26 mmol) in 3 ml of anhydrous ACN and the reaction mixture is stirred for 15 minutes; example 25za (62 mg, 0.23 mmol) is added and the resulting mixture is stirred overnight. The reaction mixture is filtered over basic alumina pad, concentrated under reduced pressure and purified by Si flash chromatography (eluent 0-100% EtOAc/cyclohexane) then by RP flash chromatography (eluent 20-100 ACN/water) to furnish the title compound (63.8 mg, 53%).

HPLC-MS (Method 7a): $R_t$=6.80 min

MS (APCI): m/z=527 (M+H)$^+$

The diastereomers of the title compound are separated by HPLC using a chiral stationary phase.

Method for Separation:

HPLC apparatus type: Waters 600 Pump; column: Daicel Chiralpack IA, 5.0 μm, 250 mm×20 mm; method: eluent hexane/IPA 85:15; flow rate: 12 mL/min, Temperature: 25° C.; UV Detection: 230 nm Example of Separation by Chiral HPLC:

Submitted to separation: 54 mg of Example 163 prepared as described above;

Obtained: 24 mg of Diastereoisomer 1 (Exp. 164) and 26 mg of Diastereoisomer 2 (Exp. 165)

| Example 164: Diastereoisomer 1 Unknown absolute stereochemistry at bridgehead | Example 165: Diastereoisomer 2 Unknown absolute stereochemistry at bridgehead |

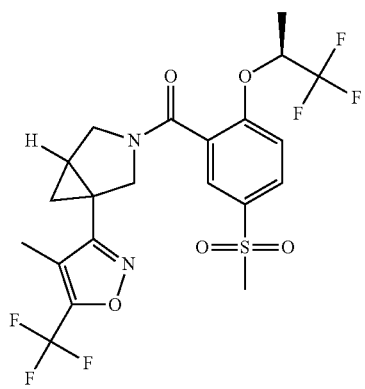 [SMILES: Cc1c(C23CC2CN(C(=O)c2cc(S(C)(=O)=O)ccc2O[C@@H](C)C(F)(F)F)C3)noc1C(F)(F)F] 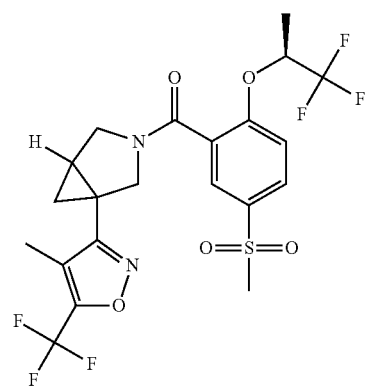 [SMILES: Cc1c(C23CC2CN(C(=O)c2cc(S(C)(=O)=O)ccc2O[C@@H](C)C(F)(F)F)C3)noc1C(F)(F)F]

| Example | Chiral HPLC $R_t$ [min] | HPLC-MS (Method 7a): $R_t$ [min] | MS (APCI): m/z |
|---|---|---|---|
| Exp. 164 | 22.45 (Method 25) | 6.95 | 527 |
| Exp. 165 | 30.04 (Method 25) | 6.95 | 527 |

The invention claimed is:
1. A compound of the formula (I)

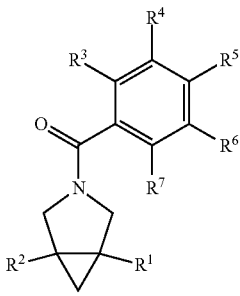

wherein
R$^1$ is selected from the group consisting of
  a) 5 or 6 membered moncyclic heteroaryl, having 1, 2, 3 or 4 heteroatoms independently selected from the group consisting of O, N and S(O)r,
  b) 5 or 6 membered moncyclic partially saturated heterocycloalkyl, having 1, 2 or 3 heteroatoms independently selected from the group consisting of O, N and S(O)r, and
  c) 9 or 10 membered bicyclic heteroaryl, having 1, 2 or 3 heteroatoms independently selected from the group consisting of O, N and S(O)$_r$,
wherein r is 0, 1 or 2;
wherein each of said groups a), b) and c) is optionally substituted with 1 or more substituents independently selected from the group consisting of C$_{1-4}$-alkyl-, C$_{1-4}$-alkyl-O—, oxetanyl, tetrahydrofuranyl, tetrahydropyranyl, C$_{3-6}$-cycloalkyl- and C$_{3-6}$-cycloalkyl-O— and in case a substituent is attached to a nitrogen ring atom said substituent is selected from the group consisting of C$_{1-4}$-alkyl-, C$_{1-4}$-alkyl-CO—, C$_{3-6}$-cycloalkyl- and C$_{3-6}$-cycloalkyl-CO—,
and wherein each of said C$_{1-4}$-alkyl-, C$_{1-4}$-alkyl-O—, C$_{1-4}$-alkyl-CO—, oxetanyl, tetrahydrofuranyl, tetrahydropyranyl, C$_{3-6}$-cycloalkyl-, C$_{3-6}$-cycloalkyl-CO— or C$_{3-6}$-cycloalkyl-O— substituents may be substituted by 1 or more substituents independently selected from the group consisting of fluoro, —CF$_3$, —CHF$_2$, —CH$_2$F and —CN;
R$^2$ is selected from the group consisting of hydrogen, C$_{1-4}$-alkyl-, C$_{1-4}$-alkyl-O—, —CN and C$_{3-6}$-cycloalkyl-,
wherein each of said C$_{1-4}$-alkyl-, C$_{1-4}$-alkyl-O— and C$_{3-6}$-cycloalkyl-group may be optionally substituted with 1, 2, 3 or more substituents independently selected from the group consisting of fluoro, —CF$_3$, —CHF$_2$, —CH$_2$F and —CN;
R$^3$ is selected from the group consisting of C$_{1-6}$-alkyl-O—, C$_{3-6}$-cycloalkyl-O—, morpholino, pyrazolyl and a 4 to 7 membered, monocyclic heterocycloalkyl-O— with 1 oxygen atom as ring member and optionally 1 or 2 heteroatoms independently selected from the group consisting of O, N and S(O)$_s$ with s=0, 1 or 2,
wherein said C$_{1-6}$-alkyl-O— and said C$_{3-6}$-cycloalkyl-O— may be optionally substituted with 1, 2, 3 or more substituents independently selected from the group consisting of fluoro, —CF$_3$, —CHF$_2$, —CH$_2$F, —CN, C$_{1-4}$-alkyl-, C$_{3-6}$-cycloalkyl-, C$_{1-6}$-alkyl-O— and C$_{3-6}$-cycloalkyl-O—;
R$^4$ is hydrogen;
or R$^3$ and R$^4$ together with the ring atoms of the phenyl group to which they are bound may form a 4, 5 or 6 membered, monocyclic, partially saturated heterocycloalkyl or a heteroaryl each of which having 1, 2 or 3 heteroatoms independently selected from the group consisting of O, N and S(O)$_s$ with s=0, 1 or 2, wherein there must be 1 ring oxygen atom that is directly attached to the ring carbon atom of said phenyl group to which R$^3$ is attached to in general formula (I);
wherein said heterocycloalkyl group may be optionally substituted with 1, 2, 3 or more substituents independently selected from the group consisting of fluoro, —CF$_3$, —CHF$_2$, —CH$_2$F, —CN, C$_{1-4}$-alkyl-, C$_{3-6}$-cycloalkyl-, C$_{1-6}$-alkyl-O—, C$_{3-6}$-cycloalkyl-O—, oxetanyl-O—, tetrahydrofuranyl-O— and tetrahydropyranyl-O—;
R$^5$ is hydrogen;
R$^6$ is selected from the group consisting of hydrogen, C$_{1-4}$-alkyl-SO$_2$—, C$_{3-6}$-cycloalkyl-SO$_2$ and —CN;
R$^7$ is hydrogen;
or one of the pairs a) R$^6$ and R$^7$ or b) R$^6$ and R$^5$ form together with the ring atoms of the phenyl group to which they are bound, a 5 or 6 membered, partially saturated monocyclic heterocycloalkyl group having 1, 2 or 3 heteroatoms independently selected from the group consisting of O, N and S(O)$_u$ with u=0, 1 or 2, wherein there must be 1 —SO$_2$— member that is directly attached to the ring carbon atom of said phenyl group to which R$^6$ is attached to in general formula (I),
wherein said heterocycloalkyl group may be optionally substituted with 1, 2, 3 or more substituents independently selected from the group consisting of fluoro, —CF$_3$, —CHF$_2$, —CH$_2$F, —CN, C$_{1-4}$-alkyl-, C$_{1-6}$-alkyl-O— and C$_{3-6}$-cycloalkyl-O—
or a salt thereof.

2. A compound according to claim 1, wherein
R$^1$ is a 5 or 6 membered moncyclic heteroaryl, having 1, 2 or 3 heteroatoms independently selected from the group consisting of O, N or S,
wherein said heteroaryl is optionally substituted with 1 or more substituents independently selected from the group consisting of C$_{1-2}$-alkyl-, C$_{1-2}$-alkyl-O—, oxetanyl, tetrahydrofuranyl, tetrahydropyranyl, cyclopropyl-, cyclobutyl-, cyclopropyl-O— and cyclobutyl-O— and in case a substituent is attached to a nitrogen ring atom said substituent is selected from the group consisting of C$_{1-2}$-alkyl- and C$_{1-2}$-alkyl-CO—,
and wherein each of said C$_{1-2}$-alkyl-, C$_{1-2}$-alkyl-O—, C$_{1-2}$-alkyl-CO—, oxetanyl, tetrahydrofuranyl, tetrahydropyranyl, cyclopropyl-, cyclobutyl, cyclopropyl-O— or cyclobutyl-O— substituents may be substituted with 1 or more substituents independently selected from the group consisting of fluoro, —CF$_3$, —CHF$_2$, —CH$_2$F and —CN;
R$^2$ is selected from the group consisting of hydrogen, methyl, ethyl, methoxy, ethoxy, —CN and cyclopropyl-,
wherein each of said groups may be optionally substituted with 1, 2 or 3 substituents independently selected from the group consisting of fluoro, —CF$_3$, —CHF$_2$, —CH$_2$F and —CN;
R$^3$ is as is selected from the group consisting of C$_{1-6}$-alkyl-O—, oxetanyl-O—, tetrahydrofuranyl-O—, tetrahydropyranyl-O— wherein said C$_{1-6}$-alkyl-O—, oxetanyl-O—, tetrahydrofuranyl-O—, tetrahydropyranyl-O— may be optionally substituted with 1, 2 or 3 substituents independently selected from the group consisting of fluoro, —$CF_3$, —$CHF_2$, —$CH_2F$, —CN, $C_{1-4}$-alkyl- and $C_{1-6}$-alkyl-O—;

$R^4$ is hydrogen;

or $R^3$ and $R^4$ together with the ring atoms of the phenyl group to which they are bound may form a 4, 5 or 6 membered, monocyclic, partially saturated heterocycloalkyl group having 1 or 2 oxygen atoms, wherein 1 ring oxygen atom is directly attached to the ring carbon atom of said phenyl group to which $R^3$ is attached to in general formula (I);

wherein said heterocycloalkyl group may be optionally substituted with 1, 2, 3 or more substituents independently selected from the group consisting of fluoro, —$CF_3$, —$CHF_2$, —$CH_2F$, —CN, $C_{1-3}$-alkyl-, cyclopropyl-, $C_{1-3}$-alkyl-O— and cyclopropyl-O—;

$R^5$ is hydrogen;

$R^6$ is selected from the group consisting of hydrogen, $C_{1-4}$-alkyl-$SO_2$—, $C_{3-6}$-cycloalkyl-$SO_2$— and —CN;

$R^7$ is hydrogen.

3. A compound according to claim 1, wherein $R^1$ is a 5 or 6 membered moncyclic heteroaryl being selected from the group consisting of oxadiazolyl, oxazolyl, isoxazolyl, thiazolyl, pyrazolyl, triazoyl, pyridinyl and pyrimidinyl, wherein said heteroaryl is optionally substituted with 1 or more substituents independently selected from the group consisting of $C_{1-2}$-alkyl-, $C_{1-2}$-alkyl-O—, cyclopropyl- and cyclopropyl-O— and in case it is a substituent of a nitrogen ring atom said substituent is selected from the group consisting of $C_{1-2}$-alkyl- and $C_{1-2}$-alkyl-CO—, and wherein each of said $C_{1-2}$-alkyl-, $C_{1-2}$-alkyl-O—, $C_{1-2}$-alkyl-CO—, cyclopropyl- or cyclopropyl-O— substituents may be substituted with 1 or more substituents independently selected from the group consisting of fluoro, —$CF_3$, —$CHF_2$, —$CH_2F$ and —CN;

$R^2$ is selected from the group consisting of hydrogen, methyl, ethyl, methoxy, ethoxy, —CN and cyclopropyl-, wherein each of said groups may be optionally substituted with 1, 2 or 3 substituents independently selected from the group consisting of fluoro, —$CF_3$, —$CHF_2$, —$CH_2F$ and —CN;

$R^3$ is as is selected from the group consisting of $C_{1-6}$-alkyl-O—, oxetanyl-O—, tetrahydrofuranyl-O—, tetrahydropyranyl-O— wherein said $C_{1-6}$-alkyl-O—, oxetanyl-O—, tetrahydrofuranyl-O—, tetrahydropyranyl-O— may be optionally substituted with 1, 2 or 3 substituents independently selected from the group consisting of fluoro, —$CF_3$, —$CHF_2$, —$CH_2F$, —CN, $C_{1-4}$-alkyl-, and $C_{1-6}$-alkyl-O—;

$R^4$ is hydrogen;

or $R^3$ and $R^4$ together with the ring atoms of the phenyl group to which they are bound may form a oxetan-, tetrahydrofuran-, tetrahydropyran- or dioxolan-group, wherein 1 oxygen atom is directly attached to the ring carbon atom of said phenyl group to which $R^3$ is attached to in general formula (I);

wherein said oxetan-, tetrahydrofuran-, tetrahydropyran- or dioxolan-group, may be optionally substituted with 1, 2, 3 or more substituents independently selected from the group consisting of fluoro, —$CF_3$, —$CHF_2$, —$CH_2F$, —CN, $C_{1-3}$-alkyl-, cyclopropyl-, $C_{1-3}$-alkyl-O and cyclopropyl-O—;

$R^5$ is hydrogen;

$R^6$ is selected from the group consisting of hydrogen, $C_{1-4}$-alkyl-$SO_2$—, $C_{3-6}$-cycloalkyl-$SO_2$- and —CN;

$R^7$ is hydrogen.

4. A compound according to claim 1, wherein $R^1$ is a 5 or 6 membered moncyclic heteroaryl being selected from the group consisting of oxadiazolyl, oxazolyl, isoxazolyl, thiazolyl, pyridinyl and pyrimidinyl, wherein said heteroaryl is optionally substituted with 1 or more substituents independently selected from the group consisting of $C_{1-2}$-alkyl-, $C_{1-2}$-alkyl-O—, cyclopropyl-, cyclopropyl-O— and in case it is a substituent of a nitrogen ring atom is selected from the group consisting of $C_{1-2}$-alkyl- and $C_{1-2}$-alkyl-CO—, and wherein each of said $C_{1-2}$-alkyl-, $C_{1-2}$-alkyl-O—, $C_{1-2}$-alkyl-CO—, cyclopropyl- or cyclopropyl-O— substituents may be substituted with 1 or more substituents independently selected from the group consisting of fluoro, —$CF_3$, —$CHF_2$, —$CH_2F$ and —CN;

$R^2$ is hydrogen or methyl;

$R^3$ is as is selected from the group consisting of $C_{1-6}$-alkyl-O—, oxetanyl-O—, tetrahydrofuranyl-O—, tetrahydropyranyl-O— wherein said $C_{1-6}$-alkyl-O—, oxetanyl-O—, tetrahydrofuranyl-O—, tetrahydropyranyl-O— may be optionally substituted with 1, 2 or 3 substituents independently selected from the group consisting of fluoro, —$CF_3$, —$CHF_2$, —$CH_2F$, —CN, $C_{1-4}$-alkyl- and $C_{1-6}$-alkyl-O—;

$R^4$ is hydrogen;

or $R^3$ and $R^4$ together with the ring atoms of the phenyl group to which they are bound may form a oxetan-, tetrahydrofuran-, tetrahydropyran- or dioxolan-group, wherein 1 oxygen atom is directly attached to the ring carbon atom of said phenyl group to which $R^3$ is attached to in general formula (I);

wherein said oxetan-, tetrahydrofuran-, tetrahydropyran- or dioxolan-group, may be optionally substituted with 1, 2, 3 or more substituents independently selected from the group consisting of fluoro, —$CF_3$, —$CHF_2$, —$CH_2F$, —CN, $C_{1-3}$-alkyl-, cyclopropyl-, $C_{1-3}$-alkyl-O— and cyclopropyl-O—;

$R^5$ is hydrogen;

$R^6$ is selected from the group consisting of $C_{1-4}$-alkyl-$SO_2$— and —CN;

$R^7$ is hydrogen.

5. A compound according to claim 1, wherein $R^1$ is a 5 or 6 membered moncyclic heteroaryl being selected from the group consisting of oxadiazolyl, oxazolyl, isoxazolyl, thiazolyl, pyridinyl and pyrimidinyl, wherein said heteroaryl is optionally substituted with 1 or more substituents independently selected from the group consisting of $C_{1-2}$-alkyl-, $C_{1-2}$-alkyl-O—, cyclopropyl-, cyclopropyl-O— and in case a substituent is attached to a nitrogen ring atom said substituent is selected from the group consisting of $C_{1-2}$-alkyl- and $C_{1-2}$-alkyl-CO—, and wherein each of said $C_{1-2}$-alkyl-, $C_{1-2}$-alkyl-O—, $C_{1-2}$-alkyl-CO—, cyclopropyl- or cyclopropyl-O— substituents may be substituted with 1 or more substituents independently selected from the group consisting of fluoro, —$CF_3$, —$CHF_2$, —$CH_2F$ and —CN;

$R^2$ is hydrogen or methyl;

$R^3$ is selected from the group consisting of $C_{1-3}$-alkyl-O—, oxetanyl-O—, tetrahydrofuranyl-O—, tetrahydropyranyl-O— wherein said $C_{1-3}$-alkyl-O—, oxetanyl-O—, tetrahydrofuranyl-O—, tetrahydropyranyl-O— may be optionally substituted with 1, 2 or 3 substituents independently selected from the group consisting of fluoro and —$CF_3$;

$R^4$ is hydrogen;
$R^5$ is hydrogen;
$R^6$ is selected from the group consisting of $C_{1-4}$-alkyl-$SO_2$— and —CN;
$R^7$ is hydrogen.

6. A compound according to claim 1, wherein
$R^1$ is a 5 or 6 membered moncyclic heteroaryl being selected from the group consisting of oxadiazolyl, oxazolyl, isoxazolyl, thiazolyl, pyridinyl and pyrimidinyl,
wherein said heteroaryl is optionally substituted with 1 or more substituents independently selected from the group consisting of $C_{1-2}$-alkyl-, $C_{1-2}$-alkyl-O—, cyclopropyl-, cyclopropyl-O— and in case a substituent is attached to a nitrogen ring atom said substituent is selected from the group consisting of $C_{1-2}$-alkyl- and $C_{1-2}$-alkyl-CO—,
and wherein each of said $C_{1-2}$-alkyl-, $C_{1-2}$-alkyl-O—, $C_{1-2}$-alkyl-CO—, cyclopropyl- or cyclopropyl-O— substituents may be substituted with 1 or more substituents independently selected from the group consisting of fluoro, —$CF_3$, —$CHF_2$, —$CH_2F$ and —CN;
$R^2$ is hydrogen;
$R^3$ is selected from the group consisting of R-1,1,1-trifluoro-2-ethoxy and S-1,1,1-trifluoro-2-ethoxy;
$R^4$ is hydrogen;
$R^5$ is hydrogen;
$R^6$ is selected from the group consisting of $C_{1-4}$-alkyl-$SO_2$— and —CN;
$R^7$ is hydrogen.

7. A compound according to claim 1, wherein the absolute configuration at $R^1$ is R.

8. A compound according to claim 1, wherein the absolute configuration at $R^1$ is S.

9. A compound according to claim 1 wherein the compound is in the form of a pharmaceutically acceptable salt.

10. A method for treating schizophrenia or Alzheimer's Disease which comprises administering to a human host suffering from said condition a therapeutically effective amount of a compound according to claim 1.

11. A pharmaceutical composition comprising a compound according to claim 1 together with at a pharmaceutical carrier.

12. A compound according to claim 1, of the formula

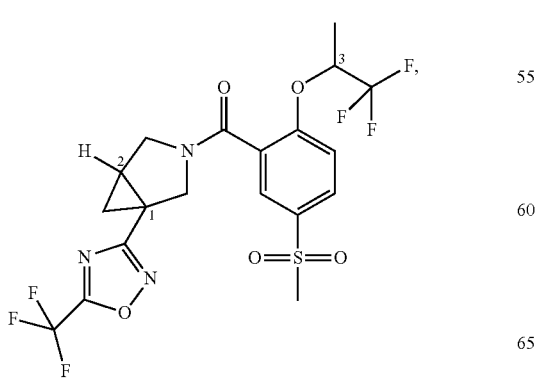

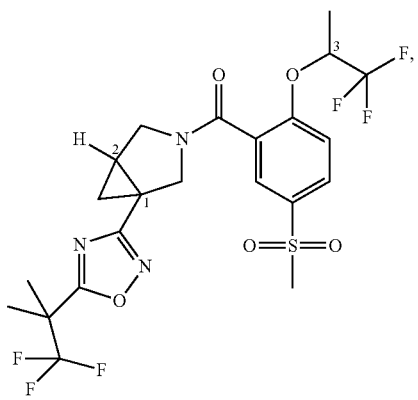

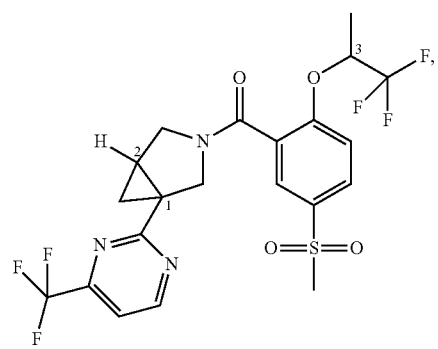 [SMILES: CC(Oc1ccc(S(C)(=O)=O)cc1C(=O)N1CC2CC2(c2nccc(C(F)(F)F)n2)C1)C(F)(F)F]

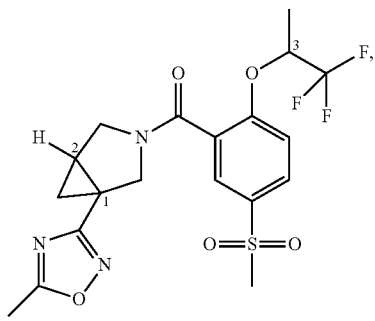

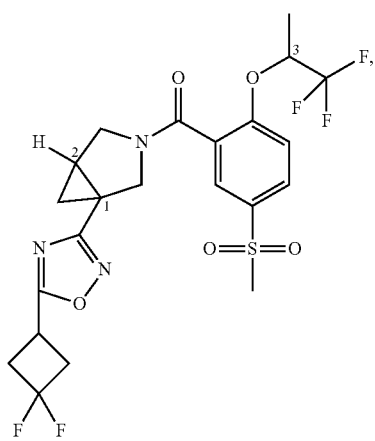

-continued
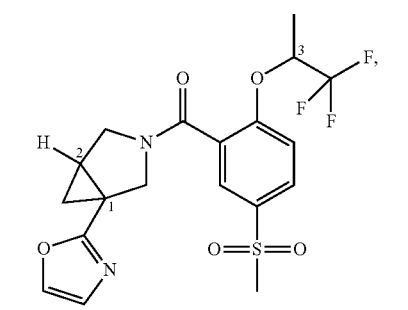
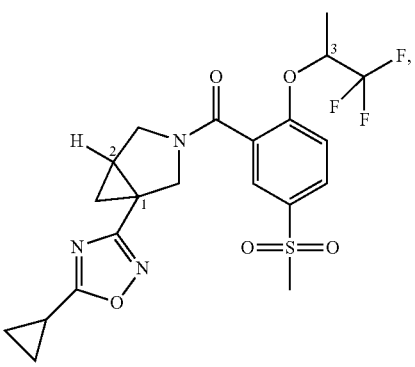
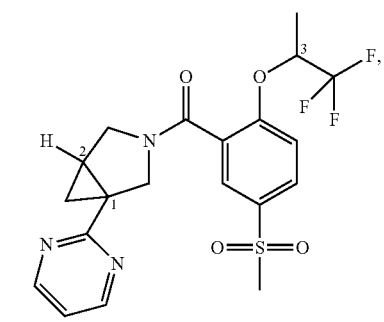
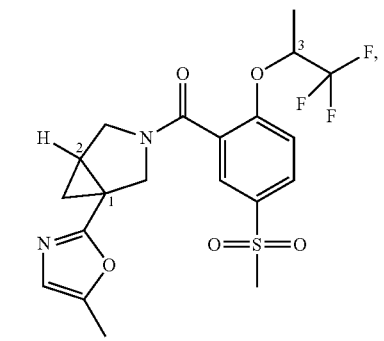
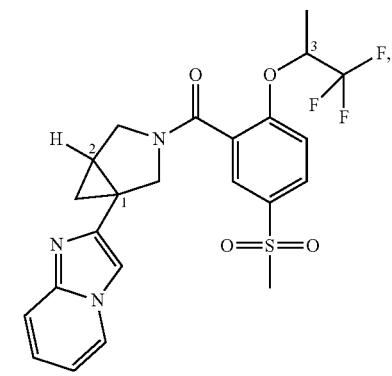
-continued
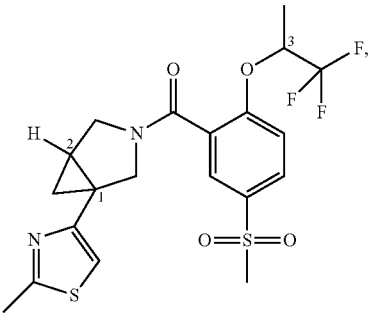
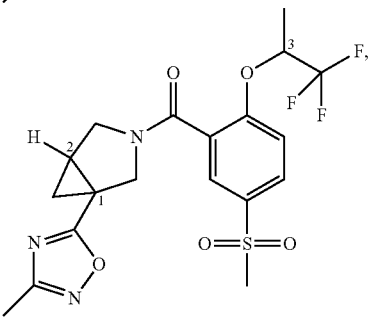
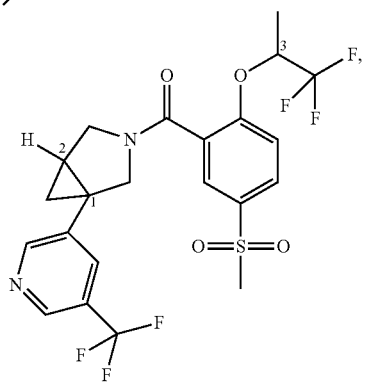
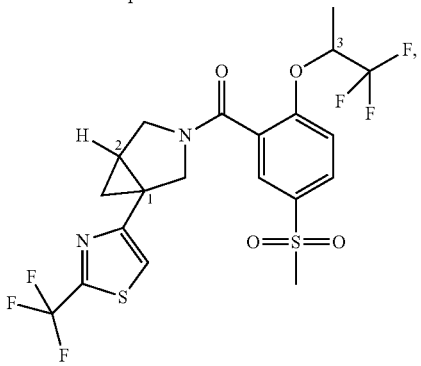
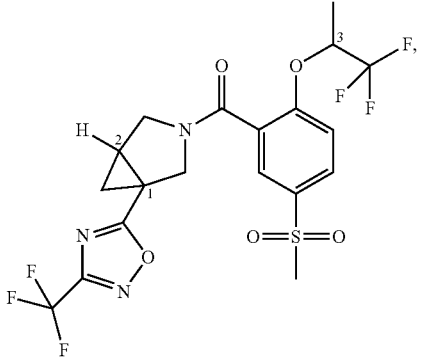

229
-continued
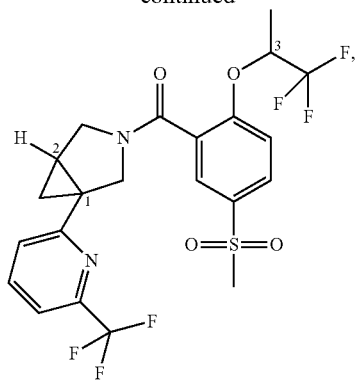
230
-continued
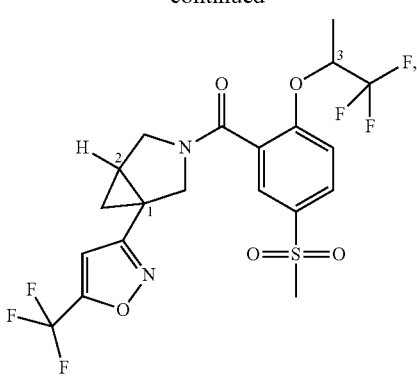
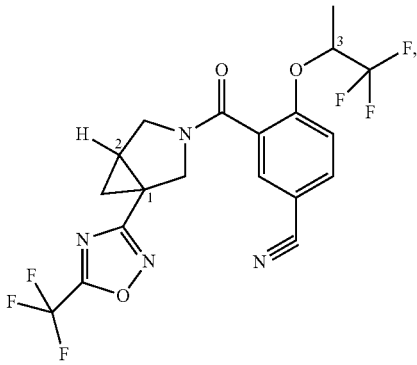
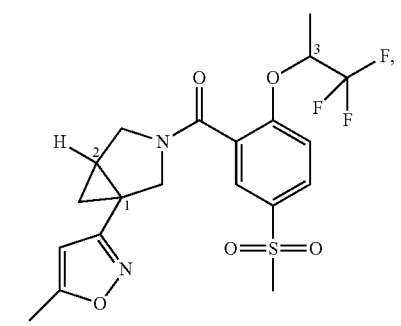
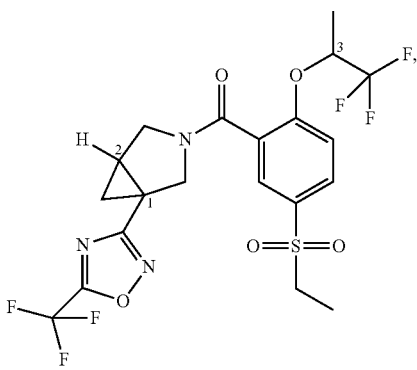

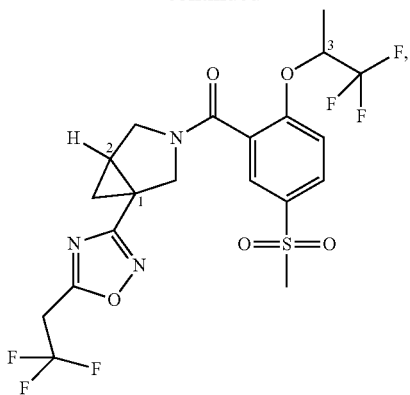
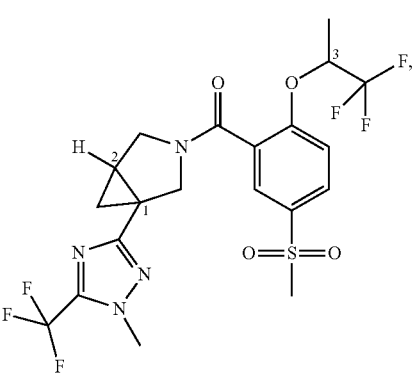
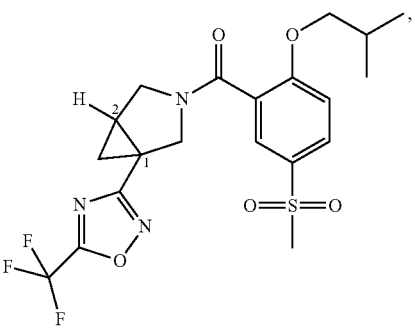
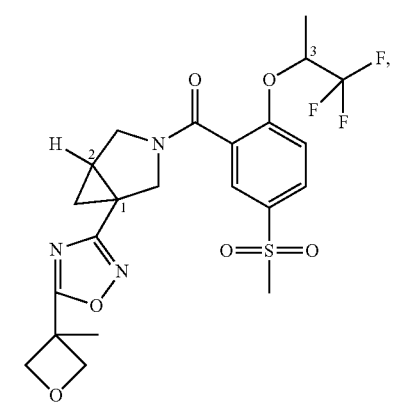
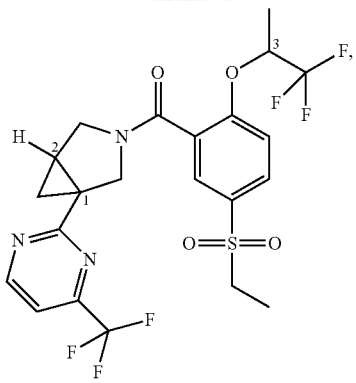
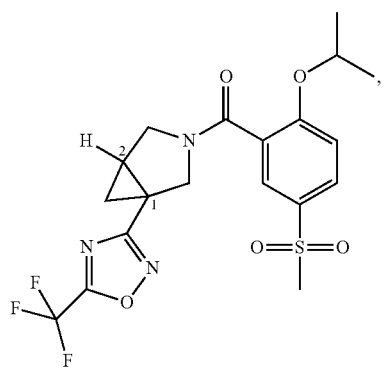
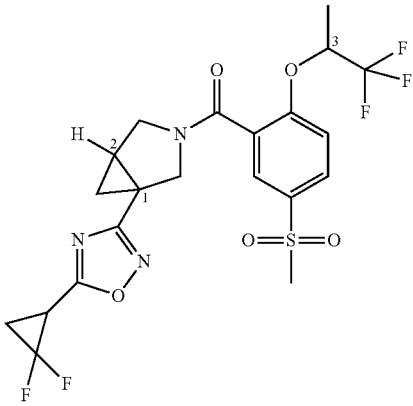
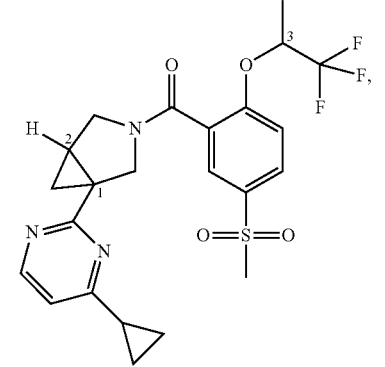

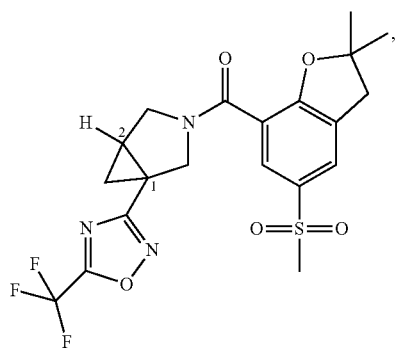
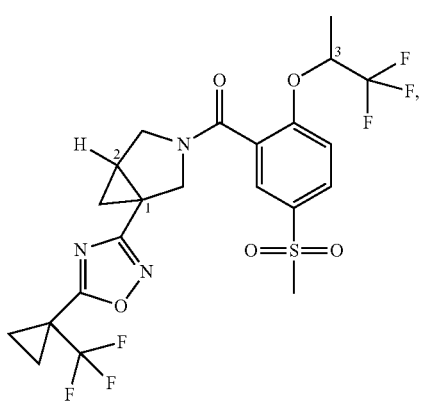
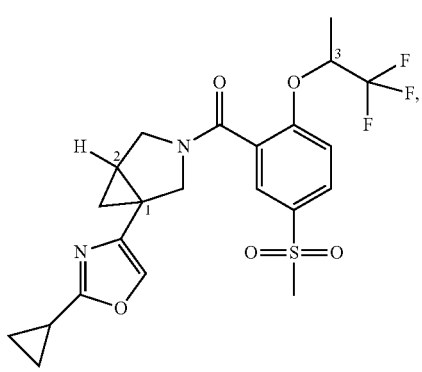
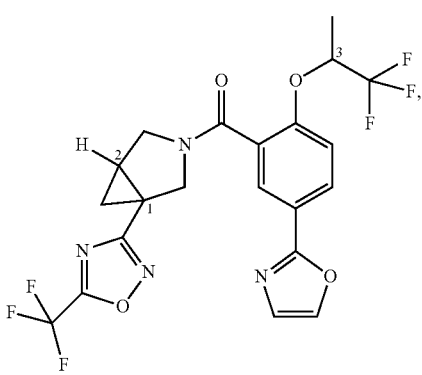
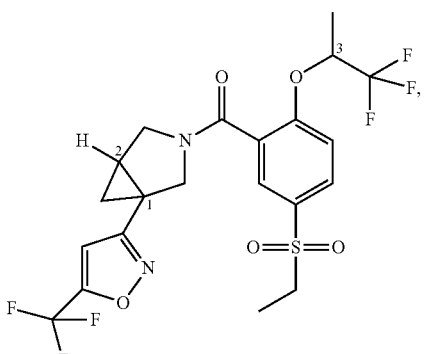
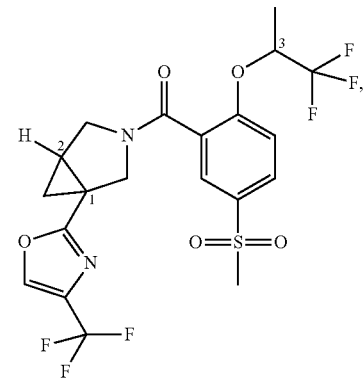
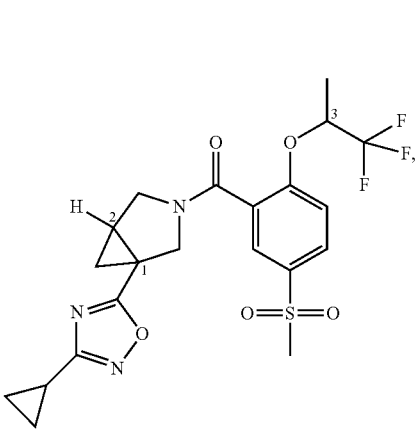
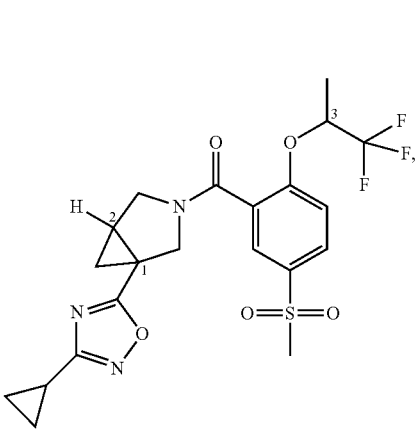

235
-continued
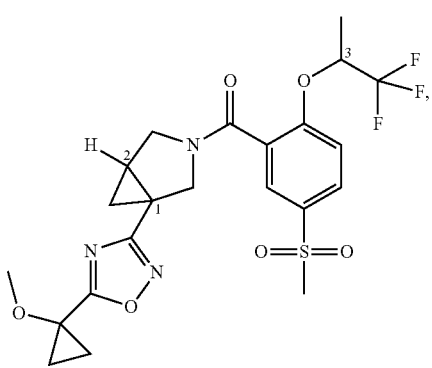
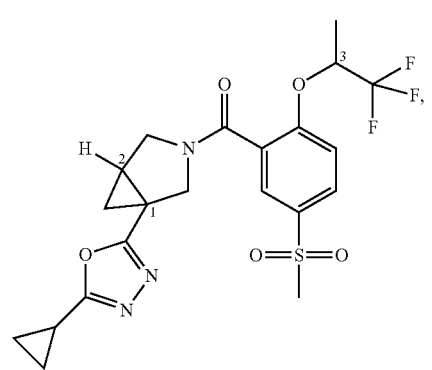
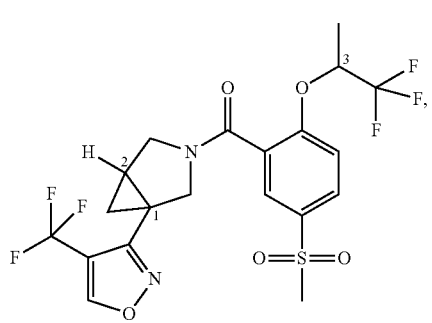
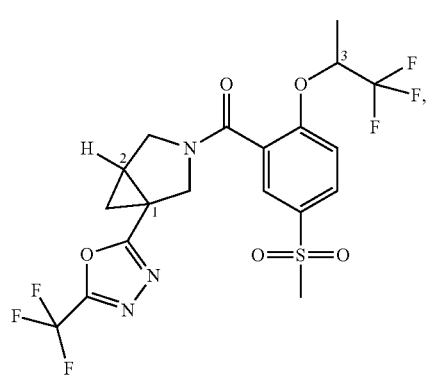
236
-continued
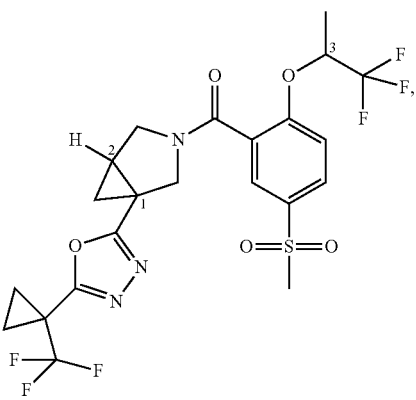
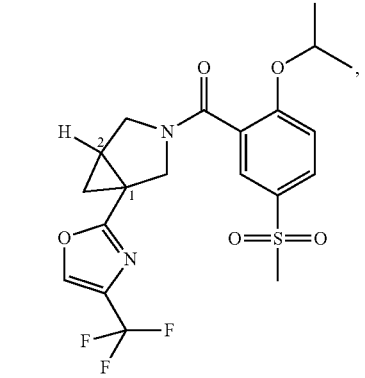
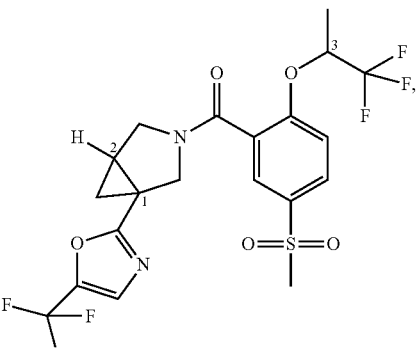
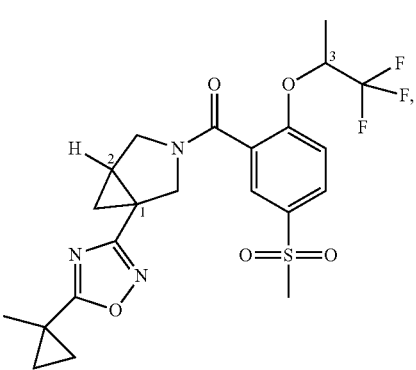

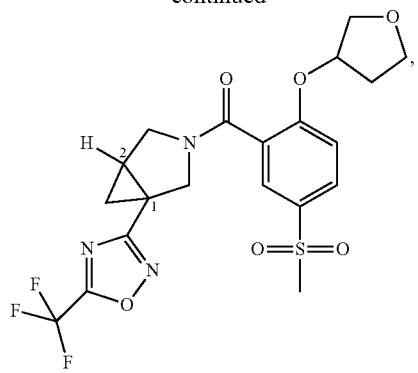
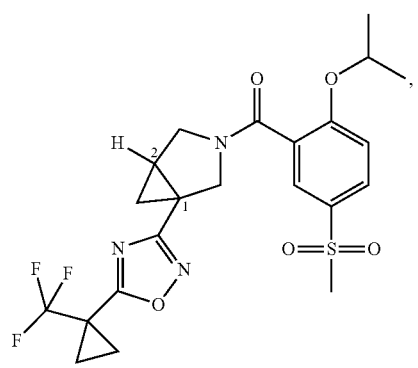
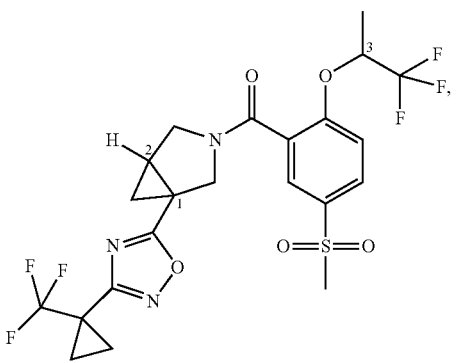
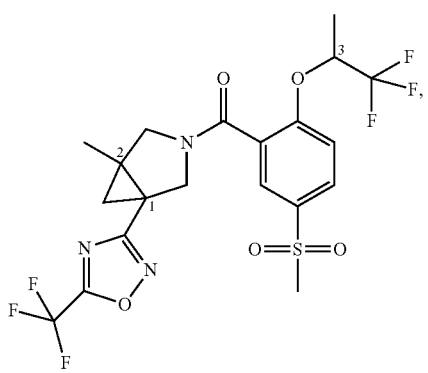

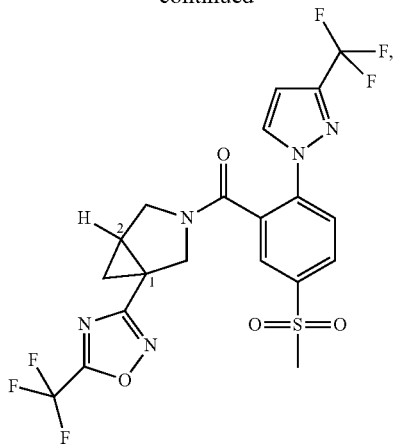
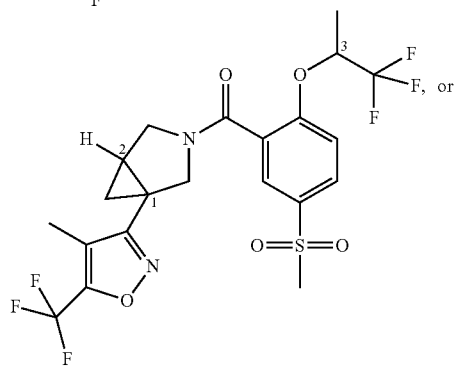
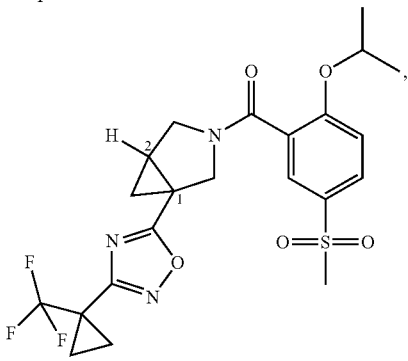

wherein said compound is selected from the group consisting of:
  the stereoisomer with R-configuration at the chiral carbon atom designated by the numeral 1 and R-configuration at the chiral carbon atom designated by the numeral 3;
  the stereoisomer with S-configuration at the chiral carbon atom designated by the numeral 1 and S-configuration at the chiral carbon atom designated by the numeral 3;
  the stereoisomer with R-configuration at the chiral carbon atom designated by the numeral 1 and S-configuration at the chiral carbon atom designated by the numeral 3;
  the stereoisomer with S-configuration at the chiral carbon atom designated by the numeral 1 and R-configuration at the chiral carbon atom designated by the numeral 3;
  wherein, in each such stereoisomer, the chiral carbon atom designated by the numeral 2 is always in the syn configuration with respect to the chiral carbon atom designated by the numeral 1;
or a mixture of two or more of the foregoing stereoisomer.

13. A compound according to claim 1, of the formula

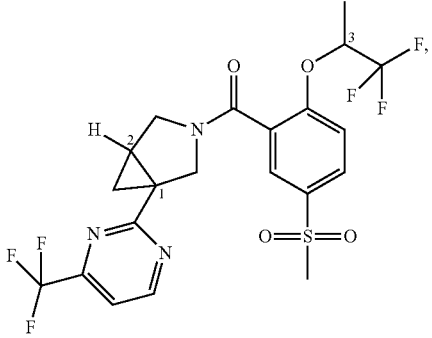

wherein said compound is selected from the group consisting of:
- the stereoisomer with R-configuration at the chiral carbon atom designated by the numeral 1 and R-configuration at the chiral carbon atom designated by the numeral 3;
- the stereoisomer with S-configuration at the chiral carbon atom designated by the numeral 1 and S-configuration at the chiral carbon atom designated by the numeral 3;
- the stereoisomer with R-configuration at the chiral carbon atom designated by the numeral 1 and S-configuration at the chiral carbon atom designated by the numeral 3; and
- the stereoisomer with S-configuration at the chiral carbon atom designated by the numeral 1 and R-configuration at the chiral carbon atom designated by the numeral 3;

wherein, in each such stereoisomer, the chiral carbon atom designated by the numeral 2 is always in the syn configuration with respect to the chiral carbon atom designated by the numeral 1;
or a mixture of two or more of the foregoing stereoisomers.

14. The compound according to claim 1, of the formula

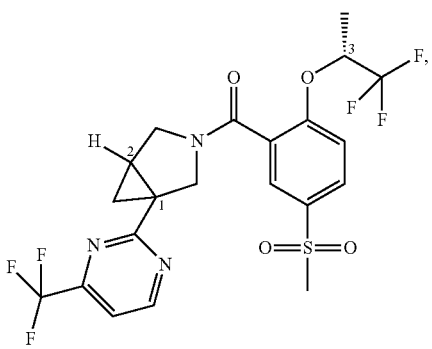 [SMILES: C[C@@H](Oc1ccc(S(C)(=O)=O)cc1C(=O)N1CC2CC2(c2nccc(C(F)(F)F)n2)C1)C(F)(F)F]

with R-configuration at the chiral carbon atom designated by the numeral 1;
wherein the chiral carbon atom designated by the numeral 2 is in the syn configuration with respect to the chiral carbon atom designated by the numeral 1.

15. The compound according to claim 1, of the formula

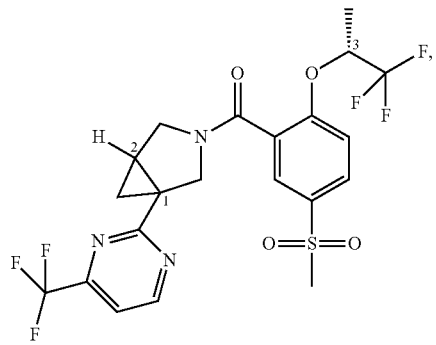 [SMILES: C[C@@H](Oc1ccc(S(C)(=O)=O)cc1C(=O)N1CC2CC2(c2nccc(C(F)(F)F)n2)C1)C(F)(F)F]

with S-configuration at the chiral carbon atom designated by the numeral 1;
wherein the chiral carbon atom designated by the numeral 2 is in the syn configuration with respect to the chiral carbon atom designated by the numeral 1.

16. The compound according to claim 1, of the formula

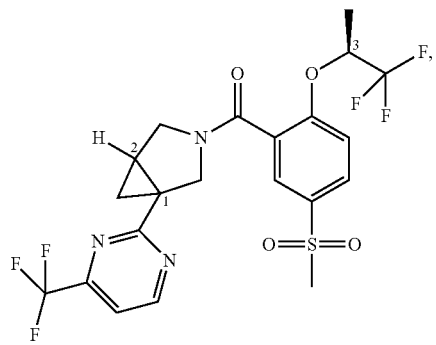 [SMILES: C[C@H](Oc1ccc(S(C)(=O)=O)cc1C(=O)N1CC2CC2(c2nccc(C(F)(F)F)n2)C1)C(F)(F)F]

with R-configuration at the chiral carbon atom designated by the numeral 1;
wherein the chiral carbon atom designated by the numeral 2 is in the syn configuration with respect to the chiral carbon atom designated by the numeral 1.

17. The compound according to claim 1, of the formula

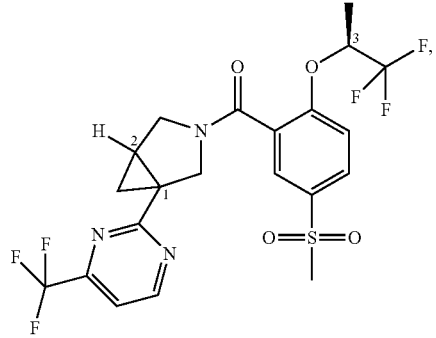 [SMILES: C[C@H](Oc1ccc(S(C)(=O)=O)cc1C(=O)N1CC2CC2(c2nccc(C(F)(F)F)n2)C1)C(F)(F)F]

with S-configuration at the chiral carbon atom designated by the numeral 1;
wherein the chiral carbon atom designated by the numeral 2 is in the syn configuration with respect to the chiral carbon atom designated by the numeral 1.

18. A compound according to claim 1, of the formula

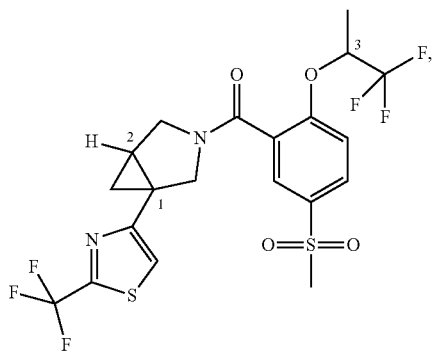

wherein said compound is selected from the group consisting of:
- the stereoisomer with R-configuration at the chiral carbon atom designated by the numeral 1 and R-configuration at the chiral carbon atom designated by the numeral 3;
- the stereoisomer with S-configuration at the chiral carbon atom designated by the numeral 1 and S-configuration at the chiral carbon atom designated by the numeral 3;
- the stereoisomer with R-configuration at the chiral carbon atom designated by the numeral 1 and S-configuration at the chiral carbon atom designated by the numeral 3; and
- the stereoisomer with S-configuration at the chiral carbon atom designated by the numeral 1 and R-configuration at the chiral carbon atom designated by the numeral 3;
- wherein, in each such stereoisomer, the chiral carbon atom designated by the numeral 2 is always in the syn configuration with respect to the chiral carbon atom designated by the numeral 1;

or a mixture of two or more of the foregoing stereoisomers.

19. The compound according to claim 1, of the formula

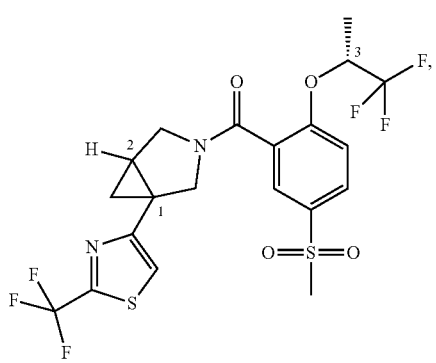 [SMILES: C[C@@H](Oc1ccc(S(C)(=O)=O)cc1C(=O)N1CC2CC2(c2csc(C(F)(F)F)n2)C1)C(F)(F)F]

with K-configuration at the chiral carbon atom designated by the numeral 1;
wherein the chiral carbon atom designated by the numeral 2 is in the syn configuration with respect to the chiral carbon atom designated by the numeral 1.

20. The compound according to claim 1, of the formula

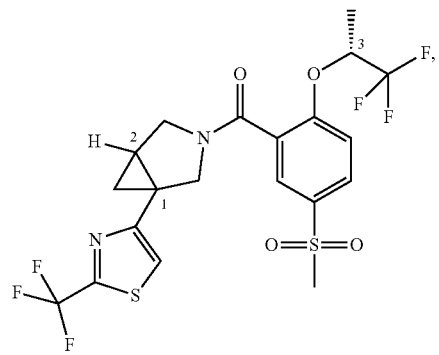

with S-configuration at the chiral carbon atom designated by the numeral 1;
wherein the chiral carbon atom designated by the numeral 2 is in the syn configuration with respect to the chiral carbon atom designated by the numeral 1.

21. The compound according to claim 1, of the formula

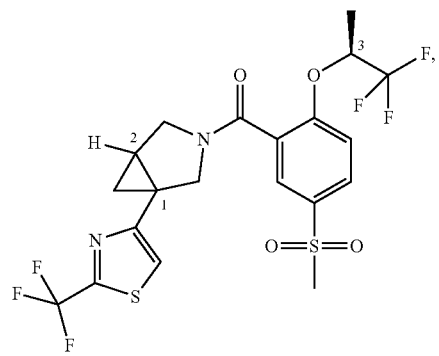 [SMILES: C[C@H](Oc1ccc(S(C)(=O)=O)cc1C(=O)N1CC2CC2(c2csc(C(F)(F)F)n2)C1)C(F)(F)F]

with R-configuration at the chiral carbon atom designated by the numeral 1;
wherein the chiral carbon atom designated by the numeral 2 is in the syn configuration with respect to the chiral carbon atom designated by the numeral 1.

22. The compound according to claim 1, of the formula

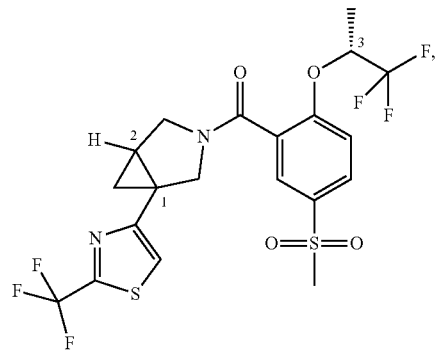

with S-configuration at the chiral carbon atom designated by the numeral 1;
wherein the chiral carbon atom designated by the numeral 2 is in the syn configuration with respect to the chiral carbon atom designated by the numeral 1.

23. A compound according to claim 1, of the formula

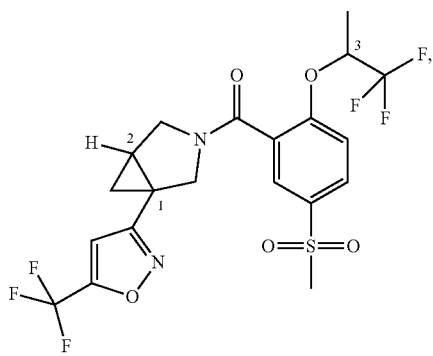 [SMILES: C[C@@H](Oc1ccc(S(C)(=O)=O)cc1C(=O)N1CC2CC2(c2cc(C(F)(F)F)on2)C1)C(F)(F)F]

wherein said compound is selected from the group consisting of:
- the stereoisomer with R-configuration at the chiral carbon atom designated by the numeral 1 and R-configuration at the chiral carbon atom designated by the numeral 3;
- the stereoisomer with S-configuration at the chiral carbon atom designated by the numeral 1 and S-configuration at the chiral carbon atom designated by the numeral 3;
- the diastereomer with R-configuration at the chiral carbon atom designated by the numeral 1 and S-configuration at the chiral carbon atom designated by the numeral 3; and
- the stereoisomer with S-configuration at the chiral carbon atom designated by the numeral 1 and R-configuration at the chiral carbon atom designated by the numeral 3;
- wherein, in each such stereoisomer, the chiral carbon atom designated by the numeral 2 is always in the syn configuration with respect to the chiral carbon atom designated by the numeral 1;

or a mixture of two or more of the foregoing stereoisomers.

24. The compound according to claim 1, of the formula

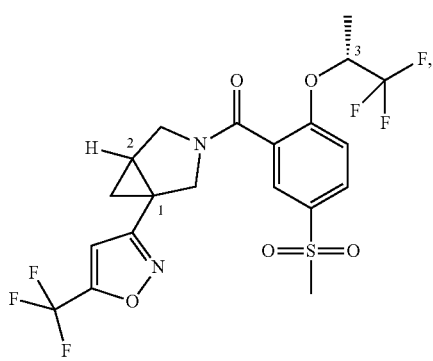 [SMILES: C[C@@H](Oc1ccc(S(C)(=O)=O)cc1C(=O)N1CC2CC2(c2cc(C(F)(F)F)on2)C1)C(F)(F)F]

with R-configuration at the chiral carbon atom designated by the numeral 1;
wherein the chiral carbon atom designated by the numeral 2 is in the syn configuration with respect to the chiral carbon atom designated by the numeral 1.

25. The compound according to claim 1, of the formula

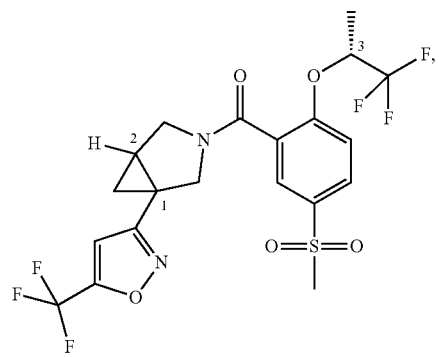

with S-configuration at the chiral carbon atom designated by the numeral 1;
wherein the chiral carbon atom designated by the numeral 2 is in the syn configuration with respect to the chiral carbon atom designated by the numeral 1.

26. The compound according to claim 1, of the formula

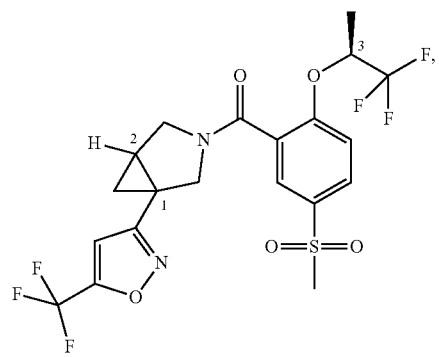 [SMILES: C[C@H](Oc1ccc(S(C)(=O)=O)cc1C(=O)N1CC2CC2(c2cc(C(F)(F)F)on2)C1)C(F)(F)F]

with R-configuration at the chiral carbon atom designated by the numeral 1;
wherein the chiral carbon atom designated by the numeral 2 is in the syn configuration with respect to the chiral carbon atom designated by the numeral 1.

27. The compound according to claim 1, of the formula

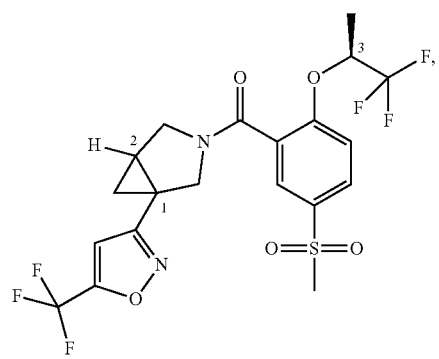 [SMILES: C[C@H](Oc1ccc(S(C)(=O)=O)cc1C(=O)N1CC2CC2(c2cc(C(F)(F)F)on2)C1)C(F)(F)F]

with S-configuration at the chiral carbon atom designated by the numeral 1;
wherein the chiral carbon atom designated by the numeral 2 is in the syn configuration with respect to the chiral carbon atom designated by the numeral 1.

28. A compound according to claim 1, of the formula

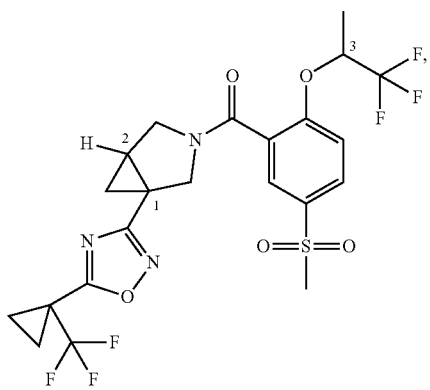 [SMILES: CC(Oc1ccc(S(C)(=O)=O)cc1C(=O)N1CC2CC2(c2noc(C3(C(F)(F)F)CC3)n2)C1)C(F)(F)F]

wherein said compound is selected from the group consisting of:
- the stereoisomer with R-configuration at the chiral carbon atom designated by the numeral 1 and R-configuration at the chiral carbon atom designated by the numeral 3;
- the stereoisomer with S-configuration at the chiral carbon atom designated by the numeral 1 and S-configuration at the chiral carbon atom designated by the numeral 3;
- the stereoisomer with R-configuration at the chiral carbon atom designated by the numeral 1 and S-configuration at the chiral carbon atom designated by the numeral 3; and
- the stereoisomer with S-configuration at the chiral carbon atom designated by the numeral 1 and R-configuration at the chiral carbon atom designated by the numeral 3;

wherein, in each such stereoisomer, the chiral carbon atom designated by the numeral 2 is always in the syn configuration with respect to the chiral carbon atom designated by the numeral 1;

or a mixture of two or more of the foregoing stereoisomers.

29. The compound according to claim 1, of the formula

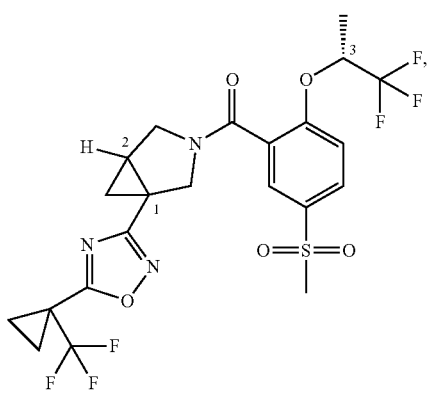 [SMILES: C[C@@H](Oc1ccc(S(C)(=O)=O)cc1C(=O)N1CC2CC2(c2noc(C3(C(F)(F)F)CC3)n2)C1)C(F)(F)F]

with R-configuration at the chiral carbon atom designated by the numeral 1;
wherein the chiral carbon atom designated by the numeral 2 is in the syn configuration with respect to the chiral carbon atom designated by the numeral 1.

30. The compound according to claim 1, of the formula

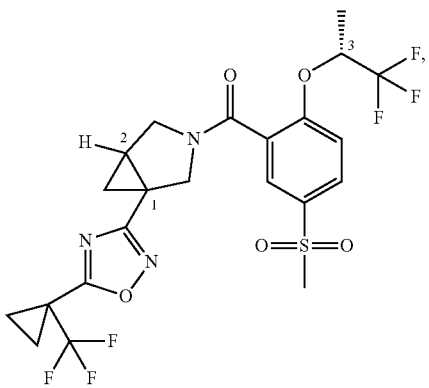

with S-configuration at the chiral carbon atom designated by the numeral 1;
wherein the chiral carbon atom designated by the numeral 2 is in the syn configuration with respect to the chiral carbon atom designated by the numeral 1.

31. The compound according to claim 1, of the formula

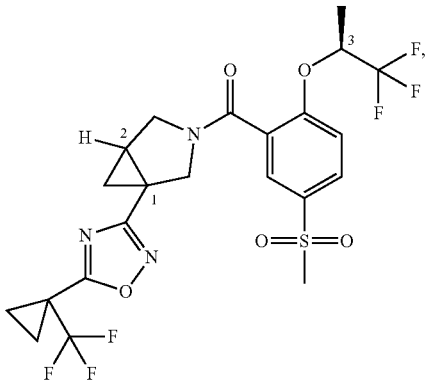 [SMILES: C[C@H](Oc1ccc(S(C)(=O)=O)cc1C(=O)N1CC2CC2(c2noc(C3(C(F)(F)F)CC3)n2)C1)C(F)(F)F]

with R-configuration at the chiral carbon atom designated by the numeral 1;
wherein the chiral carbon atom designated by the numeral 2 is in the syn configuration with respect to the chiral carbon atom designated by the numeral 1.

32. The compound according to claim 1, of the formula

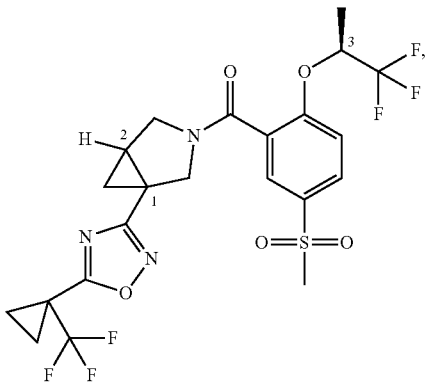 [SMILES: C[C@H](Oc1ccc(S(C)(=O)=O)cc1C(=O)N1CC2CC2(c2noc(C3(C(F)(F)F)CC3)n2)C1)C(F)(F)F]

with S-configuration at the chiral carbon atom designated by the numeral 1;

wherein the chiral carbon atom designated by the numeral 2 is in the syn configuration with respect to the chiral carbon atom designated by the numeral 1.

33. A compound according to claim 1, of the formula

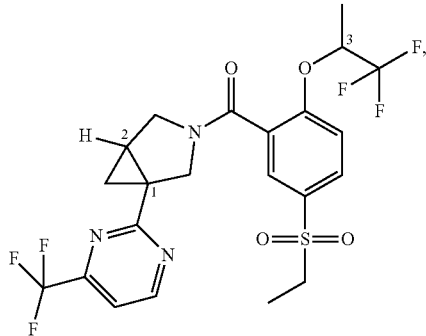

wherein said compound is selected from the group consisting of:
- the stereoisomer with R-configuration at the chiral carbon atom designated by the numeral 1 and R-configuration at the chiral carbon atom designated by the numeral 3;
- the stereoisomer with S-configuration at the chiral carbon atom designated by the numeral 1 and S-configuration at the chiral carbon atom designated by the numeral 3;
- the stereoisomer with R-configuration at the chiral carbon atom designated by the numeral 1 and S-configuration at the chiral carbon atom designated by the numeral 3; and
- the stereoisomer with S-configuration at the chiral carbon atom designated by the numeral 1 and R-configuration at the chiral carbon atom designated by the numeral 3;
- wherein, in each such stereoisomer, the chiral carbon atom designated by the numeral 2 is always in the syn configuration with respect to the chiral carbon atom designated by the numeral 1;
- or a mixture of two or more of the foregoing stereoisomers.

34. The compound according to claim 1, of the formula

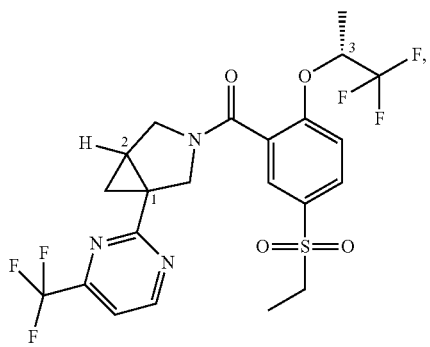 [SMILES: CCS(=O)(=O)c1ccc(O[C@H](C)C(F)(F)F)c(C(=O)N2CC3CC3(c3nccc(C(F)(F)F)n3)C2)c1]

with R-configuration at the chiral carbon atom designated by the numeral 1;
wherein the chiral carbon atom designated by the numeral 2 is in the syn configuration with respect to the chiral carbon atom designated by the numeral 1.

35. The compound according to claim 1, of the formula

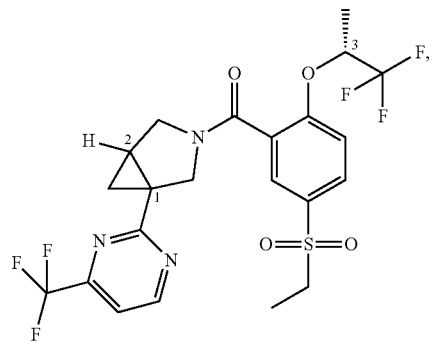 [SMILES: CCS(=O)(=O)c1ccc(O[C@H](C)C(F)(F)F)c(C(=O)N2CC3CC3(c3nccc(C(F)(F)F)n3)C2)c1]

with S-configuration at the chiral carbon atom designated by the numeral 1;
wherein the chiral carbon atom designated by the numeral 2 is in the syn configuration with respect to the chiral carbon atom designated by the numeral 1.

36. The compound according to claim 1, of the formula

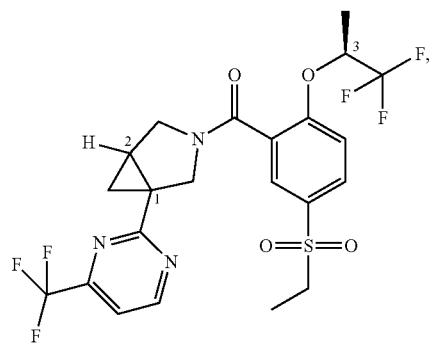 [SMILES: CCS(=O)(=O)c1ccc(O[C@@H](C)C(F)(F)F)c(C(=O)N2CC3CC3(c3nccc(C(F)(F)F)n3)C2)c1]

with R-configuration at the chiral carbon atom designated by the numeral 1;
wherein the chiral carbon atom designated by the numeral 2 is in the syn configuration with respect to the chiral carbon atom designated by the numeral 1.

37. The compound according to claim 1, of the formula

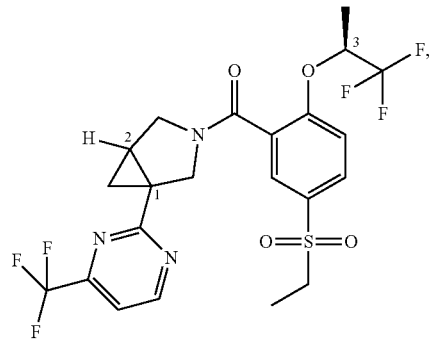 [SMILES: CCS(=O)(=O)c1ccc(O[C@@H](C)C(F)(F)F)c(C(=O)N2CC3CC3(c3nccc(C(F)(F)F)n3)C2)c1]

with S-configuration at the chiral carbon atom designated by the numeral 1;
wherein the chiral carbon atom designated by the numeral 2 is in the syn configuration with respect to the chiral carbon atom designated by the numeral 1.

38. A compound according to claim 1, of the formula

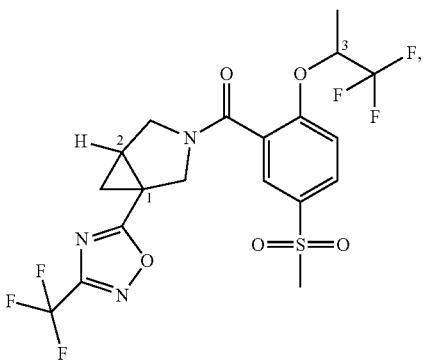

wherein said compound is selected from the group consisting of:
  the stereoisomer with R-configuration at the chiral carbon atom designated by the numeral 1 and R-configuration at the chiral carbon atom designated by the numeral 3;
  the stereoisomer with S-configuration at the chiral carbon atom designated by the numeral 1 and S-configuration at the chiral carbon atom designated by the numeral 3;
  the stereoisomer with R-configuration at the chiral carbon atom designated by the numeral 1 and S-configuration at the chiral carbon atom designated by the numeral 3; and
  the stereoisomer with S-configuration at the chiral carbon atom designated by the numeral 1 and R-configuration at the chiral carbon atom designated by the numeral 3;
  wherein, in each such stereoisomer, the chiral carbon atom designated by the numeral 2 is always in the syn configuration with respect to the chiral carbon atom designated by the numeral 1;
or a mixture of two or more of the foregoing stereoisomers.

39. The compound according to claim 1, of the formula

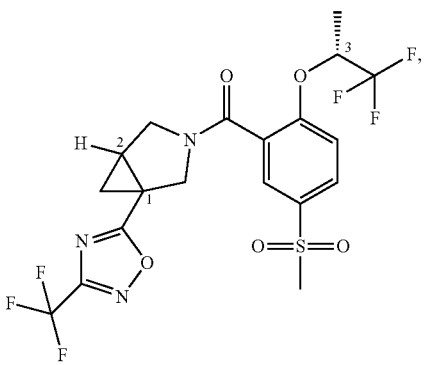

with R-configuration at the chiral carbon atom designated by the numeral 1;
wherein the chiral carbon atom designated by the numeral 2 is in the syn configuration with respect to the chiral carbon atom designated by the numeral 1.

40. The compound according to claim 1, of the formula

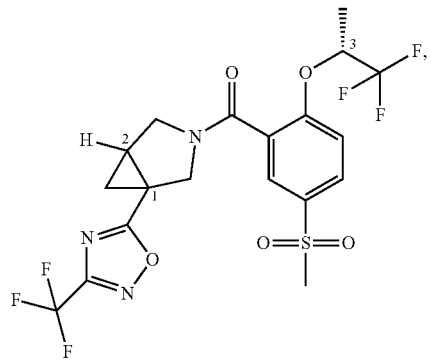 [SMILES: C[C@@H](Oc1ccc(S(C)(=O)=O)cc1C(=O)N1CC2CC2(c2nc(C(F)(F)F)no2)C1)C(F)(F)F]

with S-configuration at the chiral carbon atom designated by the numeral 1;
wherein the chiral carbon atom designated by the numeral 2 is in the syn configuration with respect to the chiral carbon atom designated by the numeral 1.

41. The compound according to claim 1, of the formula

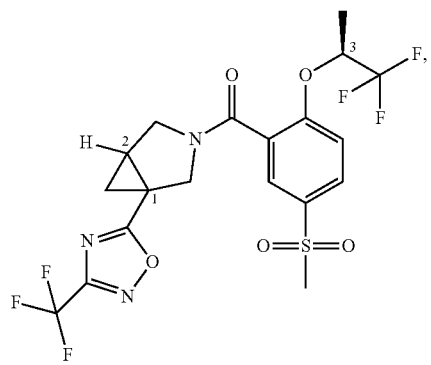 [SMILES: C[C@H](Oc1ccc(S(C)(=O)=O)cc1C(=O)N1CC2CC2(c2nc(C(F)(F)F)no2)C1)C(F)(F)F]

with R-configuration at the chiral carbon atom designated by the numeral 1;
wherein the chiral carbon atom designated by the numeral 2 is in the syn configuration with respect to the chiral carbon atom designated by the numeral 1.

42. The compound according to claim 1, of the formula

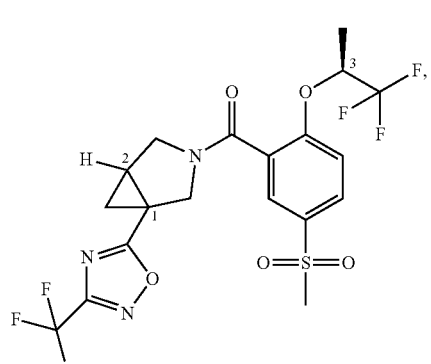

with S-configuration at the chiral carbon atom designated by the numeral 1;
wherein the chiral carbon atom designated by the numeral 2 is in the syn configuration with respect to the chiral carbon atom designated by the numeral 1.

43. A compound according to claim 1, of the formula

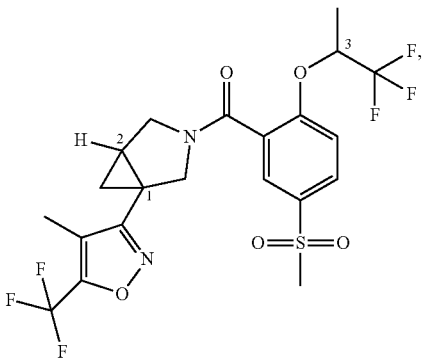 [SMILES: Cc1c(C23CC2CN(C(=O)c2cc(S(C)(=O)=O)ccc2OC(C)C(F)(F)F)C3)noc1C(F)(F)F]

wherein said compound is selected from the group consisting of:

the stereoisomer with R-configuration at the chiral carbon atom designated by the numeral 1 and R-configuration at the chiral carbon atom designated by the numeral 3;

the stereoisomer with S-configuration at the chiral carbon atom designated by the numeral 1 and S-configuration at the chiral carbon atom designated by the numeral 3;

the stereoisomer with R-configuration at the chiral carbon atom designated by the numeral 1 and S-configuration at the chiral carbon atom designated by the numeral 3; and the stereoisomer with S-configuration at the chiral carbon atom designated by the numeral 1 and R-configuration at the chiral carbon atom designated by the numeral 3;

wherein, in each such stereoisomer, the chiral carbon atom designated by the numeral 2 is always in the syn configuration with respect to the chiral carbon atom designated by the numeral 1;

or a mixture of two or more of the foregoing stereoisomers.

44. The compound according to claim 1, of the formula

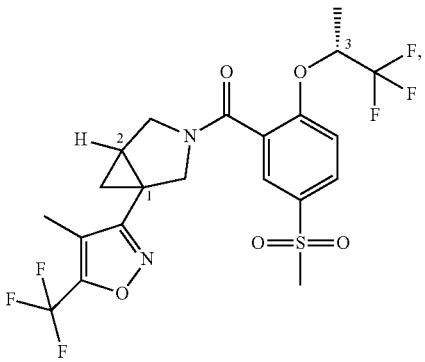

with R-configuration at the chiral carbon atom designated by the numeral 1;
wherein the chiral carbon atom designated by the numeral 2 is in the syn configuration with respect to the chiral carbon atom designated by the numeral 1.

45. The compound according to claim 1, of the formula

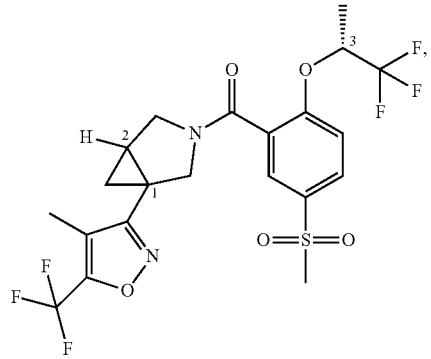 [SMILES: Cc1c(C23CC2CN(C(=O)c2cc(S(C)(=O)=O)ccc2O[C@H](C)C(F)(F)F)C3)noc1C(F)(F)F]

with S-configuration at the chiral carbon atom designated by the numeral 1;
wherein the chiral carbon atom designated by the numeral 2 is in the syn configuration with respect to the chiral carbon atom designated by the numeral 1.

46. The compound according to claim 1, of the formula

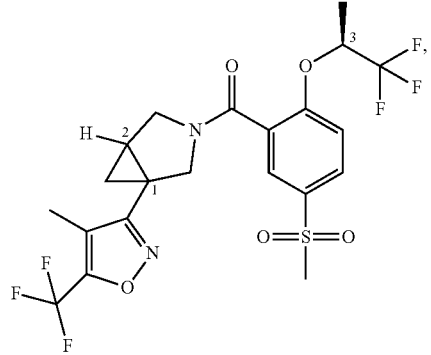 [SMILES: Cc1c(C23CC2CN(C(=O)c2cc(S(C)(=O)=O)ccc2O[C@@H](C)C(F)(F)F)C3)noc1C(F)(F)F]

with R-configuration at the chiral carbon atom designated by the numeral 1;
wherein the chiral carbon atom designated by the numeral 2 is in the syn configuration with respect to the chiral carbon atom designated by the numeral 1.

47. The compound according to claim 1, of the formula

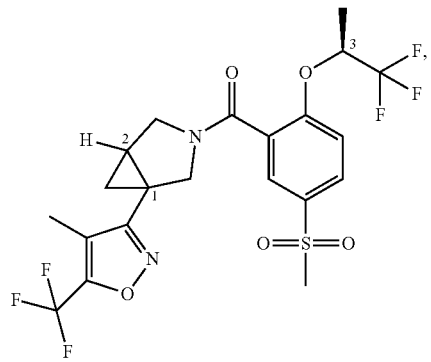 [SMILES: Cc1c(C23CC2CN(C(=O)c2cc(S(C)(=O)=O)ccc2O[C@@H](C)C(F)(F)F)C3)noc1C(F)(F)F]

with S-configuration at the chiral carbon atom designated by the numeral 1;
wherein the chiral carbon atom designated by the numeral 2 is in the syn configuration with respect to the chiral carbon atom designated by the numeral 1.

* * * * *